(12) United States Patent
Cheruvallath et al.

(10) Patent No.: US 8,563,730 B2
(45) Date of Patent: Oct. 22, 2013

(54) PYRAZOLE AND FUSED PYRAZOLE GLUCOKINASE ACTIVATORS

(75) Inventors: Zacharia Cheruvallath, San Diego, CA (US); Stephen L. Gwaltney, Escondido, CA (US); Andrew John Jennings, San Diego, CA (US); Mark Sabat, San Diego, CA (US); Jeffrey A. Stafford, San Diego, CA (US); Mingnam Tang, San Diego, CA (US); Haxia Wang, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 689 days.

(21) Appl. No.: 12/467,041

(22) Filed: May 15, 2009

(65) Prior Publication Data

US 2009/0286800 A1    Nov. 19, 2009

Related U.S. Application Data

(60) Provisional application No. 61/054,052, filed on May 16, 2008, provisional application No. 61/108,370, filed on Oct. 24, 2008.

(51) Int. Cl.
- *C07D 471/04* (2006.01)
- *C07D 231/12* (2006.01)
- *C07D 231/56* (2006.01)
- *A61K 31/437* (2006.01)

(52) U.S. Cl.
USPC ............ 546/119; 548/360.5; 548/361.1; 548/375.1; 514/303; 514/406

(58) Field of Classification Search
None
See application file for complete search history.

(56) References Cited

U.S. PATENT DOCUMENTS

| | | | |
|---|---|---|---|
| 5,612,360 A | 3/1997 | Boyd et al. | |
| 6,458,768 B1 | 10/2002 | Cozzi et al. | |
| 7,179,613 B2 | 2/2007 | Rizzo | |
| 8,008,332 B2 | 8/2011 | Cao | |
| 2002/0082260 A1 | 6/2002 | Guertin et al. | |
| 2002/0111372 A1 | 8/2002 | Corbett et al. | |
| 2003/0013633 A1 | 1/2003 | Kaddurah-Daouk | |
| 2004/0053948 A1 | 3/2004 | McDonald et al. | |
| 2004/0067939 A1 | 4/2004 | Corbett | |
| 2007/0197532 A1 | 8/2007 | Cao et al. | |
| 2007/0213349 A1 | 9/2007 | Cheruvallath et al. | |
| 2007/0244169 A1 | 10/2007 | Feng et al. | |
| 2007/0275999 A1 | 11/2007 | Kitahara | |
| 2008/0280875 A1 | 11/2008 | Pfizer | |
| 2009/0099163 A1 | 4/2009 | Cheruvallath et al. | |
| 2009/0105255 A1 | 4/2009 | Cheruvallath et al. | |

FOREIGN PATENT DOCUMENTS

| | | |
|---|---|---|
| EP | 0448206 | 9/1991 |
| EP | 1496052 | 1/2005 |
| EP | 1532980 | 5/2005 |
| EP | 1921074 | 5/2008 |
| WO | WO/95/03809 | 2/1995 |
| WO | WO/98/21239 | 5/1998 |
| WO | WO 00/58293 | 10/2000 |
| WO | WO 01/44216 | 6/2001 |
| WO | WO/01/47514 | 7/2001 |
| WO | WO 01/83478 | 11/2001 |
| WO | WO/01/85707 | 11/2001 |
| WO | WO 02/08209 | 1/2002 |
| WO | WO 02/48106 | 6/2002 |
| WO | WO/03/002062 | 1/2003 |
| WO | WO/03/055482 | 1/2003 |
| WO | WO/03/047626 | 6/2003 |
| WO | WO/2004/002481 | 1/2004 |
| WO | WO/2004/007720 | 1/2004 |
| WO | WO 2004/026226 | 4/2004 |
| WO | WO/2004/028339 | 4/2004 |
| WO | WO/2004/039412 | 5/2004 |
| WO | WO 2004/050645 | 6/2004 |
| WO | WO 2004/063179 | 7/2004 |
| WO | WO 2004/072031 | 8/2004 |
| WO | WO/2004/072031 | 8/2004 |
| WO | WO/2004/072066 | 8/2004 |
| WO | WO/2005/049019 | 5/2005 |
| WO | WO/2005/051320 | 6/2005 |
| WO | WO 2005/095418 | 10/2005 |
| WO | WO/2005/095418 | 10/2005 |
| WO | WO/2005/103021 | 11/2005 |
| WO | WO/2005/123132 | 12/2005 |
| WO | WO/2006/002121 | 1/2006 |
| WO | WO/2006/016174 | 2/2006 |
| WO | WO/2006/016194 | 2/2006 |
| WO | WO/2006/024491 | 3/2006 |

(Continued)

OTHER PUBLICATIONS

Wolff, Manfred E. "Burger's Medicinal Chemistry, 5ed, Part I", John Wiley & Sons, 1995, pp. 975-977.*

(Continued)

*Primary Examiner* — David K O Dell
(74) *Attorney, Agent, or Firm* — Matthew J. Russo; Mitchell R. Brustein

(57) ABSTRACT

Compounds are provided for use with glucokinase that comprise the formula:

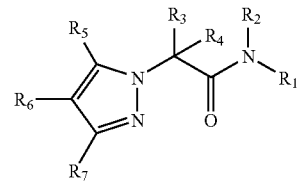

wherein the variables are as defined herein. Also provided are pharmaceutical compositions, kits and articles of manufacture comprising such compounds; methods and intermediates useful for making the compounds; and methods of using said compounds.

52 Claims, 1 Drawing Sheet

(56) References Cited

FOREIGN PATENT DOCUMENTS

| WO | WO/2006/080524 | 8/2006 |
| WO | WO/2007/001928 | 1/2007 |
| WO | WO 2007/007886 | 1/2007 |
| WO | WO/2007/041365 | 4/2007 |
| WO | WO/2007/051847 | 5/2007 |
| WO | WO 2007/061923 | 5/2007 |
| WO | WO 2007/075847 | 5/2007 |
| WO | WO 2007/104034 | 9/2007 |
| WO | WO 2007/115968 | 10/2007 |
| WO | WO/2007/122482 | 11/2007 |
| WO | WO 2007/143434 | 12/2007 |
| WO | WO/2008/005964 | 1/2008 |
| WO | WO 2008/079787 | 7/2008 |
| WO | WO/2008/084043 | 7/2008 |
| WO | WO 2008/116107 | 9/2008 |
| WO | WO/2008/153814 | 12/2008 |
| WO | WO/2009/022179 | 2/2009 |
| WO | WO/2011/115758 | 9/2011 |

OTHER PUBLICATIONS

Banker (Modern Pharmaceutics) Banker, G.S. et al, "Modern Pharmaceutics, 3ed.", Marcel Dekker, New York, 1996, pp. 451 and 596.*

West, Anthony R., Solid State Chemistry and its Applications, Wiley, New York, 1988, pp. 358 & 365.*

Bernstein "Polymorphism—A Perspective" Crystal Growth & Design, vol. 11, No. 3, 2011 pp. 632-650.*

Lang et. al. "Discovery and hit-to-lead optimization of novel allosteric glucokinase activators" Bioorg. Med. Chem. Lett. (2011), doi:10.1016/j.bmc1.2011.06.128 pp. 1-6.*

\* cited by examiner

[SEQ. I.D. No. 1]

MKLMALTLVEQILAEFQLQEEDLKKVMRRMQKEMDRGLRLETHEEASVKMLPTYVRSTPE
GSEVGDFLSLDLGGTNFRVMLVKVGEGEEGQWSVKTKHQMYSIPEDAMTGTAEMLFDYIS
ECISDFLDKHQMKHKKLPLGFTFSFPVRHEDIDKGILLNWTKGFKASGAEGNNVVGLLRD
AIKRRGDFEMDVVAMVNDTVATMISCYYEDHQCEVGMIVGTGCNACYMEEMQNVELVEGD
EGRMCVNTEWGAFGDSGELDEFLLEYDRLVDESSANPGQQLYEKLIGGKYMGELVRLVLL
RLVDENLLFHGEASEQLRTRGAFETRFVSQVESDTGDRKQIYNILSTLGLRPSTTDCDIV
RRACESVSTRAAHMCSAGLAGVINRMRESRSEDVMRITVGVDGSVYKLHPSFKERFHASV
RRLTPSCEITFIESEEGSGRGAALVSAVACKKACMLGQ

PYRAZOLE AND FUSED PYRAZOLE GLUCOKINASE ACTIVATORS

RELATED APPLICATION

This application claims the benefit of U.S. Provisional Application No. 61/054,052, filed May 16, 2008, and of U.S. Provisional Application No. 61/108,370, filed on Oct. 24, 2008, which are incorporated herein by reference.

FIELD OF THE INVENTION

The present invention relates to compounds that may be used to activate hexokinases, as well as compositions of matter, kits and articles of manufacture comprising these compounds. The invention also relates to methods for activating hexokinases and treatment methods using compounds according to the present invention. In addition, the invention relates to methods of making the compounds of the present invention, as well as intermediates useful in such methods. In particular, the present invention relates to glucokinase activators, compositions of matter, kits and articles of manufacture comprising these compounds, methods for activating glucokinase, and methods of making the activators.

BACKGROUND OF THE INVENTION

Glucokinase (GK, Hexokinase IV) is one of four hexokinases that are found in mammals (Colowick, S. P., in The Enzymes, Vol. 9 (P. Boyer, ed.) Academic Press, New York, N.Y., pages 1-48, 1973). The hexokinases catalyze the first step in the metabolism of glucose, i.e., the conversion of glucose to glucose-6-phosphate. Glucokinase is found principally in pancreatic β-cells and liver parenchymal cells, two cell types that are known to play critical roles in whole-body glucose homeostasis. Specifically, GK is a rate-controlling enzyme for glucose metabolism in these two cell types (Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994).

The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting levels (5 mM) to postprandial levels following a carbohydrate-containing meal (about 10-15 mM) (Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993). These findings suggest that GK functions as a glucose sensor in β-cells and hepatocytes (Meglasson, M. D. and Matschinsky, F. M. Amer. J. Physiol. 246, E1-E13, 1984).

More recently, studies in transgenic animals confirmed that GK does indeed play a critical role in whole-body glucose homeostasis. Animals that do not express GK die within days of birth with severe diabetes, while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). Accordingly, compounds that activate GK and, thereby, increase the sensitivity of the GK sensor system are expected to be useful in the treatment of the hyperglycemia characteristic of all type II diabetes. Glucokinase activators should increase the flux of glucose metabolism in β-cells and hepatocytes, which will be coupled to increased insulin secretion.

There is a continued need to find new therapeutic agents to treat human diseases. The hexokinases, specifically but not limited to glucokinase, are especially attractive targets for the discovery of new therapeutics due to their important role in diabetes, hyperglycemia and other diseases.

SUMMARY OF THE INVENTION

The present invention relates to compounds that activate glucokinase. The present invention also provides compositions, articles of manufacture and kits comprising these compounds. In addition, the invention relates to methods of making the compounds of the present invention, as well as intermediates useful in such methods.

In one embodiment, a pharmaceutical composition is provided that comprises a glucokinase activator according to the present invention as an active ingredient. Pharmaceutical compositions according to the invention may optionally comprise 0.001%-100% of one or more activators of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with glucokinase.

In one embodiment, a kit is provided that comprises a composition comprising at least one glucokinase activator of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one glucokinase activator of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to modulate glucokinase. In particular, the compounds, compositions, kits and articles of manufacture can be used to activate glucokinase.

In another embodiment, the compounds, compositions, kits and articles of manufacture are used to treat a disease state for which increasing glucokinase activity ameliorates the pathology and/or symptomology of the disease state.

In another embodiment, a compound is administered to a subject wherein glucokinase activity within the subject is altered and, in one embodiment, increased.

In another embodiment, a prodrug of a compound is administered to a subject that is converted to the compound in vivo where it activates glucokinase.

In another embodiment, a method of activating glucokinase is provided that comprises contacting glucokinase with a compound according to the present invention.

In another embodiment, a method of activating glucokinase is provided that comprises causing a compound according to the present invention to be present in a subject in order to activate glucokinase in vivo.

In another embodiment, a method of activating glucokinase is provided that comprises administering a first compound to a subject that is converted in vivo to a second compound wherein the second compound activates glucokinase in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by glucokinase, or which is known to be treated by glucokinase activators, is provided comprising administering to the patient a therapeutically effective amount of a compound according to the present invention.

In another embodiment, a method is provided for treating a disease state for which increasing glucokinase activity ameliorates the pathology and/or symptomology of the disease state, the method comprising: causing a compound according to the present invention to be present in a subject in a therapeutically effective amount for the disease state.

In another embodiment, a method is provided for treating a disease state for which increasing glucokinase activity ameliorates the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which increasing glucokinase activity ameliorates the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by glucokinase, or that is known to be treated by glucokinase activators.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to activating glucokinase and thus may themselves be prodrugs for another compound. Such prodrugs of another compound may or may not themselves independently have glucokinase activity.

BRIEF DESCRIPTION OF THE FIGURES

FIG. 1 illustrates SEQ. ID No. 1 referred to in this application.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $4^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$)alkenyl or a ($C_{2-3}$)alkenyl. Alternatively, "alkenyl," either alone or represented along with another radical, can be a ($C_2$)alkenyl, a ($C_3$)alkenyl or a ($C_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a ($C_{2-20}$) alkenylene, a ($C_{2-15}$) alkenylene, a ($C_{2-10}$) alkenylene, a ($C_{2-5}$) alkenylene or a ($C_{2-3}$) alkenylene. Alternatively, "alkenylene," either alone or represented along with another radical, can be a ($C_2$) alkenylene, a ($C_3$) alkenylene or a ($C_4$) alkenylene.

"Alkoxy" means an oxygen moiety having a further alkyl substituent. The alkoxy groups of the present invention can be optionally substituted.

"Alkyl" represented by itself means a straight or branched, saturated aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., ($C_{6-10}$)aryl($C_{1-3}$)alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a ($C_{1-20}$)alkyl, a ($C_{1-15}$)alkyl, a ($C_{1-10}$)alkyl, a ($C_{1-5}$)alkyl or a ($C_{1-3}$)alkyl. Alternatively, "alkyl," either alone or represented along with another radical, can be a ($C_1$)alkyl, a ($C_2$)alkyl or a ($C_3$)alkyl.

"Alkylene", unless indicated otherwise, means a straight or branched, saturated or unsaturated, aliphatic, divalent radical. ($C_X$)alkylene and ($C_{X-Y}$)alkylene are typically used where X and Y indicate the number of carbon atoms in the chain. For example, ($C_{1-6}$)alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a ($C_{1-20}$)alkylene, a ($C_{1-15}$)alkylene, a ($C_{1-10}$)alkylene, a ($C_{1-5}$)alkylene or a ($C_{1-3}$)alkylene. Alternatively, "alkylene," either alone or represented along with another radical, can be a ($C_1$)alkylene, a ($C_2$)alkylene or a ($C_3$)alkylene.

"Alkylidene" means a straight or branched, saturated or unsaturated, aliphatic radical connected to the parent molecule by a double bond. ($C_X$)alkylidene and ($C_{X-Y}$)alkylidene are typically used where X and Y indicate the number of carbon atoms in the chain. For example, ($C_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a ($C_{1-20}$)alkylidene, a ($C_{1-15}$)alkylidene, a ($C_{1-10}$)alkylidene, a ($C_{1-5}$)alkylidene or a ($C_{1-3}$)alkylidene. Alternatively, "alkylidene," either alone or represented along with another radical, can be a ($C_1$)alkylidene, a ($C_2$)alkylidene or a ($C_3$)alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a ($C_{2-20}$)alkynyl, a ($C_{2-15}$)alkynyl, a ($C_{2-10}$)alkynyl, a ($C_{2-5}$)alkynyl or a ($C_{2-3}$)alkynyl. Alternatively, "alkynyl," either alone or represented along with another radical, can be a ($C_2$)alkynyl, a ($C_3$)alkynyl or a ($C_4$)alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a ($C_{2-20}$) alkynylene, a ($C_{2-15}$) alkynylene, a ($C_{2-10}$) alkynylene, a ($C_{2-5}$) alkynylene or a ($C_{2-3}$) alkynylene. Alternatively, "alkynylene," either alone or represented along with another radical, can be a ($C_2$) alkynylene, a ($C_3$) alkynylene or a ($C_4$) alkynylene.

"Amido" means the radical —C(=O)—NR—, —C(=O)—NRR', —NR—C(=O)— and/or —NR—C(=O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH(($C_{1-10}$)alkyl), —N(($C_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp² hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $(C_X)$aryl and $(C_{X-Y})$aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene, a $(C_9)$cycloalkylene or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-15})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$) bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$) bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-3}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-$(L)_X$-R' where each L is independently selected from the group consisting of CR"R"', NR"", O, S, CO, CS, C=NR"'", SO, $SO_2$, and the like, where any two or more of R", R"', R"" and R"'" can be taken together to form a substituted or unsubstituted ring.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa $(C_{1-10})$alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid, or acid halide. For example, an oxo$(C_{1-10})$alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" include humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [$(CH_3)_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)CO$—), Arg (arginine), Asn (asparagine), Asp (aspartic acid), Cys (cysteine), Glu (glutamic acid), His (histidine), Ile (isoleucine), Leu (leucine; $(CH_3)_2CHCH_2CH(NH_2)CO$—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C$—OCO—], and the like. Suitable peptide residues include peptide residues comprising two to five, and optionally two to three, of the aforesaid amino acid residues. Examples of such peptide residues include, but are not limited to, residues of such peptides as Ala-Ala [$CH_3CH(NH_2)CO$—$NHCH(CH_3)CO$—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3C$—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$— and/or —$SO_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio($C_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $(C_1)$alkyl comprises methyl (i.e., —$CH_3$) as well as —CRR'R'' where R, R', and R'' may each independently be hydrogen or a further substituent where the atom attached to the carbon is a heteroatom or cyano. Hence, $CF_3$, $CH_2OH$ and $CH_2CN$, for example, are all $(C_1)$alkyls. Similarly, terms such as alkylamino and the like comprise dialkylamino and the like.

A compound having a formula that is represented with a dashed bond is intended to include the formulae optionally having zero, one or more double bonds, as exemplified and shown below:

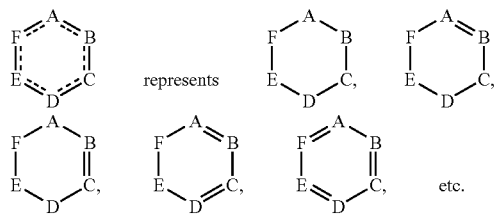

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to modulate a hexokinase and, in particular, compounds that activate glucokinase (referred to herein as "GK"). The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other hexokinase family members and thus may be used to address disease states associated with these other family members.

Glucokinase Activators

In one embodiment, glucokinase activators of the present invention have the formula:

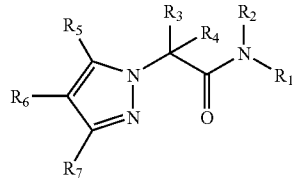

or a polymorph, solvate, ester, tautomer, enantiomer, pharmaceutically acceptable salt or prodrug thereof, wherein $R_1$ is selected from the group consisting of hetero($C_{3-12}$)cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{9-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

$R_7$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{10})$alkyl, thiocarbonyl$(C_{1-10})$alkyl, sulfonyl$(C_{10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, $(C_{9-12})$bicycloaryl $(C_{1-5})$alkyl, hetero$(C_{8-12})$bicycloaryl$(C_{1-5})$alkyl, hetero $(C_{1-10})$alkyl, $(C_{3-12})$cycloalkyl, hetero$(C_{3-12})$ cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_7$ is -$L_1$-$R_{22}$;

or any two $R_5$, $R_6$ and $R_7$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In one variation of the above embodiment, $R_1$ is not 5-(3-acetamidocyclobutyl)-1H-pyrazol-3-yl when $R_5$ and $R_6$, together with the ring to which they are attached, form an unsubstituted indazol-1-yl. In another variation of the above embodiment, $R_1$ is not 5-(2-chlorobenzyl)thiazol-2-yl when $R_3$ is phenyl and $R_2$, $R_4$, $R_5$, $R_6$ and $R_7$ are all hydrogen.

In another embodiment, glucokinase activators of the present invention have the formula:

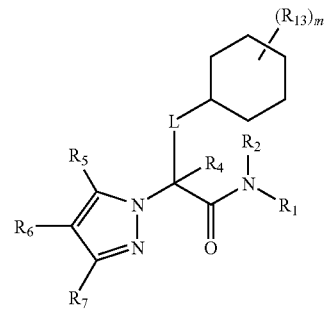

wherein m is selected from the group consisting of 0, 1, 2, 3, 4, 5, 6, 7, 8, 9, 10 and 11;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and the remaining variables are as described above.

In still another embodiment, glucokinase activators of the present invention have the formula:

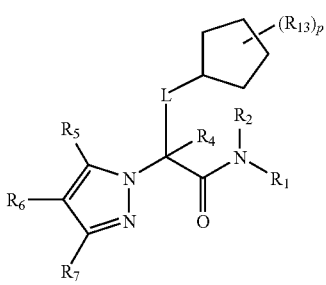

wherein
p is selected from the group consisting of 0, 1, 2, 3, 4, 5, 6, 7, 8 and 9;
$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and
the remaining variables are as described above.
In yet another embodiment, glucokinase activators of the present invention have the formula:

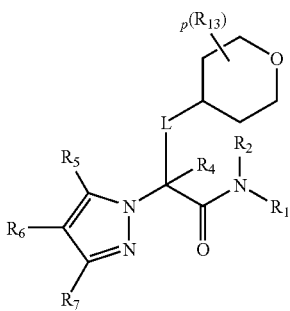

wherein
p is selected from the group consisting of 0, 1, 2, 3, 4, 5, 6, 7, 8 and 9;
$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and
the remaining variables are as described above.
In a further embodiment, glucokinase activators of the present invention have the formula:

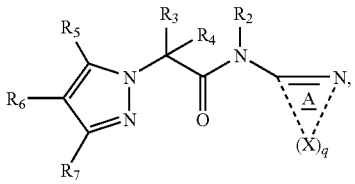

wherein
q is selected from the group consisting of 3, 4 and 5;
each X is independently selected from the group consisting of $CR_{14}R_{15}$, CO, CS, $NR_{16}$, O, S, SO and $SO_2$;
$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;
$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;
$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring, and the remaining variables are as described above.

In one variation of the above embodiment, ring A is not 5-(3-acetamidocyclobutyl)-1H-pyrazol-3-yl when $R_5$ and $R_6$, together with the ring to which they are attached, form an unsubstituted indazol-1-yl. In another variation of the above embodiment, ring A is not 5-(2-chlorobenzyl)thiazol-2-yl when $R_3$ is phenyl and $R_2$, $R_4$, $R_5$, $R_6$ and $R_7$ are all hydrogen.

In another embodiment, glucokinase activators of the present invention have the formula:

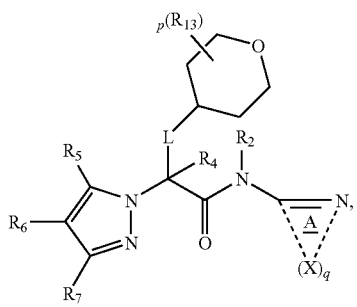

wherein p is selected from the group consisting of 0, 1, 2, 3, 4, 5, 6, 7, 8 and 9;

q is selected from the group consisting of 3, 4 and 5;

each X is independently selected from the group consisting of $CR_{14}R_{15}$, CO, CS, $NR_{16}$, O, S, SO and $SO_2$;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring, and the remaining variables are as described above.

In another embodiment, glucokinase activators of the present invention have the formula:

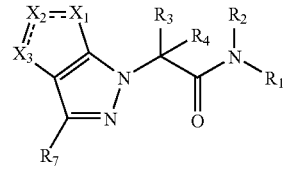

wherein $X_1$, $X_2$ and $X_3$ are each independently selected from the group consisting of $CR_9R_{10}$, CO, CS, $C(NR_{11})$, $NR_{12}$, S and O;

$R_9$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, hydroxy$(C_{1-10})$ alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$ alkyl, $(C_{1-10})$oxaalkyl, $(C_{1-10})$oxoalkyl, imino$(C_{1-10})$ alkyl, $(C_{3-12})$cycloalkyl$(C_{1-5})$alkyl, hetero$(C_{3-12})$cycloalkyl($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted; and $R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring.

In a further embodiment, glucokinase activators of the present invention have the formula:

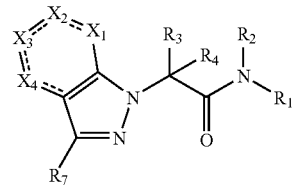

wherein $X_1$, $X_2$, $X_3$ and $X_4$ are each independently selected from the group consisting of $CR_9R_{10}$, CO, CS, $C(NR_{11})$, $NR_{12}$, S and O;

$R_9$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$) alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$) alkyl, ($C_{1-10}$)oxaalkyl, ($C_{1-10}$)oxoalkyl, imino($C_{1-10}$) alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted; and R$_{12}$ is selected from the group consisting of hydrogen, oxy, hydroxy, carbonyloxy, (C$_{1-10}$)alkoxy, (C$_{4-12}$)aryloxy, hetero(C$_{1-10}$)aryloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, with the proviso that R$_{12}$ is absent when the atom to which it is bound forms part of a double bond, or any two R$_7$, R$_9$, R$_{10}$, R$_{11}$ and R$_{12}$ are taken together to form a substituted or unsubstituted ring; and the remaining variables are as described above.

In still a further embodiment, glucokinase activators of the present invention have the formula:

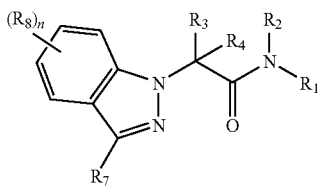

wherein n is selected from the group consisting of 0, 1, 2, 3 and 4;

R$_8$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_8$ is -L$_1$-R$_{22}$, or R$_8$ and R$_7$ or two R$_8$ are taken together to form a substituted or unsubstituted ring; and the remaining variables are as described above.

In one variation of the above embodiment, R$_1$ is not 5-(3-acetamidocyclobutyl)-1H-pyrazol-3-yl when R$_7$ and each R$_8$ are all hydrogen.

In yet a further embodiment, glucokinase activators of the present invention have the formula:

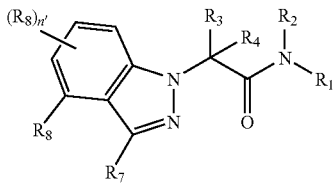

wherein n' is selected from the group consisting of 0, 1, 2 and 3;

R$_8$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_8$ is -L$_1$-R$_{22}$, or R$_8$ and R$_7$ or two R$_8$ are taken together to form a substituted or unsubstituted ring; and the remaining variables are as described above.

In one variation of the above embodiment, R$_1$ is not 5-(3-acetamidocyclobutyl)-1H-pyrazol-3-yl when R$_7$ and each R$_8$ are all hydrogen.

In still another embodiment, glucokinase activators of the present invention have the formula:

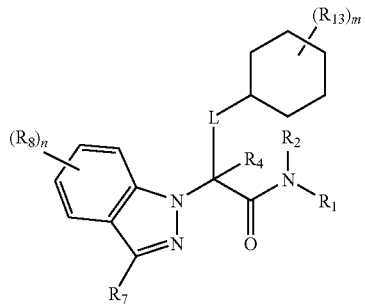

wherein n is selected from the group consisting of 0, 1, 2, 3 and 4;

m is selected from the group consisting of 0, 1, 2, 3, 4, 5, 6, 7, 8, 9, 10 and 11;

R$_8$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_8$ is -L$_1$-R$_{22}$, or R$_8$ and R$_7$ or two R$_8$ are taken together to form a substituted or unsubstituted ring;

R$_{13}$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$)

alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In yet another embodiment, glucokinase activators of the present invention have the formula:

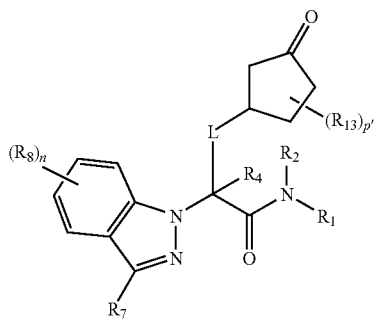

wherein n is selected from the group consisting of 0, 1, 2, 3 and 4;

p' is selected from the group consisting of 0, 1, 2, 3, 4, 5, 6 and 7;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In a further embodiment, glucokinase activators of the present invention have the formula:

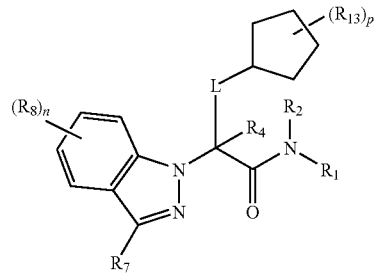

wherein n is selected from the group consisting of 0, 1, 2, 3 and 4;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In still a further embodiment, glucokinase activators of the present invention have the formula:

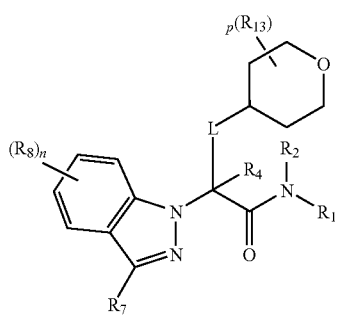

wherein
n is selected from the group consisting of 0, 1, 2, 3 and 4;
p is selected from the group consisting of 0, 1, 2, 3, 4, 5, 6, 7, 8 and 9;
$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;
$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and
the remaining variables are as described above.
In yet a further embodiment, glucokinase activators of the present invention have the formula:

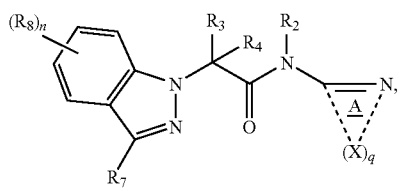

wherein
n is selected from the group consisting of 0, 1, 2, 3 and 4;
q is selected from the group consisting of 3, 4 and 5;

each X is independently selected from the group consisting of $CR_{14}R_{15}$, CO, CS, $NR_{16}$, O, S, SO and $SO_2$;
$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;
$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;
$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;
$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In one variation of the above embodiment, ring A is not 5-(3-acetamidocyclobutyl)-1H-pyrazol-3-yl when $R_7$ and each $R_8$ are all hydrogen.

In yet a further embodiment, glucokinase activators of the present invention have the formula:

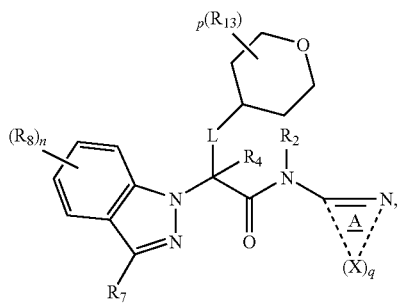

wherein n is selected from the group consisting of 0, 1, 2, 3 and 4;

p is selected from the group consisting of 0, 1, 2, 3, 4, 5, 6, 7, 8 and 9;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is $-L_1-R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is $-L_1-R_{22}$;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In another embodiment, glucokinase activators of the present invention have the formula:

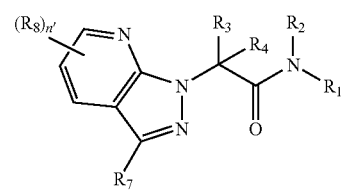

wherein n' is selected from the group consisting of 0, 1, 2 and 3;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring; and the remaining variables are as described above.

In still another embodiment, glucokinase activators of the present invention have the formula:

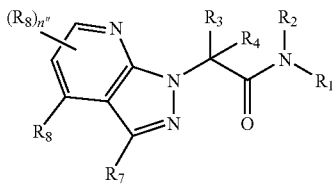

wherein n" is selected from the group consisting of 0, 1 and 2;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring; and the remaining variables are as described above.

In still another embodiment, glucokinase activators of the present invention have the formula:

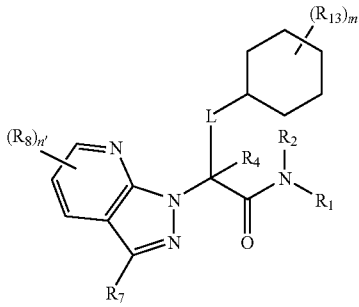

wherein n' is selected from the group consisting of 0, 1, 2 and 3;

m is selected from the group consisting of 0, 1, 2, 3, 4, 5, 6, 7, 8, 9, 10 and 11;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In yet another embodiment, glucokinase activators of the present invention have the formula:

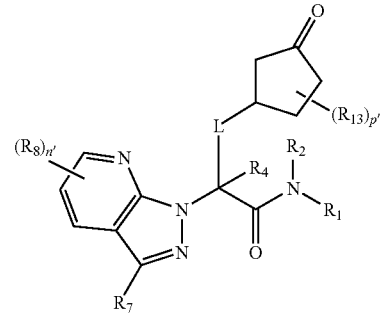

wherein n' is selected from the group consisting of 0, 1, 2 and 3;

p' is selected from the group consisting of 0, 1, 2, 3, 4, 5, 6 and 7;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-

$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and the remaining variables are as described above.

In a further embodiment, glucokinase activators of the present invention have the formula:

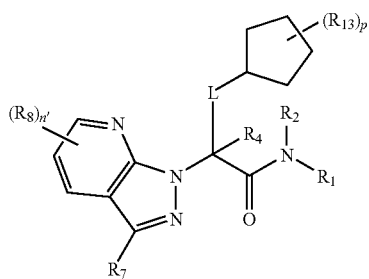

wherein n' is selected from the group consisting of 0, 1, 2 and 3;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and the remaining variables are as described above.

In still a further embodiment, glucokinase activators of the present invention have the formula:

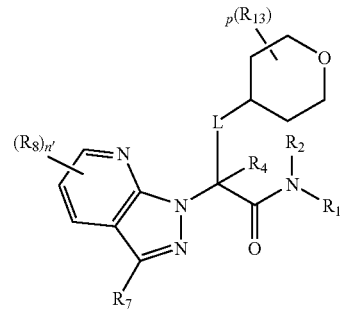

wherein n' is selected from the group consisting of 0, 1, 2 and 3;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and the remaining variables are as described above.

In yet a further embodiment, glucokinase activators of the present invention have the formula:

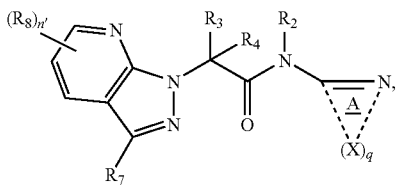

wherein n' is selected from the group consisting of 0, 1, 2 and 3;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In yet a further embodiment, glucokinase activators of the present invention have the formula:

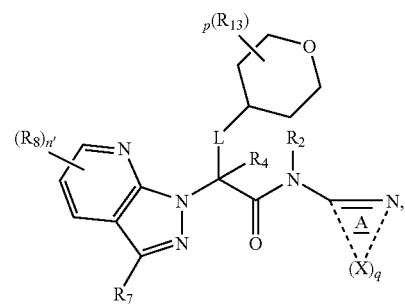

wherein n' is selected from the group consisting of 0, 1, 2 and 3;

p is selected from the group consisting of 0, 1, 2, 3, 4, 5, 6, 7, 8 and 9;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In yet another embodiment, glucokinase activators of the present invention have the formula:

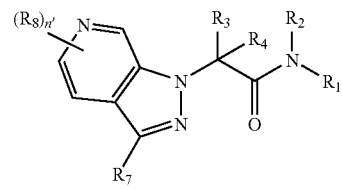

wherein n' is selected from the group consisting of 0, 1, 2 and 3;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring; and the remaining variables are as described above.

In a further embodiment, glucokinase activators of the present invention have the formula:

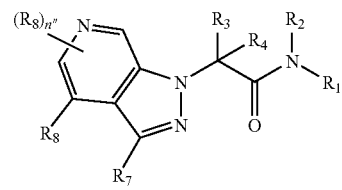

wherein n" is selected from the group consisting of 0, 1 and 2;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring; and the remaining variables are as described above.

In still another embodiment, glucokinase activators of the present invention have the formula:

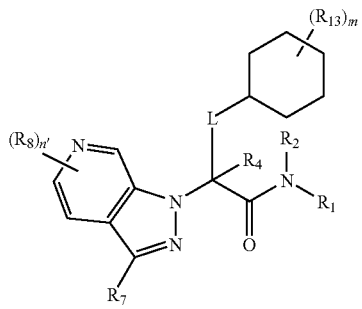

wherein
n' is selected from the group consisting of 0, 1, 2 and 3;
m is selected from the group consisting of 0, 1, 2, 3, 4, 5, 6, 7, 8, 9, 10 and 11;
$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_7$ or two $R_8$ are taken together to form a substituted or unsubstituted ring;
$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and
the remaining variables are as described above.

In yet another embodiment, glucokinase activators of the present invention have the formula:

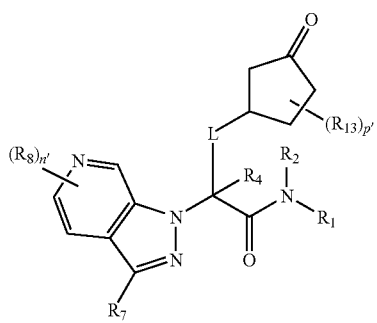

In a further embodiment, glucokinase activators of the present invention have the formula:

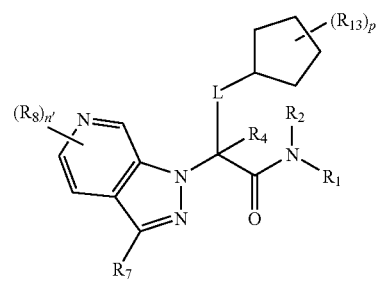

wherein
n' is selected from the group consisting of 0, 1, 2 and 3;
p is selected from the group consisting of 0, 1, 2, 3, 4, 5, 6, 7, 8 and 9;
$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In still a further embodiment, glucokinase activators of the present invention have the formula:

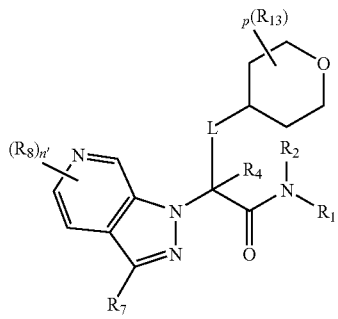

wherein n' is selected from the group consisting of 0, 1, 2 and 3;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In yet a further embodiment, glucokinase activators of the present invention have the formula:

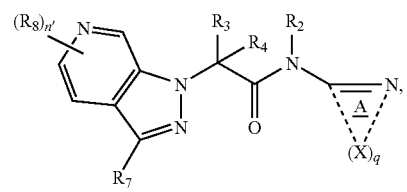

wherein n' is selected from the group consisting of 0, 1, 2 and 3;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In yet a further embodiment, glucokinase activators of the present invention have the formula:

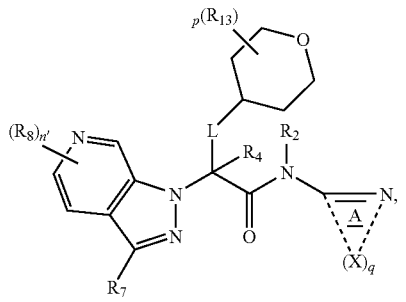

wherein n' is selected from the group consisting of 0, 1, 2 and 3;

p is selected from the group consisting of 0, 1, 2, 3, 4, 5, 6, 7, 8 and 9;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_7$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring; and the remaining variables are as described above.

In another embodiment, glucokinase activators of the present invention have the formula:

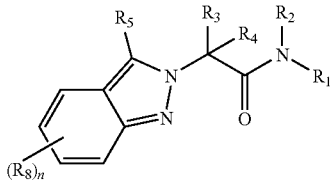

wherein n is selected from the group consisting of 0, 1, 2, 3 and 4;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_5$ or two $R_8$ are taken together to form a substituted or unsubstituted ring; and the remaining variables are as described above.

In yet another embodiment, glucokinase activators of the present invention have the formula:

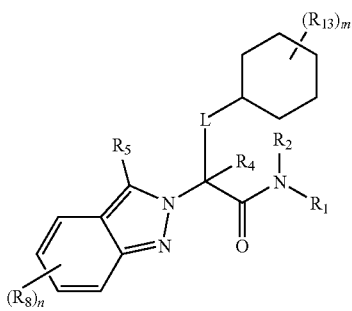

wherein n is selected from the group consisting of 0, 1, 2, 3 and 4;

m is selected from the group consisting of 0, 1, 2, 3, 4, 5, 6, 7, 8, 9, 10 and 11;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_5$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring; and the remaining variables are as described above.

In a further embodiment, glucokinase activators of the present invention have the formula:

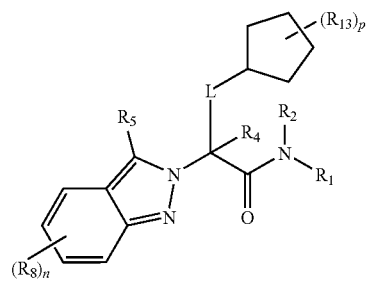

wherein n is selected from the group consisting of 0, 1, 2, 3 and 4;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_8$ is -$L_1$-$R_{22}$, or $R_8$ and $R_5$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In still a further embodiment, glucokinase activators of the present invention have the formula:

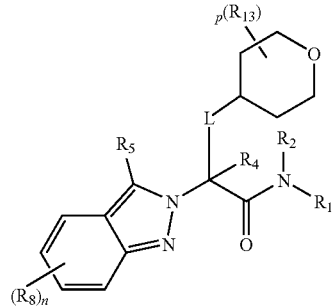

wherein n is selected from the group consisting of 0, 1, 2, 3 and 4;

p is selected from the group consisting of 0, 1, 2, 3, 4, 5, 6, 7, 8 and 9;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_5$ or two $R_8$ are taken together to form a substituted or unsubstituted ring;

$R_{13}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring; and the remaining variables are as described above.

In yet a further embodiment, glucokinase activators of the present invention have the formula:

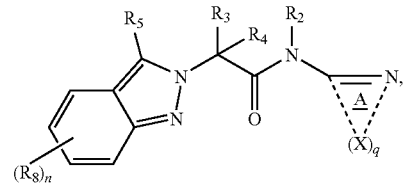

wherein n is selected from the group consisting of 0, 1, 2, 3 and 4;

q is selected from the group consisting of 3, 4 and 5;

each X is independently selected from the group consisting of $CR_{14}R_{15}$, CO, CS, $NR_{16}$, O, S, SO and $SO_2$;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is -$L_1$-$R_{22}$, or $R_8$ and $R_5$ or two $R_8$ are taken together to form a substituted or unsubstituted ring;

$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that R$_{16}$ is absent when the atom to which it is bound forms part of a double bond, or any two R$_{14}$, R$_{15}$ and R$_{16}$ are taken together to form a substituted or unsubstituted ring; and the remaining variables are as described above.

In yet a further embodiment, glucokinase activators of the present invention have the formula:

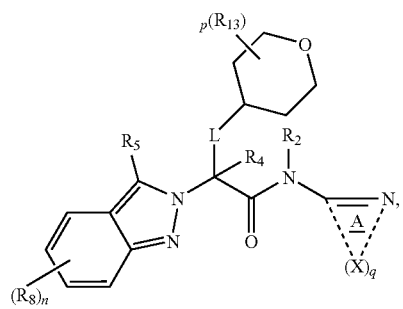

wherein n is selected from the group consisting of 0, 1, 2, 3 and 4;

p is selected from the group consisting of 0, 1, 2, 3, 4, 5, 6, 7, 8 and 9;

q is selected from the group consisting of 3, 4 and 5;

each X is independently selected from the group consisting of CR$_{14}$R$_{15}$, CO, CS, NR$_{16}$, O, S, SO and SO$_2$;

R$_8$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl (C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl (C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_8$ is -L$_1$-R$_{22}$, or R$_8$ and R$_5$ or two R$_8$ are taken together to form a substituted or unsubstituted ring;

R$_{13}$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or two R$_{13}$ are taken together to form a substituted or unsubstituted ring;

R$_{14}$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, carboxamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino (C$_{1-10}$)alkyl, imino(C$_{1-3}$)alkyl, oxa (C$_{1-5}$)alkyl, oxo(C$_{1-5}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{14}$ is -L$_1$-R$_{22}$;

R$_{15}$ is selected from the group consisting of hydrogen, halo, nitro, cyano, thio, hydroxy, alkoxy, aryloxy, heteroaryloxy, carbonyl, amino, (C$_{1-10}$)alkylamino, sulfonamido, carboxamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino (C$_{1-10}$)alkyl, imino(C$_{1-3}$)alkyl, oxa (C$_{1-5}$)alkyl, oxo(C$_{1-5}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that R$_{15}$ is absent when the atom to which it is bound forms part of a double bond;

R$_{16}$ is selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that R$_{16}$ is absent when the atom to which it is bound forms part of a double bond, or any two R$_{14}$, R$_{15}$ and R$_{16}$ are taken together to form a substituted or unsubstituted ring; and the remaining variables are as described above.

In still another embodiment, glucokinase activators of the present invention have the formula:

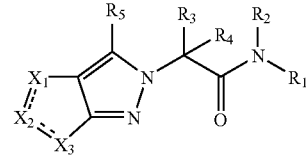

wherein

X$_1$, X$_2$ and X$_3$ are each independently selected from the group consisting of CR$_9$R$_{10}$, CO, CS, C(NR$_{11}$), NR$_{12}$, S and O;

R$_9$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{10}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_9$ and R$_{10}$ are taken together to form oxo, with the proviso that R$_{10}$ is absent when the atom to which it is bound forms part of a double bond;

R$_{11}$ is selected from the group consisting of hydrogen, hydroxy, carbonyloxy, (C$_{1-10}$)alkoxy, (C$_{4-12}$)aryloxy, hetero(C$_{1-10}$)aryloxy, oxycarbonyl, amino, (C$_{1-10}$)alkylamino, sulfonamido, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted; and R$_{12}$ is selected from the group consisting of hydrogen, oxy, hydroxy, carbonyloxy, (C$_{1-10}$)alkoxy, (C$_{4-12}$)aryloxy, hetero(C$_{1-10}$)aryloxy, carbonyl, oxycarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, with the proviso that R$_{12}$ is absent when the atom to which it is bound forms part of a double bond, or any two R$_5$, R$_9$, R$_{10}$, R$_{11}$ and R$_{12}$ are taken together to form a substituted or unsubstituted ring; and the remaining variables are as described above.

In another of its aspects, the present invention relates to methods of making compounds that are useful as glucokinase activators. In one embodiment, the methods comprise the steps of:

reacting a compound having the formula

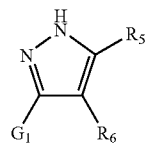

with a compound having the formula

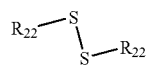

to form a first reaction product having the formula

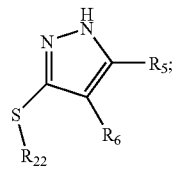

reacting the first reaction product with a compound having the formula

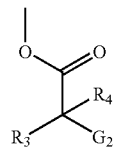

to form a second reaction product having the formula

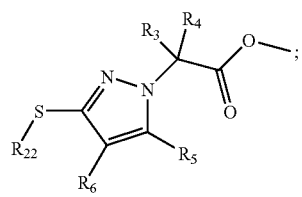

treating the second reaction product to form a third reaction product having the formula

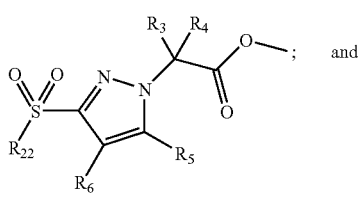

and reacting the third reaction product with a compound having the formula

NHR₁R₂ to form a fourth reaction product having the formula

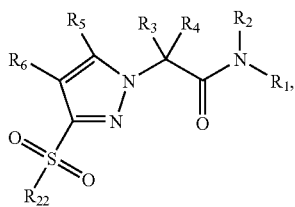

wherein
$R_1$ is selected from the group consisting of hetero($C_{3-12}$) cycloalkyl, hetero($C_{3-12}$)bicycloalkyl, heteroaryl, and hetero($C_{4-12}$)bicycloaryl, each substituted or unsubstituted;
$R_2$ is selected from the group consisting of hydrogen and a substituent convertible to hydrogen in vivo;
$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;
$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;
$R_5$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;
$R_6$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_6$ is -$L_1$-$R_{22}$;
or $R_5$ and $R_6$ are taken together to form a substituted or unsubstituted ring;
L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;
$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;
$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;
$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_1$ and $G_2$ are each independently a leaving group.

In another embodiment, the methods comprise the steps of:

reacting a compound having the formula

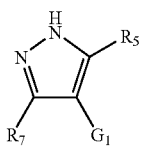

with a compound having the formula

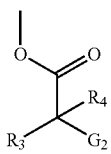

to form a first reaction product having the formula

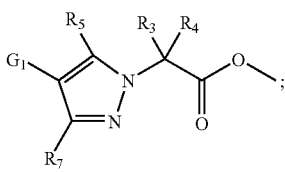

reacting the first reaction product with a compound having the formula $SHR_{22}$ to form a second reaction product having the formula

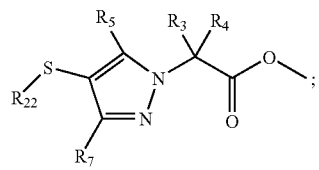

treating the second reaction product to form a third reaction product having the formula

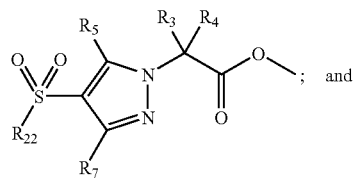

reacting the third reaction product with a compound having the formula $NHR_1R_2$ to form a fourth reaction product having the formula

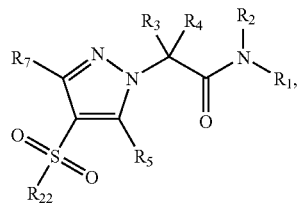

wherein $R_1$ is selected from the group consisting of hetero($C_{3-12}$)cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or R₃ and R₄ are taken together to form a substituted or unsubstituted ring;

R₅ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, amido, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, aza(C₁₋₁₀)alkyl, (C₁₋₁₀)oxaalkyl, (C₁₋₁₀)oxoalkyl, imino(C₁₋₁₀)alkyl, (C₃₋₁₂)cycloalkyl(C₁₋₅)alkyl, hetero(C₃₋₁₂)cycloalkyl(C₁₋₁₀)alkyl, aryl(C₁₋₁₀)alkyl, hetero(C₁₋₁₀)aryl(C₁₋₅)alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted;

R₇ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, amido, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, aza(C₁₋₁₀)alkyl, (C₁₋₁₀)oxaalkyl, (C₁₋₁₀)oxoalkyl, imino(C₁₋₁₀)alkyl, (C₃₋₁₂)cycloalkyl(C₁₋₅)alkyl, hetero(C₃₋₁₂)cycloalkyl(C₁₋₁₀)alkyl, aryl(C₁₋₁₀)alkyl, hetero(C₁₋₁₀)aryl(C₁₋₅)alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted, or R₇ is -L₁-R₂₂;

or R₅ and R₇ are taken together to form a substituted or unsubstituted ring;

L is a linker providing 0, 1, 2, 3, 4, 5 or 6 atom separation between the C and R₁₈ to which L is attached, wherein the atoms of the linker providing the separation are selected from the group consisting of carbon, oxygen, nitrogen, and sulfur;

L₁ is absent or a linker providing 1, 2, 3, 4, 5 or 6 atom separation between R₂₂ and the ring to which L₁ is attached, wherein the atoms of the linker providing the separation are selected from the group consisting of carbon, oxygen, nitrogen, and sulfur;

R₁₈ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, amido, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, aza(C₁₋₁₀)alkyl, (C₁₋₁₀)oxaalkyl, (C₁₋₁₀)oxoalkyl, imino(C₁₋₁₀)alkyl, (C₃₋₁₂)cycloalkyl(C₁₋₅)alkyl, hetero(C₃₋₁₂)cycloalkyl(C₁₋₁₀)alkyl, aryl(C₁₋₁₀)alkyl, hetero(C₁₋₁₀)aryl(C₁₋₅)alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted;

R₂₂ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, amido, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, aza(C₁₋₁₀)alkyl, (C₁₋₁₀)oxaalkyl, (C₁₋₁₀)oxoalkyl, imino(C₁₋₁₀)alkyl, (C₃₋₁₂)cycloalkyl(C₁₋₅)alkyl, hetero(C₃₋₁₂)cycloalkyl(C₁₋₁₀)alkyl, aryl(C₁₋₁₀)alkyl, hetero(C₁₋₁₀)aryl(C₁₋₅)alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted, or R₂₂ is —NR₂₇R₂₈;

R₂₇ and R₂₈ are each independently selected from the group consisting of hydrogen, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino(C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or R₂₇ and R₂₈ are taken together to form a substituted or unsubstituted ring; and G₁ and G₂ are each independently a leaving group.

In still another embodiment, the methods comprise the steps of:

treating a compound having the formula

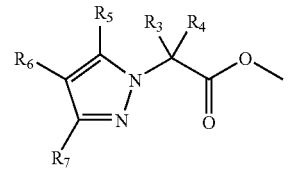

to form a first reaction product having the formula

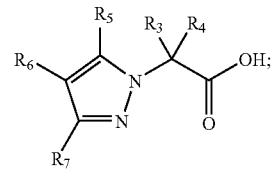

reacting the first reaction product with a compound having the formula

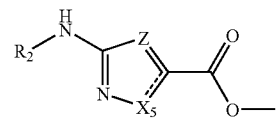

to form a second reaction product having the formula

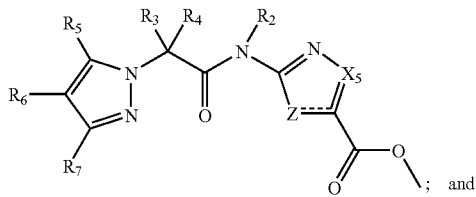

treating the second reaction product to form a third reaction product having the formula wherein $R_2$ is selected from the group consisting of hydrogen and a substituent convertible to hydrogen in vivo;

$R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_7$ is -$L_1$-$R_{22}$;

or any two $R_5$, $R_6$ and $R_7$ are taken together to form a substituted or unsubstituted ring;

$X_5$ is selected from the group consisting of $CR_9R_{10}$, CO, CS, C(NR$_{11}$), NR$_{12}$, S and O;

$R_9$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$ cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond;

Z is selected from the group consisting of $CR_{14}R_{15}$, $NR_{16}$, O and S;

$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, oxa($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur; and $L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet another embodiment, the methods comprise the steps of:

reacting a compound having the formula

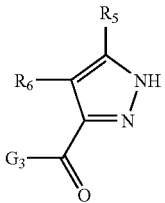

with a compound having the formula $NHR_{27}R_{28}$ to form a first reaction product having the formula

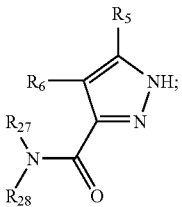

reacting the first reaction product with a compound having the formula

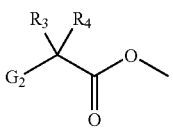

to form a second reaction product having the formula

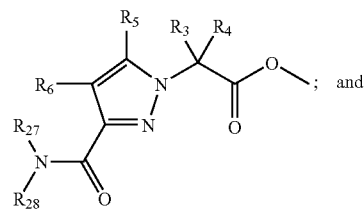; and reacting the second reaction product with a compound having the formula

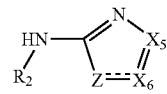

to form a third reaction product having the formula

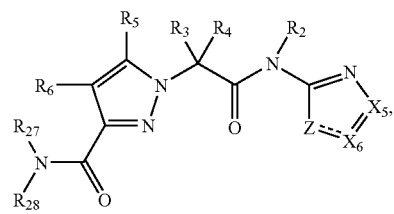

wherein $R_2$ is selected from the group consisting of hydrogen and a substituent convertible to hydrogen in vivo;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo $(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

or $R_5$ and $R_6$ are taken together to form a substituted or unsubstituted ring;

$X_5$ and $X_6$ are each independently selected from the group consisting of $CR_9R_{10}$, CO, CS, C(N$R_1$), N$R_{12}$, S and O;

$R_9$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_9$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, $(C_{1-10})$alkoxy, $(C_{4-12})$aryloxy, hetero$(C_{1-10})$aryloxy, oxycarbonyl, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{12}$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, with the proviso that $R_{12}$ is absent when the atom to which it is bound forms part of a double bond;

Z is selected from the group consisting of $CR_{14}R_{15}$, N$R_{16}$, O and S;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring; and $G_2$ and $G_3$ are each independently a leaving group.

In a further embodiment, the methods comprise the steps of:

reacting a compound having the formula

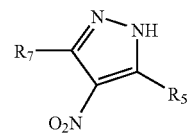

with a compound having the formula

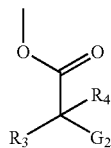

to form a first reaction product having the formula

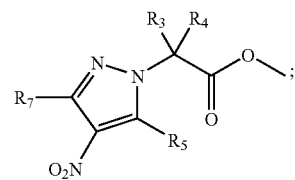

treating the first reaction product to form a second reaction product having the formula

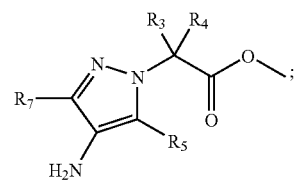

reacting the second reaction product with a compound having the formula

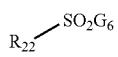

to form a third reaction product having the formula

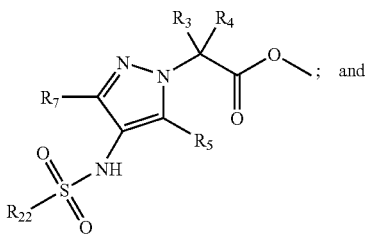

; and reacting the third reaction product with a compound having the formula

NHR$_1$R$_2$ to form a fourth reaction product having the formula

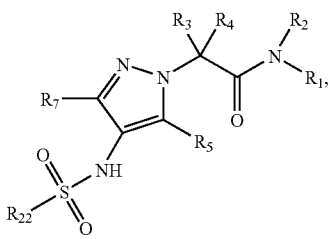

wherein

R$_1$ is selected from the group consisting of hetero(C$_{3-12}$)cycloalkyl, hetero(C$_{3-12}$)bicycloalkyl, heteroaryl, and hetero(C$_{4-12}$)bicycloaryl, each substituted or unsubstituted;

R$_2$ is selected from the group consisting of hydrogen and a substituent convertible to hydrogen in vivo;

R$_3$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ is -L-R$_{18}$;

R$_4$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ and R$_4$ are taken together to form a substituted or unsubstituted ring;

R$_5$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_7$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_7$ is -L$_1$-R$_{22}$;

or R$_5$ and R$_7$ are taken together to form a substituted or unsubstituted ring;

L is a linker providing 0, 1, 2, 3, 4, 5 or 6 atom separation between the C and R$_{18}$ to which L is attached, wherein the atoms of the linker providing the separation are selected from the group consisting of carbon, oxygen, nitrogen, and sulfur;

L$_1$ is absent or a linker providing 1, 2, 3, 4, 5 or 6 atom separation between R$_{22}$ and the ring to which L$_1$ is attached, wherein the atoms of the linker providing the separation are selected from the group consisting of carbon, oxygen, nitrogen, and sulfur;

R$_{18}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_{22}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)

cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_2$ and $G_6$ are each independently a leaving group.

In still a further embodiment, the methods comprise the steps of:

reacting a compound having the formula

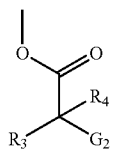

with a compound having the formula

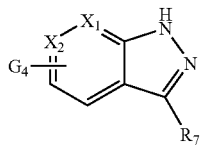

to form a first reaction product having the formula

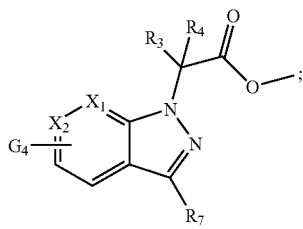

reacting the first reaction product with a compound having the formula

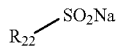

to form a second reaction product having the formula

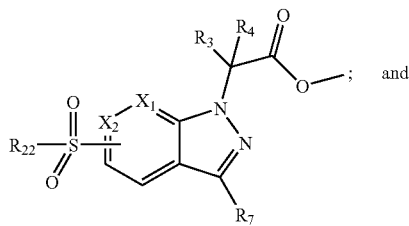

reacting the second reaction product with a compound having the formula

to form a third reaction product having the formula

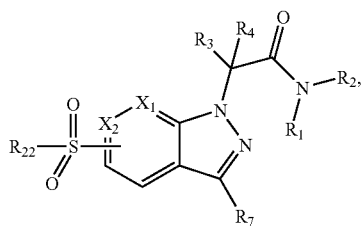

wherein $X_1$ and $X_2$ are each independently selected from the group consisting of $CR_9R_{10}$, CO, CS, C($NR_{11}$), $NR_{12}$, S and O;

$R_1$ is selected from the group consisting of hetero($C_{3-12}$) cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_7$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

$R_9$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)

bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_2$ and $G_4$ are each independently a leaving group.

In yet a further embodiment, the methods comprise the steps of:

reacting a compound having the formula

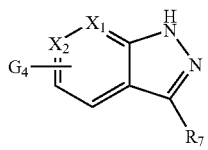

with a compound having the formula

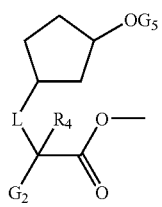

to form a first reaction product having the formula

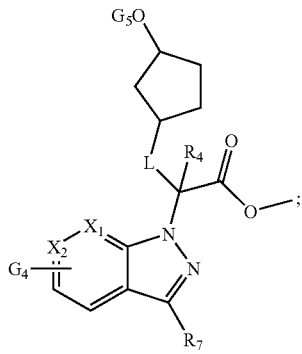

reacting the first reaction product with a compound having the formula

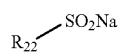

to form a second reaction product having the formula

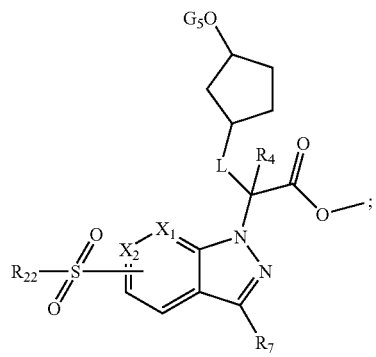

reacting the second reaction product with a compound having the formula $NHR_1R_2$ to form a third reaction product having the formula

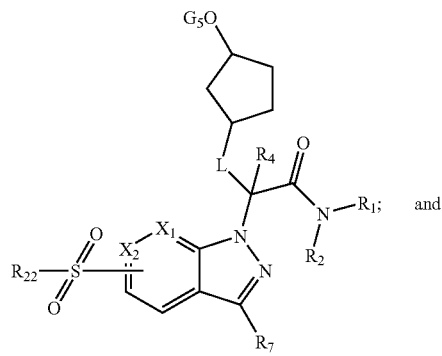

treating the third reaction product to form a fourth reaction product having the formula

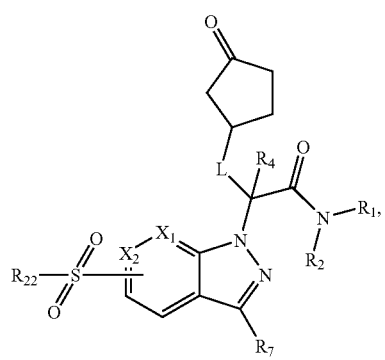

wherein $X_1$ and $X_2$ are each independently selected from the group consisting of $CR_9R_{10}$, CO, CS, $C(NR_{11})$, $NR_{12}$, S and O;

$R_1$ is selected from the group consisting of hetero($C_{3-12}$) cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted;

$R_7$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

$R_9$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$) alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$) alkyl, ($C_{1-10}$)oxaalkyl, ($C_{1-10}$)oxoalkyl, imino($C_{1-10}$) alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring;

$G_2$ and $G_4$ are each independently a leaving group; and $G_5$ is a protecting group.

In another embodiment, the methods comprise the step of: treating a first reaction product having the formula

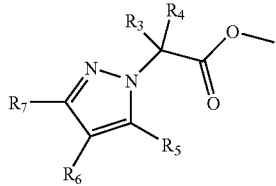

under conditions sufficient to form a second reaction product having the formula

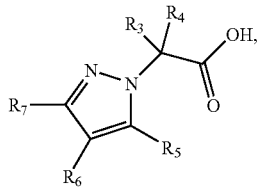

wherein $R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_7$ is -$L_1$-$R_{22}$;

or any two $R_5$, $R_6$ and $R_7$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In one variation of the above embodiment, the methods further comprise the step of:

reacting a compound having the formula

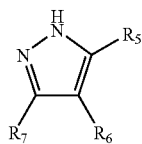

with a compound having the formula

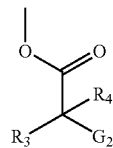

to form the first reaction, wherein $G_2$ is a leaving group.

In another variation of the above embodiment and variation, the methods further comprise the step of:

reacting the second reaction product with a compound having the formula $NHR_1R_2$ to form a third reaction product having the formula

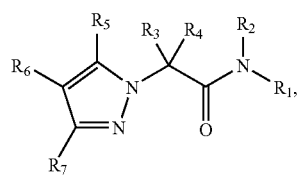

wherein $R_1$ is selected from the group consisting of hetero($C_{3-12}$) cycloalkyl, hetero($C_{3-12}$)bicycloalkyl, heteroaryl, and hetero($C_{4-12}$)bicycloaryl, each substituted or unsubstituted; and $R_2$ is selected from the group consisting of hydrogen and a substituent convertible to hydrogen in vivo.

In still another embodiment, the methods comprise the steps of:

reacting a compound having the formula

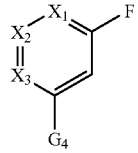

with a compound having the formula

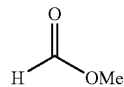

to form a first reaction product having the formula

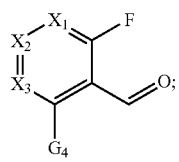

treating the first reaction product under conditions sufficient to form a second reaction product having the formula

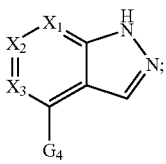

reacting the second reaction product with a compound having the formula

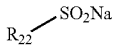

to form a third reaction product having the formula

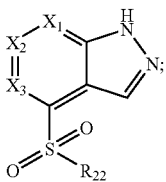

reacting the third reaction product with a compound having the formula

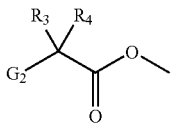

to form a fourth reaction product having the formula

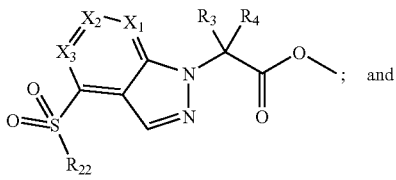; and reacting the fourth reaction product with a compound having the formula

NHR$_1$R$_2$ to form a fifth reaction product having the formula

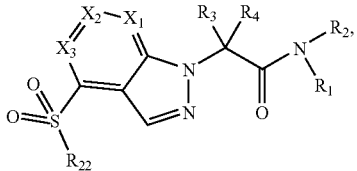

wherein

X$_1$, X$_2$ and X$_3$ are each independently selected from the group consisting of CR$_9$R$_{10}$, CO, CS, C(NR$_1$), NR$_{12}$, S and O;

R$_1$ is selected from the group consisting of hetero(C$_{3-12}$)cycloalkyl, hetero(C$_{3-12}$)bicycloalkyl, heteroaryl, and hetero(C$_{4-12}$)bicycloaryl, each substituted or unsubstituted;

R$_2$ is selected from the group consisting of hydrogen and a substituent convertible to hydrogen in vivo;

R$_3$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ is -L-R$_{18}$;

R$_4$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ and R$_4$ are taken together to form a substituted or unsubstituted ring;

R$_9$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl (C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl, each substituted or unsubstituted;

R$_{10}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_9$ and R$_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_9$, $R_{10}$, $R_{11}$ and $R_{12}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_2$ and $G_4$ are each independently a leaving group.

In yet another embodiment, the methods comprise the steps of:

reacting a compound having the formula

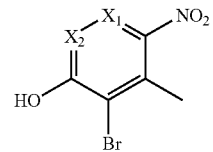

with a compound having the formula

to form a first reaction product having the formula

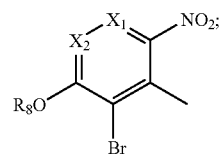

treating the first reaction product under conditions sufficient to form a second reaction product having the formula

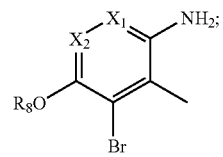

treating the second reaction product under conditions sufficient to form a third reaction product having the formula

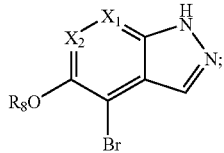

reacting the third reaction product with a compound having the formula

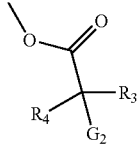

to form a fourth reaction product having the formula

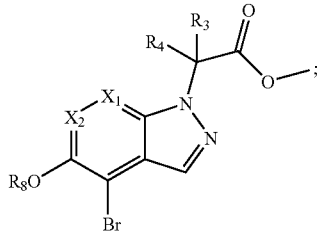

reacting the fourth reaction product with a compound having the formula

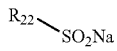

to form a fifth reaction product having the formula

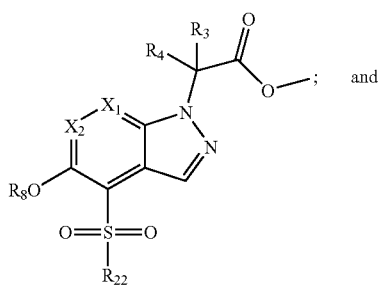

reacting the fifth reaction product with a compound having the formula

$NHR_1R_2$ to form a sixth reaction product having the formula

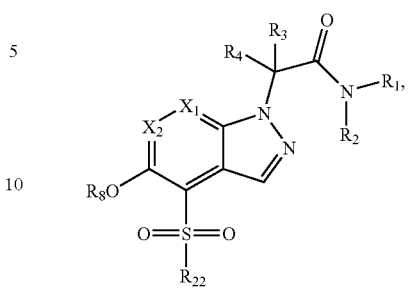

wherein $X_1$ and $X_2$ are each independently selected from the group consisting of $CR_9R_{10}$, CO, CS, $C(NR_{11})$, $NR_{12}$, S and O;

$R_1$ is selected from the group consisting of hetero($C_{3-12}$)cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is $-L-R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_8$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_8$ is $-L_1-R_{22}$, or two $R_8$ are taken together to form a substituted or unsubstituted ring;

$R_9$ is selected from the group consisting of hydrogen, halo, nitro, cyano, thio, oxy, hydroxy, carbonyloxy, ($C_{1-10}$)

alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_9$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, $(C_{1-10})$alkoxy, $(C_{4-12})$aryloxy, hetero$(C_{1-10})$aryloxy, oxycarbonyl, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{12}$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, with the proviso that $R_{12}$ is absent when the atom to which it is bound forms part of a double bond, or any two $R_9$, $R_{10}$, $R_{11}$ and $R_{12}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring;

$G_2$ is a leaving group; and $G_5$ is a protecting group.

In still another of its aspects, the present invention relates to intermediates that are useful in making glucokinase activators. In one embodiment, the intermediates comprise:

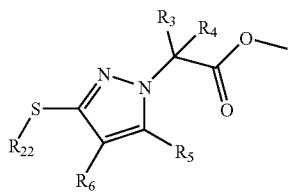

wherein $R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

or $R_5$ and $R_6$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In another embodiment, the intermediates comprise:

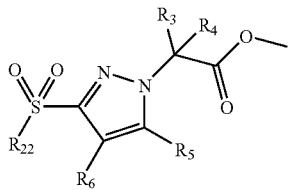

wherein $R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_6$ is -$L_1$-$R_{22}$;

or $R_5$ and $R_6$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In still another embodiment, the intermediates comprise:

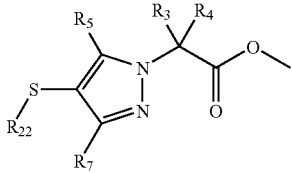

wherein $R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_7$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

or $R_5$ and $R_7$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet another embodiment, the intermediates comprise:

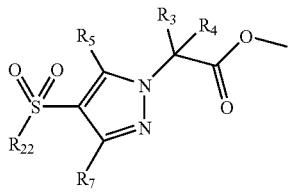

wherein $R_3$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ is -L-$R_{18}$;

$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_7$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$ alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_7$ is -$L_1$-$R_{22}$;

or $R_5$ and $R_7$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or R$_{27}$ and R$_{28}$ are taken together to form a substituted or unsubstituted ring.

In a further embodiment, the intermediates comprise:

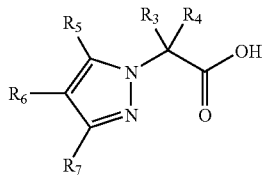

wherein

R$_3$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ is -L-R$_{18}$;

R$_4$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ and R$_4$ are taken together to form a substituted or unsubstituted ring;

R$_5$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_6$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_6$ is -L$_1$-R$_{22}$;

R$_7$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_7$ is -L$_1$-R$_{22}$;

or any two R$_5$, R$_6$ and R$_7$ are taken together to form a substituted or unsubstituted ring;

L is a linker providing 0, 1, 2, 3, 4, 5 or 6 atom separation between the C and R$_{18}$ to which L is attached, wherein the atoms of the linker providing the separation are selected from the group consisting of carbon, oxygen, nitrogen, and sulfur;

L$_1$ is absent or a linker providing 1, 2, 3, 4, 5 or 6 atom separation between R$_{22}$ and the ring to which L$_1$ is attached, wherein the atoms of the linker providing the separation are selected from the group consisting of carbon, oxygen, nitrogen, and sulfur;

R$_{18}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, aza(C$_{1-10}$)alkyl, (C$_{1-10}$) oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted;

R$_{22}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, aza(C$_{1-10}$)alkyl, (C$_{1-10}$) oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In still a further embodiment, the intermediates comprise:

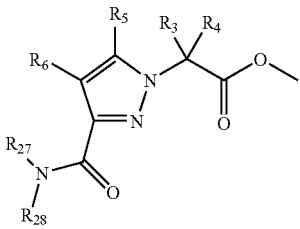

wherein $R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_6$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_6$ is -$L_1$-$R_{22}$;

or $R_5$ and $R_6$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet a further embodiment, the intermediates comprise:

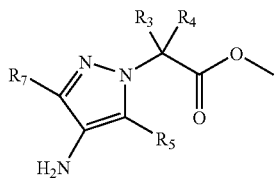

wherein $R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_5$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_7$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

or $R_5$ and $R_7$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In another embodiment, the intermediates comprise:

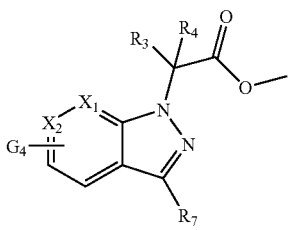

wherein $X_1$ and $X_2$ are each independently selected from the group consisting of $CR_9R_{10}$, CO, CS, $C(NR_{11})$, $NR_{12}$, S and O;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_7$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

$R_9$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$) alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$) alkyl, ($C_{1-10}$)oxaalkyl, ($C_{1-10}$)oxoalkyl, imino($C_{1-10}$) alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$) alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_4$ is a leaving group.

In still another embodiment, the intermediates comprise:

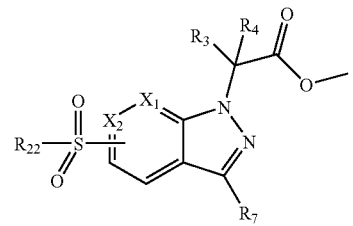

wherein $X_1$ and $X_2$ are each independently selected from the group consisting of $CR_9R_{10}$, CO, CS, C($NR_{11}$), $NR_{12}$, S and O;

$R_3$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ is -L-$R_{18}$;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_7$ is selected from the group consisting of hydrogen, halo, nitro, cyano, thio, oxy, hydroxy, carbonyloxy, ($C_{1-10}$) alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo ($C_{1-10}$)alkyl, hydroxy($C_{1-10}$)alkyl, carbonyl($C_{1-10}$) alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

$R_9$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_9$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{18}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet another embodiment, the intermediates comprise:

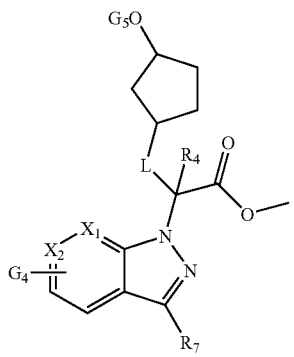

wherein
$X_1$ and $X_2$ are each independently selected from the group consisting of $CR_9R_{10}$, CO, CS, $C(NR_1)$, $NR_{12}$, S and O;
$R_4$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_3$ and $R_4$ are taken together to form a substituted or unsubstituted ring;
$R_7$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_7$ is $-L_1-R_{22}$;
$R_9$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, $(C_{3-12})$cycloalkyl sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;
$R_{10}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_5$ and $R_{10}$ are taken together to form oxo, with the proviso that $R_{10}$ is absent when the atom to which it is bound forms part of a double bond;
$R_{11}$ is selected from the group consisting of hydrogen, hydroxy, carbonyloxy, $(C_{1-10})$alkoxy, $(C_{4-12})$aryloxy, hetero$(C_{1-10})$aryloxy, oxycarbonyl, amino, $(C_{1-10})$alkylamino, sulfonamido, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;
$R_{12}$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, with the proviso that $R_{12}$ is absent when the atom to which it is bound forms part of a double bond,
or any two $R_7$, $R_9$, $R_{10}$, $R_{11}$ and $R_{12}$ are taken together to form a substituted or unsubstituted ring;
L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;
$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

R$_{22}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, aza(C$_{1-10}$)alkyl, (C$_{1-10}$) oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted, or R$_{22}$ is —NR$_{27}$R$_{28}$;

R$_{27}$ and R$_{28}$ are each independently selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{27}$ and R$_{28}$ are taken together to form a substituted or unsubstituted ring;

G$_4$ is a leaving group; and

G$_5$ is a protecting group.

In a further embodiment, the intermediates comprise:

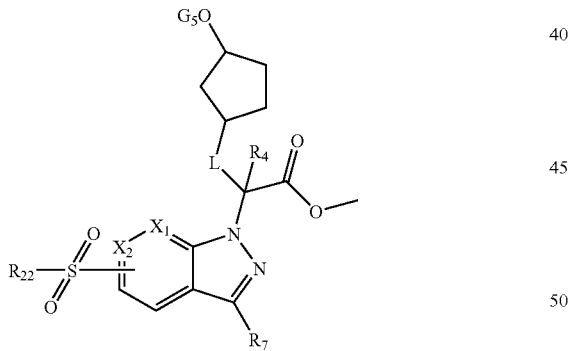

wherein

X$_1$ and X$_2$ are each independently selected from the group consisting of CR$_9$R$_{10}$, CO, CS, C(NR$_{11}$), NR$_{12}$, S and O;

R$_4$ is selected from the group consisting of hydrogen, carbonyl, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl (C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, aryl, heteroaryl, (C$_{9-12}$)bicycloaryl and hetero(C$_{4-12}$)bicycloaryl, each substituted or unsubstituted, or R$_3$ and R$_4$ are taken together to form a substituted or unsubstituted ring;

R$_7$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo (C$_{1-10}$)alkyl, hydroxy(C$_{1-10}$)alkyl, carbonyl(C$_{1-10}$) alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl (C$_{1-5}$)alkyl, hetero(C$_{3-12}$)cycloalkyl(C$_{1-10}$)alkyl, aryl (C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_7$ is -L$_1$-R$_{22}$;

R$_9$ is selected from the group consisting of hydrogen, halo, nitro, cyano, thio, oxy, hydroxy, carbonyloxy, (C$_{1-10}$) alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, (C$_{3-12}$)cycloalkyl sulfonyl, sulfinyl, (C$_{1-10}$)alkyl, halo(C$_{1-10}$)alkyl, hydroxy(C$_{1-10}$) alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$) alkyl, (C$_{1-10}$)oxaalkyl, (C$_{1-10}$)oxoalkyl, imino(C$_{1-10}$) alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl (C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl, each substituted or unsubstituted;

R$_{10}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, aza(C$_{1-10}$)alkyl, (C$_{1-10}$) oxaalkyl, (C$_{1-10}$)oxoalkyl, imino(C$_{1-10}$)alkyl, (C$_{3-12}$) cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$) bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted, or R$_5$ and R$_{10}$ are taken together to form oxo, with the proviso that R$_{10}$ is absent when the atom to which it is bound forms part of a double bond;

R$_{11}$ is selected from the group consisting of hydrogen, hydroxy, carbonyloxy, (C$_{1-10}$)alkoxy, (C$_{4-12}$)aryloxy, hetero(C$_{1-10}$)aryloxy, oxycarbonyl, amino, (C$_{1-10}$)alkylamino, sulfonamido, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$) alkyl, aza(C$_{1-10}$)alkyl, imino(C$_{1-10}$)alkyl, (C$_{3-12}$)cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_5$ is a protecting group.

In still a further embodiment, the intermediates comprise:

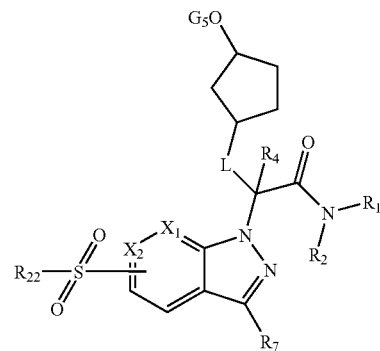

wherein $X_1$ and $X_2$ are each independently selected from the group consisting of $CR_9R_{10}$, CO, CS, C($NR_{11}$), $NR_{12}$, S and O;

$R_1$ is selected from the group consisting of hetero($C_{3-12}$)cycloalkyl, hetero($C_{3-12}$)bicycloalkyl, heteroaryl, and hetero($C_{4-12}$)bicycloaryl, each substituted or unsubstituted;

$R_2$ is selected from the group consisting of hydrogen and a substituent convertible to hydrogen in vivo;

$R_4$ is selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_3$ and $R_4$ are taken together to form a substituted or unsubstituted ring;

$R_7$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_7$ is -$L_1$-$R_{22}$;

$R_9$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, ($C_{3-12}$)cycloalkyl sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl ($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{10}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_5$ and $R_{10}$ are taken together to form oxo, with the proviso that $R_{10}$ is absent when the atom to which it is bound forms part of a double bond;

$R_{11}$ is selected from the group consisting of hydrogen, hydroxy, carbonyloxy, ($C_{1-10}$)alkoxy, ($C_{4-12}$)aryloxy, hetero($C_{1-10}$)aryloxy, oxycarbonyl, amino, ($C_{1-10}$)alkylamino, sulfonamido, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_{12}$ is selected from the group consisting of hydrogen, oxy, hydroxy, carbonyloxy, ($C_{1-10}$)alkoxy, ($C_{4-12}$)aryloxy, hetero($C_{1-10}$)aryloxy, carbonyl, oxycarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl, each substituted or unsubstituted, with the proviso that $R_{12}$ is absent when the atom to which it is bound forms part of a double bond, or any two $R_7$, $R_9$, $R_{10}$, $R_{11}$ and $R_{12}$ are taken together to form a substituted or unsubstituted ring;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$;

$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring; and $G_5$ is a protecting group.

In one variation of each of the above embodiments and variations containing $R_1$, $R_1$ is a substituted or unsubstituted heteroaryl. In another variation of each of the above embodiments and variations containing $R_1$, $R_1$ is selected from the group consisting of thiazolyl, pyrazinyl, pyrazolyl and pyridyl, each substituted or unsubstituted. In still another variation of each of the above embodiments and variations containing $R_1$, $R_1$ is selected from the group consisting of thiazol-2-yl; 2-pyridyl; 5-methyl-thiazol-2-yl; 6-methyl-pyrid-2-yl; 4-methyl-pyrid-2-yl; 5-bromo-6-methyl-pyrid-2-yl; 5-phenyl-pyrid-2-yl; benzothiazol-2-yl; a nictoinic acid methyl ester; and 5-bromo-pyrid-2-yl. In a further variation of each of the above embodiments and variations containing $R_1$, $R_1$ is a substituted or unsubstituted 2-pyrazinyl. In still a further variation of each of the above embodiments and variations containing $R_1$, $R_1$ is a substituted or unsubstituted 1-methyl-pyrazol-3-yl. In yet a further variation of each of the above embodiments and variations containing $R_1$, $R_1$ is a substituted or unsubstituted 5-fluoro-thiazol-2-yl.

In yet another variation of each of the above embodiments and variations containing $R_1$, $R_1$ comprises:

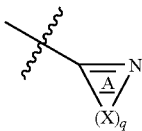

wherein q is selected from the group consisting of 3, 4 and 5;

each X is independently selected from the group consisting of $CR_{14}R_{15}$, CO, CS, $NR_{16}$, O, S, SO and $SO_2$;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In a further variation of each of the above embodiments and variations containing $R_1$, $R_1$ comprises:

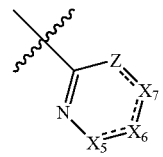

wherein $X_5$, $X_6$ and $X_7$ are each independently selected from the group consisting of $CR_{14}R_{15}$, CO, CS, $NR_{16}$, O, S, SO and $SO_2$;

Z is selected from the group consisting of $CR_{14}R_{15}$, $NR_{16}$, O and S;

$R_{14}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is -$L_1$-$R_{22}$;

R₁₅ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that R₁₅ is absent when the atom to which it is bound forms part of a double bond;

R₁₆ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that R₁₆ is absent when the atom to which it is bound forms part of a double bond, or any two R₁₄, R₁₅ and R₁₆ are taken together to form a substituted or unsubstituted ring;

L₁ is absent or a linker providing 1, 2, 3, 4, 5 or 6 atom separation between R₂₂ and the ring to which L₁ is attached, wherein the atoms of the linker providing the separation are selected from the group consisting of carbon, oxygen, nitrogen, and sulfur;

R₂₂ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or R₂₂ is —NR₂₇R₂₈; and R₂₇ and R₂₈ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or R₂₇ and R₂₈ are taken together to form a substituted or unsubstituted ring.

In another variation of each of the above embodiments and variations containing R₁, R₁ comprises:

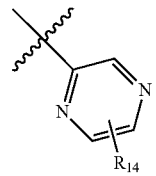

wherein

R₁₄ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or R₁₄ is -L₁-R₂₂.

In still a further variation of each of the above embodiments and variations containing R₁, R₁ comprises:

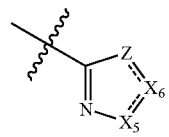

wherein

X₅ and X₆ are each independently selected from the group consisting of CR₁₄R₁₅, CO, CS, NR₁₆, O, S, SO and SO₂;

Z is selected from the group consisting of CR₁₄R₁₅, NR₁₆, O and S;

R₁₄ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or R₁₄ is -L₁-R₂₂;

$R_{15}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, carboxamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, oxa $(C_{1-5})$alkyl, oxo$(C_{1-5})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{15}$ is absent when the atom to which it is bound forms part of a double bond;

$R_{16}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{16}$ is absent when the atom to which it is bound forms part of a double bond, or any two $R_{14}$, $R_{15}$ and $R_{16}$ are taken together to form a substituted or unsubstituted ring;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is $—NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In yet a further variation of each of the above embodiments and variations containing $R_1$, $R_1$ comprises:

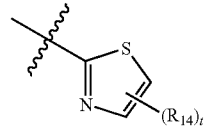

wherein t is selected from the group consisting of 0, 1 and 2; and each $R_{14}$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, carboxamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino$(C_{1-3})$alkyl, oxa$(C_{1-5})$alkyl, oxo$(C_{1-5})$alkyl, $(C_{3-12})$ cycloalkyl$(C_{1-5})$alkyl, hetero$(C_{3-12})$cycloalkyl$(C_{1-5})$ alkyl, aryl$(C_{1-10})$alkyl, heteroaryl$(C_{1-5})$alkyl, $(C_{9-12})$ bicycloaryl$(C_{1-5})$alkyl, hetero$(C_{8-12})$bicycloaryl$(C_{1-5})$ alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{14}$ is $-L_1-R_{22}$, or two $R_{14}$ are taken together to form a substituted or unsubstituted ring;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted, or $R_{22}$ is $—NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In another variation of each of the above embodiments and variations containing $R_1$, $R_1$ comprises:

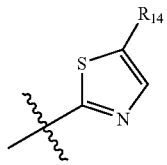

wherein
$R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;
$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;
$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and
$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In a further variation of each of the above embodiments and variations containing $R_1$, $R_1$ comprises:

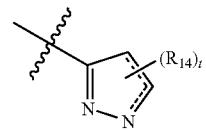

wherein
t is selected from the group consisting of 0, 1 and 2; and
each $R_{14}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, carboxamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino($C_{1-3}$)alkyl, oxa($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$, or two $R_{14}$ are taken together to form a substituted or unsubstituted ring;
$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;
$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$; and
$R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$)

alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In still a further variation of each of the above embodiments and variations containing $R_1$, $R_1$ comprises:

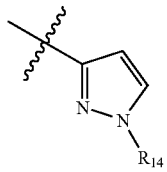

wherein $R_{14}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, carboxamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, oxa ($C_{1-5}$)alkyl, oxo($C_{1-5}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet another variation of each of the above embodiments and variations containing $R_1$, $R_1$ comprises:

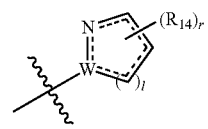

wherein l is selected from the group consisting of 1 and 2;

r is selected from the group consisting of 0, 1, 2, 3, 4, 5, 6, 7 and 8;

W is selected from the group consisting of $CR_{17}$ or N;

each $R_{14}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, carboxamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, oxa($C_{1-5}$)alkyl, oxo($C_{1-5}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{14}$ is -$L_1$-$R_{22}$, or two $R_{14}$ are taken together to form a substituted or unsubstituted ring;

$R_{17}$ is selected from the group consisting of hydrogen, halo, ($C_{1-3}$)alkyl, aryl and heteroaryl, each substituted or unsubstituted, or $R_{17}$ and $R_{14}$ are taken together to form a ring, with the proviso that $R_{17}$ is absent when the atom to which it is attached forms part of a double bond;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$) alkyl, halo($C_{1-10}$)alkyl, hydroxy($C_{1-10}$)alkyl, carbonyl ($C_{1-10}$)alkyl, thiocarbonyl($C_{1-10}$)alkyl, sulfonyl($C_{1-10}$) alkyl, sulfinyl($C_{1-10}$)alkyl, aza($C_{1-10}$)alkyl, ($C_{1-10}$) oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl ($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted, or $R_{22}$ is —$NR_{27}R_{28}$; and R$_{27}$ and R$_{28}$ are each independently selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{27}$ and R$_{28}$ are taken together to form a substituted or unsubstituted ring.

In one variation of the above variations containing W, W is CR$_{17}$. In another variation of the above variations containing W, W is N.

In another variation of each of the above embodiments and variations containing R$_1$, R$_1$ comprises:

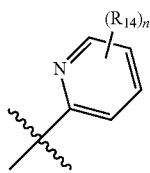

wherein
n is selected from the group consisting of 0, 1, 2, 3 and 4;
each R$_{14}$ is independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, carboxamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, oxa(C$_{1-5}$)alkyl, oxo(C$_{1-5}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{14}$ is -L$_1$-R$_{22}$, or two R$_{14}$ are taken together to form a substituted or unsubstituted ring;
L$_1$ is absent or a linker providing 1, 2, 3, 4, 5 or 6 atom separation between R$_{22}$ and the ring to which L$_1$ is attached, wherein the atoms of the linker providing the separation are selected from the group consisting of carbon, oxygen, nitrogen, and sulfur;
R$_{22}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, amido, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{22}$ is —NR$_{27}$R$_{28}$; and R$_{27}$ and R$_{28}$ are each independently selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or R$_{27}$ and R$_{28}$ are taken together to form a substituted or unsubstituted ring.

In yet another variation of each of the above embodiments and variations containing ring A, ring A is a substituted or unsubstituted heteroaryl. In a further variation of each of the above embodiments and variations containing ring A, ring A is selected from the group consisting of thiazolyl, pyrazinyl, pyrazolyl and pyridyl, each substituted or unsubstituted. In a further variation of each of the above embodiments and variations containing A, A is a substituted or unsubstituted 2-pyrazinyl. In still a further variation of each of the above embodiments and variations containing A, A is a substituted or unsubstituted 1-methyl-pyrazol-3-yl. In yet a further variation of each of the above embodiments and variations containing A, A is a substituted or unsubstituted 5-fluoro-thiazol-2-yl.

In still a further variation of each of the above embodiments and variations containing Z, Z is S.

In yet a further variation of each of the above embodiments and variations containing X$_1$, X$_1$ is —CH=. In yet another variation of each of the above embodiments and variations containing X$_1$, X$_1$ is —N=.

In another variation of each of the above embodiments and variations containing X$_2$, X$_2$ is —CH=. In yet another variation of each of the above embodiments and variations containing X$_2$, X$_2$ is —N=.

In a further variation of each of the above embodiments and variations containing X$_3$, X$_3$ is —CR$_9$=. In still another variation of each of the above embodiments and variations containing X$_3$, X$_3$ is —CH=.

In a further variation of each of the above embodiments and variations containing X$_4$, X$_4$ is —CR$_9$=. In still another variation of each of the above embodiments and variations containing X$_4$, X$_4$ is —CH=.

In a further variation of each of the above embodiments and variations containing X$_1$, X$_2$, X$_3$ and X$_4$, X$_1$ is —CH=, X$_2$ is —N=, X$_3$ is —CH= and X$_4$ is —CR$_9$=. In still a further variation of each of the above embodiments and variations containing X$_1$, X$_2$, X$_3$ and X$_4$, X$_1$ is —CH=, X$_2$ is —CH=, X$_3$ is —CR$_9$= and X$_4$ is —CR$_9$=.

In still another variation of each of the above embodiments and variations containing X$_5$, X$_5$ is —CH=.

In still another variation of each of the above embodiments and variations containing X$_6$, X$_6$ is —CH=.

In still another variation of each of the above embodiments and variations containing X$_7$, X$_7$ is —CH=. In a further variation of each of the above embodiments and variations containing X$_7$, X$_7$ is —N=.

In yet another variation of each of the above embodiments and variations containing $R_2$, $R_2$ is hydrogen.

In a further variation of each of the above embodiments and variations containing $R_3$, $R_3$ is -L-$R_{18}$;

L is a linker providing 0, 1, 2, 3, 4, 5 or 6 atom separation between the C and $R_{18}$ to which L is attached, wherein the atoms of the linker providing the separation are selected from the group consisting of carbon, oxygen, nitrogen, and sulfur; and $R_{18}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further variation of each of the above embodiments and variations containing $R_3$, $R_3$ comprises:

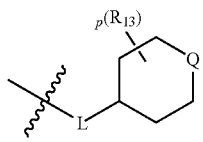

wherein p is selected from the group consisting of 0, 1, 2, 3, 4, 5, 6, 7, 8 and 9;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;

Q is selected from the group consisting of O, S, CS, CO, SO, $SO_2$, $CR_{19}R_{20}$ and $NR_{21}$;

$R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring;

$R_{19}$ and $R_{20}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{21}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In yet a further variation of each of the above embodiments and variations containing $R_3$, $R_3$ comprises:

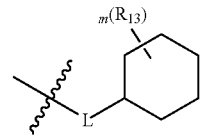

wherein m is selected from the group consisting of 0, 1, 2, 3, 4, 5, 6, 7, 8, 9, 10 and 11;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In another variation of each of the above embodiments and variations containing $R_3$, $R_3$ comprises:

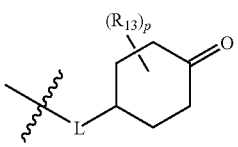

wherein p is selected from the group consisting of 0, 1, 2, 3, 4, 5, 6, 7, 8 and 9;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In still another variation of each of the above embodiments and variations containing $R_3$, $R_3$ comprises:

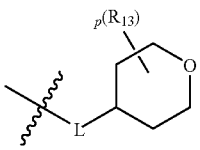

wherein p is selected from the group consisting of 0, 1, 2, 3, 4, 5, 6, 7, 8 and 9;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In yet another variation of each of the above embodiments and variations containing $R_3$, $R_3$ is selected from the group consisting of $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of each of the above embodiments and variations containing $R_3$, $R_3$ comprises:

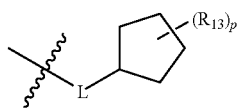

wherein p is selected from the group consisting of 0, 1, 2, 3, 4, 5, 6, 7, 8 and 9;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In still a further variation of each of the above embodiments and variations containing $R_3$, $R_3$ comprises:

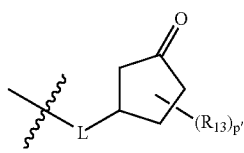

wherein p' is selected from the group consisting of 0, 1, 2, 3, 4, 5, 6 and 7;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In yet a further variation of each of the above embodiments and variations containing $R_3$, $R_3$ comprises:

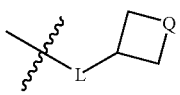

wherein

Q is selected from the group consisting of O, S, CS, CO, SO, $SO_2$, $CR_{19}R_{20}$ and $NR_{21}$;

L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur;

$R_{19}$ and $R_{20}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{21}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In another variation of each of the above embodiments and variations containing $R_3$, $R_3$ is selected from the group consisting of (C$(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, and heteroaryl$(C_{1-5})$alkyl, each substituted or unsubstituted. In still another variation of each of the above embodiments and variations containing $R_3$, $R_3$ is selected from the group consisting of butyl; hexylmethyl; benzyl; imidazol-4-ylmethyl, phenyl and (tetrahydro-2H-pyran-4-yl)methyl. In yet another variation of each of the above embodiments and variations containing $R_3$, $R_3$ is a substituted or unsubstituted (tetrahydro-2H-pyran-4-yl)methyl. In a further variation of each of the above embodiments and variations containing $R_3$, $R_3$ is selected from the group consisting of butyl; hexylmethyl; benzyl; imidazol-4-ylmethyl and phenyl. In still a further variation of each of the above embodiments and variations containing $R_3$, $R_3$ is selected from the group consisting of alkyl, cycloalkyl-alkyl, dihaloaryl-alkyl, alkoxyaryl-alkyl, alkoxycycloalkyl-alkyl, tetrahydrofuranyl-alkyl, furanyl-alkyl and tetrahydro-2H-pyranyl-alkyl, each substituted or unsubstituted.

In yet a further variation of each of the above embodiments and variations containing L, L is —$CH_2$—. In another variation of each of the above embodiments and variations containing L, L is selected from the group consisting of —$CH_2$—, —$CH_2CH_2$—, —$CH_2CH_2CH_2$—, —$CH_2C(O)$—, —$CH_2$—$C(O)CH_2$—, —$CH_2CH_2C(O)$—, —$CH_2O$—, —$CH_2OCH_2$—, —$CH_2CH_2O$—, —$CH_2NH$—, —$CH_2NHCH_2$—, —$CH_2CH_2NH$—, —$CH_2NHC(O)$—, —$CH_2C(O)NH$—, —$CH_2S$—, —$CH_2SCH_2$—, —$CH_2CH_2S$—, —$CH_2C(O)S$— and —$CH_2SC(O)$—, each substituted or unsubstituted. In still another variation of each of the above embodiments and variations containing L, L is selected from the group consisting of —$CH_2$—, —$CH_2CH_2$—, —$CH_2CH_2CH_2$—, —C(O)—, —$CH_2C(O)$—, —$C(O)CH_2$—, —$CH_2$—$C(O)CH_2$—, —$C(O)CH_2CH_2$—, —$CH_2CH_2C(O)$—, —O—, —$OCH_2$—, —$CH_2O$—, —$CH_2OCH_2$—, —$OCH_2CH_2$—, —$CH_2CH_2O$—, —$N(CH_3)$—, —$NHCH_2$—, —$CH_2NH$—, —$CH_2NHCH_2$—, —$NHCH_2CH_2$—, —$CH_2CH_2NH$—, —NH—C(O)—, —$NCH_3$—C(O)—, —C(O)NH—, —C(O)$NCH_3$—, —$NHC(O)CH_2$—, —$C(O)NHCH_2$—, —$C(O)CH_2NH$—, —$CH_2NHC(O)$—, —$CH_2C(O)NH$—, —$NHCH_2C(O)$—, —S—, —$SCH_2$—, —$CH_2S$—, —$SCH_2CH_2$—, —$CH_2SCH_2$—, —$CH_2CH_2S$—, —C(O)S—, —$C(O)SCH_2$—, —$CH_2C(O)S$—, —$C(O)CH_2S$—, and —$CH_2SC(O)$—, each substituted or unsubstituted.

In yet another variation of each of the above embodiments and variations containing L, L is selected from the group consisting of —$(CR_{24}R_{25})_s$—;

s is selected from the group consisting from the group consisting of 1, 2, 3, 4, 5 and 6; and $R_{24}$ and $R_{25}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations containing Q, Q is —$CR_{19}R_{20}$—. In still a further variation of each of the above embodiments and variations containing Q, Q is —$CH_2$—. In yet a further variation of each of the above embodiments and variations containing Q, Q is —$NR_{21}$—. In another variation of each of the above embodiments and variations containing Q, Q is —NH—. In a further variation of each of the above embodiments and variations containing Q, Q is —O—.

In still another variation of each of the above embodiments and variations containing $R_4$, $R_4$ is selected from the group consisting of carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$ bicycloaryl and hetero$(C_{4-12})$bicycloaryl, each substituted or unsubstituted.

In yet another variation of each of the above embodiments and variations containing $R_4$, $R_4$ is selected from the group consisting of hydrogen, $(C_{1-10})$alkyl, $(C_{3-12})$cycloalkyl$(C_{1-5})$ alkyl, hetero$(C_{3-12})$cycloalkyl$(C_{1-5})$alkyl, aryl$(C_{1-10})$alkyl, and heteroaryl$(C_{1-5})$alkyl, each substituted or unsubstituted. In a further variation of each of the above embodiments and variations containing $R_4$, $R_4$ is selected from the group consisting of $(C_{1-10})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, and heteroaryl $(C_{1-5})$alkyl, each substituted or unsubstituted. In still a further variation of each of the above embodiments and variations containing $R_4$, $R_4$ is selected from the group consisting of hydrogen; butyl; cyclohexylmethyl; benzyl; imidazol-4-ylmethyl and phenyl. In yet a further variation of each of the above embodiments and variations containing $R_4$, $R_4$ is selected from the group consisting of butyl; cyclohexylmethyl; benzyl; imidazol-4-ylmethyl and phenyl. In another variation of each of the above embodiments and variations containing $R_4$, $R_4$ is hydrogen.

In still another variation of each of the above embodiments and variations containing $R_5$, $R_5$ is hydrogen. In yet another variation of each of the above embodiments and variations containing $R_5$, $R_5$ is halo. In a further variation of each of the above embodiments and variations containing $R_5$, $R_5$ is a substituted or unsubstituted $(C_{1-3})$alkyl.

In still a further variation of each of the above embodiments and variations containing $R_6$, $R_6$ is hydrogen. In yet a further variation of each of the above embodiments and variations containing $R_6$, $R_6$ is halo. In another variation of each of the above embodiments and variations containing $R_6$, $R_6$ is a substituted or unsubstituted $(C_{1-3})$alkyl. In still another variation of each of the above embodiments and variations containing $R_6$, $R_6$ is a substituted or unsubstituted $(C_{1-3})$alkylsulfonyl. In yet another variation of each of the above embodiments and variations containing $R_6$, $R_6$ is a substituted or unsubstituted $(C_{1-6})$cycloalkylsulfonyl. In yet a further variation of each of the above embodiments and variations containing $R_6$, $R_6$ is selected from the group consisting of methylsulfonyl, cyclopropylsulfonyl and cyclopentylsulfonyl, each substituted or unsubstituted.

In another variation of each of the above embodiments and variations containing $R_6$, $R_6$ is -$L_1$-$R_{22}$;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In still another variation of each of the above embodiments and variations containing $R_6$, $R_6$ is —$SO_2$—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$ alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$ oxaalkyl, $(C_{1-10})$oxoalkyl, imino$(C_{1-10})$alkyl, $(C_{3-12})$ cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$ alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl$(C_{1-5})$ alkyl, $(C_{9-12})$bicycloaryl$(C_{1-5})$alkyl, hetero$(C_{8-12})$ bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In yet another variation of each of the above embodiments and variations containing $R_6$, $R_6$ is —CO—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In a further variation of each of the above embodiments and variations containing $R_6$, $R_6$ is —$NH—SO_2—R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In still a further variation of each of the above embodiments and variations containing $R_6$, $R_6$ is —$NH—CO—R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In yet a further variation of each of the above embodiments and variations containing $R_6$, $R_6$ is —$CO—NH—R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In another variation of each of the above embodiments and variations containing $R_7$, $R_7$ is hydrogen. In still another variation of each of the above embodiments and variations containing $R_7$, $R_7$ is halo. In yet another variation of each of the above embodiments and variations containing $R_7$, $R_7$ is a substituted or unsubstituted $(C_{1-3})$alkyl.

In a further variation of each of the above embodiments and variations containing $R_7$, $R_7$ is -$L_1$-$R_{22}$;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In a further variation of each of the above embodiments and variations containing $R_7$, $R_7$ is —CO—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In still a further variation of each of the above embodiments and variations containing $R_7$, $R_7$ is —NH—$SO_2$—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In yet a further variation of each of the above embodiments and variations containing $R_5$ and $R_6$, $R_5$ and $R_6$, together with the atoms to which they are attached, form a substituted or unsubstituted aryl. In another variation of each of the above embodiments and variations containing $R_5$ and $R_6$, $R_5$ and $R_6$, together with the atoms to which they are attached, form a substituted or unsubstituted phenyl. In still another variation of each of the above embodiments and variations containing $R_5$ and $R_6$, $R_5$ and $R_6$, together with the atoms to which they are attached, form a substituted or unsubstituted heteroaryl.

In yet another variation of each of the above embodiments and variations containing $R_6$ and $R_7$, $R_6$ and $R_7$, together with the atoms to which they are attached, form a substituted or unsubstituted aryl. In a further variation of each of the above embodiments and variations containing $R_6$ and $R_7$, $R_6$ and $R_7$, together with the atoms to which they are attached, form a substituted or unsubstituted phenyl. In still a further variation of each of the above embodiments and variations containing $R_6$ and $R_7$, $R_6$ and $R_7$, together with the atoms to which they are attached, form a substituted or unsubstituted heteroaryl.

In yet a further variation of each of the above embodiments and variations containing $R_8$, $R_8$ is hydrogen. In another variation of each of the above embodiments and variations containing $R_8$, $R_8$ is halo. In another variation of each of the above embodiments and variations containing $R_8$, $R_8$ is a substituted or unsubstituted $(C_{1-3})$alkyl. In still another variation of each of the above embodiments and variations containing $R_8$, $R_8$ is a substituted or unsubstituted sulfonyl$(C_{1-3})$alkyl. In a further variation of each of the above embodiments and variations containing $R_8$, $R_8$ is a substituted or unsubstituted $(C_{1-3})$alkylsulfonyl. In still a further variation of each of the above embodiments and variations containing $R_8$, $R_8$ is a substituted or unsubstituted $(C_{3-12})$cycloalkylsulfonyl. In yet another variation of each of the above embodiments and variations containing $R_8$, $R_8$ is selected from the group consisting of sulfonylmethyl, methylsulfonyl, cyclopropylsulfonyl and cyclopentylsulfonyl, each substituted or unsubstituted. In a further variation of each of the above embodiments and variations containing $R_8$, $R_8$ is a substituted or unsubstituted cyclopropylsulfonyl. In still a further variation of each of the above embodiments and variations containing $R_8$, $R_8$ is cyano. In yet a further variation of each of the above embodiments and variations containing $R_8$, $R_8$ is a substituted or unsubstituted $(C_{1-6})$alkoxy. In another variation of each of the above embodiments and variations containing $R_8$, $R_8$ is methoxy.

In a further variation of each of the above embodiments and variations containing $R_8$, $R_8$ is -$L_1$-$R_{22}$;

$L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur;

$R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In still a further variation of each of the above embodiments and variations containing $R_8$, $R_8$ is —$SO_2$—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In yet a further variation of each of the above embodiments and variations containing $R_8$, $R_8$ is —CO—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{27}$ and $R_{28}$ are taken together to form a substituted or unsubstituted ring.

In another variation of each of the above embodiments and variations containing $R_5$, $R_5$ is —NH—$SO_2$—$R_{22}$; $R_{22}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, amido, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$ cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In still another variation of each of the above embodiments and variations containing $R_8$, $R_8$ is —NH—CO—$R_{22}$; $R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet another variation of each of the above embodiments and variations containing $R_8$, $R_8$ is —CO—NH—$R_{22}$; $R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In a further variation of each of the above embodiments and variations containing $R_3$ and $R_8$, $R_3$ is a substituted or unsubstituted(tetrahydro-2H-pyran-4-yl)methyl and $R_8$ is a substituted or unsubstituted cyclopropylsulfonyl.

In another variation of each of the above embodiments and variations containing $R_9$, $R_9$ is a substituted or unsubstituted cyclopropylsulfonyl. In still another variation of each of the above embodiments and variations containing $R_9$, $R_9$ is a substituted or unsubstituted ($C_{1-3}$)alkoxy. In yet another variation of each of the above embodiments and variations containing $R_9$, $R_9$ is methoxy.

In still a further variation of each of the above embodiments and variations containing $R_3$ and $R_9$, $R_3$ is a substituted or unsubstituted(tetrahydro-2H-pyran-4-yl)methyl and $R_9$ is a substituted or unsubstituted cyclopropylsulfonyl.

In still another variation of each of the above embodiments and variations containing $R_{10}$, $R_{10}$ is hydrogen. In yet another variation of each of the above embodiments and variations containing $R_{10}$, $R_{10}$ is halo. In a further variation of each of the above embodiments and variations containing $R_{10}$, $R_{10}$ is a substituted or unsubstituted ($C_{1-3}$)alkyl.

In still another variation of each of the above embodiments and variations containing $R_{11}$, $R_{11}$ is hydrogen. In a further variation of each of the above embodiments and variations containing $R_{11}$, $R_{11}$ is a substituted or unsubstituted ($C_{1-3}$)alkyl.

In still another variation of each of the above embodiments and variations containing $R_{12}$, $R_{12}$ is hydrogen. In a further variation of each of the above embodiments and variations containing $R_{12}$, $R_{12}$ is a substituted or unsubstituted ($C_{1-3}$)alkyl.

In still another variation of each of the above embodiments and variations containing $R_{13}$, $R_{13}$ is hydrogen. In yet another variation of each of the above embodiments and variations containing $R_{13}$, $R_{13}$ is halo. In a further variation of each of the above embodiments and variations containing $R_{13}$, $R_{13}$ is a substituted or unsubstituted ($C_{1-3}$)alkyl.

In another variation of each of the above embodiments and variations containing $R_{14}$, each $R_{14}$ is independently selected from the group consisting of hydrogen, halo, a substituted or unsubstituted ($C_{1-5}$)alkyl and a substituted or unsubstituted carboxamido. In a further variation of each of the above embodiments and variations containing $R_{14}$, at least one $R_{14}$ is a substituted or unsubstituted carboxamido. In still a further variation of each of the above embodiments and variations containing $R_{14}$, at least one $R_{14}$ is hydrogen. In yet a further variation of each of the above embodiments and variations containing $R_{14}$, at least one $R_{14}$ is halo. In another variation of each of the above embodiments and variations containing $R_{14}$, at least one $R_{14}$ is fluoro. In still another variation of each of the above embodiments and variations containing $R_{14}$, at least one $R_{14}$ is chloro. In another variation of each of the above embodiments and variations containing $R_{14}$, at least one $R_{14}$ is a substituted or unsubstituted ($C_{1-5}$)alkyl. In another variation of each of the above embodiments and variations containing $R_{14}$, at least one $R_{14}$ is methyl. In still another variation of each of the above embodiments and variations containing $R_{14}$, two $R_{14}$, together with the atoms to which they are attached, are taken together to form a substituted or unsubstituted ring.

In still another variation of each of the above embodiments and variations containing $R_{14}$, $R_{14}$ is oxa($C_{1-5}$)alkyl. In yet another variation of each of the above embodiments and variations containing $R_{14}$, $R_{14}$ is oxo($C_{1-5}$)alkyl. In a further variation of each of the above embodiments and variations containing $R_{14}$, $R_{14}$ is -$L_1$-$R_{22}$, where $L_1$ is absent or a linker providing 1, 2, 3, 4, 5 or 6 atom separation between $R_{22}$ and the ring to which $L_1$ is attached, wherein the atoms of the linker providing the separation are selected from the group consisting of carbon, oxygen, nitrogen, and sulfur; $R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In still a further variation of each of the above embodiments and variations containing $R_{14}$, $R_{14}$ is selected from the group consisting of hydrogen, halo, cyano, —$OR_{22}$, —$SO_2$—$R_{22}$, —NH—$SO_2$—$R_{22}$ and —$SO_2$—NH—$R_{22}$; $R_{22}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl ($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring. In yet a further variation of each of the above embodiments and variations containing $R_{14}$, $R_{14}$ is selected from the group consisting of halo, ($C_{1-5}$)alkyl, oxa($C_{1-5}$)alkyl and oxo($C_{1-5}$)alkyl, each substituted or unsubstituted.

In yet another variation of each of the above embodiments and variations containing $R_{15}$, $R_{15}$ is hydrogen. In a further variation of each of the above embodiments and variations containing $R_{15}$, $R_{15}$ is halo. In yet a further variation of each of the above embodiments and variations containing $R_{15}$, $R_{15}$ is a substituted or unsubstituted ($C_{1-5}$)alkyl.

In a further variation of each of the above embodiments and variations containing $R_{16}$, $R_{16}$ is ($C_{1-5}$)alkyl. In another variation of each of the above embodiments and variations containing $R_{16}$, $R_{16}$ is methyl.

In another variation of each of the above embodiments and variations containing $R_{17}$, $R_{17}$ is absent. In still another variation of each of the above embodiments and variations containing $R_{17}$, $R_{17}$ is hydrogen. In yet another variation of each of the above embodiments and variations containing $R_{17}$, $R_{17}$ is ($C_{1-3}$)alkyl. In another variation of each of the above embodiments and variations containing $R_{17}$, $R_{17}$ is methyl. In a further variation of each of the above embodiments and variations containing $R_{17}$, $R_{17}$ is halo.

In another variation of each of the above embodiments and variations containing $R_{18}$, $R_{18}$ is selected from the group consisting of alkyl, cycloalkyl, heterocycloalkyl, aryl and heteroaryl, each substituted or unsubstituted.

In still another variation of each of the above embodiments and variations containing $R_{19}$, $R_{19}$ is hydrogen. In yet another variation of each of the above embodiments and variations containing $R_{19}$, $R_{19}$ is halo. In a further variation of each of the above embodiments and variations containing $R_{19}$, $R_{19}$ is a substituted or unsubstituted ($C_{1-3}$)alkyl.

In still another variation of each of the above embodiments and variations containing $R_{20}$, $R_{20}$ is hydrogen. In yet another variation of each of the above embodiments and variations containing $R_{20}$, $R_{20}$ is halo. In a further variation of each of the above embodiments and variations containing $R_{20}$, $R_{20}$ is a substituted or unsubstituted ($C_{1-13}$)alkyl.

In still another variation of each of the above embodiments and variations containing $R_{21}$, $R_{21}$ is hydrogen. In a further variation of each of the above embodiments and variations containing $R_{21}$, $R_{21}$ is a substituted or unsubstituted ($C_{1-3}$) alkyl.

In still another variation of each of the above embodiments and variations containing $R_{22}$, $R_{22}$ is a substituted or unsubstituted ($C_{1-5}$)alkyl. In yet another variation of each of the above embodiments and variations containing $R_{22}$, $R_{22}$ is a substituted or unsubstituted ($C_{3-6}$)cycloalkyl. In a further variation of each of the above embodiments and variations containing $R_{22}$, $R_{22}$ is a substituted or unsubstituted ($C_{4-8}$) aryl. In still a further variation of each of the above embodiments and variations containing $R_{22}$, $R_{22}$ is a substituted or unsubstituted phenyl. In yet a further variation of each of the above embodiments and variations containing $R_{22}$, $R_{22}$ is a substituted or unsubstituted hetero($C_{1-6}$)aryl. In another variation of each of the above embodiments and variations containing $R_{22}$, $R_{22}$ is cyclopropyl.

In still another variation of each of the above embodiments and variations containing $R_{22}$, $R_{22}$ is —$NR_{27}R_{28}$; and $R_{27}$ and $R_{28}$ are each independently selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{27}$ and $R_{28}$ are taken together to form a substituted or unsubstituted ring.

In yet a further variation of each of the above embodiments and variations containing $L_1$, $L_1$ is selected from the group consisting of —($CR_{24}R_{25}$)$_s$—, —$NR_{26}$—, —O—, —S—, —CO—, —CS—, —SO—, —SO$_2$—, and combinations thereof;

s is selected from the group consisting from the group consisting of 1, 2, 3, 4, 5 and 6;

$R_{24}$ and $R_{25}$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_{26}$ is selected from the group consisting of hydrogen, cyano, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In another variation of each of the above embodiments and variations containing $L_1$, $L_1$ is —$SO_2$—. In still another variation of each of the above embodiments and variations containing $L_1$, $L_1$ is —C(O)—$NR_{26}$— and $R_{26}$ is selected from the group consisting of hydrogen, cyano, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In yet another variation of each of the above embodiments and variations containing $L_1$, $L_1$ is —C(S)—$NR_{26}$— and $R_{26}$ is selected from the group consisting of hydrogen, cyano, hydroxy, carbonyloxy, ($C_{1-10}$)alkoxy, ($C_{4-12}$)aryloxy, hetero($C_{1-10}$)aryloxy, carbonyl, oxycarbonyl, amido, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In a further variation of each of the above embodiments and variations containing $R_{24}$, $R_{24}$ is selected from the group consisting of H and a substituted or unsubstituted ($C_{1-5}$)alkyl.

In still a further variation of each of the above embodiments and variations containing $R_{25}$, $R_{25}$ is selected from the group consisting of H and a substituted or unsubstituted ($C_{1-5}$)alkyl.

In yet a further variation of each of the above embodiments and variations containing $R_{26}$, $R_{26}$ is selected from the group consisting of hydrogen and a substituted or unsubstituted ($C_{1-10}$)alkyl.

In yet another variation of each of the above embodiments and variations containing $R_{27}$, $R_{27}$ is a substituted or unsubstituted ($C_{3-12}$)cycloalkyl. In a further variation of each of the above embodiments and variations containing $R_{27}$, $R_{27}$ is a substituted or unsubstituted cyclopropyl.

In still a further variation of each of the above embodiments and variations containing $R_{28}$, $R_{28}$ is hydrogen.

In another variation of each of the above embodiments and variations containing l, l is 1.

In still another variation of each of the above embodiments and variations containing m, m is 0. In yet another variation of each of the above embodiments and variations containing m, m is 1. In a further variation of each of the above embodiments and variations containing m, m is 2.

In a further variation of each of the above embodiments and variations containing n, n is 0. In still a further variation of each of the above embodiments and variations containing n, n is 1. In yet a further variation of each of the above embodiments and variations containing n, n is 2.

In a further variation of each of the above embodiments and variations containing n', n' is 0. In still a further variation of each of the above embodiments and variations containing n', n' is 1. In yet a further variation of each of the above embodiments and variations containing n', n' is 2.

In a further variation of each of the above embodiments and variations containing n", n" is 0. In still a further variation of each of the above embodiments and variations containing n", n" is 1. In yet a further variation of each of the above embodiments and variations containing n", n" is 2.

In another variation of each of the above embodiments and variations containing p, p is 0. In still another variation of each of the above embodiments and variations containing p, p is 1. In yet another variation of each of the above embodiments and variations containing p, p is 2.

In another variation of each of the above embodiments and variations containing p', p' is 0. In still another variation of each of the above embodiments and variations containing p', p' is 1. In yet another variation of each of the above embodiments and variations containing p', p' is 2.

In a further variation of each of the above embodiments and variations containing q, q is 3. In still a further variation of each of the above embodiments and variations containing q, q is 4.

In another variation of each of the above embodiments and variations containing r, r is 1.

In a further variation of each of the above embodiments and variations containing s, s is 0. In still a further variation of each of the above embodiments and variations containing s, s is 1.

In another variation of each of the above embodiments and variations containing t, t is 1.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent, such as hydrogen. It is further noted that the compound may be present in a mixture of stereoisomers, or the compound may comprise a single stereoisomer.

The present invention also provides a pharmaceutical composition comprising as an active ingredient a compound according to any one of the above embodiments and variations. In one particular variation, the composition is a solid formulation adapted for oral administration.

In another particular variation, the composition is a liquid formulation adapted for oral administration. In yet another particular variation, the composition is a tablet. In still another particular variation, the composition is a liquid formulation adapted for parenteral administration.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of activating glucokinase comprising contacting glucokinase with a compound of any one of the above embodiments and variations.

In yet another of its aspects, there is provided a method of activating glucokinase comprising causing a compound of any one of the above embodiments and variations to be present in a subject in order to activate glucokinase in vivo.

In a further of its aspects, there is provided a method of activating glucokinase comprising administering a first compound to a subject that is converted in vivo to a second compound wherein the second compound activates glucokinase in vivo, the second compound being a compound according to any one of the above embodiments and variations.

In another of its aspects, there is provided a method of treating a disease state for which increasing glucokinase activity ameliorates the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which increasing glucokinase activity ameliorates the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which increasing glucokinase activity ameliorates the pathology and/or symptomology of the disease state, the method comprising administering a first compound to a subject that is converted in vivo to a second compound wherein the second compound activates glucokinase in vivo, the second compound being a compound according to any one of the above embodiments and variations.

In one variation of each of the above methods the disease state is selected from the group consisting of hyperglycemia, diabetes, dyslipidaemia, obesity, insulin resistance, metabolic syndrome X, impaired glucose tolerance, polycystic ovary syndrome, and cardiovascular disease.

Salts, Hydrates, and Prodrugs of Glucokinase Activators

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, Protecting *Groups in Organic Synthesis*, $3^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising Glucokinase Activators

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The glucokinase activators and compositions comprising them may be administered or coadministered in any conventional dosage form. Co-administration in the context of this invention is intended to mean the administration of more than one therapeutic agent, one of which includes a glucokinase activator, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an activator of the present invention to increase glucokinase activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more glucokinase activators, optionally 0.1-95%, and optionally 1-95%.

Salts, preferably sodium salts, of the activators may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an activator in the parenteral formulation may be adjusted so that an injection administers a pharmaceutically effective amount sufficient to produce the desired pharmacological effect. The exact concentration of an activator and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the glucokinase activator to the treated tissue(s). The activator may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The glucokinase activator may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a glucokinase activator is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the activator.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The glucokinase activators may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The activators may also be formulated for local or topical application, such as for topical application to the skin and mucous membranes, such as in the eye, in the form of gels, creams, and lotions and for application to the eye or for intracistemal or intraspinal application. Topical administration is contemplated for transdermal delivery and also for administration to the eyes or mucosa, or for inhalation therapies. Nasal solutions of the glucokinase activator alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |

-continued

ORAL FORMULATION

| | |
|---|---:|
| Sodium Hydroxide | 18 mg |
| Flavoring | |
| Water | q.s. to 100 mL |

INTRAVENOUS FORMULATION

| | |
|---|---:|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

TABLET FORMULATION

| | |
|---|---:|
| Compound of the Present Invention | 1% |
| Microcrystalline Cellulose | 73% |
| Stearic Acid | 25% |
| Colloidal Silica | 1%. |

Kits Comprising Glucokinase Activators

The invention is also directed to kits and other articles of manufacture for treating diseases associated with glucokinase. It is noted that diseases are intended to cover all conditions for which increasing glucokinase activity (e.g., upregulation of glucokinase) ameliorates the pathology and/or symptomology of the condition.

In one embodiment, a kit is provided that comprises a composition comprising at least one activator of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one activator of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as glucokinase activators for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety of therapeutic agents may have a therapeutic additive or synergistic effect with GK activators according to the present invention. In particular, the present invention also relates to the use of the GK activators of the present invention in combination with one or more other antidiabetic compounds. Examples of such other antidiabetic compounds include, but are not limited to S9 proteases, like dipeptidyl peptidase IV (DPP-IV) inhibitors; insulin signaling pathway modulators, like protein tyrosine phosphatase (PTPase) inhibitors, and glutamine-fructose-6-phosphate amidotransferase (GFAT) inhibitors; compounds influencing a dysregulated hepatic glucose production, like glucose-6-phosphatase (G6Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors; pyruvate dehydrogenase kinase (PDHK) inhibitors; insulin sensitivity enhancers (insulin sensitizers); insulin secretion enhancers (insulin secretagogues); alpha-glucosidase inhibitors; inhibitors of gastric emptying; other glucokinase (GK) activators; GLP-1 receptor agonists; UCP modulators; RXR modulators; GSK-3 inhibitors; PPAR modulators; metformin; insulin; and $\alpha_2$-adrenergic antagonists.

The one or more antidiabetic compounds administered in combination with the GK activators of the present invention may also optionally be DPP-IV inhibitors selected from the group consisting of Alogliptin (Nesina; Takeda Pharmaceutical Company Limited), Sitagliptin (Januvia; Merck), Saxagliptin (Onglyza; Bristol Myers Squibb), and Vildagliptin (Galvus; Novartis). In addition, the one or more antidiabetic compounds administered in combination with the GK activators of the present invention may also optionally be DPP-IV inhibitors combined with metformin such as, for example, Alogliptin plus metformin(Takeda Pharmaceutical Company Limited), Sitagliptin plus metformin (Janumet; Merck), Saxagliptin plus metformin (Bristol Myers Squibb), and Vildagliptin plus metformin (Eucreas; Novartis).

The one or more antidiabetic compounds administered in combination with the GK activators of the present invention may also optionally be selected from the group consisting of protein tyrosine phosphatase inhibitors, glutamine-fructose-6-phosphate amidotransferase inhibitors, glucose-6-phosphatase inhibitors, fructose-1,6-bisphosphatase inhibitors, glycogen phosphorylase inhibitors, glucagon receptor antagonists, phosphoenolpyruvate carboxykinase inhibitors, pyruvate dehydrogenase kinase inhibitors, alpha-glucosidase inhibitors, inhibitors of gastric emptying, glucokinase activators, GLP-1 receptor agonists, GLP-2 receptor agonists, UCP modulators, RXR modulators, GSK-3 inhibitors, PPAR modulators, metformin, insulin, and U2-adrenergic antagonists.

The one or more antidiabetic compounds administered in combination with the GK activators of the present invention may also optionally be selected from the group consisting of GSK-3 inhibitors, retinoid X receptor agonists, Beta-3 AR agonists, UCP modulators, antidiabetic thiazolidinediones, non-glitazone type PPAR gamma agonists, dual PPAR gamma/PPAR alpha agonists, antidiabetic vanadium containing compounds and biguanides.

The one or more antidiabetic compounds administered in combination with the GK activators of the present invention may also optionally be thiazolidinediones selected from the group consisting of (S)-((3,4-dihydro-2-(phenyl-methyl)-2H-1-benzopyran-6-yl)methyl-thiazolidine-2,4-dione, 5-{[4-(3-(5-methyl-2-phenyl-4-oxazolyl)-1-oxo-propyl)-phenyl]-methyl}-thiazolidine-2,4-dione, 5-{[4-(1-methyl-cyclohexyl)methoxy)-phenyl]methyl}-thiazolidine-2,4-dione, 5-{[4-(2-(1-indolyl)ethoxy)phenyl]methyl}-thiazolidine-2,4-dione, 5-{4-[2-(5-methyl-2-phenyl-4-oxazoly)-ethoxy)] benzyl}-thiazolidine-2,4-dione, 5-(2-naphthylsulfonyl)-thiazolidine-2,4-dione, bis{4-[(2,4-dioxo-5-thiazolidinyl)-methyl]phenyl}methane, 5-{4-[2-(5-methyl-2-phenyl-4-oxazolyl)-2-hydroxyethoxy]-benzyl}-1-thiazolidine-2,4-dione, 5-[4-(1-phenyl-1-cyclopropanecarbonylamino)-benzyl]-thiazolidine-2,4-dione, 5-{[4-(2-(2,3-dihydroindol-1-yl)ethoxy)phenylmethyl]-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione, 5-{[4-(2-(5-ethyl-2-pyridyl)ethoxy)phenyl]-methyl}-thiazolidine-2,4-dione, 5-{[4-((3,4-dihydro-6-hydroxy-2,5,7,8-tetramethyl-2H-1-benzopyran-2-yl)methoxy)-phenyl]-methyl)-thiazolidine-2,4-dione, 5-[6-(2-fluoro-benzyloxy)-naphthalen-2-ylmethyl]-thiazolidine-2,4-dione, 5-([2-(2-naphthyl)-benzoxazol-5-yl]-methyl}thiazolidine-2,4-dione and 5-(2,4-dioxothiazolidin-5-ylmethyl)-2-methoxy-N-(4-trifluoromethyl-benzyl) benzamide, including any pharmaceutically acceptable salts thereof.

In one variation, the one or more antidiabetic compounds administered in combination with the GK activators of the present invention includes metformin. In one particular variation, the metformin in this combination comprises one or more pharmaceutically acceptable salts thereof. In another particular variation, the metformin in this combination comprises a metformin HCl salt. In still another particular variation, the metformin in this combination is administered in a daily dose of between 125 and 2550 mg. In yet another variation, the metformin in this combination is administered in a daily dose of between 250 and 2550 mg.

In another variation, the one or more antidiabetic compounds administered in combination with the GK activators of the present invention includes one or more sulphonyl urea derivatives.

The one or more antidiabetic compounds administered in combination with the GK activators of the present invention may also optionally be selected from the group consisting of glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof. In one variation, the one or more antidiabetic compounds administered in combination with the GK activators of the present invention includes glimepiride.

The one or more antidiabetic compounds administered in combination with the GK activators of the present invention may also optionally be selected from the group consisting of incretin hormones or mimics thereof, beta-cell imidazoline receptor antagonists, and short-acting insulin secretagogues.

In another variation, the one or more antidiabetic compounds administered in combination with the GK activators of the present invention includes insulin.

The one or more antidiabetic compounds administered in combination with the GK activators of the present invention may also optionally be one or more GLP-1 agonists including, for example, extendatide.

The one or more antidiabetic compounds administered in combination with the GK activators of the present invention may also optionally be one or more GLP-2 agonists including, for example, human recombinant GLP-2.

The one or more antidiabetic compounds administered in combination with the GK activators of the present invention may also optionally be one or more antidiabetic D-phenylalanine derivatives.

The one or more antidiabetic compounds administered in combination with the GK activators of the present invention may also optionally be selected from the group consisting of repaglinide, mitiglinide, and nateglinide, including any pharmaceutically acceptable salts thereof. In one variation, the one or more antidiabetic compounds administered in combination with the GK activators of the present invention includes mitiglinide calcium salt hydrate.

The one or more antidiabetic compounds administered in combination with the GK activators of the present invention may also optionally be one or more alpha-Glucosidase inhibitors.

The one or more antidiabetic compounds administered in combination with the GK activators of the present invention may also optionally be selected from the group consisting of acarbose, voglibose and miglitol, including any pharmaceutically acceptable salts thereof. In one variation, the one or more antidiabetic compounds administered in combination with the GK activators of the present invention includes voglibose. In another variation, the voglibose in this combination is administered in a daily dose of between 0.1 and 1 mg.

The one or more antidiabetic compounds administered in combination with the GK activators of the present invention may also optionally be rosiglitazone, including any pharmaceutically acceptable salts thereof. In one variation, the rosiglitazone in this combination comprises a rosiglitazone maleate salt.

The one or more antidiabetic compounds administered in combination with the GK activators of the present invention may also optionally be tesaglitazar, muraglitazar or naveglitazar, including any pharmaceutically acceptable salts thereof.

The one or more antidiabetic compounds administered in combination with the GK activators of the present invention may also optionally be pioglitazone, including any pharmaceutically acceptable salts thereof. In one variation, the pioglitazone in this combination comprises a pioglitazone HCl salt. In another variation, the pioglitazone in this combination is administered in a daily dose of between 7.5 and 60 mg. In still another variation, the pioglitazone in this combination is administered in a daily dose of between 15 and 45 mg.

The one or more antidiabetic compounds administered in combination with the GK activators of the present invention may also optionally comprise metformin and pioglitazone. In one variation, the pioglitazone in this combination comprises one or more pharmaceutically acceptable salts thereof. In another variation, the pioglitazone in this combination comprises a pioglitazone HCl salt. In still another variation, the pioglitazone in this combination is administered in a daily dose of between 7.5 and 60 mg. In yet another variation, the pioglitazone in this combination is administered in a daily dose of between 15 and 45 mg. In another variation of each of the above variations, the metformin in this combination comprises one or more pharmaceutically acceptable salts thereof. In one particular variation, the metformin in this combination comprises a metformin HCl salt. In another particular variation, the metformin in this combination is administered in a daily dose of between 125 and 2550 mg. In still another variation, the metformin in this combination is administered in a daily dose of between 250 and 2550 mg.

In the case of combination therapy with compounds of the present invention, the other antidiabetic compound may be administered (e.g., route and dosage form) in a manner known per se for such compound. Compounds of the present invention and the other antidiabetic compound may be administered sequentially (i.e., at separate times) or at the same time, either one after the other separately in two separate dose forms or in one combined, single dose form. In one particular embodiment, the other antidiabetic compound is administered with compounds of the present invention as a single, combined dosage form. The dose of the antidiabetic compound may be selected from the range known to be clinically employed for such compound. Any of the therapeutic compounds of diabetic complications, antihyperlipemic compounds or antiobestic compounds can be used in combination with compounds of the present invention in the same manner as the above antidiabetic compounds.

EXAMPLES

Preparation of Glucokinase Activators

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| μL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |

| | |
|---|---|
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

General synthetic routes for producing compounds of the present invention are shown below.

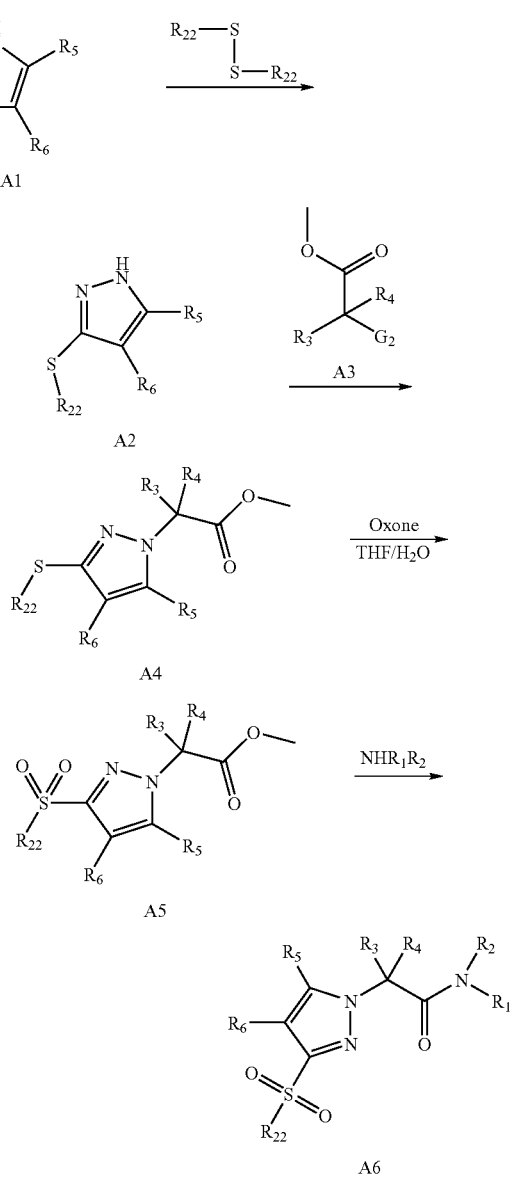

Referring to Scheme A, a halo-pyrazole (A1, wherein G$_1$ is a leaving group (e.g., halo such as bromo)) and a disulfide are treated with NiBr and Zn in the presence of 2,2'-bipyridine to give intermediates A2. Subsequent treatment of A2 with base and reagent A3 (wherein G$_2$ is a leaving group (e.g., halo such as bromo)) affords intermediates A4. Oxidation of the sulfur functionality of A4 with Oxone® gives analogs A5 which are then treated with various amine containing molecules to afford amides A6.

Scheme B

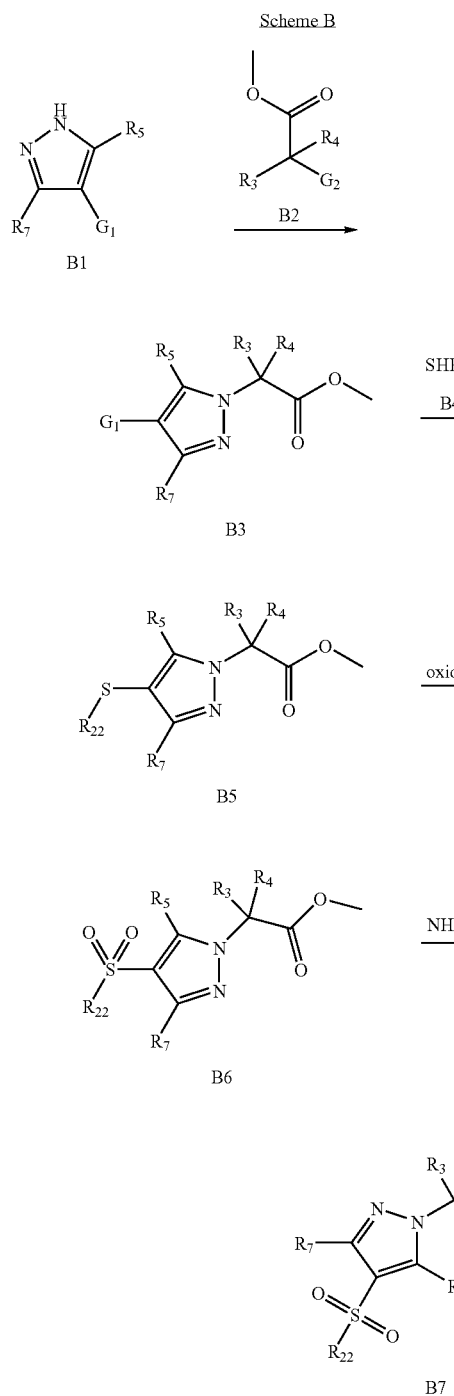

Scheme C

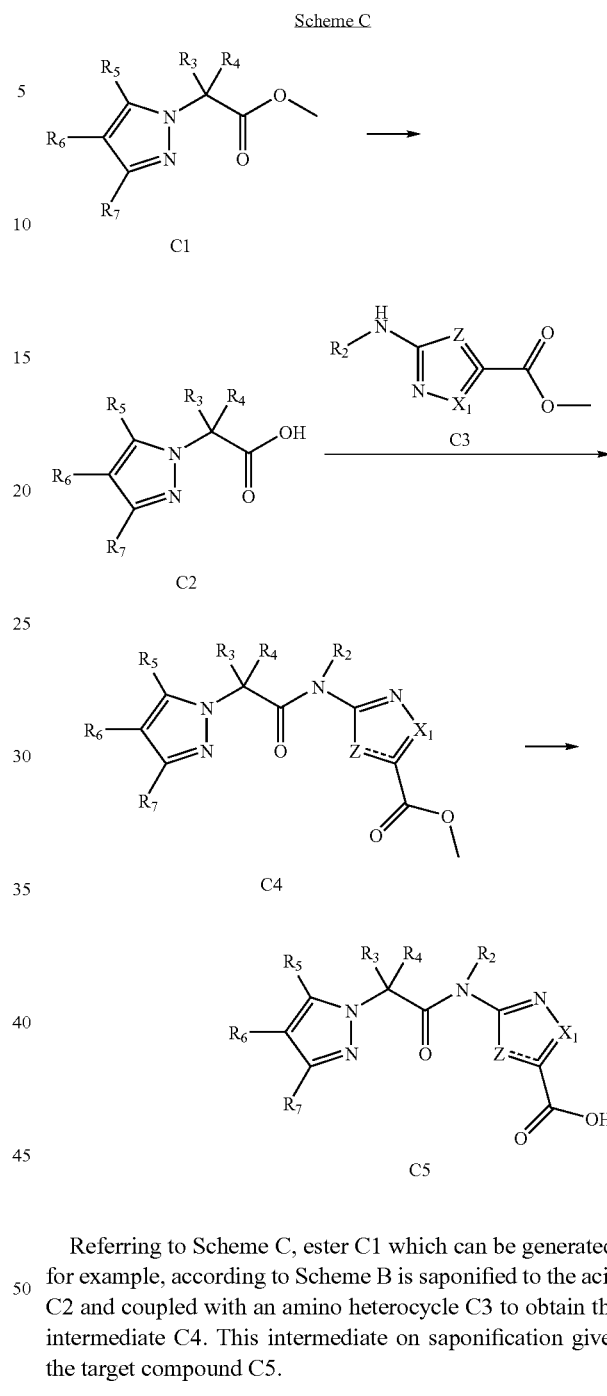

Referring to Scheme C, ester C1 which can be generated, for example, according to Scheme B is saponified to the acid C2 and coupled with an amino heterocycle C3 to obtain the intermediate C4. This intermediate on saponification gives the target compound C5.

Referring to Scheme B, a halo-pyrazole (B1, wherein $G_1$ is a leaving group (e.g., halo such as bromo)) is treated with base and reagent B2 (wherein $G_2$ is a leaving group (e.g., halo such as bromo)) to afford intermediates B3. Subsequent treatment of this material with various mercaptans in the presence of tris(dibenzylacetone)dipalladium and 4,5-bis(diphenylphosphino)-9,9-dimethylxanthene affords B5. Oxidation of the sulfur functionality of B5 gives analogs B6 which are then treated with various amine containing molecules to give amides B7.

Scheme D

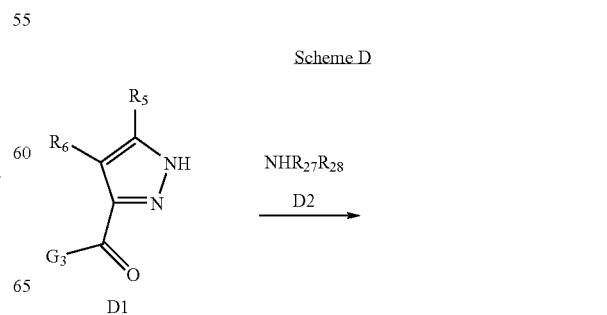

177
-continued

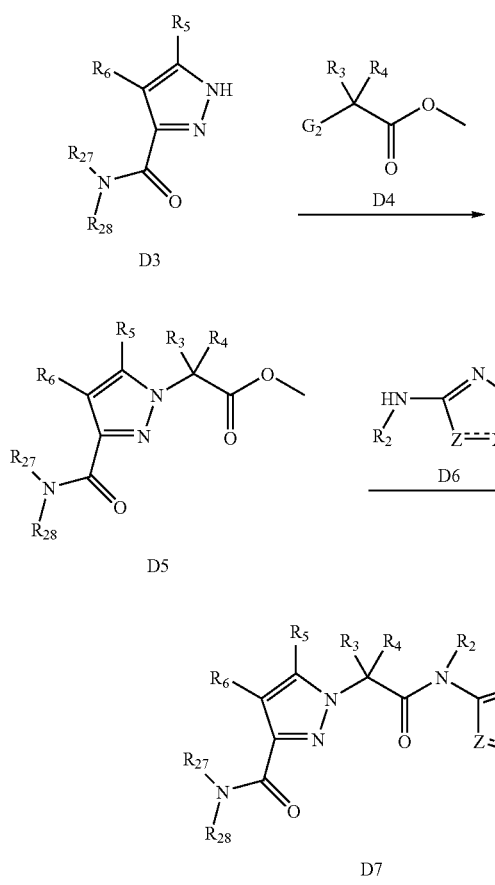

178
-continued

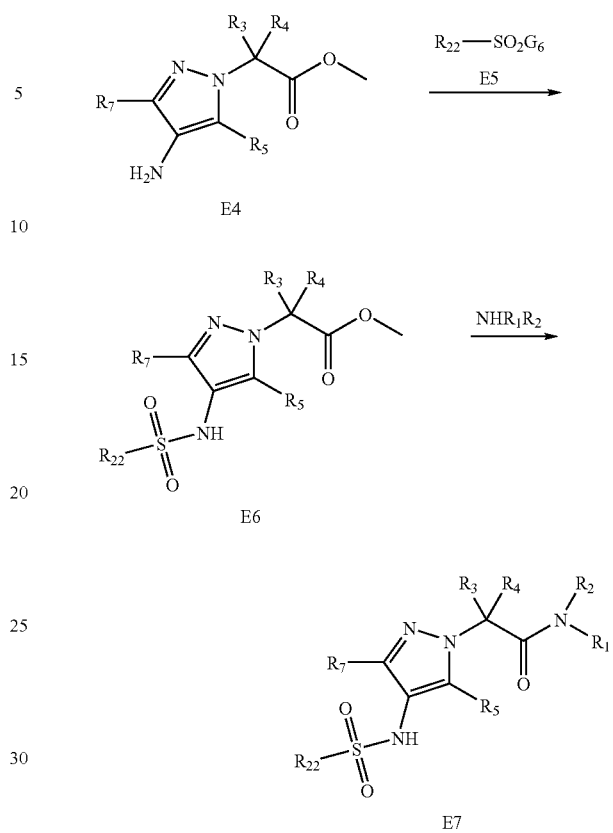

Referring to Scheme D, intermediate D3 can be obtained by treatment of a substituted pyrazole-3-carbonyl chloride (D1, wherein $G_3$ is a leaving group (e.g., halo such as chloro)) with an amine D2 in the presence of a base. Alkylation followed by coupling with the amino heterocycle D6 can be done using an analogous procedure as in Scheme A to obtain the target compound D7.

Referring to Scheme E, a nitro pyrazole E1 is treated with a base and reagent E2 (wherein $G_2$ is a leaving group (e.g., halo such as bromo)) to afford intermediate E3. Reduction of the nitro group followed by treatment with an electrophile E5 (wherein $G_6$ is a leaving group (e.g., halo such as chloro)) in the presence of a base gives the intermediate E6. Coupling with an amine gives the target compound E7.

Scheme E

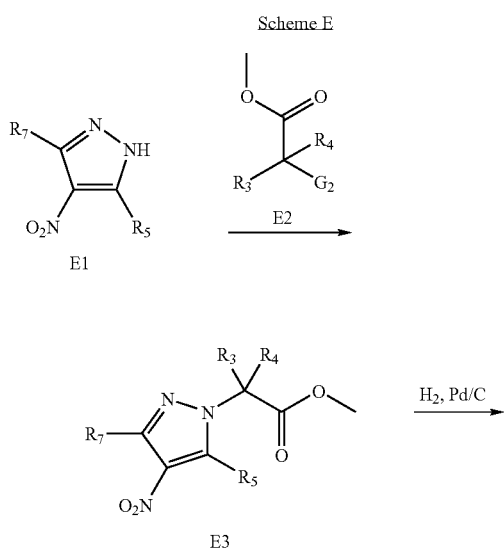

Scheme F

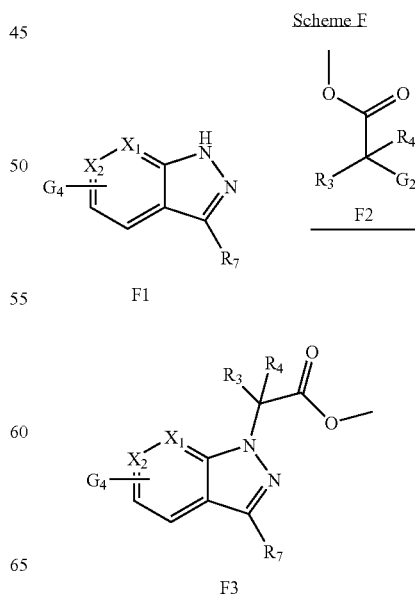

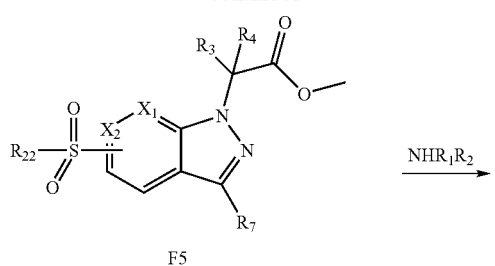

F5

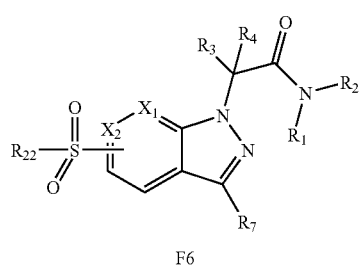

F6

Referring to Scheme F, a substituted indazole (F1, wherein $G_4$ is a leaving group (e.g., halo such as bromo)) is treated with reagent F2 (wherein $G_2$ is a leaving group (e.g., halo such as bromo)) in the presence of a base to obtain a mixture of N-1 and N-2 alkylated products F3 which can be separated by flash column chromatography. Introduction of the sulfone group can be achieved by coupling in the presence of Pd or Cu to obtain intermediate F5, which is then treated with an amine to obtain the desired target F6.

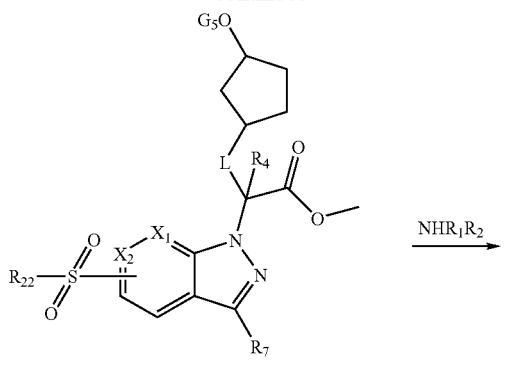

G5

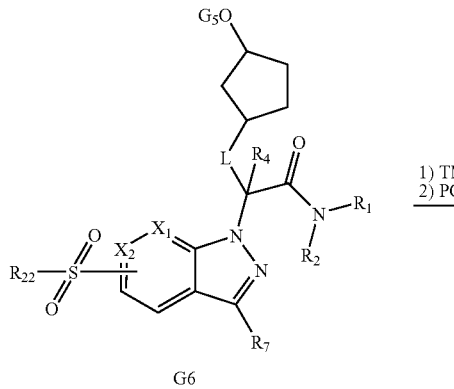

G6

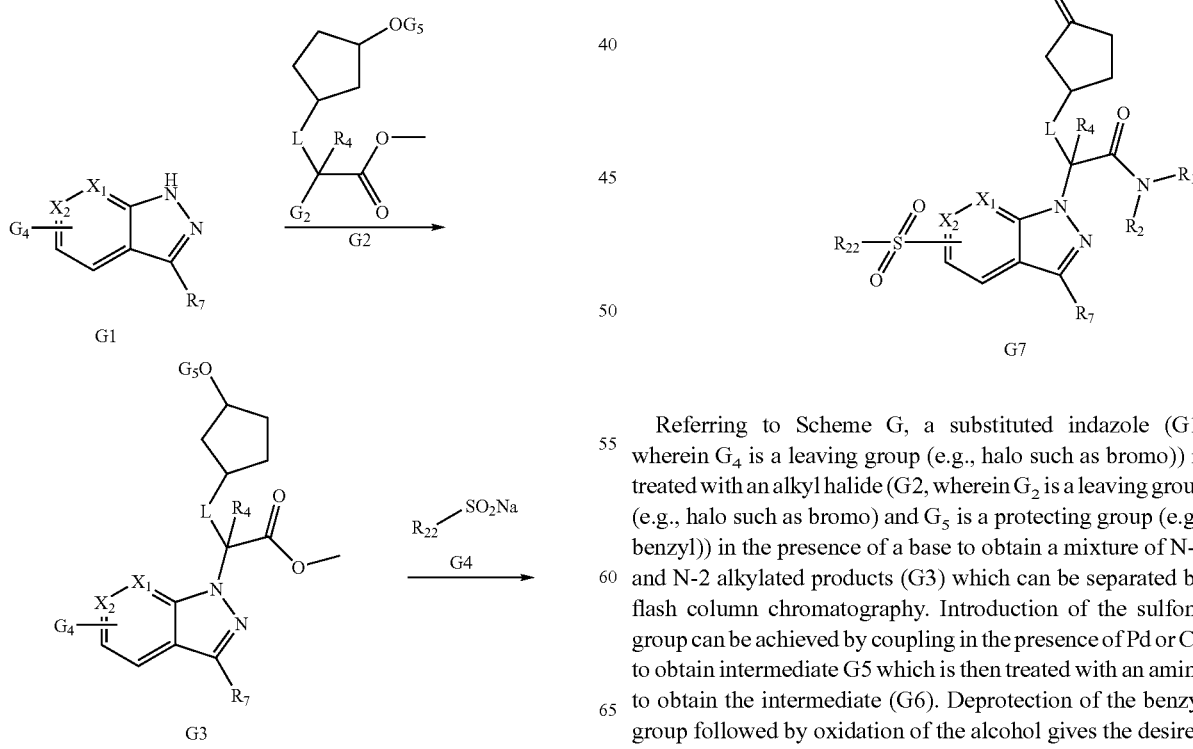

Referring to Scheme G, a substituted indazole (G1, wherein $G_4$ is a leaving group (e.g., halo such as bromo)) is treated with an alkyl halide (G2, wherein $G_2$ is a leaving group (e.g., halo such as bromo) and $G_5$ is a protecting group (e.g., benzyl)) in the presence of a base to obtain a mixture of N-1 and N-2 alkylated products (G3) which can be separated by flash column chromatography. Introduction of the sulfone group can be achieved by coupling in the presence of Pd or Cu to obtain intermediate G5 which is then treated with an amine to obtain the intermediate (G6). Deprotection of the benzyl group followed by oxidation of the alcohol gives the desired target (G7).

Scheme H
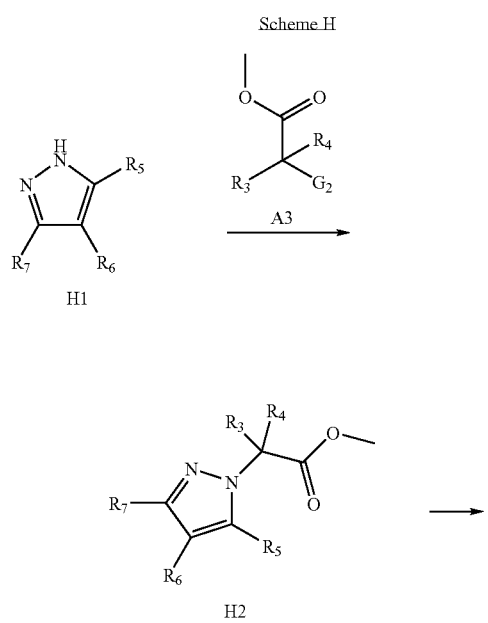
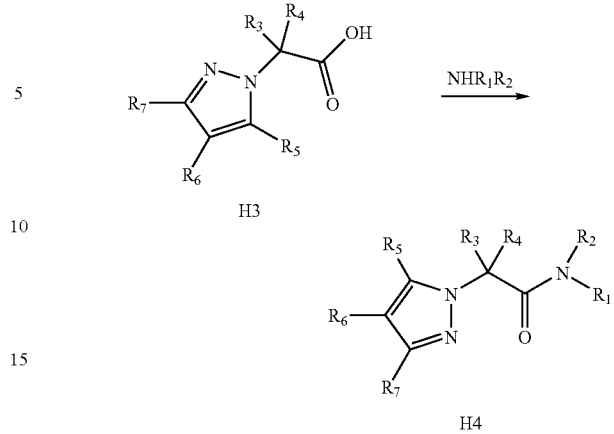
Referring to Scheme H, a substituted pyrazole H1, is treated with reagent A3 (wherein $G_2$ is a leaving group (e.g., halo such as bromo)) in the presence of a base to obtain a mixture of alkylated products H2 which can be separated by column chromatography. Hydrolysis of the ester to H3, followed by coupling with an amine gives the target compound H4
Scheme I
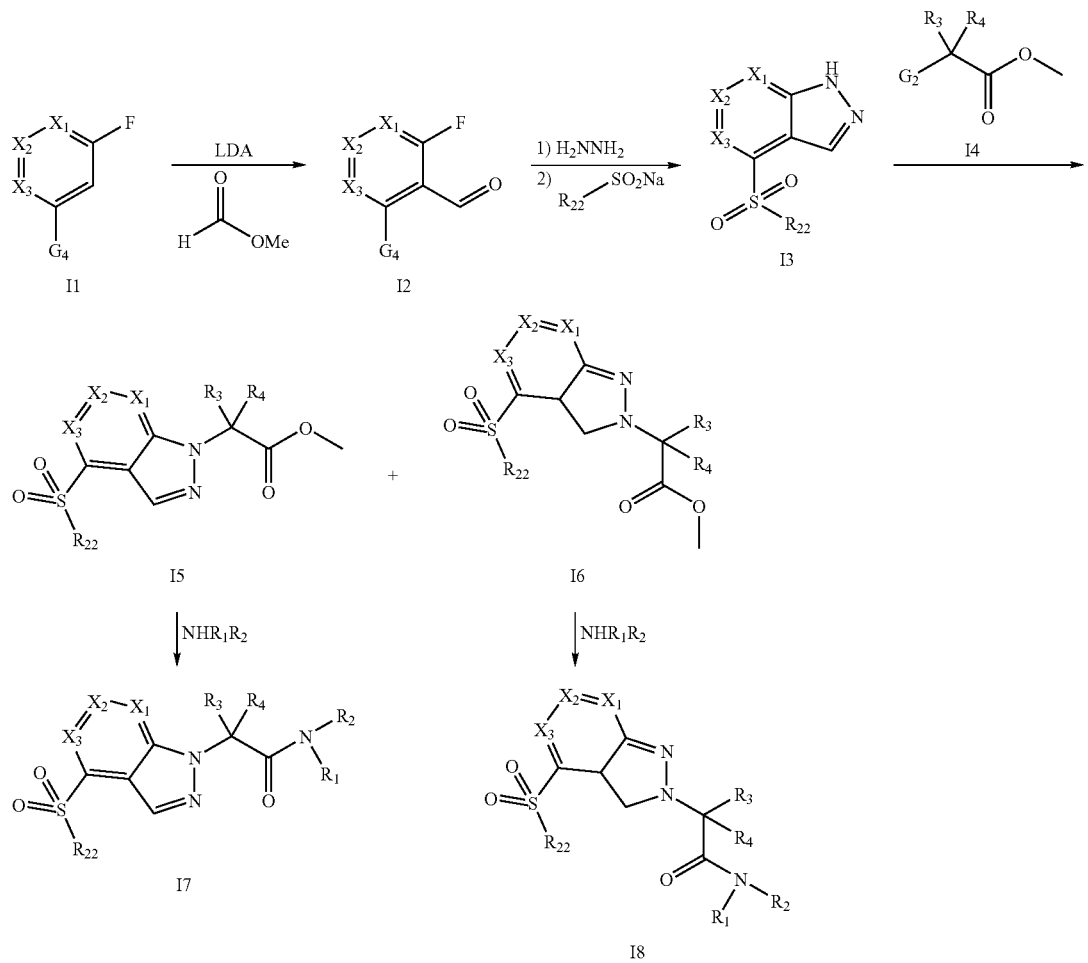

Referring to Scheme I, ortho lithiation of I1, wherein $G_4$ is a leaving group (e.g., halo such as fluoro), followed by introduction of the aldehyde ortho to the fluoride gives I2. Treatment with hydrazine gives the hydrazone which cyclizes to an intermediate indazole on heating. Introduction of the sulfone group can be achieved either by displacement with a sulfinate or by coupling in the presence of Pd or Cu to obtain intermediate I3. The indazole I3 is treated with reagent I4 (wherein $G_2$ is a leaving group (e.g., halo such as bromo)) in the presence of a base to obtain a mixture of N-1 and N-2 alkylated products 15 and 16, which can be separated by flash column chromatography. Treatment of 15 and/or 16 with an amine gives the desired targets 17 and 18, respectively.

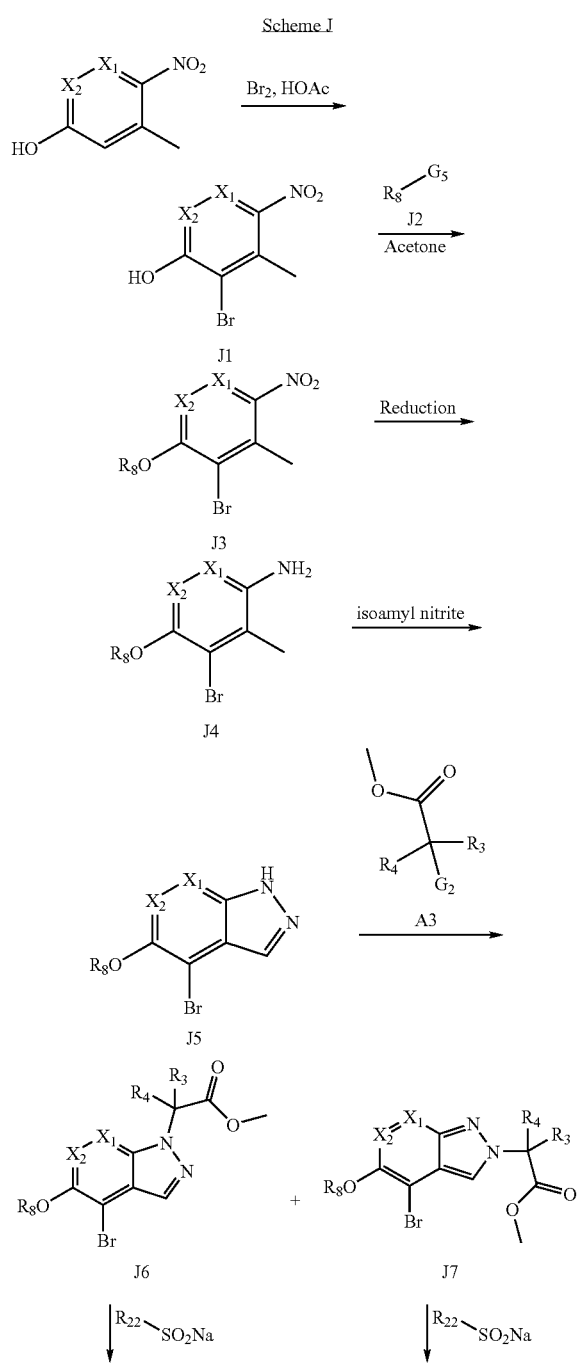

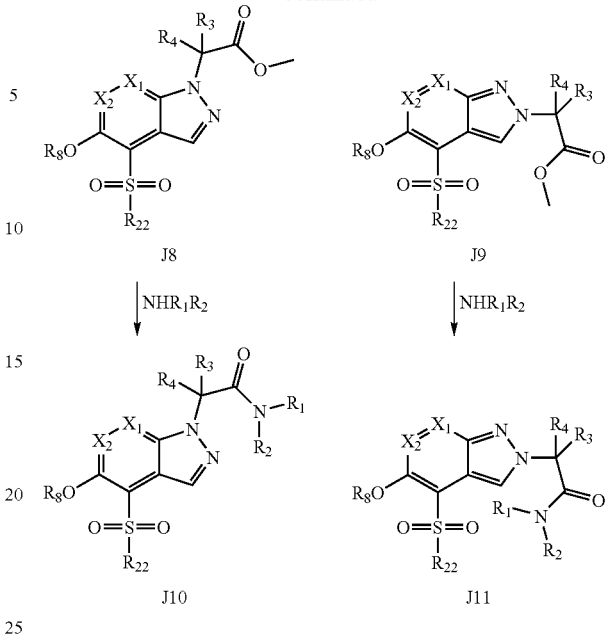

Referring to Scheme J, bromination of 3-methyl-4-nitrophenol gives a mixture of regioisomers which can be separated by column chromatography. Treatment of J1 with an alkyl halide (J2, wherein G5 is a leaving group (e.g., halo such as bromine)) in the presence of a base gives J3. Reduction of the nitro group yields J4 which can then be treated with isoamyl nitrite in the presence of a base to obtain the substituted indazole J5. The substituted indazole J5 is treated with reagent A3 (wherein $G_2$ is a leaving group (e.g., halo such as bromo)) in the presence of a base to obtain a mixture of N-1 and N-2 alkylated products J6 and J7, which can be separated by flash column chromatography. Introduction of a sulfone group on J6 and/or J7 can be achieved by coupling in the presence of Pd or Cu to obtain intermediates J8 and J9, respectively. J8 and/or J9 can then be treated with an amine to obtain J10 and J11, respectively.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10µ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction schemes are set forth herein.

Examples of Glucokinase Activators

The present invention is further exemplified, but not limited by, the following examples that describe the synthesis of particular compounds according to the invention.

Compound 1: 2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide

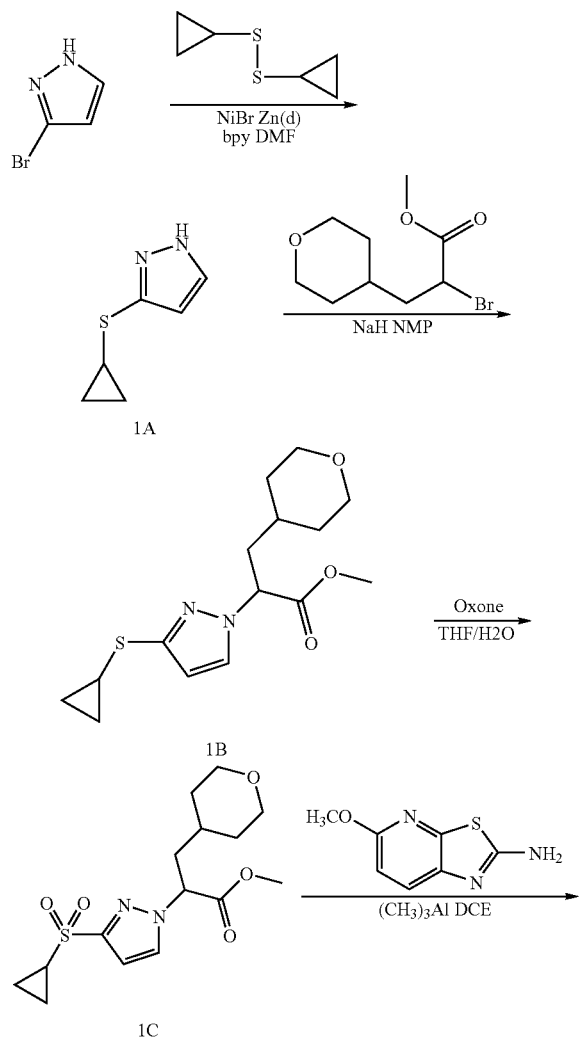

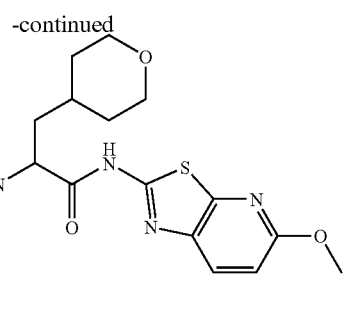

3-bromo-1H-pyrazole (1.0 g, 6.8 mmole), NiBr (0.148 g, 0.68 mmole), 2,2'-bipyridine (0.106 g, 0.68 mmole), Zinc dust (0.993 g, 13.6 mmole) and 1,2-dicyclopropyldisulfane (0.993 g, 6.8 mmole) were added to a solution of DMF (20 mL) and the mixture was heated under $N_2$ for 18 h at 80° C. The solvent was removed from the crude reaction mixture under vacuum and the orange gum was treated with MeOH. The resulting ppt was filtered and discarded. Purification of the filtrate with preparative scale HPLC afforded compound 1A as light brown oil (367 mg). [M+H] calc'd for $C_6H_9N_2S$, 141.04; found 141.0. $^1$H NMR (400 MHz, CHLOROFORM-d) δ ppm 0.73 (q, J=5.05 Hz, 2 H) 1.02-1.17 (m, 2 H) 2.26 (ddd, J=7.58, 3.66, 3.41 Hz, 1 H) 6.48 (br. s., 1 H) 7.82 (br. s., 1 H).

3-(cyclopropylthio)-1H-pyrazole (1A) (0.083 g, 0.6 mmole) was dissolved in NMP (2 mL) and the solution was chilled to 0° C. NaH (0.060 g, 1.8 mmole) was added and when the reaction subsided methyl 2-bromo-3-(tetrahydro-2H-pyran-4-yl)propanoate (0.060 g, 1.8 mmole) was introduced, and the reaction was heated at 80° C. for 1 h. The reaction was cooled and quenched with a small volume of MeOH and the crude mixture was purified using preparative scale HPLC. Compound 1B as well as a small amount of the carboxylic acid of 1B were collected. Removal of the solvent and treatment of the acid with $TMSCH_2N_2$ followed by combination with 1B afforded title compound as oil (81 mg). [M+H] calc'd for $C_{15}H_{23}N_2O_3S$ (1B ester), 311.14; found 311.0; [M+H] calc'd for $C_{14}H_{21}N_2O_3S$ (1B acid), 297.12; found 297.0.

Compound 1B used directly from the preceding step was treated with Oxone® (0.147 g, 0.24 mmole) in a 1:1 solution of $THF/H_2O$ (10 mL). After oxidation was judged complete the solvent was removed and the residue was portioned between EtOAc and $H_2O$. The organic layer was separated, dried and concentrated to yield crude compound 1C as oil. This material was purified using preparative scale HPLC and used directly in the next step, [M+H] calc'd for $C_{15}H_{23}N_2O_5S$, 343.12; found 343.3.

5-Methoxythiazolo[5,4-b]pyridin-2-amine (0.048 g, 0.26 mmole) was added to a microwave vial followed by DCE (2 mL). The reaction mixture was cooled to 0° C. under a $N_2$ atmosphere. Trimethyl aluminum (2M in hexanes) (0.13 mL, 0.26 mmole) was added and when the reaction subsided the cooling bath was removed, the solution was then stirred at RT for 15 min. To this was added a solution of methyl 2-(3-(cyclopropylsulfonyl)-1H-pyrazol-1-yl)-3-(tetrahydro-2H-pyran-4-yl)propanoate 1C (0.015 g, 0.04 mmole) in DCE (2 mL) and the reaction mixture was heated in a microwave at 110° C. for 1 h. The reaction was then quenched with 1N HCl and extracted 2× with DCM. The organic layers were pooled, dried over $Na_2SO_4$; the solvent was removed and the crude residue was purified by preparative scale HPLC to afford compound 1 (46 mg). [M+H] calc'd for $C_{21}H_{26}N_5O_5S_2$, 492.13; found 492.0. $^1$H NMR (400 MHz, MeOD) δ ppm 1.07 (dd, J=7.96, 2.15 Hz, 2H) 1.18-1.42 (m, 6 H) 1.52 (d, J=9.35 Hz, 1H) 1.74 (d, J=2.02 Hz, 1H) 2.14 (t, J=6.32 Hz, 1H) 2.32 (t, J=10.48 Hz, 1H) 2.61-2.80 (m, 1H) 3.29 (m, 1H, under MeOD signal) 3.79-3.98 (m, 5H) 5.50 (ddd, J=10.80, 5.68, 5.49 Hz, 1H) 6.81-6.90 (m, 2H) 7.94 (d, J=8.84 Hz, 1H) 8.10 (d, J=2.53 Hz, 1H)

Compounds 2 and 3: (S)-2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide and (R)-2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide

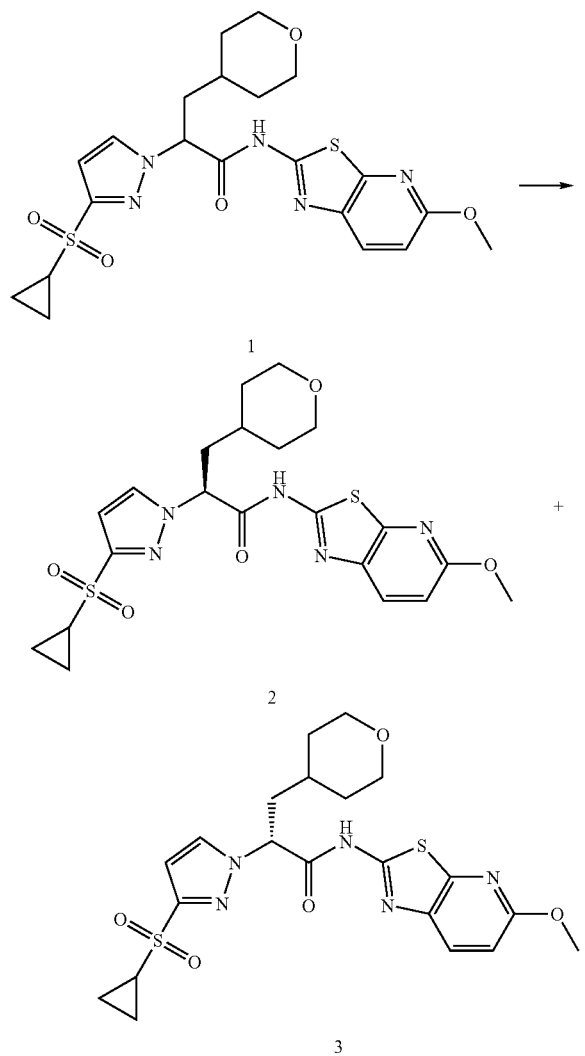

Compound 1 was subjected to chiral separation on a Berger SFC instrument. For this particular compound, it was found that using Chiralpak AD-H media eluting with 16% MeOH to afford Compounds 2 and 3 was optimal.

Compound 2: [M+H] calc'd for $C_{21}H_{26}N_5O_5S_2$, 492.13; found 492.0. $^1$H NMR (400 MHz, MeOD) δ ppm 1.07 (dd, J=7.96, 2.15 Hz, 2H) 1.18-1.42 (m, 6H) 1.52 (d, J=9.35 Hz, 1H) 1.74 (d, J=2.02 Hz, 1H) 2.14 (t, J=6.32 Hz, 1H) 2.32 (t, J=10.48 Hz, 1H) 2.61-2.80 (m, 1H) 3.29 (m, 1H, under MeOD signal) 3.79-3.98 (m, 5H) 5.50 (ddd, J=10.80, 5.68, 5.49 Hz, 1H) 6.81-6.90 (m, 2H) 7.94 (d, J=8.84 Hz, 1H) 8.10 (d, J=2.53 Hz, 1H)

Compound 3: [M+H] calc'd for $C_{21}H_{26}N_5O_5S_2$, 492.13; found 492.0. $^1$H NMR (400 MHz, MeOD) δ ppm 1.07 (dd, J=7.96, 2.15 Hz, 2H) 1.18-1.42 (m, 6H) 1.52 (d, J=9.35 Hz, 1H) 1.74 (d, J=2.02 Hz, 1H) 2.14 (t, J=6.32 Hz, 1H) 2.32 (t, J=10.48 Hz, 1H) 2.61-2.80 (m, 1H) 3.29 (m, 1H, under MeOD signal) 3.79-3.98 (m, 5H) 5.50 (ddd, J=10.80, 5.68, 5.49 Hz, 1H) 6.81-6.90 (m, 2H) 7.94 (d, J=8.84 Hz, 1H) 8.10 (d, J=2.53 Hz, 1H)

Compound 4: N-(5-chlorothiazol-2-yl)-2-(4-(cyclopropylsulfonyl)-1H-pyrazol-1-yl)-3-(tetrahydro-2H-pyran-4-yl)propanamide

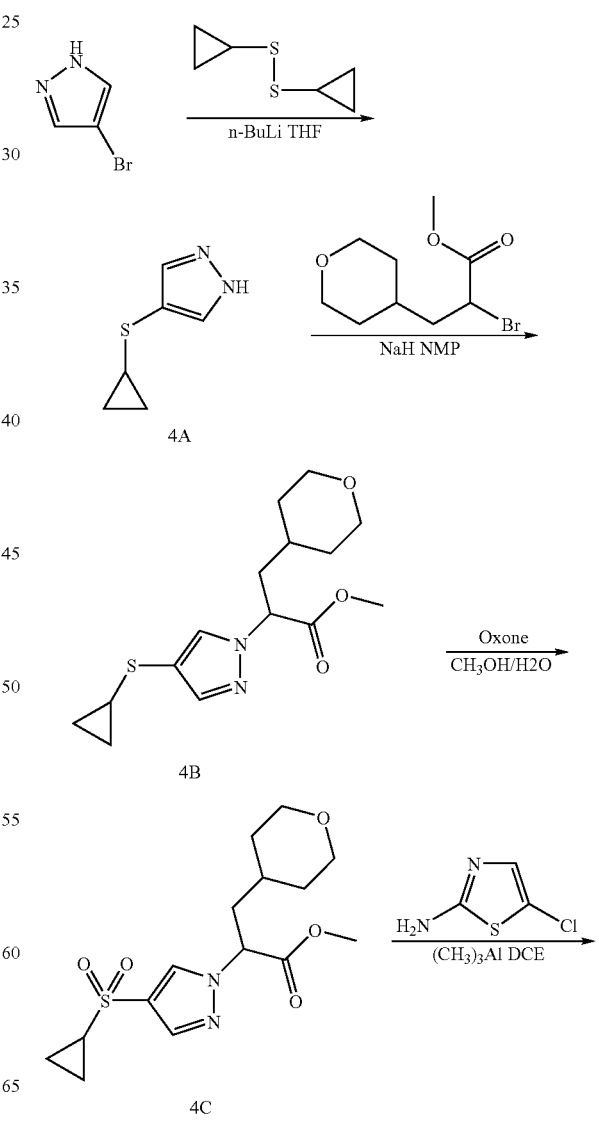

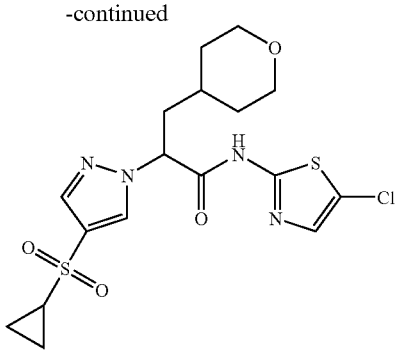

4-bromo-1H-pyrazole (4.0 g, 26.9 mmole) was dissolved in THF (100 mL) and chilled to 0° C. 1.6 M n-BuLi in THF was added and the reaction mixture was stirred for 1 h at RT. The reaction was then cooled to 0° C. and 1,2-dicyclopropyldisulfane (3.9 g, 26.9 mmole) was added; the reaction was stirred for 1 h at 0° C. and quenched with sat NH$_4$Cl and extracted with EtOAc. The crude product was obtained as an oil and used directly in the next step. [M+H] calc'd for $C_6H_9N_2S$, 141.04; found 141.9.

4-(cyclopropylthio)-1H-pyrazole (4A) (1.0 g, 7.14 mmole) was dissolved in NMP (5 mL) and the solution was chilled to 0° C. NaH (0.263 g, 7.9 mmole) was added and when the reaction subsided methyl 2-bromo-3-(tetrahydro-2H-pyran-4-yl)propanoate (1.1 g, 7.9 mmole) was introduced, and the reaction was heated at 80° C. for 1 h. The reaction was cooled and quenched with a small volume of MeOH and the crude mixture was purified using preparative scale HPLC. Compound 4B as well as a small amount of the carboxylic acid of 4B were collected. Removal of the solvent and treatment of the acid with TMSCH$_2$N$_2$ followed by combination with 4B afforded title compound as oil (0.68 g). [M+H] calc'd for $C_{15}H_{23}N_2O_3S$ (4B ester), 311.14; found 311.2; [M+H] calc'd for $C_{14}H_{21}N_2O_3S$ (4B acid), 297.12; found 297.1.

Compound 4B (0.68 g, 1.9 mmole) was treated with Oxone® (2.4 g, 3.8 mmole) in a 1:1 solution of MeOH/H$_2$O (20 mL). After oxidation was judged complete the solvent was removed and the residue was portioned between EtOAc and H$_2$O. The organic layer was separated, dried and concentrated to yield crude compound 4C as oil (0.729 g). This material was purified using preparative scale HPLC and used directly in the next step, [M+H] calc'd for $C_{15}H_{23}N_2O_5S$, 343.12; found 343.0.

5-chlorothiazol-2-amine (0.519 g, 3.03 mmole) was added to a microwave vial followed by DCE (3 mL). The reaction mixture was cooled to 0° C. under a N$_2$ atmosphere. Trimethyl aluminum (2M in hexanes) (2.6 mmole) was added and when the reaction subsided the cooling bath was removed, the solution was then stirred at RT for 15 min. To this was added a solution of methyl 2-(4-(cyclopropylsulfonyl)-1H-pyrazol-1-yl)-3-(tetrahydro-2H-pyran-4-yl)propanoate 4C (0.173 g, 0.51 mmole) in DCE (2 mL) and the reaction mixture was heated in a microwave at 110° C. for 1 h. The reaction was then quenched with 1N HCl and extracted 2× with DCM. The organic layers were pooled, dried over Na$_2$SO$_4$ and the solvent was removed. This crude residue was purified by preparative scale HPLC to afford compound 4 (0.21 g). [M+H] calc'd for $C_{17}H_{22}ClN_4O_4S_2$, 445.07; found 445.2. $^1$H NMR (400 MHz, CHLOROFORM-d) δ ppm 0.93-1.75 (m, 9H) 2.19 (br. s., 2H) 2.55 (br. s., 1H) 3.31 (br. s., 2H) 3.94 (br. s., 2H) 5.10 (br. s., 1H) 7.32 (s, 1H) 8.01 (d, J=9.35 Hz, 2H) 10.35 (bs, 1H)

Compound 5: N-(5-chlorothiazol-2-yl)-2-(4-(cyclopentylsulfonyl)-1H-pyrazol-1-yl)-3-(tetrahydro-2H-pyran-4-yl)propanamide

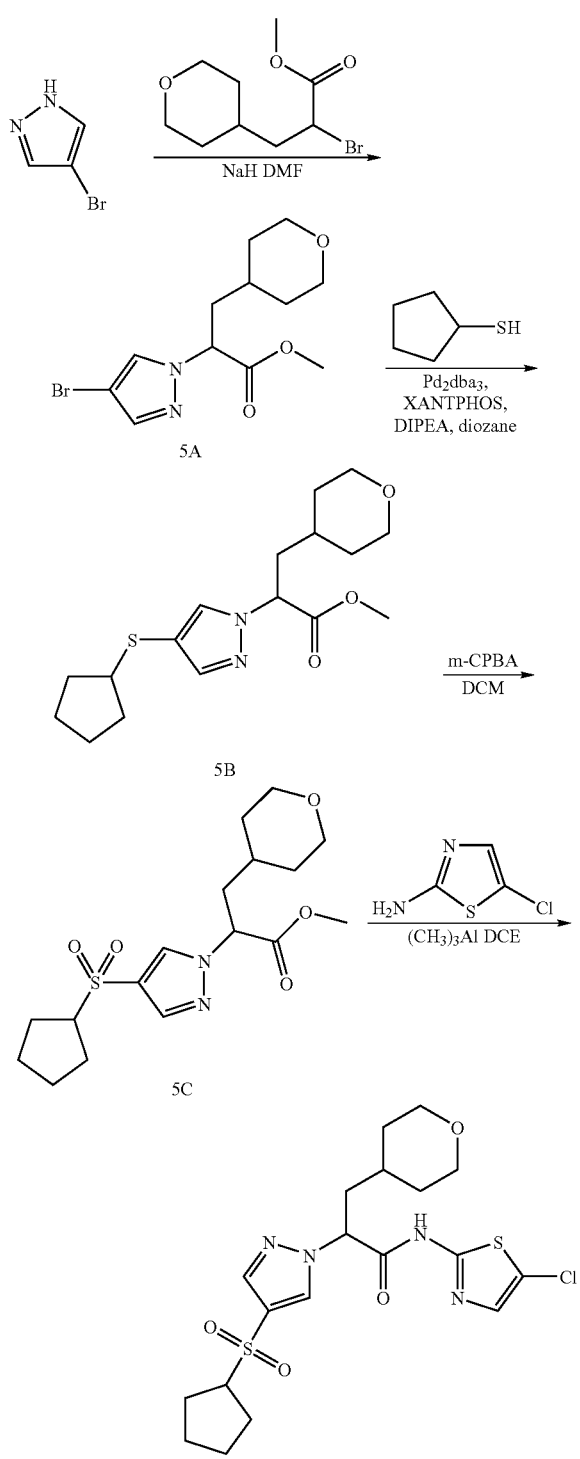

Sodium hydride (63 mg, 2.47 mmol) was suspend in DMF (5 ml), and was cooled to 0° C. A solution of 4-bromo-1H-pyrazole (300 mg, 2.06 mmole) in DMF (5 mL) was added dropwise. After stirring for 20 min at 0° C., methyl 2-bromo-3-(tetrahydro-2H-pyran-4-yl)propanoate (620 mg, 2.47 mmol) was added. The reaction mixture was stirred at room temperature for 2 hours. The reaction was quenched with sat. ammonium chloride and extracted into ethyl acetate. The organic layer was washed with water, dried over MgSO$_4$, concentrated by high vacuum to yield crude compound 5A (492 mg). [M+H] calc'd for $C_{12}H_{17}BrN_2O_3$ 318.18; found 318.

Compound 5A (492 mg, 1.56 mmol) was dissolved in dioxane (5 ml). Cyclopentylmercaptan (159 mg, 1.56 mmol) was added, followed by diisopropylethylamine (0.54 ml, 3.12 mmol) tris(dibenzylacetone)dipalladium (71 mg, 0.078 mmol) and 4,5-bis(diphenylphosphino)-9,9-dimethylxanthene (90 mg, 0.156 mmol). The reaction mixture was heated at 100° C. in sealed vial over night. After cooling to room temperature, the solution was poured to water, extracted with ethyl acetate, washed with water, dried over MgSO$_4$, concentrated by high vacuum to crude compound 5B (695 mg). [M+H] calc'd for $C_{17}H_{26}N_2O_3S$ 339.46; found 339.

Compound 5B (695 mg, 2.06 mmol) was dissolved in dichloromethane (20 ml) and cooled to 0° C. m-chloroperoxybenzoic acid (1.84 g, 8.22 mmol) was added. After stirring 3 hours at room temperature, the reaction solution was diluted with dichloromethane, washed with 1 N NaOH, water, dried over MgSO$_4$, concentrated by vacuum to afford crude compound 5C (593 mg). [M+H] calc'd for $C_{17}H_{26}N_2O_5S$ 371.46; found 371.

Compound 5 was synthesized according to the procedure described in connection with Compound 4. [M+H] calc'd for $C_{19}H_{25}FN_4O_4S_2$ 457.56.01; found 457. $^1$H NMR (400 MHz, CHLOROFORM-d) δ ppm 1.34 (m, 3H) 1.50 (m, 1H) 1.65 (m, 3H) 1.77 (m, 2H) 2.02 (m, 4H) 2.16 (m, 1H), 2.24 (m, 1H) 3.29 (m, 2H) 3.50 (m, 1H) 3.94 (t, J=16, 16 Hz, 2H) 5.13 (m, 1H) 7.08 (d, J=4 Hz, 1H) 7.98 (s, 1H) 8.06 (s, 1H)

Compound 6: Methyl 2-(3-cyclopentyl-2-(4-(cyclopropylsulfonyl)-1H-pyrazol-1-yl)propanamido)thiazole-5-carboxylate

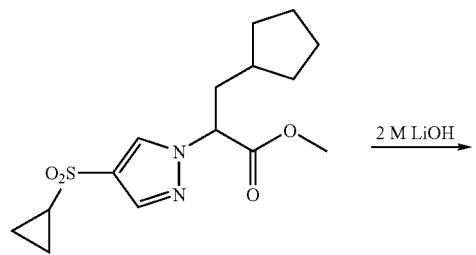

6A

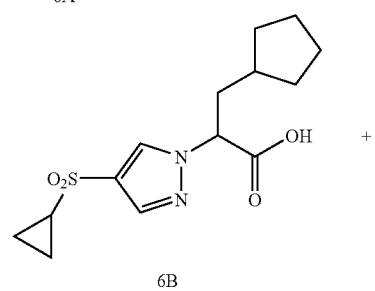

6B

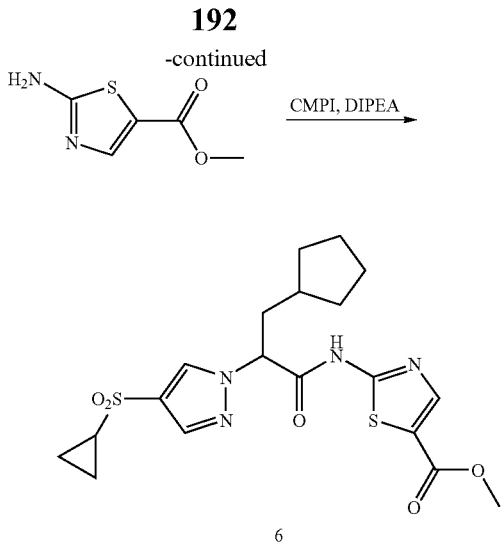

6

Compound 6A (1.663 g, 5.1 mmol), which was generated according to the procedure described in connection with Compound 1, was dissolved in dioxane (15 ml). 2 M LiOH (5.1 ml, 10.2 mmol) was added and the reaction mixture was stirred at room temperature overnight. The reaction solution was concentrated, poured to water, acidified with 20% HCl, extracted with ethyl acetate, dried over Na$_2$SO$_4$, concentrated by vacuum to crude compound 6B (1.494 g). [M+H] calc'd for $C_{14}H_{20}N_2O_4S$ 313.38; found 313.

Compound 6B (200 mg, 0.64 mmol) was dissolved in NMP (5 ml). Methyl 2-aminothioazole-5-carboxylate (184 mg, 1.282 mmol) was added, followed by 2-chloro-1-methylpyridinium iodide (360 mg, 1.41 mmol), diisopropylethylamine (0.25 ml, 1.41 mmol). The reaction mixture was heated at 90° C. in sealed vial overnight. After cooling to room temperature, the reaction solution poured to water, extracted with ethyl acetate, concentrated. Residue was purified with HPLC to yield compound 6 (85 mg). [M+H] calc'd for $C_{19}H_{24}N_4O_5S_2$ 453.55; found 453. $^1$H NMR (400 MHz, MeOD). δ ppm 1.23 (m, 6H) 1.60 (m, 6H) 1.82 (m, 1H) 2.20 (m, 1H) 2.34 (m, 1H) 2.75 (m, 1H), 3.86 (s, 3H) 5.34 (m, 1H) 7.90 (s, 1H) 8.10 (s, 1H) 8.47 (s, 1H)

Compound 7: 2-(3-cyclopentyl-2-(4-(cyclopropylsulfonyl)-1H-pyrazol-1-yl)propanamido)thiazole-5-carboxylic Acid

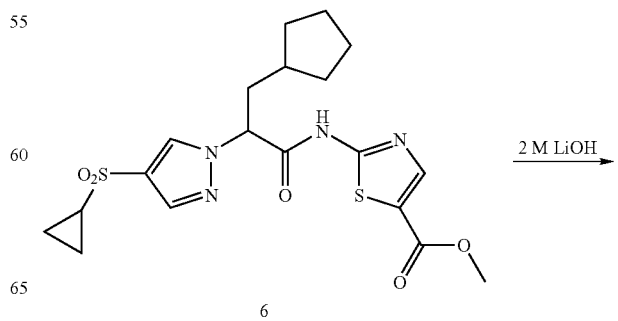

6

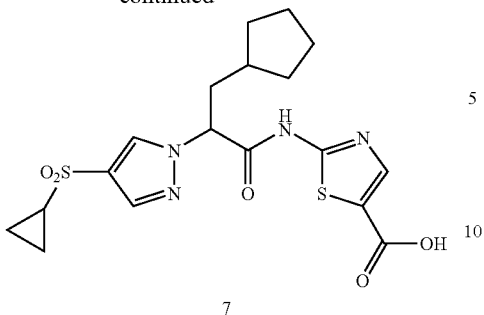

7

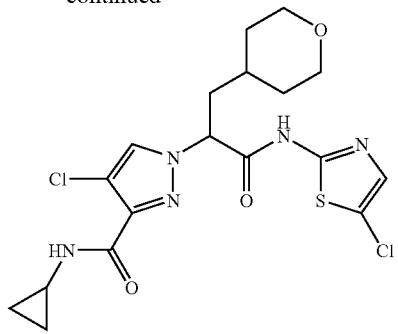

8

Compound 6 (67 mg, 0.149 mmol) was dissolved in dioxane (3 ml) and a 2 M LiOH (0.15 ml, 0.3 mmol) solution was added. After stirring at room temperature overnight, water (10 ml) was added and the reaction mixture was acidified with 20% HCl followed by extraction with ethyl acetate. The organic layer was separated, dried and concentrated. This material was purified using prep HPLC to afford compound 7 (36.3 mg). [M+H] calc'd for $C_{18}H_{22}N_4O_5S_2$ 439.52; found 439. $^1$H NMR (400 MHz, MeOD). δ ppm 1.09 (m, 3H) 1.23 (m, 3H) 1.52 (m, 2H) 1.65 (m, 4H) 1.82 (m, 1H) 2.19 (m, 1H), 2.34 (m, 1H) 2.75 (m, 1H) 5.35 (m, 1H) 7.90 (s, 1H) 8.06 (s, 1H) 8.48 (s, 1H).

Compound 8: 4-chloro-1-(1-(5-chlorothiazol-2-ylamino)-1-oxo-3-(tetrahydro-2H-pyran-4-yl)propan-2-yl)-N-cyclopropyl-1H-pyrazole-3-carboxamide

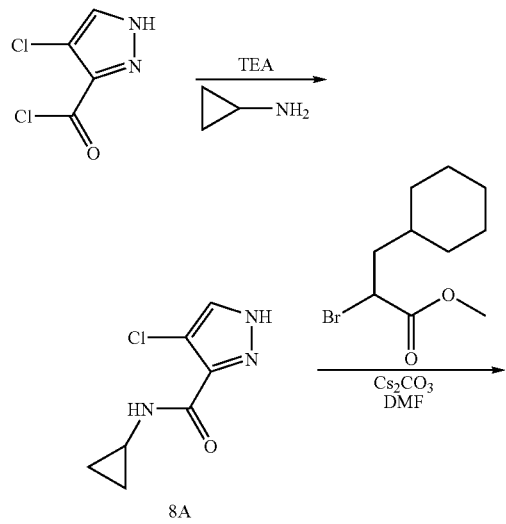

8A

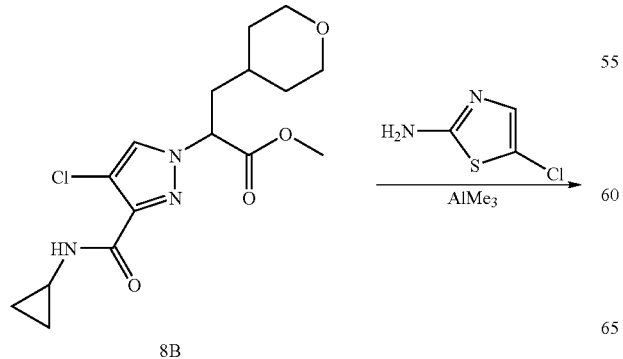

8B

To 4-chloro-1H-pyrazole-3-carbonyl chloride (0.5 g, 3.03 mmol) in dichloromethane (10 ml) at 0° C. was added TEA (0.46 ml, 3.33 mmol) followed by the dropwise addition of cyclopropylamine (0.419 ml, 6.06 mmol). The reaction mixture was allowed to warm to room temperature and stirred overnight. The reaction mixture was concentrated in vacuo, extracted into ethyl acetate and washed with sat. bicarbonate and brine solution. The organic layer was dried over $Na_2SO_4$, concentrated to obtain 0.55 g of 8A as an oil and used as is in the next step. [M+H] calc'd for $C_7H_8ClN_3O$, 186.61; found 186.6

To compound 8A (0.20 g, 1.08 mmol) in DMF (6 ml) was added $Cs_2CO_3$ (0.373 g, 1.14 mmol) and methyl 2-bromo-3-(tetrahydro-2H-pyran-4-yl)propanoate (0.271 g, 1.08 mmol) in 2 ml of DMF. The reaction mixture was stirred overnight at room temperature, extracted into ethyl acetate and washed with sat. brine solution. The organic layer was dried over $Na_2SO_4$ and concentrated to an oil. This material was purified by silica gel flash column (75% ethyl acetate in hexanes) to obtain 0.3 g of compound 8B. [M+H] calc'd for $C_{16}H_{22}ClN_3O_4$, 356.82; found 356.80

Compound 8 was synthesized using methyl 2-(4-chloro-3-(cyclopropylcarbamoyl)-1H-pyrazol-1-yl)-3-(tetrahydro-2H-pyran-4-yl)propanoate (8B) as starting material using the analogous procedure described in connection with Compound 1. [M+H] calc'd for $C_{18}H_{21}Cl_2N_5O_3S$, 459.36; found 459.30. $^1$H NMR (400 MHz, DMSO-$d_6$) δ ppm 0.52-0.60 (m, 2H) 0.61-0.71 (m, 2H) 1.13-1.38 (m, 3H) 1.44-1.65 (m, 2H) 1.89-2.05 (m, 1H) 2.26-2.38 (m, 1H) 2.76 (td, J=7.33, 4.04 Hz, 1H) 3.19 (q, J=11.79 Hz, 2H) 3.71-3.90 (m, 2H) 5.35 (dd, J=10.99, 4.42 Hz, 1H) 7.58 (s, 1H) 8.18 (d, J=4.29 Hz, 1H) 8.37 (s, 1 H) 13.01 (s, 1H)

Compound 9: N-(5-chlorothiazol-2-yl)-2-(4-(cyclopropanesulfonamido)-1H-pyrazol-1-yl)-3-(tetrahydro-2H-pyran-4-yl)propanamide

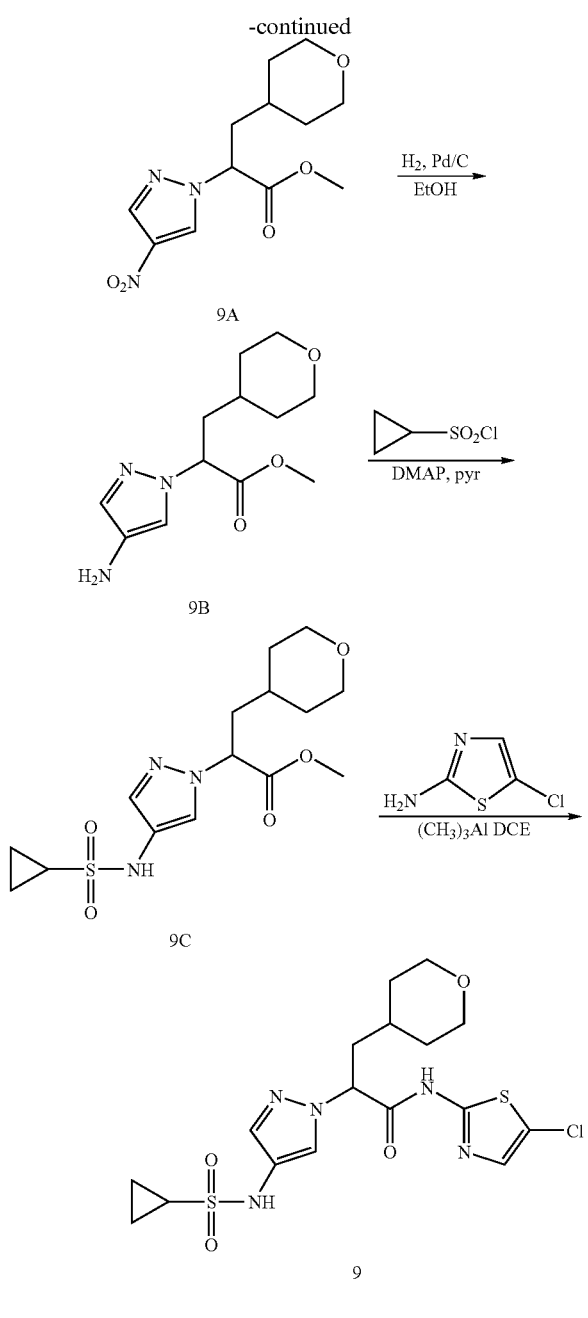

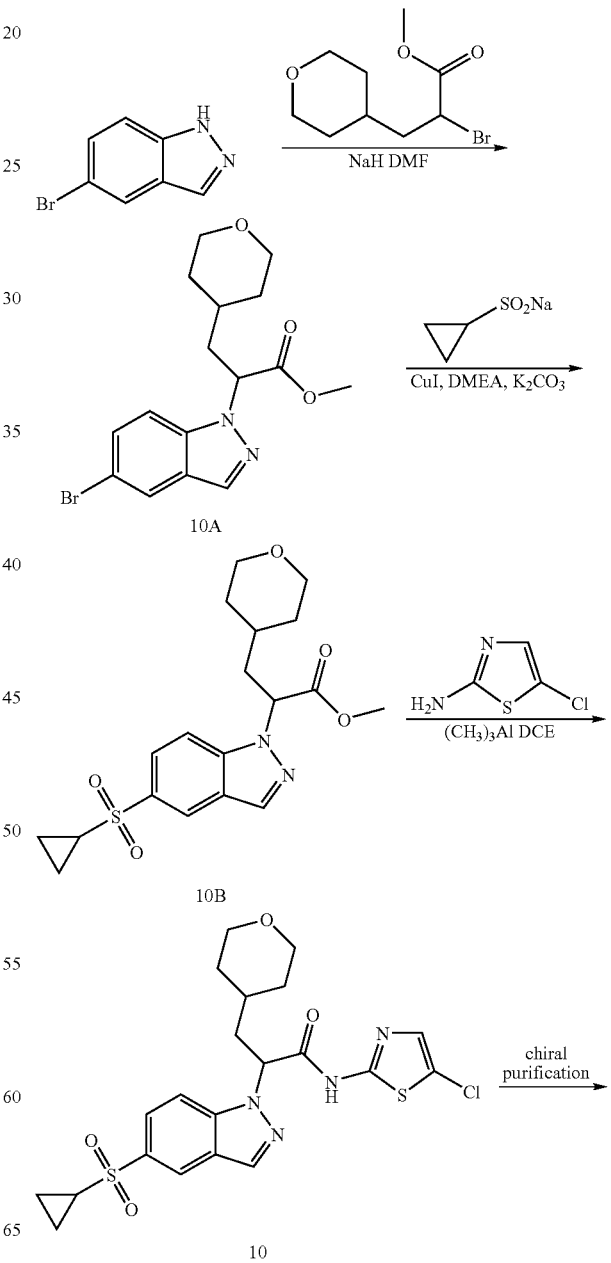

Compound 9 was synthesized using methyl 2-(4-(cyclopropanesulfonamido)-1H-pyrazol-1-yl)-3-(tetrahydro-2H-pyran-4-yl)propanoate (9C) as starting material using the analogous procedure described in connection with Compound 1. [M+H] calc'd for $C_{17}H_{22}ClN_5O_4S_2$ 460.97, found 461.0; $^1H$ NMR (400 MHz, DMSO-$d_6$) δ ppm 0.80-0.87 (m, 2H) 0.88-0.96 (m, 2H) 1.14-1.31 (m, 3H) 1.46 (d, J=10.36 Hz, 1H) 1.59 (d, J=9.35 Hz, 1H) 1.92-2.02 (m, 1H) 2.12-2.23 (m, 1H) 2.54-2.57 (m, 1H) 3.09-3.21 (m, 3H) 3.74-3.86 (m, 2H) 5.30 (dd, J=10.10, 5.31 Hz, 1H) 7.36 (s, 1H) 7.57 (s, 1H) 7.82 (s, 1H) 9.22 (s, 1H) 12.87 (s, 1H)

Compound 10: N-(5-chlorothiazol-2-yl)-2-(5-(cyclopropylsulfonyl)-1H-indazol-1-yl)-3-(tetrahydro-2H-pyran-4-yl)propanamide Compound 9A was synthesized using 4-nitro-1H-pyrazole and methyl 2-bromo-3-(tetrahydro-2H-pyran-4-yl)propanoate as starting material using the analogous procedure described in connection with Compound 1.

Compound 9A (0.37 g) was dissolved in EtOH (15 mL). A catalytic amount of Pd—C was added. The suspension was purged with $H_2$ gas 3 times, and then stirred at room temperature under $H_2$ overnight. The suspension was then filtered and the filtrate was concentrated in vacuo to yield 9B (0.121 g). [M+H] calc'd for $C_{12}H_{19}N_3O_3$, 254.3, found, 254.3

To the amine 9B (0.120 g) in 10 ml of DCM at 0° C. was added pyridine (0.038 ml), DMAP (0.057 g), followed by the dropwise addition of methane sulfonyl chloride (0.052 ml). The reaction mixture was allowed to warm to room temperature and stirred overnight. The reaction mixture was washed with water and brine, dried over $Na_2SO_4$, and concentrated in vacuo to obtain intermediate 9C as an oil. [M+H] calc'd for $C_{15}H_{23}N_3O_5S$, 358.4 found, 358.4.

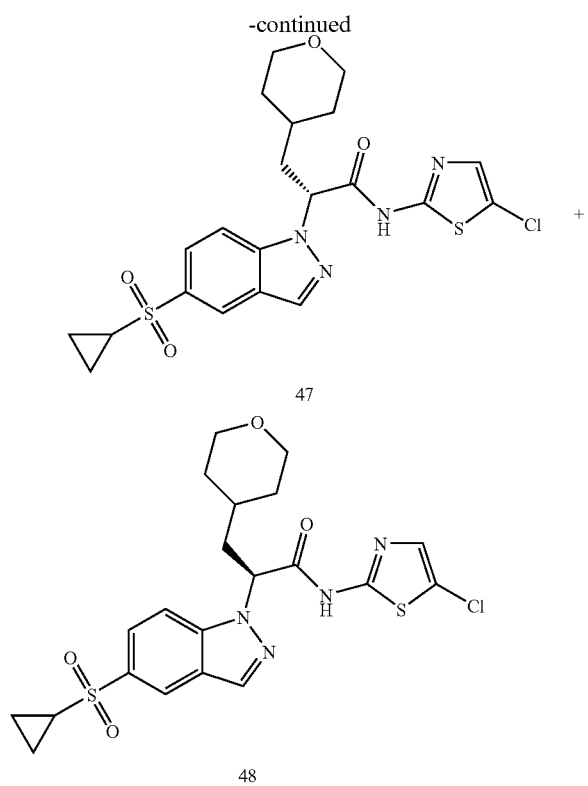

47

48

Compound 10A was synthesized using 5-bromo-1H-indazole and methyl 2-bromo-3-(tetrahydro-2H-pyran-4-yl)propanoate as starting material using the analogous procedure described in connection with Compound 1. A mixture (~4:1) of the N-1 vs. N-2 alkylated product was obtained. Purification using flash column chromatography (4:1, hexane:ethyl acetate) gave compound 10A.

To methyl 2-(5-bromo-1H-indazol-1-yl)-3-(tetrahydro-2H-pyran-4-yl)propanoate (0.22 g) in 10 ml of DMSO, was added sodium cyclopropanesulfinate (0.23 g), copper iodide (0.011 g), dimethylethylenediamine (0.013 ml) and $K_2CO_3$ (0.167 g). The reaction was heated at 100° C. overnight. The reaction mixture was extracted into ethyl acetate, washed with water and brine, dried over $Na_2SO_4$, and concentrated in vacuo to obtain intermediate 10B as an oil. [M+H] calc'd for $C_{19}H_{24}N_2O_5S$, 393.47 found, 393.5

Compound 10 was synthesized using methyl 2-(5-(cyclopropylsulfonyl)-1H-indazol-1-yl)-3-(tetrahydro-2H-pyran-4-yl)propanoate (10B) as starting material using the analogous procedure described in connection with Compound 1. [M+H] calc'd for $C_{21}H_{23}ClN_4O_4S_2$ 496.01, found 496.1. $^1H$ NMR (400 MHz, CHLOROFORM-d) δ ppm 1.01-1.11 (m, 2H) 1.18-1.29 (m, 1H) 1.31-1.52 (m, 5H) 1.59-1.71 (m, 1H) 2.31 (ddd, J=14.02, 8.72, 4.80 Hz, 1H) 2.45-2.59 (m, 2H) 3.20 (m, J=19.48, 11.67, 11.67, 2.15 Hz, 2H) 3.84-3.97 (m, 2H) 5.51 (dd, J=10.36, 4.80 Hz, 1H) 7.26 (s, 1H) 7.61 (d, J=8.84 Hz, 1H) 7.94 (dd, J=8.84, 1.52 Hz, 1H) 8.35 (s, 1H) 8.44 (s, 1H)

Compound 10 was subjected to chiral separation on a Berger SFC instrument using Chiralpak AD-H media eluting with 40% MeOH to afford Compounds 47 and 48.

Compound 70 was obtained using an analogous procedure with the N-2 isomer of an indazole related to Compound 10B.

Compound 11: N-(5-chlorothiazol-2-yl)-2-(4-(cyclopropylsulfonyl)-1H-indazol-1-yl)-3-((R)-3-oxocyclopentyl)propanamide

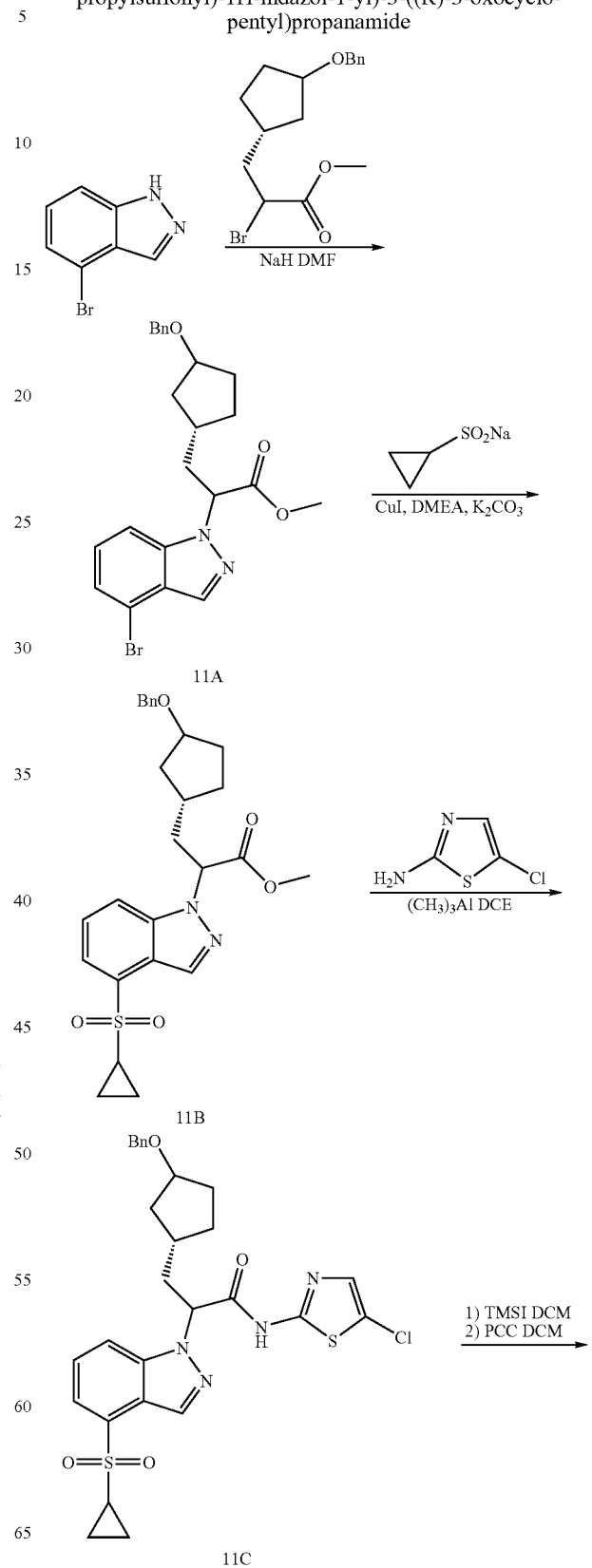

11A

11B

11C

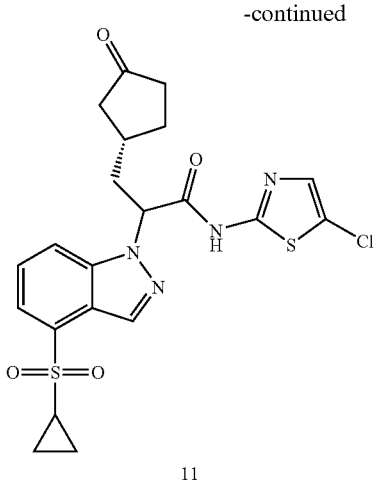

11

Compound 11A was synthesized using 4-bromo-1H-indazole and methyl 3-((1R)-3-(benzyloxy)cyclopentyl)-2-bromopropanoate as starting material using the analogous procedure described in connection with Compound 1. A mixture of the N-1 vs. N-2 alkylated product was obtained. Purification using flash column chromatography (3:1, hexane:ethyl acetate) gave compound 11A. [M+H] calc'd for $C_{23}H_{26}BrN_2O_3$, 457.1 found 457.1.

To methyl 3-((1R)-3-(benzyloxy)cyclopentyl)-2-(4-bromo-1H-indazol-1-yl)propanoate (0.327 g) in 10 ml of DMSO, was added sodium cyclopropanesulfinate (0.57 g), copper iodide (0.085 g), dimethylethylenediamine (0.096 ml). The reaction was heated at 150° C. overnight. The reaction mixture was cooled and washed with water and brine, dried over $Na_2SO_4$, and concentrated in vacuo to afford 11B. [M+H] calc'd for $C_{26}H_{31}N_2O_5S$, 483.19 found 483.2

5-chlorothiazol-2-amine (0.35 g, 2.04 mmole) was added to a microwave vial followed by DCE (3 mL). The reaction mixture was cooled to 0° C. under a $N_2$ atmosphere. Trimethyl aluminum (2M in hexanes) (2.0 mmole) was added and when the reaction subsided the cooling bath was removed, the solution was then stirred at RT for 15 min. To this was added a solution of methyl 3-((1R)-3-(benzyloxy)cyclopentyl)-2-(4-(cyclopropylsulfonyl)-1H-indazol-1-yl)propanoate 11B (0.165 g, 0.34 mmole) in DCE (2 mL) and the reaction mixture was heated in a microwave at 110° C. for 1 h. The reaction was then quenched with 1N HCl and extracted 2× with DCM. The organic layers were pooled, dried over $Na_2SO_4$ and the solvent was removed. This crude residue was purified by preparative scale HPLC to afford compound 11C as a yellow oil (0.193 g). [M+H] calc'd for $C_{28}H_{29}ClN_4O_4S_2$, 585.13; found 585.2.

Compound 11 was synthesized by treating compound 11C (0.142 g) with an excess of TMSI at 50° C. for 0.5 h. The reaction mixture was quenched with MeOH, the solvent was the removed in vacuo and the residue was portioned between EtOAc and $NaHCO_3$ soln., the organics were dried over $Na_2SO_4$ and concentrated in vacuo. The crude material was subsequently redissolved in DCM and treated with pyridinium chlorochromate 20% on basic aluminum. After oxidation was complete the reaction mixture was filtered through a pad of celite and concentrated. Purification by preparative scale HPLC afforded compound 11 (0.040 g). [M+H] calc'd for $C_{21}H_{31}ClN_4O_4S_2$, 493.07; found 493.1. $^1$H NMR (MeOD) δ ppm: 8.48 (s, 1H), 8.07 (dd, J=8.6, 3.0 Hz, 1H), 7.75 (d, J=7.1 Hz, 1H), 7.64 (dd, J=8.6, 7.3 Hz, 1H), 7.30 (s, 1H), 5.59-5.73 (m, 1H), 2.73-2.85 (m, 1H), 2.52-2.70 (m, 1H), 2.24-2.42 (m, 1H), 1.76-1.87 (m, 2H), 1.57-1.75 (m, 3H), 1.42-1.56 (m, 1H), 1.18-1.35 (m, 3H), 0.98-1.11 (m, 2H).

Compound 12: 2-(4-(cyclopropylsulfonyl)-6-(difluoromethoxy)-1H-indazol-1-yl)-N-(1-methyl-1H-pyrazol-3-yl)-3-(tetrahydro-2H-pyran-4-yl)propanamide

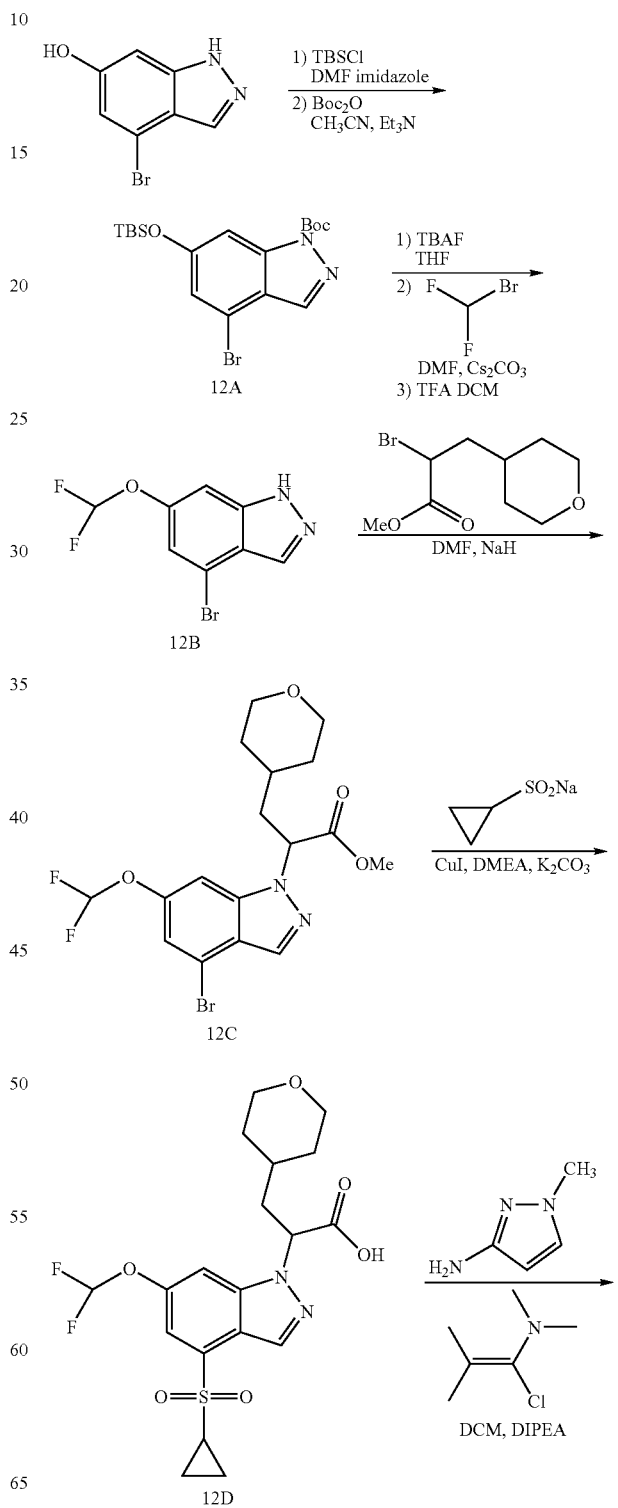

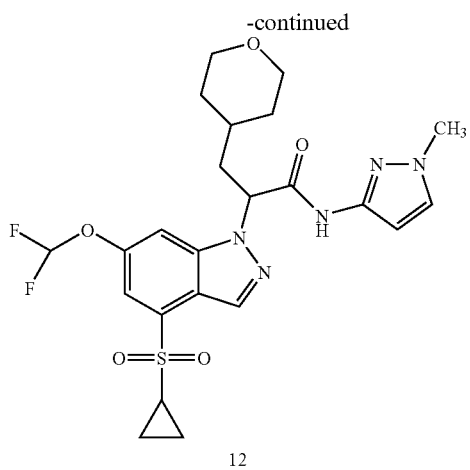

12

Compound 12A was synthesized by treating 4-bromo-1H-indazol-6-ol (1.0 g, 4.7 mmol) with TBSCl (0.78 g, 5.2 mmol) and imidazole (0.35 g, 5.2 mmol) in 5 ml of DMF and stirring the solution at RT overnight. The reaction mixture was worked up using standard protecting group introduction protocol and the resulting orange red oil crystallized on standing (1.2 g). This material was dissolved in $CH_3CN$ (10 mL) and treated with $Boc_2$ (0.88 g, 4.03 mmol), $Et_3N$ (0.48 g, 4.8 mmol) and a catalytic amount of DMAP. The reaction was stirred at RT overnight, concentrated under vacuum and partitioned between DCM and 1N HCl. The organic layer was dried over $MgSO_4$ and concentrated. Purification using flash column chromatography afforded the title material as a clear oil (519 mg, 33% yield) [M+H] calc'd for $C_{18}H_{28}BrN_2O_3Si$, 427.1 found 427.1.

Compound 12B was synthesized by treating 12A (0.52 g, 1.2 mmol) in THF (5 mL) with 1M TBAF (2.4 mmol) at 0° C. for 15 min. The reaction mixture was poured into $NH_4Cl$ sat and extracted with EtOAc. The organics were dried over $Na_2SO_4$ and concentrated under vacuum. The resulting material was dried under high vacuum prior to use in the next step. Transfer of this compound to a pressure bottle was achieved with 1-2 mL of DMF; followed by the addition of $Cs_2CO_3$ (0.39 g, 1.2 mmol). This suspension was chilled and an excess of difluorobromomethane was condensed into the reaction mixture. The pressure bottle was sealed, allowed to warm to RT and stirred continuously for 2d. Subsequent warming to 50° C. for 1d afforded a 70/30 mixture of the product and starting material, which was separated with flash column chromatography. This material was treated with a 1:1 mixture of TFA/DFCM at RT for 1 h. Removal of solvent and portioning of the residue between EtOAc and sat. $NaHCO_3$ gave the title compound (0.18 g, 57% yield).

Compound 12C was synthesized from 12B (0.18 g, 0.67 mmol) and methyl 2-bromo-3-(tetrahydro-2H-pyran-4-yl)propanoate (0.25 g, 1.0 mmol) using an analogous procedure described in connection with Compound 1. The title compound (yellow oil) was isolated as a crude N1 & N2 mixture (70/30) with the desired N1 material dominant. The regioisomers were separated with flash column chromatography; [M+H] calc'd for $C_{17}H_{20}BrF_2N_2O_4$, 433.1 found 433.2.

Compound 12D was synthesized from 12C using an analogous procedure described in connection with Compound 10. The title material was isolated and purified using preparative HPLC; [M+H] calc'd for $C_{19}H_{23}F_2N_2O_6S$ 445.1 found 445.3.

Compound 12 was synthesized from 12D (0.08 g, 0.17 mmol) which was dissolved in DCM (5 mL). To this solution was added 1-chloro-N,N,2-trimethylprop-1-en-1-amine (0.04 g, 0.3 mmol) at RT and the mixture was stirred for 30 min. 1-methyl-1H-pyrazol-3-amine (0.03 g, 0.3 mmol) was subsequently added along with DIPEA (0.04 g, 0.3 mmol). The solvent was removed under reduced pressure and the residue was partitioned between EtOAc and sat. bicarbonate soln. The organics were dried and purified by flash column chromatography to afford compound 12 (0.044 g). [M+H] calc'd for $C_{23}H_{28}F_2N_5O_5S$, 524.2; found 524.4. $^1H$ NMR (MeOD) δ ppm: 0.94-1.13 (m, 2H) 1.22-1.46 (m, 5H) 1.52 (dd, J=9.47, 1.89 Hz, 1H) 1.72 (dd, J=9.98, 1.89 Hz, 1H) 2.05-2.29 (m, 1H) 2.54 (ddd, J=14.15, 10.23, 4.17 Hz, 1H) 2.84 (tt, J=7.96, 4.80 Hz, 1H) 3.12-3.29 (m, 2H) 3.65 (s, 1H) 3.73-3.80 (m, 3H) 3.80-3.96 (m, 2H) 5.63 (dd, J=10.36, 5.31 Hz, 1H) 6.45 (d, J=2.27 Hz, 1H) 7.42 (d, J=2.27 Hz, 1H) 7.54 (d, J=1.77 Hz, 1H) 7.89 (d, J=2.27 Hz, 1H) 8.46 (s, 1H).

Compound 13: 2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide

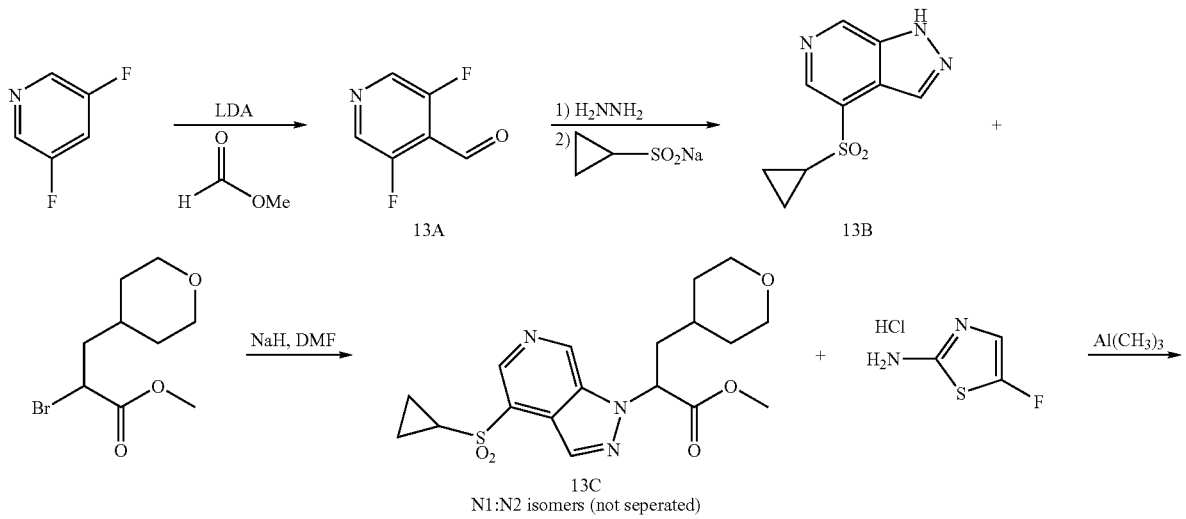

13C
N1:N2 isomers (not seperated)

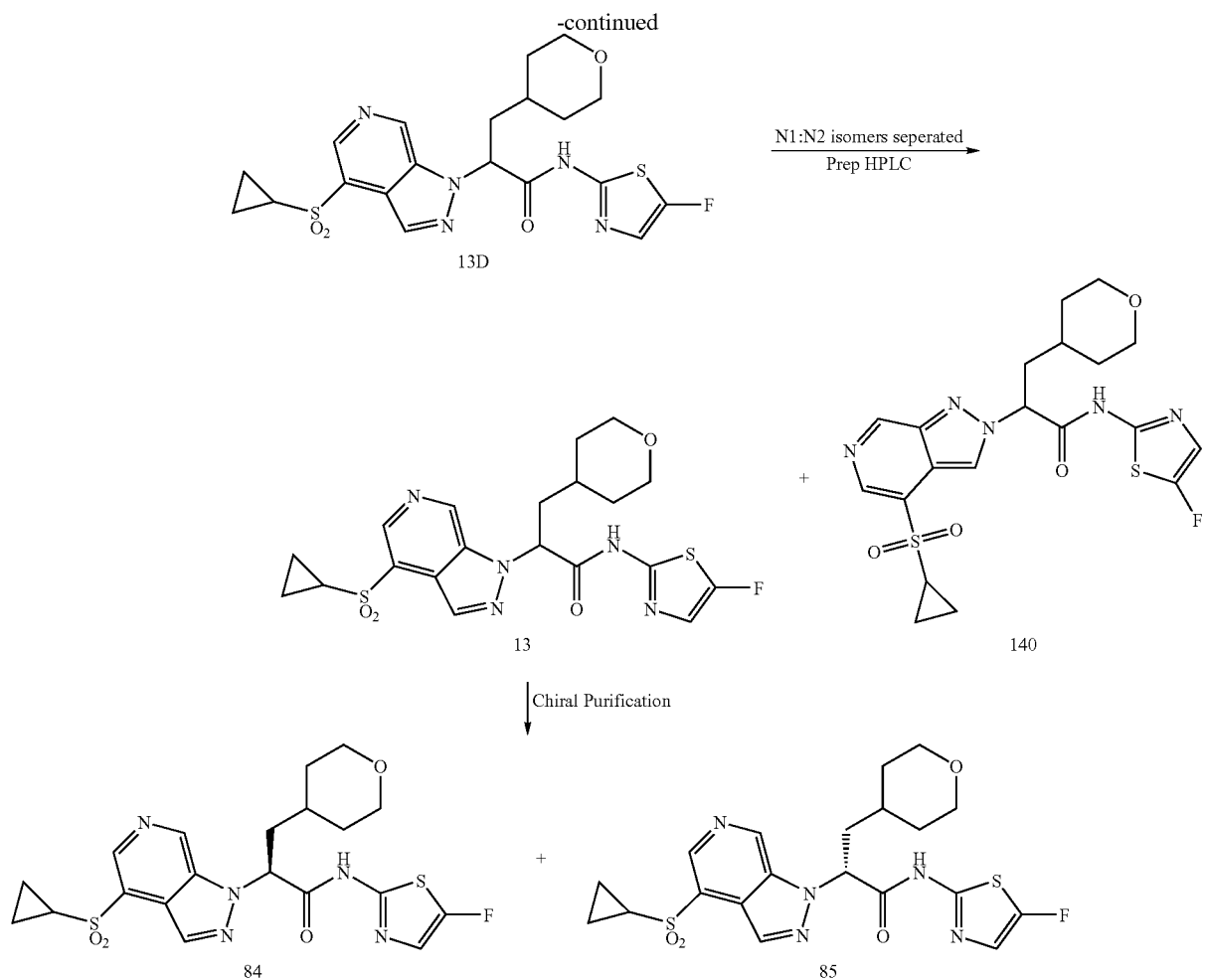

Compound 13A: LDA (68 ml, 478 mmol) and THF (500 ml) were cooled to 0° C. while stirring under nitrogen and n-BuLi (192 ml, 478 mmol, 2.5 M in hexanes) was added dropwise. After 30 min, the mixture was cooled to −78° C. (dry ice/acetone bath) and 3,5-difluoropyridine (50 g, 434 mmol) dissolved in 500 ml of THF was added dropwise while maintaining the temperature below −69° C. After 4 h, methyl formate (54 ml, 868 mmol) dissolved in 135 ml of THF was added dropwise (completed addition in 1.25 h). In a separate flask, 1 L sat. NaHCO$_3$ was cooled to 0° C. while stirring. The reaction mixture was added to the NaHCO$_3$ solution while stirring and the mixture was allowed to warm to room temperature. The organic layer was separated and the water layer was extracted with ethyl acetate (4×, 250 mL). The combined organic extracts were washed with sat. brine, dried over Na$_2$SO$_4$ and concentrated to obtain a dark purple oil. Purification using flash column chromatography gave 32.5 g (52% yield) of compound 13A.

Compound 13B: To a solution of 3,5-difluoroisonicotinaldehyde (10.15 g, 70.60 mmol) in NMP (50 ml) at 0° C. was added anhydrous hydrazine (2.3 ml, 70.69 mmol) dropwise. The reaction solution was stirred at R.T. for 2 hrs (monitored by LC-MS for completion of reaction to hydrazone). The reaction mixture was then heated at 140° C. overnight for conversion to the indazole (monitored by LC-MS for completion of reaction). Cyclopropylsulfinic acid sodium salt (18.1 g, 141.38 mmol) was then added to the reaction mixture and it was heated at 180° C. overnight. When reaction was complete (monitored by LC-MS), the reaction mixture was concentrated using a high vacuum pump to remove NMP and then extracted into ethyl acetate. The organic layer was washed with water and any solid obtained was filtered through celite. The combined organic layers were washed with H$_2$O, dried over MgSO$_4$, filtered, and concentrated in vacuo. The oil was purified by flash column chromatography (80% EtOAc in hexanes to 100% EtOAc) to yield 5.492 g (54% yield) of compound 13B. [M+H] calc'd for C$_9$H$_9$N$_3$O$_2$S 224.2; found, 224.25.

Compound 13C: Sodium hydride (557 mg, 22.0 mmol) was suspended in DMF (5 ml), and cooled to 0° C. A solution of Compound 13B (3.77 g, 16.92 mmole) in DMF (15 mL) was added dropwise to it. After stirring for 20 min at 0° C., methyl 2-bromo-3-(tetrahydro-2H-pyran-4-yl)propanoate (5.52 g, 22.0 mmol) was added dropwise to the reaction mixture and it was allowed to warm at room temperature and stirred for 2 hours. The reaction mixture was quenched with sat. ammonium chloride and extracted into ethyl acetate. The organic layer was washed with water, dried over MgSO$_4$, filtered, and concentrated under reduced pressure to yield crude compound 13C (5.94 g; 89% yield). [M+H] calc'd for C$_{18}$H$_{23}$N$_3$O$_5$S 394.4; found, 394.46.

Compound 13D: To a suspension of 5-fluorothiazol-2-amine hydrochloride (9.36 g, 60.5 mmole) in DCE (30 mL) at 0° C. under a N$_2$ atmosphere was added trimethyl aluminum (2M in hexanes) (30.3 mL, 60.5 mmole) dropwise. After stirring at room temperature for 30 minutes, a solution of Compound 13C (5.94 g; 15.12 mmol) in DCE (30 ml) was added dropwise and the reaction mixture was heated at 100° C. for 2 hours. After cooling to 0° C., the reaction mixture was quenched with 1N HCl and extracted 2× with DCM. The organic layers was combined, dried over Na$_2$SO$_4$, filtered and concentrated under reduced pressure to yield the crude Compound 13D.

Compounds 13 and 140 were obtained from compound 13D as a TFA salt, after purification using prep HPLC (Waters System: Column is Phenomenex C18, 5μ, 150×50 mm, mobile phase A: 0.05% TFA in H2O and mobile phase B is 0.035% TFA in acetonitrile, Solvent gradient is 40-55% B); [M+H] calc'd for C$_{20}$H$_{22}$FN$_5$O$_4$S$_2$ 480.5; found, 480.55.

Compound 13 was obtained as a free base by concentration of the HPLC fractions, followed by extraction into ethyl acetate and washing with satd. NaHCO$_3$. The organic layer was dried over Na$_2$SO$_4$, filtered and concentrated under reduced pressure to obtain compound 13.

Compound 13 was subjected to chiral separation on a Berger SFC instrument using Chiralpak AD-H media eluting with 40% MeOH to afford Compounds 84 and 85.

Compound 14: 6-(2-(4-(cyclopropylsulfonyl)-1H-indazol-1-yl)-3-(tetrahydro-2H-pyran-4-yl)propanamido)nicotinamide

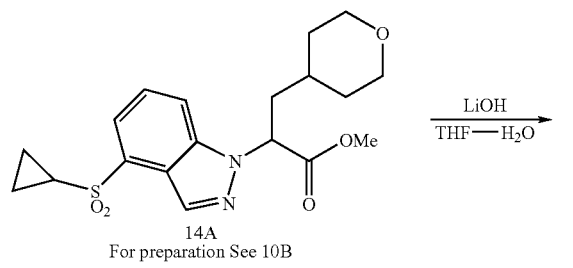
14A
For preparation See 10B

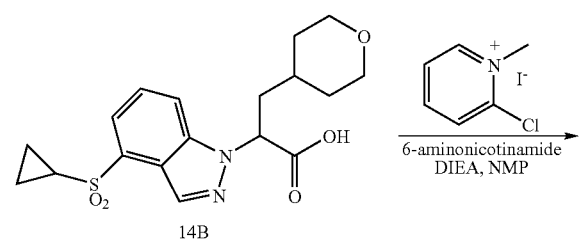
14B

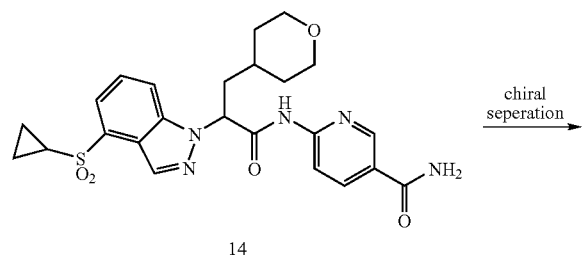
14

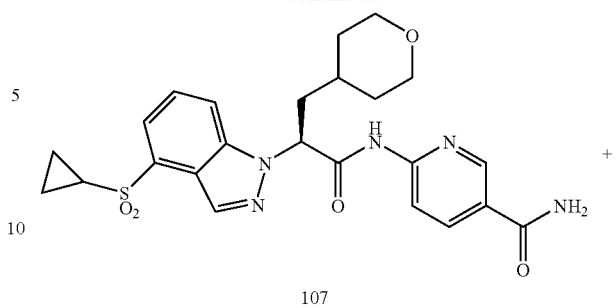
107

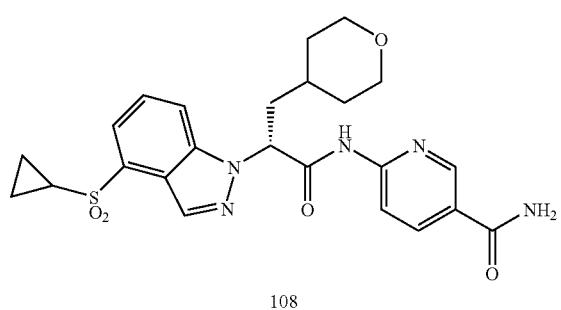
108

Compound 14A was synthesized using 4-bromo-1H-indazole and methyl 2-bromo-3-(tetrahydro-2H-pyran-4-yl)propanoate as starting material using the analogous procedure described in connection with Compound 10. A mixture (~3:1) of the N-1 vs. N-2 alkylated product was obtained. Purification using flash column chromatography (4:1, hexane:ethyl acetate) gave compound 14A.

Compound 14B was synthesized by treating 14A (0.4 g, 1.0 mmol) in THF-H$_2$O (5:1, 10 mL) with 1M LiOH (3.0 mmol) at 0° C. for 15 min. and the mixture was stirred for 18 h at room temperature. The reaction mixture was acidified with 1N HCl and extracted with EtOAc. The organics were dried over Na$_2$SO$_4$ and concentrated under vacuum. The resulting material was dried under high vacuum prior to use in the next step.

Compound 14 was synthesized from 14B (0.15 g, 0.39 mmol) which was dissolved in NMP (5 mL). To this solution was added 6-aminonicotinamide (0.109 g, 0.79 mmol). 2-chloro-1-methylpyridiniumidodide (0.15 g, 0.58 mmol) was subsequently added along with DIPEA (0.092 mL, 0.53 mmol) at RT and the mixture was stirred for 18 h at 80° C. The reaction mixture was cooled and partitioned between EtOAc and sat. NaCl soln. The organic layer were dried and purified by prep HPLC (Waters System: Column is SunFire C18, 5μ, 30×75 mm, mobile phase A: 0.05% TFA in H2O and mobile phase B is 0.035% TFA in acetonitrile, Solvent gradient is 30-45% B); to afford compound 14 (158 mg). [M+H] calc'd for C$_{24}$H$_{28}$N$_5$O$_5$S, 498.3; found 498.6. $^1$H NMR (400 MHz, DMSO-d$_6$) δ ppm 0.94-1.13 (m, 2H) 1.13-1.43 (m, 5H) 1.43-1.67 (m, 2H) 2.12-2.28 (m, 1H) 2.50 (ddd, J=14.21, 10.42, 5.18 Hz, 1H) 2.93-3.22 (m, 3H) 3.79-3.95 (m, 2H) 5.89 (dd, J=9.47, 4.93 Hz, 1H) 7.48 (br. s., 1 H) 7.61-7.77 (m, 2H) 7.95-8.12 (m, 2H) 8.12-8.28 (m, 2H) 8.43 (s, 1H) 8.83 (d, J=1.77 Hz, 1H) 11.32 (s, 1H).

Compound 14 was subjected to chiral separation on a Berger SFC instrument using Chiralpak AD-H media eluting with 40% MeOH to afford Compounds 107 and 108.
Compound 15: 2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide
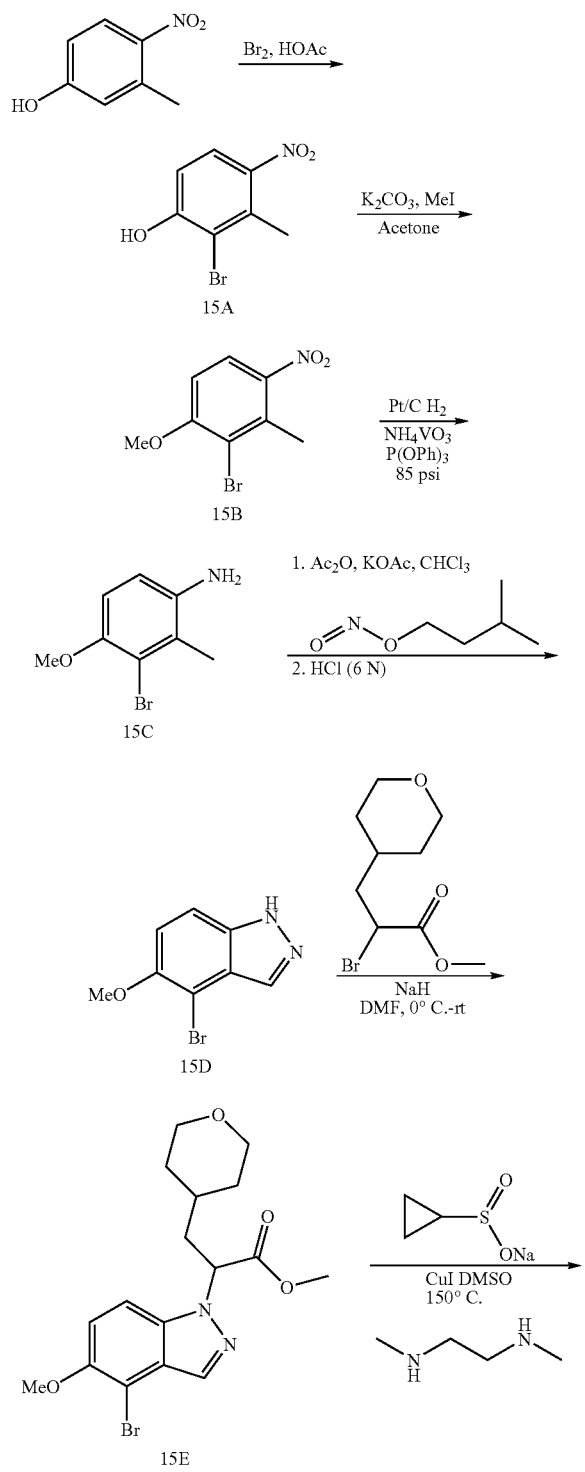
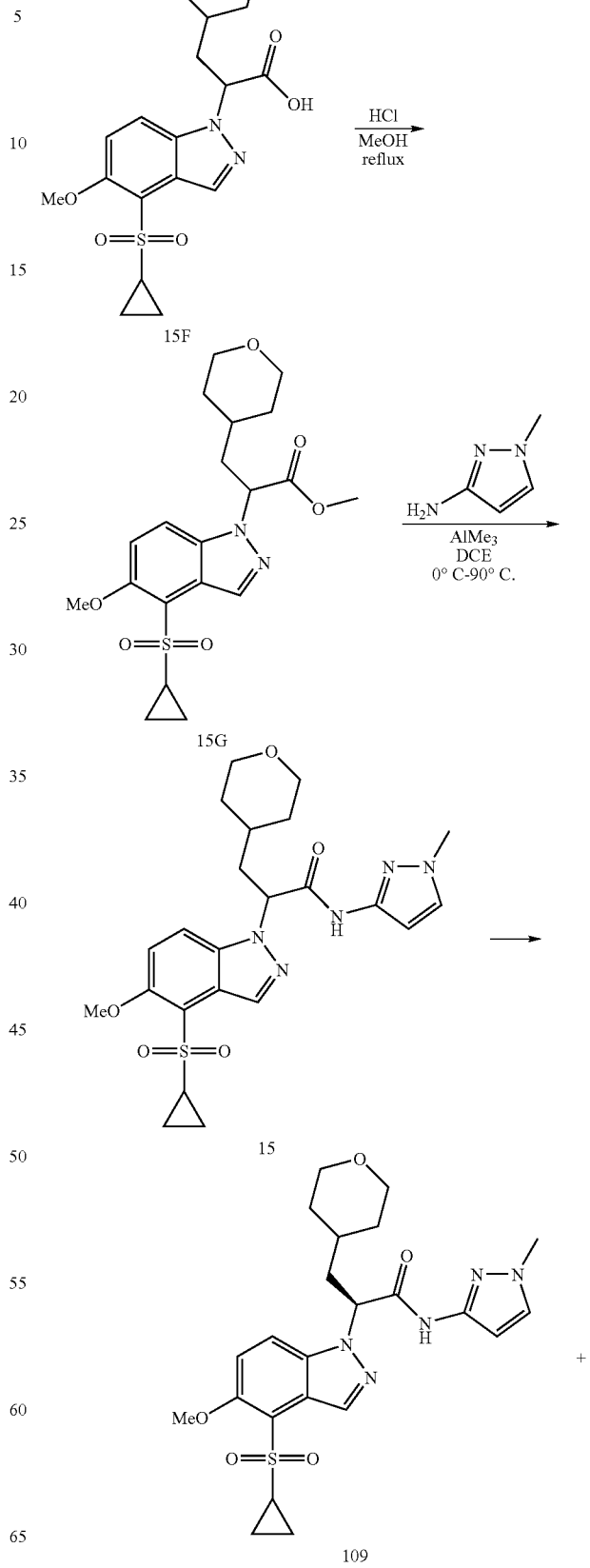

-continued

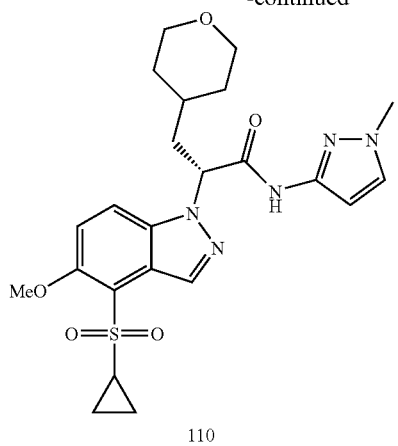

110

Compound 15A: A solution of bromine (15.69 g, 0.097 mol) in acetic acid (8.88 ml) was added dropwise to a solution of 3-methyl-4-nitrophenol (14.8 g, 0.097 mol) in acetic acid (118 ml) over 45 min, and the mixture stirred for another 3 h hour. Since the reaction was not complete as monitored for completeness using LC-MS, 1 ml Bromine in acetic acid (2 ml) was added to the reaction mixture, and the mixture was stirred overnight. The solvent was removed under reduced pressure and the residue was suspended in water and extracted with ethyl acetate. The mixture was filtered through Celite. The organic layer was separated, washed with brine, dried over $Na_2SO_4$, and concentrated to afford crude compound Compound 15A (15 g) and the other regioisomer (3-methyl-4-nitro-6-bromophenol) in a 2:1 ratio. The crude compound is taken on to the next step without purification.

Compound 15B: To the crude compound 15A (104 g, 0.45 mol) in acetone (1000 ml), $K_2CO_3$ (68 g, 0.49 mol) and methyl iodide (74 g, 0.52 mol) were added at room temperature. The mixture was refluxed for 1.5 hour. Since the reaction was not complete as monitored for completeness by LC-MS, $K_2CO_3$ (325 mesh) (22.6 g, 0.16 mol) and MeI (10 ml, 0.16 mol) was added to the reaction mixture, and the mixture was allowed to reflux overnight. The reaction was again monitored for completeness by LC-MS. Additional $K_2CO_3$ (325 mesh) (8 g, 0.058 mol) and MeI (4 ml) was added to the reaction mixture, and the mixture allowed to reflux for another hour. The reaction mixture was then cooled to room temperature, filtered, and concentrated. The residue was portioned between EtOAc and $H_2O$. The organic layer was separated, dried and concentrated to yield crude compound 15B (152 g) as a brown solid.

Compound 15C: To a solution of compound 15B (76.4 g, 0.311 mol) in DCM (160 ml) was added $NH_4VO_3$ (2.18 g, 0.0186 mol), $P(OPh)_3$ (0.964 g, 0.00311 mol) and Pt/C (5%) (15.5 g). The mixture was stirred under $H_2$ at 85 psi overnight. The reaction mixture was filtered through Celite and concentrated to give 64.9 g crude compound 15C. The crude compound 15C containing the other regioisomer (5-bromo-4-methoxy-2-methylaniline) was separated at this stage by flash column chromatography (0-100% ethyl acetate in hexanes) to afford compound 15C (34.66 g).

Compound 15D: To compound 15C (32.2 g, 0.149 mol) in $CHCl_3$ (470 ml) was added $Ac_2O$ (32.65 ml, 0.345 mol). The reaction mixture was stirred at room temperature for 40 min. KOAc (4.47 g, 0.0455 mol) and isoamyl nitrite (44.3 ml, 0.33 µmol) was added to the reaction mixture. The reaction mixture was refluxed overnight, cooled in an ice bath and neutralized with 1N NaOH. The organic layer was separated from the aqueous layer, washed with brine and dried over $Na_2SO_4$ and concentrated. The residue was taken up in a methanol (296 ml) and 6N HCl solution (90 ml). The reaction mixture was heated to reflux for one hour. After cooling, the reaction mixture was concentrated. The solid was neutralized with a saturated aqueous $NaHCO_3$ solution, isolated by filtration, washed with water and dried to afford compound 15D (23 g)

Compound 15E: Compound 15D (12 g, 0.0529 mol) was dissolved in DMF (140 mL) and the solution was chilled to 0° C. NaH (2.65 g, 0.0663 mole) was added and when the reaction subsided, methyl 2-bromo-3-(tetrahydro-2H-pyran-4-yl)propanoate (15.9 g, 0.0635 mole) was added to the reaction mixture. The reaction mixture was then warmed to room temperature and stirred overnight. When the reaction was complete as monitored by LC-MS (N1:N2 ratio was 3:1), the reaction mixture was cooled in an ice bath, quenched with a small volume of water and extracted into EtOAc. The organic layer was dried over $Na_2SO_4$, filtered and concentrated to obtain an oil which was purified by flash column chromatography to afford Compound 15E (7.54 g).

Compound 15G: To compound 15E (7 g, 0.0177 mol) in 48 ml of DMSO was added sodium cyclopropanesulfinate (6.93 g, 0.0546 mol), copper iodide (3.46 g, 0.0182 mol) and dimethylethylenediamine (1.96 ml, 0.0182 mol). The reaction was heated at 150° C. for 40 min. The reaction mixture was then cooled in an ice bath, diluted with EtOAc and filtered through celite. The organic layer was dried over $Na_2SO_4$ and concentrated to afford a mixture of compound 15F and compound 15G. The residue was dissolved in MeOH (100 ml) and HCl (6N, 10 ml) was added to it. The reaction mixture was heated to reflux and stirred overnight. After the reaction mixture was cooled to room temperature, it was concentrated under vacuum, and extracted into EtOAc. The organic layer was washed with water and brine, dried over $Na_2SO_4$, filtered and concentrated to obtain an oil. The crude oil was purified by flash column chromatography to give compound 15G (2.7 g).

Compound 15: To a solution of 1-methyl-1H-pyrazol-3-amine (2.50 g, 25.78 mmol) in DCE (25 ml) at 0° C. under a $N_2$ atmosphere was added trimethyl aluminum (2M in hexanes) (12.89 mL, 25.8 mmole). After 15 min, a solution of compound 15G (2.72 g, 6.46 mmole) in DCE (12 ml) was added to the reaction mixture and the solution was heated at 90° C. for 2 h. The reaction mixture was then cooled in ice bath, quenched with 1N HCl and extracted 2× with EtOAc. The organic layer was dried over $Na_2SO_4$ and the crude residue was purified by flash column chromatography (Hexanes/EtOAc, 30%-100%) to afford compound 15 (2.7 g). [M+H] calc'd for $C_{23}H_{29}N_5O_5S$ 488, found 488, $^1H$ NMR(CHLOROFORM-d, 400 MHz): δ=8.72 (s, 1H), 8.64 (s, 1H), 7.67 (d, J=9.3 Hz, 1H), 7.30 (d, J=9.1 Hz, 1H), 7.22 (d, J=2.5 Hz, 1H), 6.61 (d, J=2.3 Hz, 1H), 5.27 (dd, J=10.6, 4.8 Hz, 1H), 4.07 (s, 3H), 3.82-3.92 (m, 2H), 3.75 (s, 3H), 3.09-3.29 (m, 3H), 2.44-2.56 (m, 1H), 2.28 (d, J=5.1 Hz, 1H), 1.42-1.52 (m, 2H), 1.29-1.40 (m, 3H), 1.21 (d, J=6.1 Hz, 2H), 0.95-1.09 ppm (m, 2H)

Compound 15 was subjected to chiral separation on a Berger SFC instrument using Chiralpak OD-H media and eluting with 25% Isopropanol to afford Compounds 109 and 110.

Compound 16: 2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide
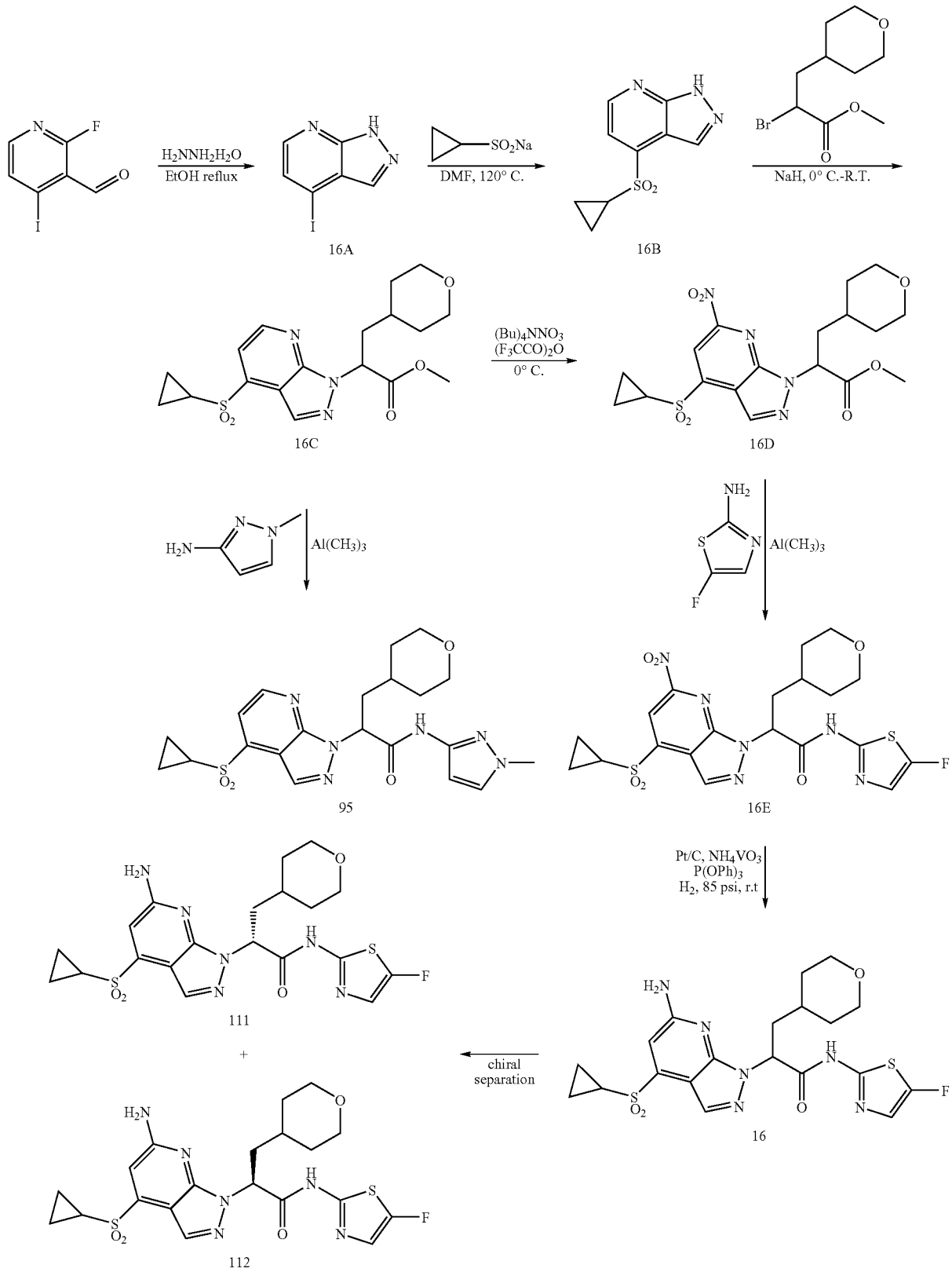

Compound 16A: To a solution of 2-fluoro-4-iodonicotinaldehyde (3.0 g, 11.95 mmol) in ethanol (45 ml) was added hydrazine monohydrate (1.12 g, 14.34 mmol) and the reaction mixture was heated at 120° C. in a sealed vial overnight. The reaction mixture was cooled to room temperature, and then was concentrated under reduced pressure. The residue was treated with water (30 ml) and 1 N NaOH (20 ml) and extracted with CHCl$_3$ (40×4 ml). The organic layer was separated, dried over MgSO$_4$ and concentrated to yield crude compound 16A as solid (2.74 g). [M+H] calc'd for $C_6H_{41}N_3$ 246; found 246.

Compound 16B: To a solution of 16A (1.00 g, 4.02 mmol) in DMF (12 ml) was added sodium cyclopropanesulfinate (1.57 g, 12.2 mmol) and the reaction was heated at 120° C. for 4 hours. After cooling to room temperature, the reaction mixture was concentrated and the residue was treated with water, followed by extracted into ethyl acetate. The organic layer was separated, dried over MgSO$_4$ and concentrated under reduced pressure to yield crude 16B (0.98 g). [M+H] calc'd for $C_9H_9N_3O_2S$ 224; found 224.

Compound 16C was synthesized from compound 16B using an analogous procedure described in connection with Compound 10 to yield crude 16C as solid (1.496 g, 86%). [M+H] calc'd for $C_{18}H_{23}N_3O_5S$ 394; found 394.

Compound 16D: To a solution of compound 16C (878 mg, 2.23 mmol) in DCM (10 ml) was added tetrabutylammonium nitrate (1.021 g, 3.35 mmol) and the solution was cooled to 0° C. Trifluoroacetic anhydride (0.47 ml, 3.35 mmol) was then added dropwise to the reaction mixture and it was stirred at 0° C. for 1.5 h. after which another 1.5 eq. of tetrabutylammonium nitrate and trifluoroacetic anhydride was added to the reaction mixture at 0° C. and stirred for 1.5 h. The reaction mixture was diluted with DCM and washed with water. The organic layer was separated, dried over MgSO$_4$ and concentrated under reduced pressure. The residue obtained was purified by prep. HPLC (Waters System: Column is Phenomenex C18, 5µ, 150×50 mm, mobile phase A: 0.05% TFA in H2O and mobile phase B is 0.035% TFA in acetonitrile, Solvent gradient is 40-55% B); to yield 16D as solid (176 mg, 18%). [M+H] calc'd for $C_{18}H_{22}N_4O_7S$ 439; found 439.

Compound 16E was synthesized from compound 16D using an analogous procedure described in connection with Compound 10 to yield crude 16E (233 mg). [M+H] calc'd for $C_{20}H_{21}FN_6O_6S_2$ 525; found 525.

Compound 16: To a vial charged with ammonium metavanadate (5 mg, 0.032 mmol) and triphenylphosphite (2 mg, 0.05 mmol) was added a solution of compound 16E (233 mg, 0.54 mmol) in THF (12 ml), followed by a catalytic mount of Pt/C (5%). The reaction mixture was stirred under hydrogen (85 psi) for 24 hours. The reaction mixture was then filtered through Celite and concentrated under reduced pressure to obtain a residue which was purified via prep. HPLC (Waters System: Column is Phenomenex C18, 5µ, 150×50 mm, mobile phase A: 0.05% TFA in H2O and mobile phase B is 0.035% TFA in acetonitrile, Solvent gradient is 40-55% B); to yield compound 16 (54 mg). [M+H] calc'd for $C_{20}H_{23}FN_6O_4S_2$ 496, found 496. $^1$H NMR (400 MHz, METHANOL-d$_4$) δ ppm 0.99-1.07 (m, 9H) 1.29-1.42 (m, 22H) 1.47-1.54 (m, 4H) 1.71-1.78 (m, 4H) 2.09-2.19 (m, 4H) 2.52-2.63 (m, 5H) 2.90 (tt, J=8.08, 4.80 Hz, 5H) 3.12-3.28 (m, 9H) 3.80-3.90 (m, 9H) 5.86 (dd, J=10.99, 4.42 Hz, 5H) 7.08 (d, J=2.53 Hz, 4H) 8.15 (s, 4H) 8.32 (s, 4H).

Compound 16 was subjected to chiral separation on a Berger SFC instrument. For this particular compound it was found that using Chiralpak AD-H media eluting with 40% MeOH afforded Compounds 111 and 112

Compound 95 was synthesized from compound 16C using an analogous procedure described in connection with Compound 10. The crude compound was purified by prep. HPLC (Waters System: Column is Phenomenex C18, 5µ, 150×50 mm, mobile phase A: 0.05% TFA in H2O and mobile phase B is 0.035% TFA in acetonitrile, Solvent gradient is 40-55% B) to yield compound 95. [M+H] calc'd for $C_{21}H_{27}N_6O_4S$ 459, found 459. $^1$H NMR (400 MHz, METHANOL-d$_4$) δ ppm 1.08-1.18 (m, 2H) 1.28-1.44 (m, 5H) 1.54 (d, J=9.35 Hz, 1H) 1.74 (dd, J=10.11, 1.77 Hz, 1H) 2.17-2.27 (m, 1H) 2.67 (ddd, J=14.21, 10.93, 3.66 Hz, 1H) 2.89 (tt, J=7.86, 4.77 Hz, 1H) 3.10-3.28 (m, 2H) 3.76 (s, 3H) 3.85 (dd, J=10.74, 4.93 Hz, 2H) 5.99 (dd, J=10.99, 4.67 Hz, 1H) 6.42 (d, J=2.53 Hz, 1H) 7.42 (d, J=2.27 Hz, 1H) 7.69 (d, J=4.80 Hz, 1H) 8.51 (s, 1H) 8.81 (d, 1H)

Compound 19: 2-(6-cyano-4-(cyclopropylsulfonyl)-1H-indazol-1-yl)-N-(1-methyl-1H-pyrazol-3-yl)-3-(tetrahydro-2H-pyran-4-yl) propanamide

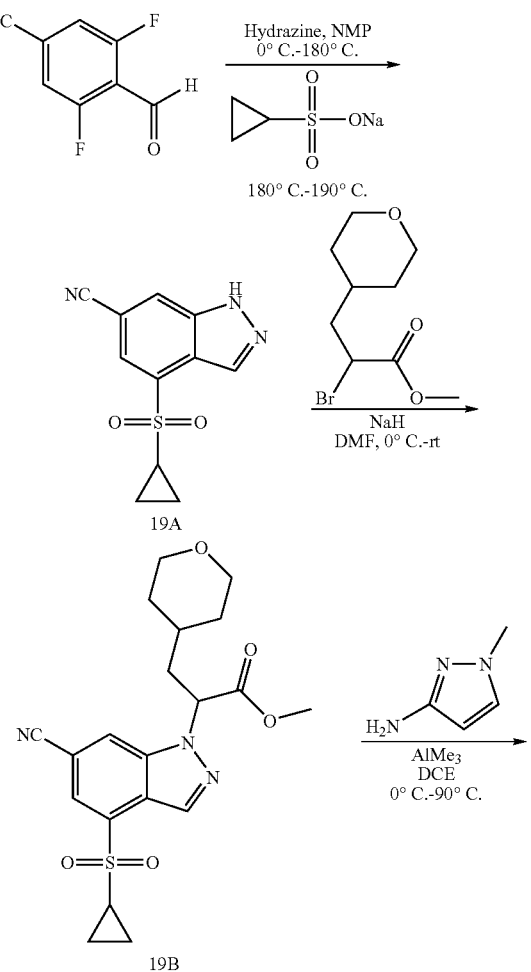

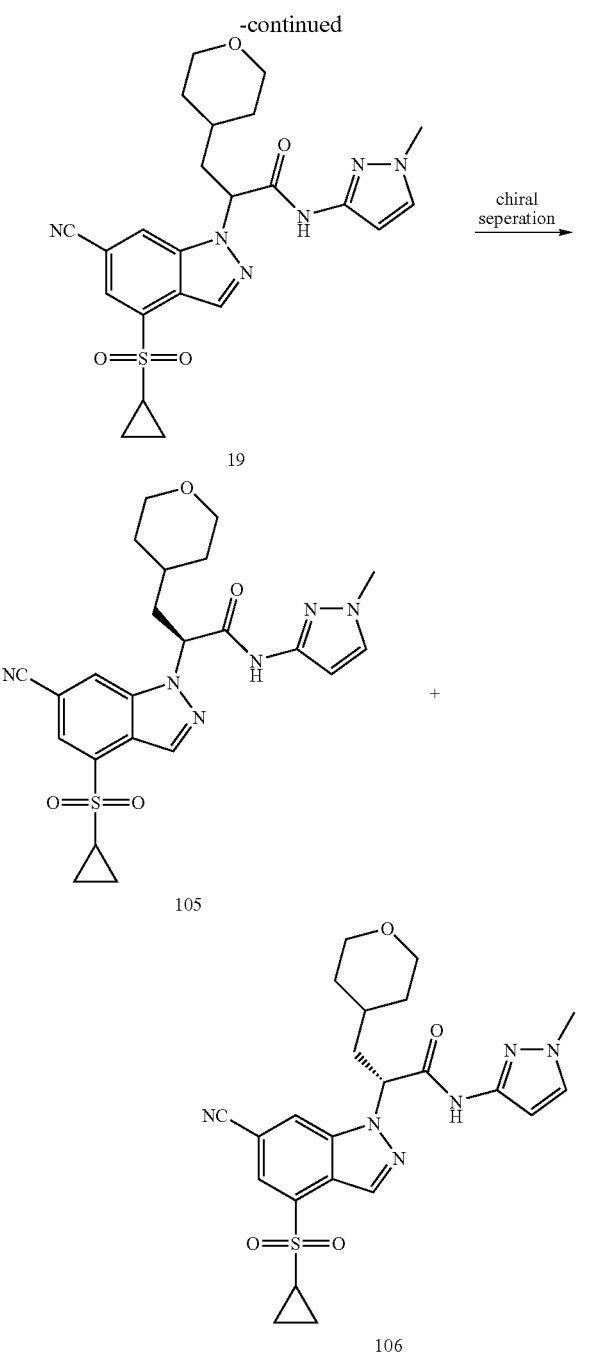

and concentrated to obtain a residue which was purified by flash column chromatography to yield compound 19A (8.5 g). [M+H] calc'd for $C_{11}H_9N_3O_2S$ 248, found 248

Compound 19B: Compound 19A (4.2 g, 16.99 mmol) was dissolved in DMF (50 mL) and the solution was chilled to 0° C. NaH (0.88 g, 22.08 mmol) was added and when the reaction subsided, methyl 2-bromo-3-(tetrahydro-2H-pyran-4-yl)propanoate (5.54, 22.08 mmol) was added to the reaction mixture. The reaction mixture was then warmed to room temperature and stirred overnight. When the reaction was complete as monitored by LC-MS (N1:N2 ratio was 3; 1), the reaction mixture was cooled in an ice bath, quenched with a small volume of water and extracted into EtOAc. The organic layer was dried over $Na_2SO_4$, filtered and concentrated to obtain an oil which was purified by flash column chromatography to afford the NI isomer as Compound 19B (1.8 g, 25%) [M+H] calc'd for $C_{20}H_{23}N_3O_5S$ 418, found 418

Compound 19: To a solution of 1-methyl-1H-pyrazol-3-amine (5.21 g, 53.7 mmol) in DCE (70 ml) at 0° C. under a $N_2$ atmosphere was added trimethyl aluminum (2M in hexanes) (26.8 mL, 53.7 mmole). After 15 min, a solution of compound 19B (5.6 g, 13.41 mmole) in DCE (15 ml) was added to the reaction mixture and the solution was heated overnight at 90° C. The reaction mixture was then cooled in ice bath, quenched with 1N HCl and extracted 2× with EtOAc. The organic layer was dried over $Na_2SO_4$ and the crude residue was purified by flash column chromatography (Hexanes/EtOAc, 40%-100%) to afford compound 19 as a free base (4.47 g, 69%). [M+H] calc'd for $C_{23}H_{26}N_6O_4S$ 483, found 483. $^1$H NMR (400 MHz, CHLOROFORM-d) δ 8.60-8.71 (m, 2H), 8.24 (s, 1H), 7.96 (d, J=1.01 Hz, 1H), 7.22-7.28 (m, 1H), 6.62 (d, J=2.27 Hz, 1H), 5.45 (dd, J=5.56, 9.85 Hz, 1H), 3.84-3.98 (m, 2H), 3.77 (s, 3H), 3.13-3.32 (m, 2H), 2.55-2.67 (m, 1H), 2.44-2.55 (m, 1H), 2.35 (dd, J=7.71, 13.77 Hz, 1H), 1.63 (d, J=12.13 Hz, 1H), 1.31-1.58 (m, 6H), 1.06-1.19 (m, 2H)

Compound 19 was also purified via prep. HPLC (Waters System: Column is Phenomenex C18, 5μ, 150×50 mm, mobile phase A: 0.05% TFA in H2O and mobile phase B is 0.035% TFA in acetonitrile, Solvent gradient is 40-55% B); to yield compound 19 as a TFA salt.

Compound 19 was subjected to chiral separation on a Berger SFC instrument using Chiralpak AD-H media eluting with 20% IPOH to afford Compounds 105 and 106.

Compound 20: 2-(4-(cyclopropylsulfonyl)-1H-pyrazolo[3,4-c]pyridin-1-yl)-N-(pyrazin-2-yl)-3-(tetrahydro-2H-pyran-4-yl)propanamide

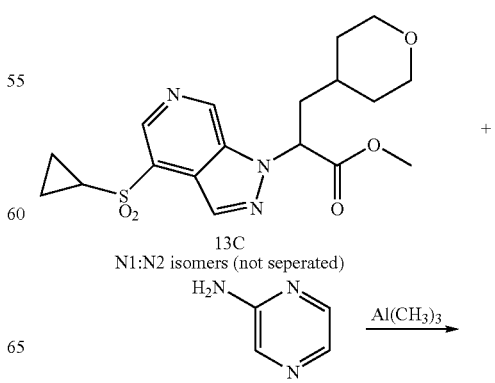

13C
N1:N2 isomers (not seperated)

Compound 19A: To a solution of 3,5-difluoro-4-formylbenzonitrile (9.76 g, 0.058 mol) in N-Methyl-2-pyrrolidinone (100 ml) at 0° C. was added anhydrous hydrazine (2.06 g, 0.064 mol) and the reaction mixture was stirred at 0° C. for 1 h. The solution was then allowed to warm to room temperature and stirred for 2 h (monitored by LC-MS for completion of reaction to hydrazone). The reaction mixture was then heated to 180° C. for 4 h. The solution was cooled to room temperature and sodiumcyclopropanesulfinate (9.73 g, 0.076 mol) was added. The reaction mixture was then heated overnight at 180° C. followed by heating at 190° C. for another 5 h. The reaction mixture was cooled to room temperature, diluted with EtOAc and filtered through a pad of Celite. The filtrate was washed with brine solution, dried over $Na_2SO_4$

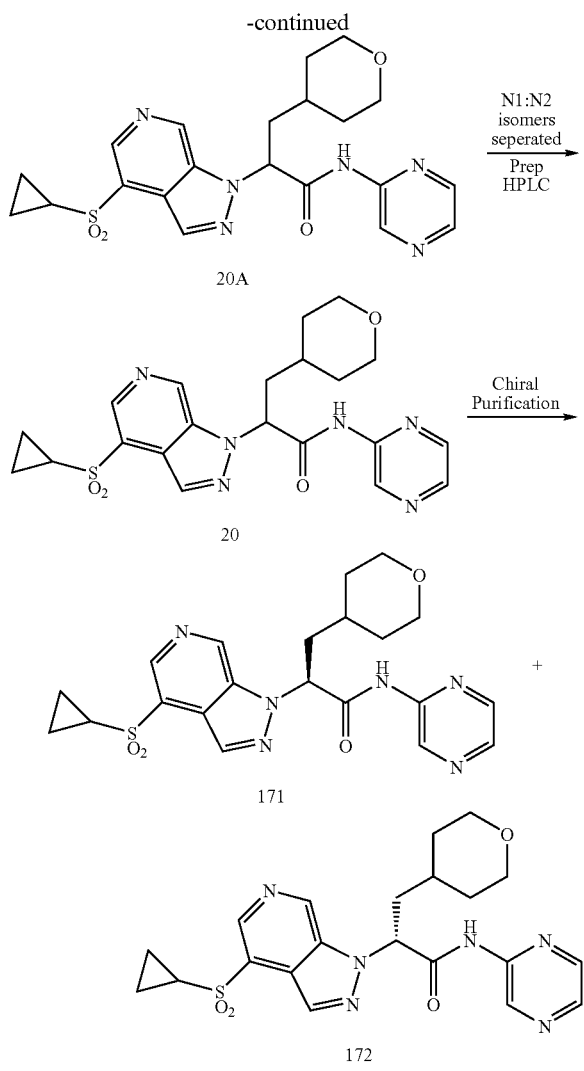

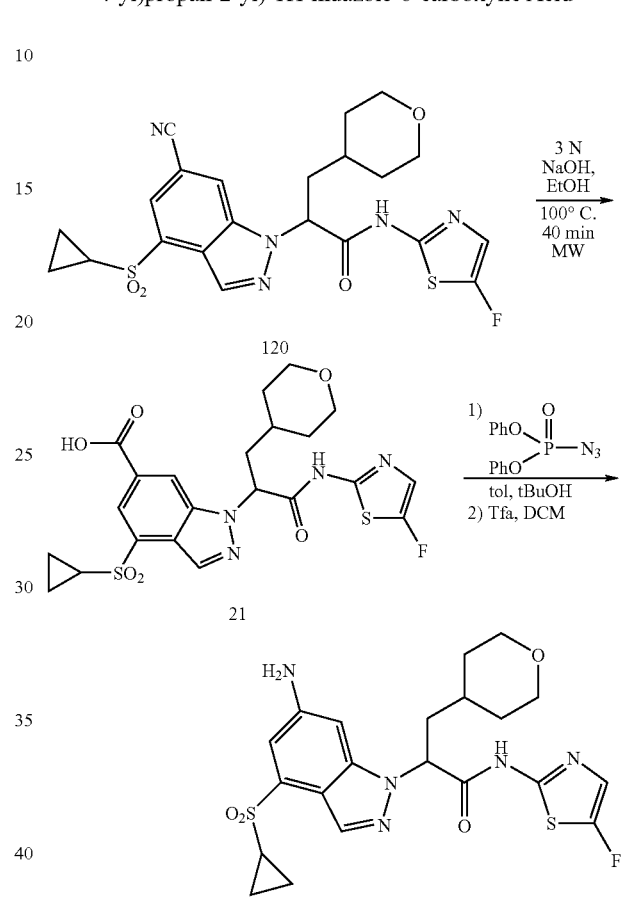

Compound 20A: To a solution of amino-pyrazine (3.4 g, 35.8 mmol) in DCE (40 ml) at 0° C. under a N₂ atmosphere was added trimethyl aluminum (2M in hexanes) (17.89 mL, 35.8 mmole). After 15 min, a solution of compound 13C (3.52 g, 8.95 mmole) in DCE (20 ml) was added to the reaction mixture and the solution was heated overnight at 90° C. The reaction mixture was then cooled in ice bath, quenched with 1N HCl and extracted 2× with EtOAc. The organic layer was dried over Na₂SO₄ and the crude residue as compound 20A Compound 20 was obtained from compound 20A as a TFA salt after purification using prep HPLC (Waters System: Column is Phenomenex C18, 5μ, 150×50 mm, mobile phase A: 0.05% TFA in H₂O and mobile phase B is 0.035% TFA in acetonitrile, Solvent gradient is 40-55% B); [M+H] calc'd for C₂₁H₂₄N₆O₄S 457.5; found, 457.55 ¹H NMR (400 MHz, DMSO-d₆) δ ppm 1.06-1.12 (m, 2H) 1.20-1.37 (m, 5H) 1.50 (d, J=11.62 Hz, 1H) 1.66 (d, J=11.12 Hz, 1H) 2.25-2.35 (m, 1H) 2.52-2.58 (m, 1H) 3.04-3.17 (m, 3H) 3.71-3.83 (m, 2H) 6.06 (dd, J=10.11, 5.31 Hz, 1H) 8.40 (d, J=2.53 Hz, 1H) 8.42-8.46 (m, 1H) 8.55 (s, 1H) 8.70 (s, 1H) 9.24 (d, J=1.26 Hz, 1H) 9.68 (s, 1H).

Compound 20 was obtained as a free base after purification using prep HPLC (Waters System: Column is Phenomenex C18, 5μ, 150×50 mm, mobile phase A: 10 mM NH₄HCO₃ in H₂O and mobile phase B is 10 mM NH₄HCO₃ in 80% acetonitrile, Solvent gradient is 30-35% B).

Compound 20 was subjected to chiral separation on a Berger SFC instrument using Chiralpak AD-H media eluting with 40% MeOH to afford Compounds 171 and 172.

Compound 21: 4-(cyclopropylsulfonyl)-1-(1-(5-fluorothiazol-2-ylamino)-1-oxo-3-(tetrahydro-2H-pyran-4-yl)propan-2-yl)-1H-indazole-6-carboxylic Acid A solution of 2-(6-cyano-4-(cyclopropylsulfonyl)-1H-indazol-1-yl)-N-(5-fluorothiazol-2-yl)-3-(tetrahydro-2H-pyran-4-yl)propanamide 120 (006 g, 0.11 mmol) in EtOH (5 mL) was added to a microwave vial followed by 3N NaOH (1 mL) and the mixture was heated at 100° C. for 40 min. The solvent was removed under vacuum and the residue was partitioned between 1N HCl and EtOAc. The organic layer was dried over Na₂SO₄ to give the crude carboxylic acid 21. [M+H] calc'd for C₂₂H₂₄FN₄O₆S₂ 523.1, found 523.3.

4-(cyclopropylsulfonyl)-1-(1-(5-fluorothiazol-2-ylamino)-1-oxo-3-(tetrahydro-2H-pyran-4-yl)propan-2-yl)-1H-indazole-6-carboxylic acid 21 (0.1 g, 0.19 mmol), diphenyl phosphorazidate (0.05 g, 0.19 mmol), triethylamine (0.03 g, 0.3 mmol), and tBuOH (0.016 g, 0.21 mmol) were combined in toluene (10 mL) and refluxed for 2 h. The solvent was removed and the residue treated with TFA/DCM (1/1) for 15 min. The mixture was concentrated under reduced pressure and purified using prep HPLC (Waters System: Column is Phenomenex C18, 5μ, 150×50 mm, mobile phase A: 0.05% TFA in H₂O and mobile phase B is 0.035% TFA in acetonitrile) to give Compound 142 as a reddish brown solid (50 mg); [M+H] calc'd for C₂₁H₂₅FN₅O₄S₂ 494.1, found 494.4

Compound 22: 2-(5-chloro-4-(cyclopropylsulfonyl)-1H-indazol-1-yl)-N-(5-fluorothiazol-2-yl)-3-(tetrahydro-2H-pyran-4-yl)propanamide
Compound 23: 2-(7-chloro-4-(cyclopropylsulfonyl)-1H-indazol-1-yl)-N-(5-flourothiazol-2-yl)-3-(tetrahydro-2H-pyran-4-yl)propanamide
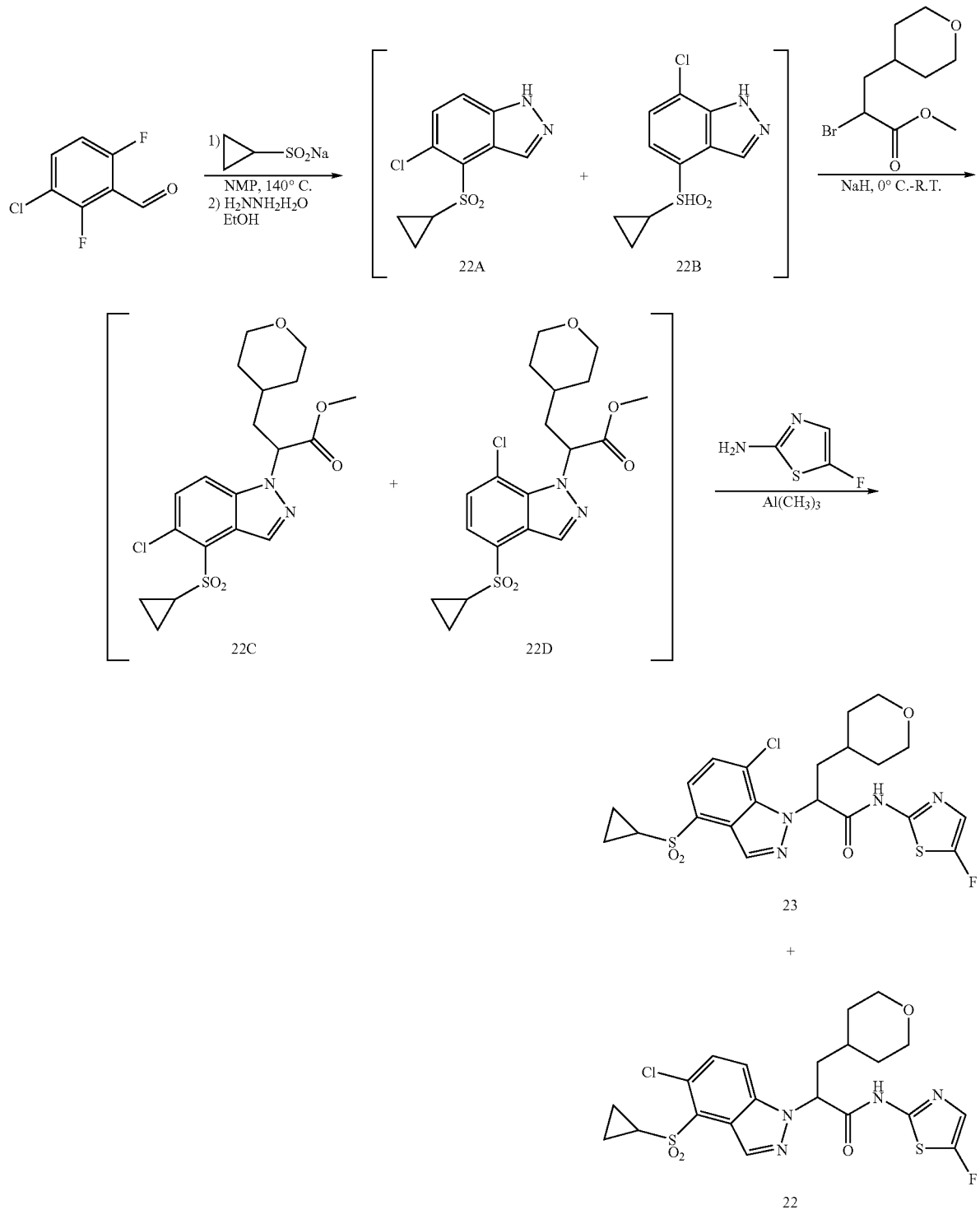

3-chloro-2,6-difluorobenzaldehyde (0.22 g, 1.23 mmol) and sodium cyclopropanesulfinate (0.19 g, 1.35 mmol) were combined in NMP (3 mL) and heated at 140° C. for 0.5 h. The reaction mixture was diluted with MeOH and purified using HPLC to give a mixture of 5-chloro-4-(cyclopropylsulfonyl)-1H-indazole 22A and 7-chloro-4-(cyclopropylsulfonyl)-1H-indazole 22 B as a white solid (0.14 g); [M+H] calc'd for $C_{10}H_{10}ClN_2O_2S$ 257.0, found 257.1. $^1$HNMR analysis confirmed the mixture of regioisomers in an approximate 1:1 ratio.

The mixture of 22A and 22 B (0.14 g, 0.54 mmol) was dissolved in DMF (4 mL) and the solution was chilled to 0° C. NaH (0.02 g, 0.65 mmol) was added and, when the reaction subsided, methyl 2-bromo-3-(tetrahydro-2H-pyran-4-yl)propanoate (0.20, 0.81 mmol) was added to the reaction mixture. The reaction mixture was then warmed to room temperature and stirred for 1 h. The reaction was quenched with a small volume of MeOH and concentrated under vacuum. The residue was portioned between EtOAc and 1N HCl. The organic layer was dried over $Na_2SO_4$, filtered and purified by flash column chromatography to afford compounds 22C and 22D as a clear oil (0.41 g); [M+H] calc'd for $C_{19}H_{24}ClN_2O_5S$ 427.1, found 427.3. The mixture of isomers was used as is in the next step.

Compounds 22 and 23: To a solution of 5-fluorothiazol-2-amine (0.29 g, 1.9 mmol) in DCE (5 ml) at 0° C. under a $N_2$ atmosphere was added trimethyl aluminum (2M in hexanes) (1.9 mmol). After 15 min, a solution of Compounds 22C and 22D (0.41 g, 0.96 mmole) in DCE (3 ml) was added to the reaction mixture and the solution was heated in a microwave oven at 100° C. for 1 h. The reaction mixture was then cooled in an ice bath, quenched with 1N HCl and extracted 2× with EtOAc. The organic layer was dried over $Na_2SO_4$ and the crude residue was purified by flash column chromatography using (DCM/MeOH, 0%-10%) to afford pure compounds 22 and 23. Compound 22: [M+H] calc'd for $C_{21}H_{23}ClFN_4O_4S_2$ 513.1, found 513.2; $^1$H NMR (400 MHz, CHLOROFORM-d) δ ppm 0.96-1.14 (m, 2H) 1.28-1.48 (m, 5H) 1.54 (br. s., 1H) 1.71 (d, J=7.58 Hz, 1H) 2.32-2.60 (m, 3H) 3.19-3.37 (m, 2H) 3.78-4.06 (m, 2H) 5.42 (dd, J=9.22, 6.19 Hz, 1H) 7.08 (br. s., 1H) 7.45-7.60 (m, 1H) 7.68 (d, J=7.58 Hz, 1H) 8.60 (s, 1H). Compound 23 [M+H] calc'd for $C_{21}H_{23}ClFN_4O_4S_2$ 513.1, found 513.2; $^1$H NMR (400 MHz, CHLOROFORM-d) δ ppm 0.93-1.20 (m, 1H) 1.30-1.60 (m, 5H) 1.67 (br. s., 3H) 2.16-2.38 (m, 1H) 2.46-2.74 (m, 2H) 3.17-3.44 (m, 2H) 3.79-4.01 (m, 2H) 6.49 (br. s., 1 H) 7.00 (d, J=2.53 Hz, 1H) 7.60 (dd, J=7.83, 4.04 Hz, 1H) 7.67-7.80 (m, 1H) 8.72 (s, 1H).

In addition to the foregoing, the above reaction schemes and variations thereof can be used to prepare the following.

| Ex. | Structure | Method | LCMS | NMR data |
| --- | --- | --- | --- | --- |
| 24 | 2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide | See Cmpd. 1 | [M + H] calc'd for $C_{21}H_{26}N_5O_5S_2$, 492.13; found 492.0 | $^1$H NMR (400 MHz, MeOD) δ ppm 1.00-1.14 (m, 2H) 1.16-1.47 (m, 6H) 1.66-1.84 (m, 2H) 2.15 (br. s., 1H) 2.32 (dd, J = 14.40, 6.82 Hz, 1H) 2.63-2.87 (m, 1H) 3.77 (s, 3H) 3.85-3.98 (m, 4H) 5.47 (dd, J = 10.23, 5.43 Hz, 1H) 6.84 (d, J = 8.84 Hz, 1H) 7.90-7.95 (m, 1H) 8.51 (s, 1H). |
| 25 | (R)-2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide | See Cmpds. 2 and 3 | [M + H] calc'd for $C_{21}H_{26}N_5O_5S_2$, 492.13; found 492.0 | $^1$H NMR (400 MHz, MeOD) δ ppm 1.00-1.14 (m, 2H) 1.16-1.47 (m, 6H) 1.66-1.84 (m, 2H) 2.15 (br. s., 1H) 2.32 (dd, J = 14.40, 6.82 Hz, 1H) 2.63-2.87 (m, 1H) 3.77 (s, 3H) 3.85-3.98 (m, 4H) 5.47 (dd, J = 10.23, 5.43 Hz, 1H) 6.84 (d, J = 8.84 Hz, 1H) 7.90-7.95 (m, 1H) 8.51 (s, 1H). |

| Ex. | Structure | Method | LCMS | NMR data |
|---|---|---|---|---|
| 26 | (S)-2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide | See Cmpds. 2 and 3 | [M + H] calc'd for $C_{21}H_{26}N_5O_5S_2$, 492.13; found 492.0 | $^1$H NMR (400 MHz, MeOD) δ ppm 1.00-1.14 (m, 2H) 1.16-1.47 (m, 6H) 1.66-1.84 (m, 2H) 2.15 (br. s., 1H) 2.32 (dd, J = 14.40, 6.82 Hz, 1H) 2.63-2.87 (m, 1H) 3.77 (s, 3H) 3.85-3.98 (m, 4H) 5.47 (dd, J = 10.23, 5.43 Hz, 1H) 6.84 (d, J = 8.84 Hz, 1H) 7.90-7.95 (m, 1H) 8.51 (s, 1H). |
| 27 | 2-(4-(cyclopropylsulfonyl)-3,5-dimethyl-1H-pyrazol-1-yl)-N-(5-fluorothiazol-2-yl)-3-(tetrahydro-2H-pyran-4-yl)propanamide | See Cmpd. 4 | [M + H] calc'd for $C_{19}H_{26}FN_4O_4S_2$, 457.13; found 457 | 1H NMR (400 MHz, CHLOROFORM-d) δ ppm 1.03 (d, J = 8.08 Hz, 2H) 1.21-1.45 (m, 5H) 1.50-1.63 (m, 2H) 2.09-2.31 (m, 2H) 2.48 (d, J = 3.28 Hz, 1H) 2.51 (s, 3H) 2.54 (s, 3H) 3.33 (d, J = 9.60 Hz, 2H) 3.87-4.01 (m, 2H) 4.96 (dd, J = 9.35, 5.81 Hz, 1H) 7.06 (d, J = 2.78 Hz, 1H) |
| 28 | 2-(4-(cyclopropylsulfonyl)-1H-pyrazol-1-yl)-N-(5-fluorothiazol-2-yl)-3-(tetrahydro-2H-pyran-4-yl)propanamide | See Cmpd. 4 | [M + H] calc'd for $C_{17}H_{22}FN_4O_4S_2$, 429.10, found 429 | 1H NMR (400 MHz, CHLOROFORM-d) δ ppm 1.09 (dq, J = 7.86, 2.43 Hz, 2H) 1.27-1.46 (m, 5H) 1.53 (d, J = 9.35 Hz, 1H) 1.68 (d, J = 11.87 Hz, 1H) 2.23 (d, J = 14.15 Hz, 1H) 2.07-2.31 (m, 1H) 2.51-2.62 (m, 1H) 3.33 (dd, J = 11.37, 2.27 Hz, 2H) 3.95 (t, J = 11.87 Hz, 2H) 5.19 (dd, J = 9.73, 5.68 Hz, 1H) 6.40 (br.s., 1H) 7.11 (d, J = 2.53 Hz, 1H) 7.94 (s, 1H) 8.09 (s, 1H) |

-continued

| Ex. | Structure | Method | LCMS | NMR data |
|---|---|---|---|---|
| 29 | 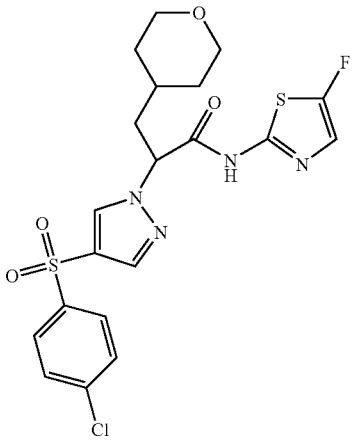 [SMILES: O=C(Nc1ncc(F)s1)C(CC1CCOCC1)n1cc(S(=O)(=O)c2ccc(Cl)cc2)cn1]<br>2-(4-(4-chlorophenylsulfonyl)-1H-pyrazol-1-yl)-N-(5-fluorothiazol-2-yl)-3-(tetrahydro-2H-pyran-4-yl)propanamide | See Cmpd. 4 | [M + H] calc'd for $C_{20}H_{21}ClFN_4O_4S_2$, 499.06, found 499 | 1H NMR (400 MHz, CHLOROFORM-d) δ ppm 1.32 (br. s., 2H) 1.34 (d, J = 4.29 Hz, 1H) 1.48 (br. s., 1H) 1.62 (br. s., 1H) 2.16 (d, J = 6.57 Hz, 2H) 3.23-3.34 (m, 2H) 3.93 (dd, J = 16.42, 11.87 Hz, 2H) 5.11 (dd, J = 9.47, 6.19 Hz, 1H) 5.50 (br. s., 1H) 7.08 (d, J = 2.78 Hz, 1H) 7.51 (d, J = 8.59 Hz, 2H) 7.87-7.93 (m, 3H) 8.10 (s, 1H) |
| 30 | 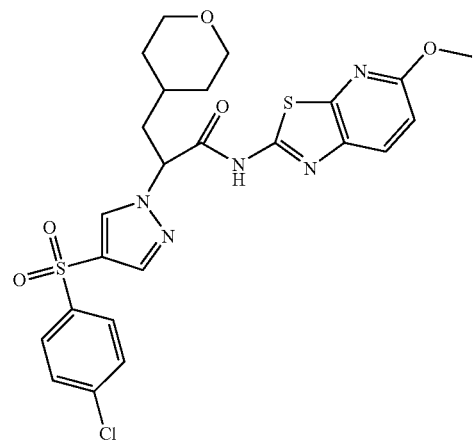 [SMILES: COc1ccc2nc(NC(=O)C(CC3CCOCC3)n3cc(S(=O)(=O)c4ccc(Cl)cc4)cn3)sc2n1]<br>2-(4-(4-chlorophenylsulfonyl)-1H-pyrazol-1-yl)-N-(5-methoxythiazolo[5,4-b]pyridin-2-yl)-3-(tetrahydro-2H-pyran-4-yl)propanamide | See Cmpd. 4 | [M + H] calc'd for $C_{24}H_{25}ClN_5O_5S_2$, 562.09, found 562 | 1H NMR (400 MHz, CHLOROFORM-d) δ ppm 1.34 (t, J = 10.11 Hz, 2H) 1.36 (br. s., 1H) 1.50 (br. s., 1H) 1.65 (br. s., 1H) 2.24 (d, J = 4.55 Hz, 1H) 2.21 (t, J = 6.06 Hz, 1H) 3.27-3.36 (m, 2H) 4.00 (s, 3H), 3.87-3.98 (m, 2H) 5.17 (dd, J = 9.35, 6.06 Hz, 1H) 6.87 (d, J = 8.84 Hz, 1H) 7.51 (d, J = 8.34 Hz, 2H) 7.86-7.93 (m, 3H) 7.95 (s, 1H) 8.11 (s, 1H) |
| 31 | 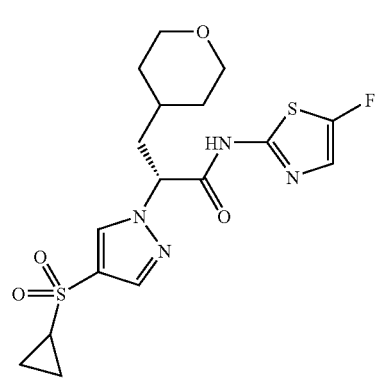 [SMILES: O=C(Nc1ncc(F)s1)[C@@H](CC1CCOCC1)n1cc(S(=O)(=O)C2CC2)cn1]<br>(R)-2-(4-(cyclopropylsulfonyl)-1H-pyrazol-1-yl)-N-(5-fluorothiazol-2-yl)-3-(tetrahydro-2H-pyran-4-yl)propanamide | See Cmpds. 2 and 3 | [M + H] calc'd for $C_{17}H_{22}FN_4O_4S_2$, 429.10, found 429 | 1H NMR (400 MHz, CHLOROFORM-d) δ ppm 1.09 (dq, J = 7.86, 2.43 Hz, 2H) 1.27-1.46 (m, 5H) 1.53 (d, J = 9.35 Hz, 1H) 1.68 (d, J = 11.87 Hz, 1H) 2.23 (d, J = 14.15 Hz, 1H) 2.07-2.31 (m, 1H) 2.51-2.62 (m, 1H) 3.33 (dd, J = 11.37, 2.27 Hz, 2H) 3.95 (t, J = 11.87 Hz, 2H) 5.19 (dd, J = 9.73, 5.68 Hz, 1H) 6.40 (br. s., 1H) 7.11 (d, J = 2.53 Hz, 1H) 7.94 (s, 1H) 8.09 (s, 1H) |

| Ex. | Structure | Method | LCMS | NMR data |
|---|---|---|---|---|
| 32 | 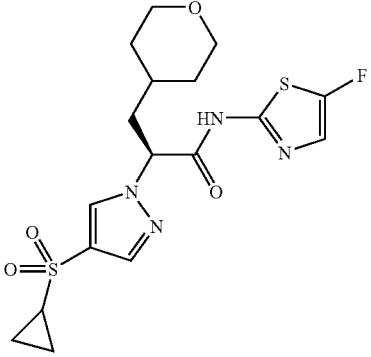 [SMILES: O=C(Nc1ncc(F)s1)[C@H](CC1CCOCC1)n1cc(S(=O)(=O)C2CC2)cn1]<br>(S)-2-(4-(cyclopropylsulfonyl)-1H-pyrazol-1-yl)-N-(5-fluorothiazol-2-yl)-3-(tetrahydro-2H-pyran-4-yl)propanamide | See Cmpds. 2 and 3 | [M + H] calc'd for $C_{17}H_{22}FN_4O_4S_2$, 429.10, found 429 | 1H NMR (400 MHz, CHLOROFORM-d) δ ppm 1.09 (dq, J = 7.86, 2.43 Hz, 2H) 1.27-1.46 (m, 5H) 1.53 (d, J = 9.35 Hz, 1H) 1.68 (d, J = 11.87 Hz, 1H) 2.23 (d, J = 14.15 Hz, 1H) 2.07-2.31 (m, 1H) 2.51-2.62 (m, 1H) 3.33 (dd, J = 11.37, 2.27 Hz, 2H) 3.95 (t, J = 11.87 Hz, 2H) 5.19 (dd, J = 9.73, 5.68 Hz, 1H) 6.40 (br. s., 1H) 7.11 (d, J = 2.53 Hz, 1H) 7.94 (s, 1H) 8.09 (s, 1H) |
| 33 | 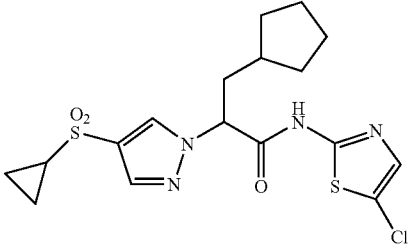 [SMILES: O=C(Nc1ncc(Cl)s1)C(CC1CCCC1)n1cc(S(=O)(=O)C2CC2)cn1]<br>N-(5-chlorothiazol-2-yl)-3-cyclopentyl-2-(4-(cyclopropylsulfonyl)-1H-pyrazol-1-yl)propanamide | See Cmpd. 4 | [M + H] calc'd for $C_{17}H_{22}ClN_5O_3S_2$, 429.07, found 429 | $^1$H NMR (400 MHz, CHLOROFORM-d) δ ppm 1.15 (m, 4H) 1.36 (m, 2H) 1.59 (m, 6H) 1.79 (m, 1H) 2.29 (m, 2H) 2.56 (m, 1H), 5.03 (m, 1H) 7.35 (s, 1H) 7.99 (s, 1H) 8.06 (m, 1H) |
| 34 | 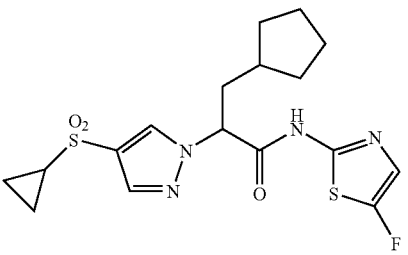 [SMILES: O=C(Nc1ncc(F)s1)C(CC1CCCC1)n1cc(S(=O)(=O)C2CC2)cn1]<br>3-cyclopentyl-2-(4-(cyclopropylsulfonyl)-1H-pyrazol-1-yl)-N-(5-fluorothiazol-2-yl)propanamide | See Cmpd. 4 | [M + H] calc'd for $C_{17}H_{22}FN_4O_3S_2$, 413.50, found 413 | $^1$H NMR (400 MHz, CHLOROFORM-d) δ ppm 1.13 (m, 4H) 1.37 (m, 2H) 1.57 (m, 6H) 1.79 (m, 1H) 2.25 (m, 2H) 2.55 (m, 1H), 5.02 (m, 1H) 7.14 (s, 1H) 7.97 (s, 1H) 8.17 (s, 1H) |
| 35 | 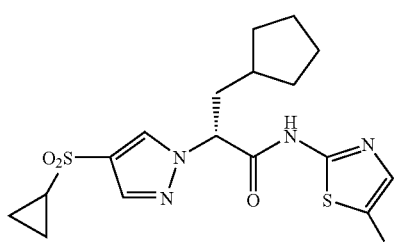<br>(R)-3-cyclopentyl-2-(4-(cyclopropylsulfonyl)-1H-pyrazol-1-yl)-N-(5-fluorothiazol-2-yl)propanamide | See Cmpd. 4 | [M + H] calc'd for $C_{17}H_{22}FN_4O_3S_2$, 413.50, found 413.36 | $^1$H NMR (400 MHz, CHLOROFORM-d) δ ppm 1.13 (m, 4H) 1.37 (m, 2H) 1.57 (m, 6H) 1.79 (m, 1H) 2.25 (m, 2H) 2.55 (m, 1H), 5.02 (m, 1H) 7.14 (s, 1H) 7.97 (s, 1H) 8.17 (s, 1H) |

| Ex. | Structure | Method | LCMS | NMR data |
|---|---|---|---|---|
| 36 | 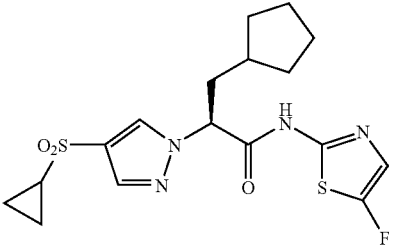 [SMILES: O=C(Nc1ncc(F)s1)[C@H](CC1CCCC1)n1cc(S(=O)(=O)C2CC2)cn1]<br>(S)-3-cyclopentyl-2-(4-(cyclopropylsulfonyl)-1H-pyrazol-1-yl)-N-(5-fluorothiazol-2-yl)propanamide | See Cmpd. 4 | [M + H] calc'd for $C_{17}H_{22}FN_4O_3S_2$, 413.50, found 413.36 | $^1$H NMR (400 MHz, CHLOROFORM-d) δ ppm 1.13 (m, 4H) 1.37 (m, 2H) 1.57 (m, 6H) 1.79 (m, 1H) 2.25 (m, 2H) 2.55 (m, 1H), 5.02 (m, 1H) 7.14 (s, 1H) 7.97 (s, 1H) 8.17 (s, 1H) |
| 37 | 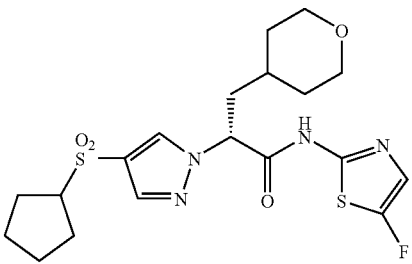 [SMILES: O=C(Nc1ncc(F)s1)[C@@H](CC1CCOCC1)n1cc(S(=O)(=O)C2CCCC2)cn1]<br>2-(4-(cyclopentylsulfonyl)-1H-pyrazol-1-yl)-N-(5-fluorothiazol-2-yl)-3-(tetrahydro-2H-pyran-4-yl)propanamide | See Cmpd. 5 | [M + H] calc'd for $C_{19}H_{26}FN_4O_4S_2$, 457.56, found 457 | $^1$H NMR (400 MHz, CHLOROFORM-d) δ ppm 1.34 (m, 3H) 1.50 (m, 1H) 1.65 (m, 3H) 1.77 (m, 2H) 2.02 (m, 4H) 2.16 (m, 1H), 2.24 (m, 1H) 3.29 (m, 2H) 3.50 (m, 1H) 3.94 (t, J = 16, 16 Hz, 2H) 5.13 (m, 1H) 7.08 (d, J = 4 Hz, 1H) 7.98 (s, 1H) 8.06 (s, 1H) |
| 38 | 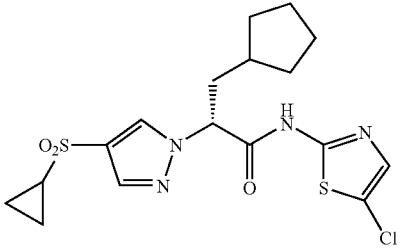 [SMILES: O=C(Nc1ncc(Cl)s1)[C@@H](CC1CCCC1)n1cc(S(=O)(=O)C2CC2)cn1]<br>(R)-N-(5-chlorothiazol-2-yl)-3-cyclopentyl-2-(4-(cyclopropylsulfonyl)-1H-pyrazol-1-yl)propanamide | See Cmpd. 4 | [M + H] calc'd for $C_{17}H_{22}ClN_4O_3S_2$, 429.96, found 429.36 | $^1$H NMR (400 MHz, CHLOROFORM-d) δ ppm 1.15 (m, 4H) 1.36 (m, 2H) 1.59 (m, 6) 1.79 (m, 1H) 2.29 (m, 2H) 2.56 (m, 1H), 5.03 (m, 1H) 7.35 (s, 1H) 7.99 (s, 1H) 8.06 (m, 1H) |
| 39 | 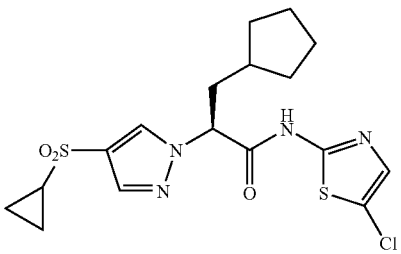 [SMILES: O=C(Nc1ncc(Cl)s1)[C@H](CC1CCCC1)n1cc(S(=O)(=O)C2CC2)cn1]<br>(S)-N-(5-chlorothiazol-2-yl)-3-cyclopentyl-2-(4-(cyclopropylsulfonyl)-1H-pyrazol-1-yl)propanamide | See Cmpd. 4 | [M + H] calc'd for $C_{17}H_{22}ClN_4O_3S_2$, 429.96, found 429.3 | $^1$H NMR (400 MHz, CHLOROFORM-d) δ ppm 1.15 (m, 4H) 1.36 (m, 2H) 1.59 (m, 6) 1.79 (m, 1H) 2.29 (m, 2H) 2.56 (m, 1H), 5.03 (m, 1H) 7.35 (s, 1H) 7.99 (s, 1H) 8.06 (m, 1H) |

| Ex. | Structure | Method | LCMS | NMR data |
|---|---|---|---|---|
| 40 | (R)-N-(5-chlorothiazol-2-yl)-2-(4-(cyclopropylsulfonyl)-1H-pyrazol-1-yl)-3-(tetrahydro-2H-pyran-4-yl)propanamide | See Cmpds. 2 and 3 | [M + H] calc'd for $C_{17}H_{22}ClN_4O_4S_2$, 445.07; found 445.2. | 1H NMR (400 MHz, CHLOROFORM-d) δ ppm 0.93-1.75 (m, 9H) 2.19 (br. s., 2H) 2.55 (br. s., 1H) 3.31 (br. s., 2H) 3.94 (br. s., 2H) 5.10 (br. s., 1H) 7.32 (s, 1H) 8.01 (d, J = 9.35 Hz, 2H) 10.35 (bs, 1H) |
| 41 | N-(5-fluorothiazol-2-yl)-2-(4-(methylsulfonyl)-1H-indazole-1-yl)-3-(tetrahydro-2H-pyran-4-yl)propanamide | See Cmpd 10 | [M + H] calc'd for $C_{19}H_{21}FN_4O_4S_2$, 454, found 454 | $^1$H NMR (400 MHz, METHANOL-$d_4$) δ ppm 1.21-1.42 (m, 3H) 1.42-1.49 (m, 1H) 1.66-1.74 (m, 1H) 2.13-2.22 (m, 1H) 2.49-2.58 (m, 1H) 3.13-3.26 (m, 2H) 3.29 (br. s., 3H) 3.78-3.89 (m, 2H) 5.65 (dd, J = 10.61, 4.80 Hz, 1H) 7.08 (d, J = 2.53 Hz, 1H) 7.30-7.41 (m, 2H) 7.67 (d, J = 8.08 Hz, 1H) 8.11 (s, 1H) |
| 42 | (S)-N-(5-chlorothiazol-2-yl)-2-(4-(cyclopropylsulfonyl)-1H-pyrazol-1-yl)-3-(tetrahydro-2H-pyran-4-yl)propanamide | See Cmpds. 2 and 3 | [M + H] calc'd for $C_{17}H_{22}ClN_4O_4S_2$, 445.07; found 445.2. | 1H NMR (400 MHz, CHLOROFORM-d) δ ppm 0.93-1.75 (m, 9H) 2.19 (br. s., 2H) 2.55 (br. s., 1H) 3.31 (br. s., 2H) 3.94 (br. s., 2H) 5.10 (br. s., 1H) 7.32 (s, 1H) 8.01 (d, J = 9.35 Hz, 2H) 10.35 (bs, 1H) |
| 43 | (R)-2-(4-(cyclopentylsulfonyl)-1H-pyrazol-1-yl)-N-(5-fluorothiazol-2-yl)-3-(tetrahydro-2H-pyran-4-yl)propanamide | See Cmpd. 5 | [M + H] calc'd for $C_{19}H_{26}FN_4O_4S_2$, 457.56, found 457 | $^1$H NMR (400 MHz, CHLOROFORM-d) δ ppm 1.34 (m, 3H) 1.50 (m, 1H) 1.65 (m, 3H) 1.77 (m, 2H) 2.02 (m, 4H) 2.16 (m, 1H), 2.24 (m, 1H) 3.29 (m, 2H) 3.50 (m, 1H) 3.94 (t, J = 16, 16 Hz, 2H) 5.13 (m, 1H) 7.08 (d, J = 4 Hz, 1H) 7.98 (s, 1H) 8.06 (s, 1H) |

| Ex. | Structure | Method | LCMS | NMR data |
|---|---|---|---|---|
| 44 | 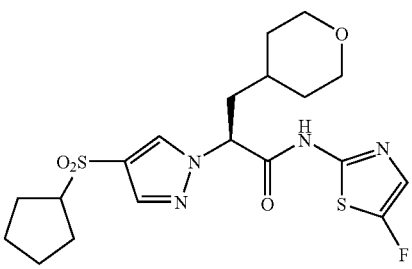 [SMILES: O=C(Nc1ncc(F)s1)[C@H](CC1CCOCC1)n1cc(S(=O)(=O)C2CCCC2)cn1]<br>(S)-2-(4-(cyclopentylsulfonyl)-1H-pyrazol-1-yl)-N-(5-fluorothiazol-2-yl)-3-(tetrahydro-2H-pyran-4-yl)propanamide | See Cmpd. 5 | [M + H] calc'd for $C_{19}H_{26}FN_4O_4S_2$, 457.56, found 457 | $^1$H NMR (400 MHz, CHLOROFORM-d) δ ppm 1.34 (m, 3H) 1.50 (m, 1H) 1.65 (m, 3H) 1.77 (m, 2H) 2.02 (m, 4H) 2.16 (m, 1H) 2.24 (m, 1H) 3.29 (m, 2H) 3.50 (m, 1H) 3.94 (t, J = 16, 16 Hz, 2H) 5.13 (m, 1H) 7.08 (d, J = 4 Hz, 1H) 7.98 (s, 1H) 8.06 (s, 1H) |
| 45 | 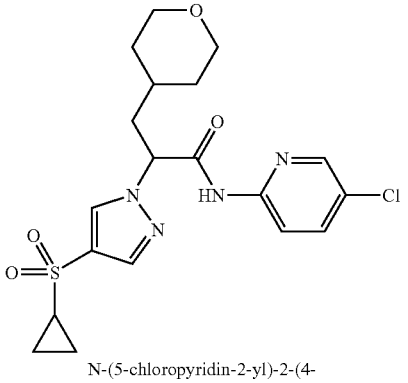<br>N-(5-chloropyridin-2-yl)-2-(4-(cyclopropylsulfonyl)-1H-pyrazol-1-yl)-3-(tetrahydro-2H-pyran-4-yl)propanamide | See Cmpd. 4 | [M + H] calc'd for $C_{19}H_{24}ClN_4O_4S$, 439.11, found 439 | 1H NMR (400 MHz, CHLOROFORM-d) δ ppm 1.08 (dd, J = 8.08, 2.02 Hz, 2H) 130-1.44 (m, 1H) 1.36 (dd, J = 4.42, 2.15 Hz, 4H) 1.53 (d, J = 9.09 Hz, 1H) 1.68 (d, J = 9.85 Hz, 1H) 2.19 (t, J = 6.32 Hz, 1H) 2.25 (dd, J = 9.85, 4.04 Hz, 1H) 2.57 (ddd, J = 7.96, 4.80, 3.16 Hz, 1H) 3.31 (td, J = 11.24, 8.08 Hz, 1H) 3.25-3.37 (m, 1H) 3.88-4.00 (m, 2H) 5.12 (dd, J = 9.73, 5.68 Hz, 1H) 7.74 (dd, J = 8.84, 2.53 Hz, 1H) 7.98 (s, 1H) 8.11 (s, 1H) 8.20 (d, J = 8.84 Hz, 1H) 8.24 (d, J = 2.27 Hz, 1H) 9.66 (br. s., 1H) |
| 46 | 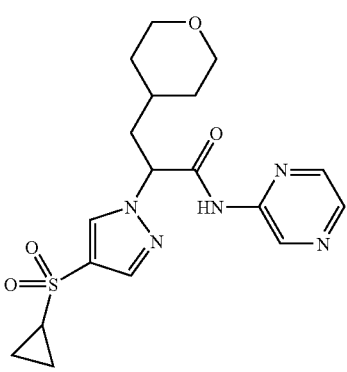 [SMILES: O=C(Nc1cnccn1)C(CC1CCOCC1)n1cc(S(=O)(=O)C2CC2)cn1]<br>2-(4-(cyclopropylsulfonyl)-1H-pyrazol-1-yl)-N-(pyrazin-2-yl)-3-(tetrahydro-2H-pyran-4-yl)propanamide | See Cmpd. 4 | [M + H] calc'd for $C_{18}H_{24}N_5O_4S$, 406.15, found 406 | 1H NMR (400 MHz, CHLOROFORM-d) δ ppm 1.09 (dd, J = 7.71, 1.64 Hz, 2H) 1.29-1.47 (m, 5H) 1.54 (br. s., 1H) 1.66 (br. s., 1H) 2.14-2.38 (m, 2H) 2.51-2.63 (m, 1H) 3.23-3.42 (m, 2H) 3.87-4.03 (m, 2H) 5.07 (dd, J = 9.60, 5.56 Hz, 1H) 8.03 (d, J = 6.57 Hz, 2H) 8.32 (s, 1H) 8.42 (d, J = 2.27 Hz, 1H) 9.27 (br. s., 1H) 9.50 (s, 1H) |

-continued

| Ex. | Structure | Method | LCMS | NMR data |
|---|---|---|---|---|
| 47 | 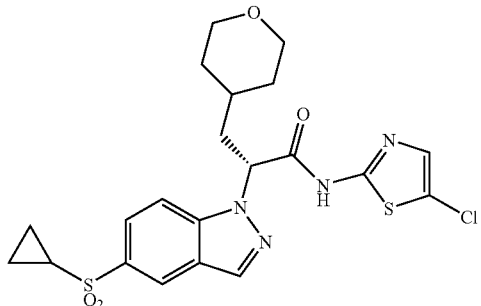<br>(R)-N-(5-chlorothiazol-2-yl)-2-(5-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | |
| 48 | 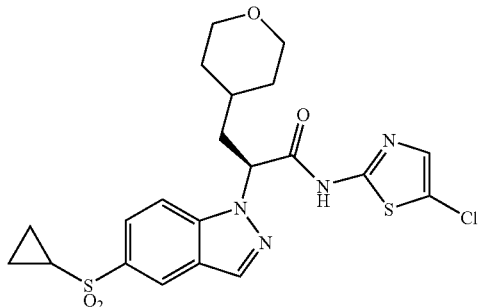<br>(S)-N-(5-chlorothiazol-2-yl)-2-(5-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | |
| 49 | 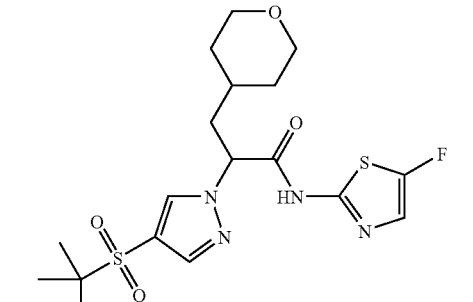<br>2-(4-(tert-butylsulfonyl)-1H-pyrazol-1-yl)-N-(5-fluorothiazol-2-yl)-3-(tetrahydro-2H-pyran-4-yl)propanamide | See Cmpd. 4 | [M + H] calc'd for $C_{18}H_{26}FN_4O_4S_2$ 445.13, found 445.3 | 1H NMR (400 MHz, CHLOROFORM-d) δ ppm 1.29-1.45 (m, 3H) 1.38 (s, 9H) 1.51 (d, J = 2.27 Hz, 1H) 1.64 (d, J = 11.62 Hz, 1H) 2.04-2.29 (m, 2H) 3.14-3.35 (m, 2H) 3.80-4.02 (m, 2H) 5.12 (dd, J = 9.85, 5.81 Hz, 1H) 7.12 (d, J = 2.78 Hz, 1H) 7.95 (s, 1H) 8.03 (s, 1H) |
| 50 | 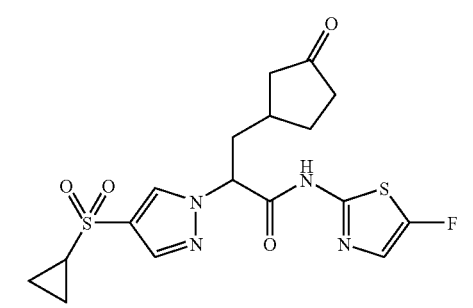 [SMILES: O=C1CCC(CC(C(=O)Nc2ncc(F)s2)n2cc(S(=O)(=O)C3CC3)cn2)C1]<br>2-(4-(cyclopropylsulfonyl)-1H-pyrazol-1-yl)-N-(5-fluorothiazol-2-yl)-3-(3-oxocyclopentyl)propanamide | See Cmpd. 4 | [M + H] calc'd for $C_{17}H_{20}FN_4O_4S_2$ 427.08, found 427.1 | |

-continued

| Ex. | Structure | Method | LCMS | NMR data |
|---|---|---|---|---|
| 51 | 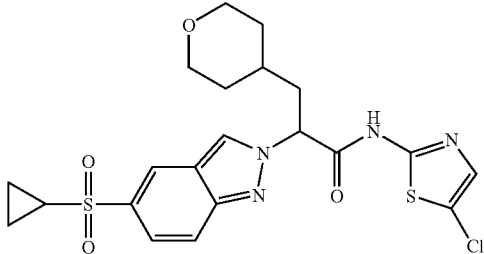 [SMILES: O=C(Nc1ncc(Cl)s1)C(CC1CCOCC1)n1cc2cc(S(=O)(=O)C3CC3)ccc2n1]<br>N-(5-chlorothiazol-2-yl)-2-(5-(cyclopropylsulfonyl)-2H-indazol-2-yl)-3-(tetrahydro-2H-pyran-4-yl)propanamide | See Cmpd. 10 | [M + H] calc'd for $C_{21}H_{24}ClN_4O_4S_2$ 496.01, found 496.1 | $^1$H NMR (400 MHz, CHLOROFORM-d) δ ppm 1.00-1.13 (m, 2H) 1.20-1.64 (m, 7H) 1.76 (d, J = 12.38 Hz, 1H) 2.27-2.42 (m, 1H) 2.43-2.60 (m, 2H) 3.30 (t, J = 10.86 Hz, 2H) 3.87-4.08 (m, 2H) 5.57 (dd, J = 9.73, 5.18 Hz, 1H) 7.32 (br. s., 1H) 7.70-7.82 (m, 1H) 7.87 (d, J = 9.09 Hz, 1H) 8.42 (d, J = 5.56 Hz, 2H) |
| 52 | 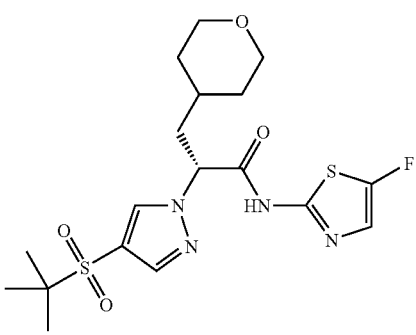 [SMILES: CC(C)(C)S(=O)(=O)c1cnn([C@H](CC2CCOCC2)C(=O)Nc2ncc(F)s2)c1]<br>(R)-2-(4-(tert-butylsulfonyl)-1H-pyrazol-1-yl)-N-(5-fluorothiazol-2-yl)-3-(tetrahydro-2H-pyran-4-yl)propanamide | See Cmpds. 2 and 3 | [M + H] calc'd for $C_{18}H_{26}FN_4O_4S_2$ 445.13, found 445.3 | 1H NMR (400 MHz, CHLOROFORM-d) δ ppm 1.29-1.45 (m, 3H) 1.38 (s, 9H) 1.51 (d, J = 2.27 Hz, 1H) 1.64 (d, J = 11.62 Hz, 1H) 2.04-2.29 (m, 2H) 3.14-3.35 (m, 2H) 3.80-4.02 (m, 2H) 5.12 (dd, J = 9.85, 5.81 Hz, 1H) 7.12 (d, J = 2.78 Hz, 1H) 7.95 (s, 1H) 8.03 (s, 1H) |
| 53 | 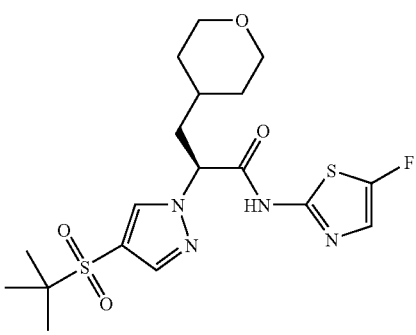 [SMILES: CC(C)(C)S(=O)(=O)c1cnn([C@@H](CC2CCOCC2)C(=O)Nc2ncc(F)s2)c1]<br>(S)-2-(4-(tert-butylsulfonyl)-1H-pyrazol-1-yl)-N-(5-fluorothiazol-2-yl)-3-(tetrahydro-2H-pyran-4-yl)propanamide | See Cmpds. 2 and 3 | [M + H] calc'd for $C_{18}H_{26}FN_4O_4S_2$ 445.13, found 445.3 | 1H NMR (400 MHz, CHLOROFORM-d) δ ppm 1.29-1.45 (m, 3H) 1.38 (s, 9H) 1.51 (d, J = 2.27 Hz, 1H) 1.64 (d, J = 11.62 Hz, 1H) 2.04-2.29 (m, 2H) 3.14-3.35 (m, 2H) 3.80-4.02 (m, 2H) 5.12 (dd, J = 9.85, 5.81 Hz, 1H) 7.12 (d, J = 2.78 Hz, 1H) 7.95 (s, 1H) 8.03 (s, 1H) |
| 54 | 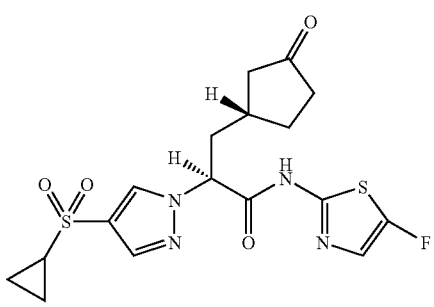 [SMILES: O=C1CC[C@H](C[C@@H](C(=O)Nc2ncc(F)s2)n2cc(S(=O)(=O)C3CC3)cn2)C1]<br>(S)-2-(4-(cyclopropylsulfonyl)-1H-pyrazol-1-yl)-N-(5-fluorothiazol-2-yl)-3-((R)-3-oxocyclopentyl)propanamide | See Cmpd. 4 | [M + H] calc'd for $C_{17}H_{20}FN_4O_4S_2$ 427.08, found 427.1 | |

| Ex. | Structure | Method | LCMS | NMR data |
|---|---|---|---|---|
| 55 | 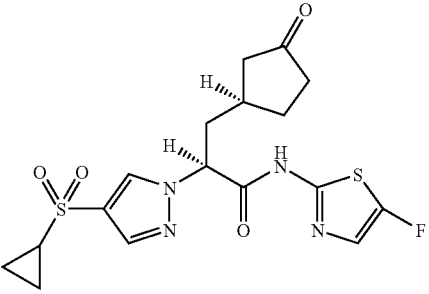 [SMILES: O=C1CC[C@@H](C[C@@H](C(=O)Nc2ncc(F)s2)n2cc(S(=O)(=O)C3CC3)cn2)C1]<br>(S)-2-(4-(cyclopropylsulfonyl)-1H-pyrazol-1-yl)-N-(5-fluorothiazol-2-yl)-3-((S)-3-oxocyclopentyl)propanamide | See Cmpd. 4 | [M + H] calc'd for $C_{17}H_{20}FN_4O_4S_2$ 427.08, found 427.1 | |
| 56 | 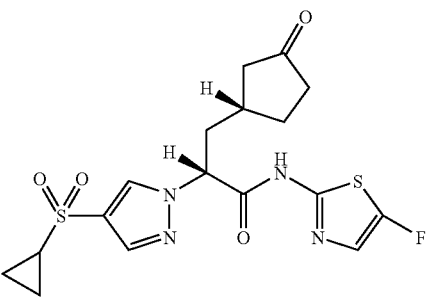 [SMILES: O=C1CC[C@H](C[C@H](C(=O)Nc2ncc(F)s2)n2cc(S(=O)(=O)C3CC3)cn2)C1]<br>(R)-2-(4-(cyclopropylsulfonyl)-1H-pyrazol-1-yl)-N-(5-fluorothiazol-2-yl)-3-((R)-3-oxocyclopentyl)propanamide | See Cmpd. 4 | [M + H] calc'd for $C_{17}H_{20}FN_4O_4S_2$ 427.08, found 427.1 | |
| 57 | 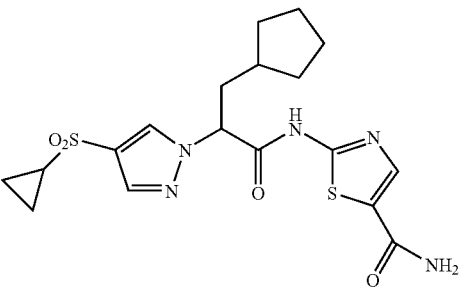 [SMILES: NC(=O)c1cnc(NC(=O)C(CC2CCCC2)n2cc(S(=O)(=O)C3CC3)cn2)s1]<br>(2-(3-cyclopentyl-2-(4-(cyclopropylsulfonyl)-1H-pyrazol-1-yl)propanamido)thiazole-5-carboxamide | See Cmpds. 6 and 7 | [M + H] calc'd for $C_{18}H_{24}N_5O_4S_2$ 438.54, found 438 | $^1$H NMR (400 MHz, DMSO-d6). δ ppm 1.06 (m, 4H) 1.27 (m, 1H) 1.56 (m, 6H) 2.11 (m, 1H) 2.33 (m, 1H) 2.84 (m, 1H), 3.75 (s, 2H) 5.36 (m, 1H) 7.95 (s, 1H) 8.08 (s, 1H) 8.63 (s, 1H) |
| 58 | 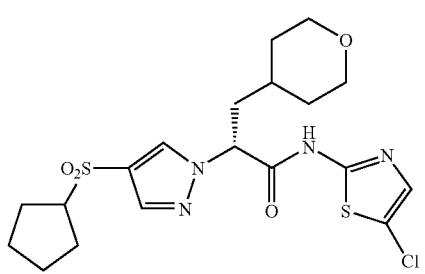 [SMILES: O=C(Nc1ncc(Cl)s1)[C@@H](CC1CCOCC1)n1cc(S(=O)(=O)C2CCCC2)cn1]<br>(R)-N-(5-chlorothiazol-2-yl)-2-(4-(cyclopentylsulfonyl)-1H-pyrazol-1-yl)-3-(tetrahydro-2H-pyran-4-yl)propanamide | See Cmpd. 5 | [M + H] calc'd for $C_{19}H_{26}ClN_4O_4S_2$ 474.01, found 474 | $^1$H NMR (400 MHz, CHLOROFORM-d) δ ppm 1.34 (m, 3H) 1.50 (m, 1H) 1.65 (m, 3H) 1.77 (m, 2H) 2.02 (m, 4H) 2.19 (m, 2H), 3.29 (m, 2H) 3.52 (m, 1H) 3.95 (t, J = 12, 12 Hz, 2H) 5.16 (m, 1H) 7.32 (d, J = 4 Hz, 1H) 7.98 (s, 1H) 8.06 (s, 1H) |

| Ex. | Structure | Method | LCMS | NMR data |
|---|---|---|---|---|
| 59 | 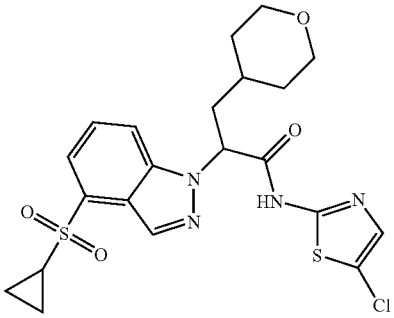 [SMILES: O=C(Nc1ncc(Cl)s1)C(CC1CCOCC1)n1ncc2c(S(=O)(=O)C3CC3)cccc21]<br>N-(5-chlorothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | $^1$H NMR (400 MHz, DMSO-$d_6$) δ ppm 1.00-1.12 (m, 2H) 1.14-1.38 (m, 5H) 1.45 (br. s., 1H) 1.60 (br. s., 1H) 2.26 (d, J = 6.57 Hz, 1H) 2.46 (br. s., 1H) 2.91-3.21 (m, 3H) 3.68-3.84 (m, 2H) 5.87 (dd, J = 9.98, 4.93 Hz, 1H) 7.56 (s, 1H) 7.63-7.76 (m, 2H) 8.18 (d, J = 8.34 Hz, 1H) 8.45 (s, 1H) |
| 60 | 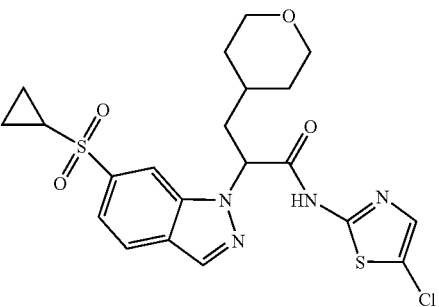 [SMILES: O=C(Nc1ncc(Cl)s1)C(CC1CCOCC1)n1ncc2ccc(S(=O)(=O)C3CC3)cc21]<br>N-(5-chlorothiazol-2-yl)-2-(6-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | $^1$H NMR (400 MHz, DMSO-$d_6$) δ ppm 1.00-1.09 (m, 2H) 1.12-1.37 (m, 5H) 1.45 (d, J = 8.08 Hz, 1H) 1.60 (d, J = 12.13 Hz, 1H) 2.21-2.33 (m, 1H) 2.35-2.47 (m, 1H) 2.83-2.94 (m, 1H) 3.00-3.17 (m, 2H) 3.70-3.85 (m, 2H) 5.93 (dd, J = 9.60, 5.31 Hz, 1H) 7.56 (s, 1H) 7.64-7.72 (m, 1H) 8.08 (d, J = 8.59 Hz, 1H) 8.41 (d, J = 10.86 Hz, 2H) |
| 61 | 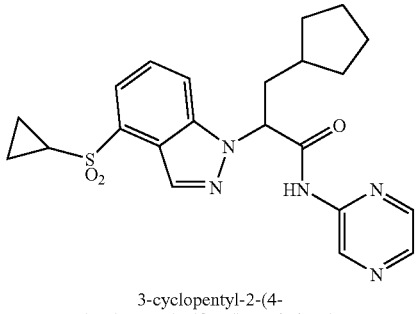<br>3-cyclopentyl-2-(4-(cyclopropylsulfonyl)-1H-indazol-1-yl)-N-(pyrazin-2-yl)propanamide | See Cmpd. 10 | [M + H] calc'd for $C_{22}H_{26}N_5O_3S$ 440.53; found 440 | $^1$H NMR (400 MHz, MeOD). δ ppm 1.06 (m, 3H) 1.29 (m, 3H) 1.43 (m, 2H) 1.60 (m, 4H) 1.74 (m, 1H) 2.31 (m, 1H) 2.64 (m, 1H) 2.81 (m, 1H) 5.64 (m, 1H) 7.74 (d, J = 4 Hz, 1H) 8.11 (d, J = 8 Hz, 1H) 8.30 (s, 1H) 8.34 (s, 1H) 8.50 (s, 1H) |
| 62 | 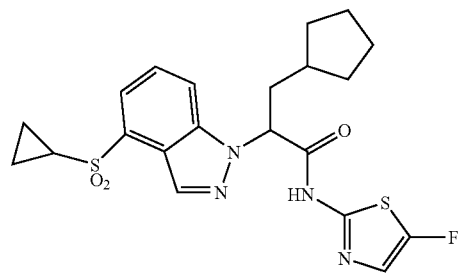 [SMILES: O=C(Nc1ncc(F)s1)C(CC1CCCC1)n1ncc2c(S(=O)(=O)C3CC3)cccc21]<br>3-cyclopentyl-2-(4-(cyclopropylsulfonyl)-1H-indazol-1-yl)-N-(5-fluorothiazol-2-yl)propanamide | See Cmpd. 10 | [M + H] calc'd for $C_{21}H_{24}FN_4O_3S_2$ 463.56; found 463 | $^1$H NMR (400 MHz, MeOD). δ ppm 1.07 (m, 3H) 1.29 (m, 3H) 1.45 (m, 3H) 1.60 (m, 3H) 1.74 (m, 1H) 2.29 (m, 1H) 2.60 (m, 1H) 2.80 (m, 1H) 5.64 (m, 1H) 7.09 (d, J = 4 Hz, 1H) 7.64 (t, J = 8, 8 Hz, 1H) 7.74 (d, J = 8 Hz, 1H) 8.09 (d, J = 12 Hz, 1H) 8.47 (s, 1H) |

| Ex. | Structure | Method | LCMS | NMR data |
|---|---|---|---|---|
| 63 | 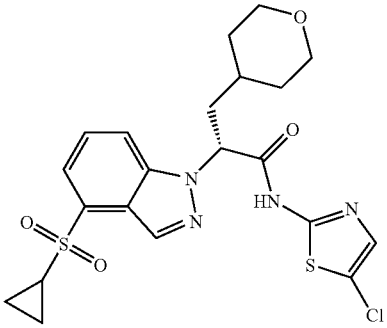 [SMILES: O=C(Nc1ncc(Cl)s1)[C@@H](CC1CCOCC1)n1ncc2c(S(=O)(=O)C3CC3)cccc21]<br>(R)-N-(5-chlorothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | |
| 64 | 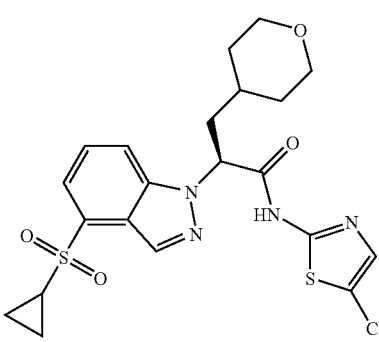<br>(S)-N-(5-chlorothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{21}H_{24}ClN_4O_4S_2$ 496.01, found 496.1 | |
| 65 | 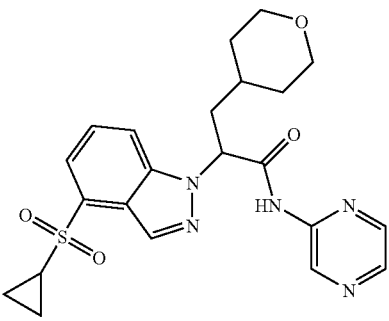 [SMILES: O=C(Nc1cnccn1)C(CC1CCOCC1)n1ncc2c(S(=O)(=O)C3CC3)cccc21]<br>2-(4-(cyclopropylsulfonyl)-1H-indazol-1-yl)-N-(pyrazin-2-yl)-3-(tetrahydro-2H-pyran-4-yl)propanamide | See Cmpd. 10 | [M + H] calc'd for $C_{22}H_{26}N_5O_4S$ 456.53, found 456.5 | $^1$H NMR (400 MHz, MeOD) δ ppm 0.91-1.03 (m, 2H) 1.16-1.35 (m, 5H) 1.38-1.47 (m, 1H) 1.59-1.70 (m, 1H) 2.10-2.21 (m, 1H) 2.47-2.59 (m, 1H) 2.72 (tt, J = 7.89, 4.74 Hz, 1H) 3.05-3.18 (m, 2H) 3.68-3.83 (m, 2H) 5.71 (dd, J = 10.61, 4.80 Hz, 1H) 7.51-7.59 (m, 1H) 7.63-7.69 (m, 1H) 8.02 (d, J = 8.59 Hz, 1H) 8.24 (d, J = 15.92 Hz, 2H) 8.40 (s, 1H) 9.23 (br. s., 1H) |

| Ex. | Structure | Method | LCMS | NMR data |
|---|---|---|---|---|
| 66 | 2-(4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_4S_2$ 479.56, found 479.5 | $^1$H NMR (400 MHz, MeOD) δ ppm 0.94-1.00 (m, 2H) 1.17-1.32 (m, 5H) 1.35-1.43 (m, 1H) 1.58-1.67 (m, 1H) 2.08-2.18 (m, 1H) 2.48 (ddd, J = 14.46, 10.42, 4.42 Hz, 1H) 2.72 (tt, J = 7.96, 4.80 Hz, 1H) 3.04-3.17 (m, 2H) 3.69-3.82 (m, 2H) 5.66 (dd, J = 10.61, 5.05 Hz, 1H) 6.99 (d, J = 2.53 Hz, 1H) 7.55 (dd, J = 8.34, 7.33 Hz, 1H) 7.66 (d, J = 6.57 Hz, 1H) 7.97 (d, J = 8.59 Hz, 1H) 8.38 (s, 1H) |
| 67 | N-(5-chlorothiazol-2-yl)-2-(4-(cyclopropylsulfonyl)-6-fluoro-1H-indazol-1-yl)-3-(tetrahydro-2H-pyran-4-yl)propanamide | See Cmpd. 10 | [M + H] calc'd for $C_{21}H_{23}ClFN_4O_4S_2$ 514.01, found 514 | $^1$H NMR (40 MHz, MeOD) δ ppm 1.09 (m, 2H) 1.32 (m, 5H) 1.47 (m, 1H) 1.70 (m, 1H) 2.23 (m, 1H) 2.56 (m, 1H) 2.86 (m, 1H) 3.20 (m, 2H) 3.85 (m, 2H) 5.71 (m, 1H) 7.56 (m, 1H) 7.87 (m, 1H) 8.47 (s, 1H) |
| 68 | (R)-2-(4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_4S_2$ 479.56, found 479.5 | |
| 69 | (S)-2-(4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_4S_2$ 479.56, found 479.5 | |

| Ex. | Structure | Method | LCMS | NMR data |
|---|---|---|---|---|
| 70 | 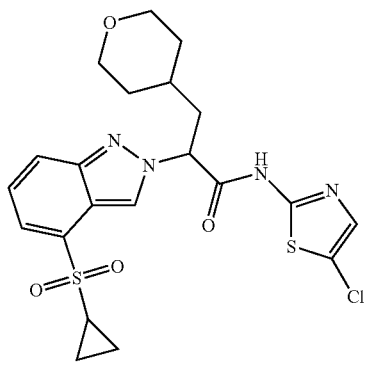 [SMILES: O=C(Nc1ncc(Cl)s1)C(CC1CCOCC1)n1cc2c(S(=O)(=O)C3CC3)cccc2n1]<br>N-(5-chlorothiazol-2-yl)-2-(4-(cyclopropylsulfonyl)-2H-indazol-2-yl)-3-(tetrahydro-2H-pyran-4-yl)propanamide | See Cmpd. 10 | [M + H] calc'd for $C_{21}H_{24}ClN_4O_4S_2$ 496.01, found 496.1 | $^1$H NMR (400 MHz, MeOD) δ ppm 0.93-1.00 (m, 2H) 1.16-1.36 (m, 5H) 1.39-1.47 (m, 1H) 1.64-1.74 (m, 1H) 2.09-2.21 (m, 1H) 2.40 (ddd, J = 14.46, 10.17, 4.67 Hz, 1H) 2.71-2.75 (m, 1H) 3.11-3.20 (m, 2H) 3.70-3.84 (m, 2H) 5.63 (dd, J = 10.36, 5.31 Hz, 1H) 7.24 (s, 1H) 7.41 (dd, J = 8.59, 7.07 Hz, 1H) 7.62 (d, J = 6.32 Hz, 1H) 7.89 (d, J = 8.84 Hz, 1H) 8.67 (d, J = 1.01 Hz, 1H) |
| 71 | 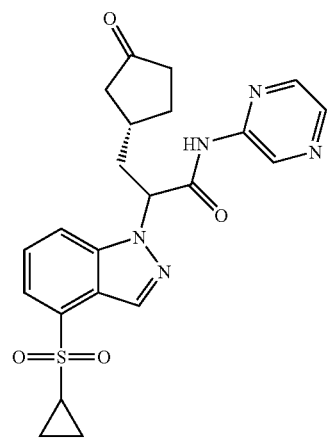 [SMILES: O=C1CC[C@H](CC(C(=O)Nc2cnccn2)n2ncc3c(S(=O)(=O)C4CC4)cccc32)C1]<br>2-(4-(cyclopropylsulfonyl)-1H-indazol-1-yl)-3-((R)-3-oxocyclopentyl)-N-(pyrazin-2-yl)propanamide | See Cmpd. 11 | [M + H] calc'd for $C_{22}H_{24}N_5O_4S$ 454.2, found 454.0 | see separated diastereomers for $^1$H NMR |
| 72 | 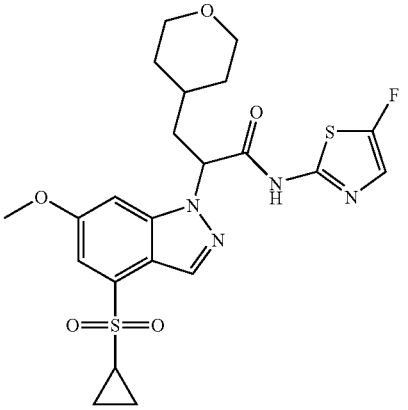 [SMILES: COc1cc(S(=O)(=O)C2CC2)c2cnn(C(CC3CCOCC3)C(=O)Nc3ncc(F)s3)c2c1]<br>2-(4-(cyclopropylsulfonyl)-6-methoxy-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{26}FN_4O_5S_2$ 509, found 509 | $^1$H NMR (CHLOROFORM-d, 400 MHz): δ = 8.52 (s, 1H), 7.45 (d, J = 1.8 Hz, 1H), 7.00 (br. s., 1H), 6.96 (s, 1H), 5.30 (s, 1H), 3.95 (s, 3H), 3.78-3.93 (m, 2H), 3.13-3.30 (m, 2H), 2.57-2.73 (m, 1H), 2.50 (br. s., 1H), 2.25 (d, J = 5.6 Hz, 1H), 1.59 (d, J = 12.4 Hz, 1H), 1.44-1.55 (m, 2H), 1.28-1.44 (m, 4H), 1.01-1.16 ppm (m, 2H) |

-continued

| Ex. | Structure | Method | LCMS | NMR data |
|---|---|---|---|---|
| 73 | 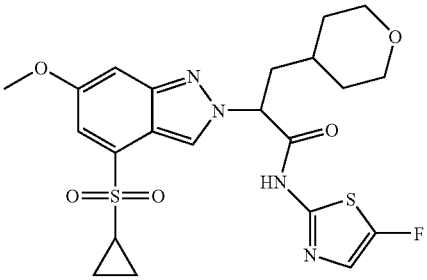 [SMILES: COc1cc(S(=O)(=O)C2CC2)c2cn(C(CC3CCOCC3)C(=O)Nc3ncc(F)s3)nc2c1]<br>2-(4-(cyclopropylsulfonyl)-6-methoxy-2H-indazol-2-yl)-N-(5-fluorothiazol-2-yl)-3-(tetrahydro-2H-pyran-4-yl)propanamide | See Cmpd. 10 | [M + H] calc'd for $C_{22}H_{26}FN_4O_5S_2$ 509, found 509 | $^1$H NMR (CHLOROFORM-d, 400 MHz): δ = 8.37 (s, 1H), 7.45 (d, J = 2.0 Hz, 1H), 7.27 (d, J = 2.0 Hz, 1H), 7.02 (d, J = 2.8 Hz, 1H), 5.25 (dd, J = 10.0, 5.4 Hz, 1H), 3.95 (s, 3H), 3.73-3.91 (m, 2H), 3.20-3.33 (m, 2H), 2.49-2.58 (m, 1H), 2.37-2.48 (m, 1H), 2.21-2.32 (m, 1H), 1.69 (d, J = 12.1 Hz, 1H), 1.51 (dd, J = 9.3, 2.0 Hz, 1H), 1.28-1.45 (m, 5H), 0.99-1.08 ppm (m, 2H) |
| 74 | 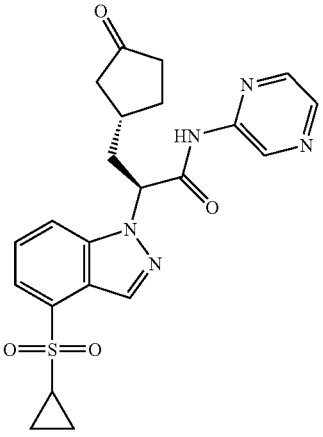 [SMILES: O=C1CC[C@H](C[C@@H](C(=O)Nc2cnccn2)n2ncc3c(S(=O)(=O)C4CC4)cccc32)C1]<br>(S)-2-(4-(cyclopropylsulfonyl)-1H-indazol-1-yl)-3-((R)-3-oxocyclopentyl)-N-(pyrazin-2-yl)propanamide | See Cmpd. 11 | [M + H] calc'd for $C_{22}H_{24}N_5O_4S$ 454.2, found 454.0 | $^1$H NMR (400 MHz, MeOD) δ ppm 1.01-1.14 (m, 2H) 1.16-1.32 (m, 2H) 1.62-1.85 (m, 2H) 2.00-2.13 (m, 3H) 2.15-2.29 (m, 2H) 2.52 (ddd, J = 14.08, 7.14, 5.05 Hz, 1H) 2.65-2.86 (m, 2H) 5.79 (dd, J = 10.11, 5.05 Hz, 1H) 7.55-7.72 (m, 1H) 7.76 (d, J = 6.57 Hz, 1H) 8.14 (d, J = 8.59 Hz, 1H) 8.24-8.44 (m, 2H) 8.51 (s, 1H) 9.29-9.37 (m, 1H) |
| 75 | 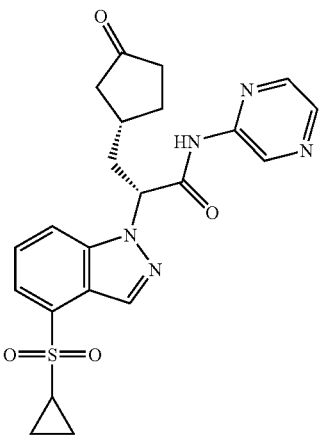 [SMILES: O=C1CC[C@H](C[C@H](C(=O)Nc2cnccn2)n2ncc3c(S(=O)(=O)C4CC4)cccc32)C1]<br>(R)-2-(4-(cyclopropylsulfonyl)-1H-indazol-1-yl)-3-((R)-3-oxocyclopentyl)-N-(pyrazin-2-yl)propanamide | See Cmpd. 11 | [M + H] calc'd for $C_{22}H_{24}N_5O_4S$ 454.2, found 454.0 | $^1$H NMR (400 MHz, MeOD) δ ppm 0.92-1.13 (m, 2H) 1.18-1.37 (m, 2H) 1.50-1.68 (m, 1H) 1.89-2.13 (m, 4H) 2.14-2.39 (m, 2H) 2.44 (ddd, J = 13.96, 8.91, 4.93 Hz, 1H) 2.70-2.92 (m, 2H) 5.73 (dd, J = 10.61, 4.80 Hz, 1H) 7.52-7.73 (m, 1H) 7.75 (d, J = 6.82 Hz, 1H) 8.13 (d, J = 8.59 Hz, 1H) 8.35 (br. s., 2H) 8.51 (s, 1H) 9.33 (br. s., 1H) |

| Ex. | Structure | Method | LCMS | NMR data |
|---|---|---|---|---|
| 76 | 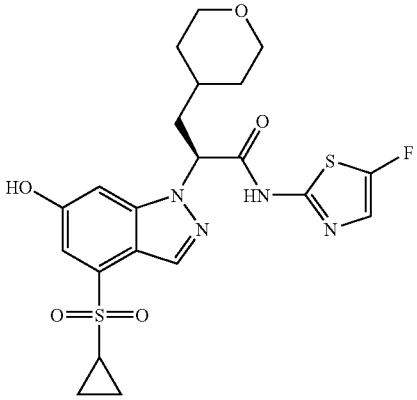 [SMILES: O=C(Nc1ncc(F)s1)[C@H](CC1CCOCC1)n1ncc2c(S(=O)(=O)C3CC3)cc(O)cc21]<br>(S)-2-(4-(cyclopropylsulfonyl)-6-hydroxy-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_5S_2$ 495, found 495 | $^1$H NMR (DMSO-d$_6$, 400 MHz): δ = 12.70 (s, 1H), 10.48 (s, 1H), 8.23 (s, 1H), 7.33-7.36 (m, 2H), 7.23 (d, J = 1.8 Hz, 1H), 5.62 (d, J = 4.3 Hz, 1H), 3.71-3.85 (m, 3H), 3.06-3.21 (m, 2H), 2.24-2.41 (m, 1H), 2.09-2.24 (m, 1H), 1.54-1.63 (m, 1H), 1.48 (br. s., 1H), 1.28 (br. s., 3H), 1.16 (br. s., 2H), 1.06 ppm (dd, J = 7.8, 2.0 Hz, 2H) |
| 77 | 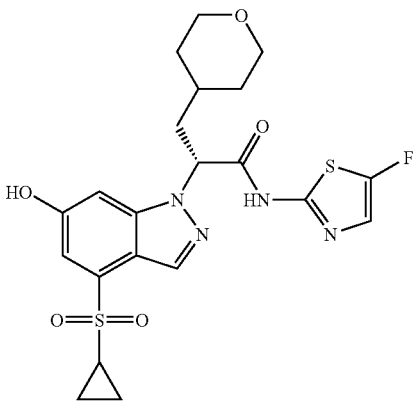 [SMILES: O=C(Nc1ncc(F)s1)[C@@H](CC1CCOCC1)n1ncc2c(S(=O)(=O)C3CC3)cc(O)cc21]<br>(R)-2-(4-(cyclopropylsulfonyl)-6-hydroxy-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_5S_2$ 495, found 495 | $^1$H NMR (DMSO-d$_6$, 400 MHz): δ = 12.70 (s, 1H), 10.48 (s, 1H), 8.23 (s, 1H), 7.33-7.36 (m, 2H), 7.23 (d, J = 1.8 Hz, 1H), 5.62 (d, J = 4.3 Hz, 1H), 3.71-3.85 (m, 3H), 3.06-3.21 (m, 2H), 2.24-2.41 (m, 1H), 2.09-2.24 (m, 1H), 1.54-1.63 (m, 1H), 1.48 (br. s., 1H), 1.28 (br. s., 3H), 1.16 (br. s., 2H), 1.06 ppm (dd, J = 7.8, 2.0 Hz, 2H) |
| 78 | 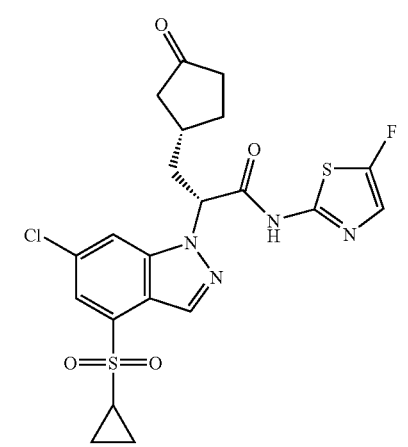 [SMILES: O=C1CC[C@H](C[C@H](C(=O)Nc2ncc(F)s2)n2ncc3c(S(=O)(=O)C4CC4)cc(Cl)cc32)C1]<br>(R)-2-(6-chloro-4-(cyclopropylsulfonyl)-1H-indazol-1-yl)-N-(5-fluorothiazol-2-yl)-3-((R)-3-oxocyclopentyl)propanamide | See Cmpd. 11 | [M + H] calc'd for $C_{21}H_{21}ClFN_4O_4S_2$ 511.1, found 511.3 | $^1$H NMR (400 MHz, CHLOROFORM-d) δ ppm 1.07-1.31 (m, 2H) 1.34-1.57 (m, 2H) 1.57-1.84 (m, 3H) 1.93-2.21 (m, 3H) 2.32 (dd, J = 18.32, 8.21 Hz, 1H) 2.47-2.70 (m, 2H) 2.97-3.20 (m, 1H) 5.33 (dd, J = 9.98, 5.18 Hz, 1H) 6.93-7.13 (m, 1H) 7.71-7.91 (m, 2H) 8.49-8.69 (m, 1H) |

| Ex. | Structure | Method | LCMS | NMR data |
|---|---|---|---|---|
| 79 | 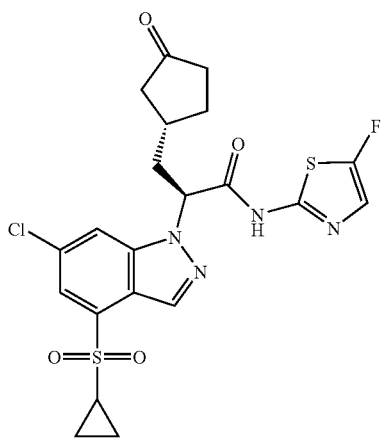 [SMILES: O=C1CC[C@H](C[C@@H](C(=O)Nc2ncc(F)s2)n2ncc3c(S(=O)(=O)C4CC4)cc(Cl)cc32)C1]<br>(S)-2-(6-chloro-4-(cyclopropylsulfonyl)-1H-indazol-1-yl)-N-(5-fluorothiazol-2-yl)-3-((R)-3-oxocyclopentyl)propanamide | See Cmpd. 11 | [M + H] calc'd for $C_{21}H_{21}ClFN_4O_4S_2$ 511.1, found 511.3 | $^1$H NMR (400 MHz, CHLOROFORM-d) δ ppm 1.07-1.31 (m, 2H) 1.39-1.69 (m, 4H) 1.81-1.92 (m, 1H) 1.93-2.14 (m, 2H) 2.18-2.38 (m, 2H) 2.46 (ddd, J = 14.02, 8.84, 5.18 Hz, 1H) 2.53-2.79 (m, 2H) 5.27 (dd, J = 10.48, 4.93 Hz, 1H) 7.03 (d, J = 3.03 Hz, 1H) 7.71-7.93 (m, 2H) 8.63 (s, 1H) |
| 80 | 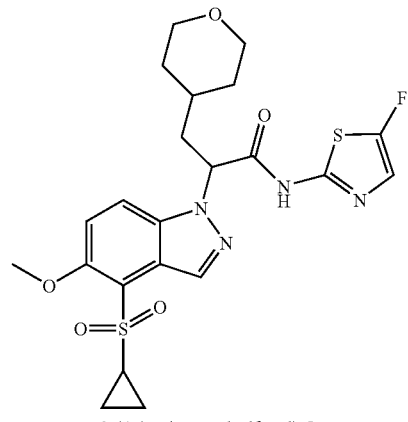<br>2-(4-(cyclopropylsulfonyl)-5-methoxy-1H-indazol-1-yl)-N-(5-fluorothiazol-2-yl)-3-(tetrahydro-2H-pyran-4-yl)propanamide | See Cmpd. 15 | [M + H] calc'd for $C_{22}H_{26}FN_4O_5S_2$ 509, found 509 | $^1$H NMR (CHLOROFORM-d, 400 MHz): δ = 8.74 (s, 1H), 7.67 (d, J = 9.1 Hz, 1H), 7.33 (d, J = 9.3 Hz, 1H), 7.02 (d, J = 2.8 Hz, 1H), 5.37 (dd, J = 10.6, 4.8 Hz, 1H), 4.08 (s, 3H), 3.82-3.95 (m, 2H), 3.05-3.29 (m, 3H), 2.49 (ddd, J = 14.2, 10.5, 5.1 Hz, 1H), 2.23 (ddd, J = 14.0, 8.8, 4.8 Hz, 1H), 1.53-1.66 (m, 1H), 1.42-1.49 (m, 2H), 1.27-1.42 (m, 3H), 1.21 (dd, J = 7.5, 3.9 Hz, 1H), 1.02 ppm (dddd, J = 16.8, 8.1, 6.5, 4.9 Hz, 2H) |
| 81 | 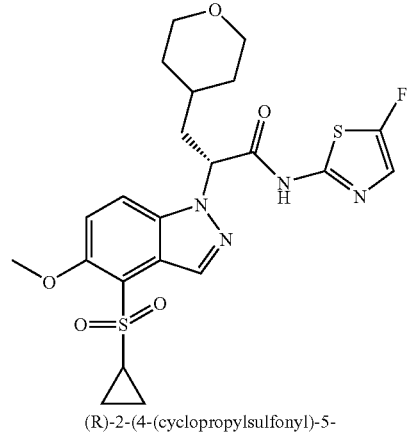<br>(R)-2-(4-(cyclopropylsulfonyl)-5-methoxy-1H-indazol-1-yl)-N-(5-fluorothiazol-2-yl)-3-(tetrahydro-2H-pyran-4-yl)propanamide | See Cmpd. 15 | [M + H] calc'd for $C_{22}H_{26}FN_4O_5S_2$ 509, found 509 | $^1$H NMR (CHLOROFORM-d, 400 MHz): δ = 8.74 (s, 1H), 7.67 (d, J = 9.1 Hz, 1H), 7.33 (d, J = 9.3 Hz, 1H), 7.02 (d, J = 2.8 Hz, 1H), 5.37 (dd, J = 10.6, 4.8 Hz, 1H), 4.08 (s, 3H), 3.82-3.95 (m, 2H), 3.05-3.29 (m, 3H), 2.49 (ddd, J = 14.2, 10.5, 5.1 Hz, 1H), 2.23 (ddd, J = 14.0, 8.8, 4.8 Hz, 1H), 1.53-1.66 (m, 1H), 1.42-1.49 (m, 2H), 1.27-1.42 (m, 3H), 1.21 (dd, J = 7.5, 3.9 Hz, 1H), 1.02 ppm (dddd, J = 16.8, 8.1, 6.5, 4.9 Hz, 2H) |

| Ex. | Structure | Method | LCMS | NMR data |
|---|---|---|---|---|
| 82 | 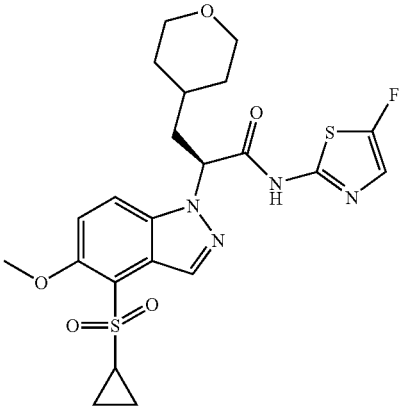 [SMILES: COc1ccc2c(cnn2[C@@H](CC2CCOCC2)C(=O)Nc2ncc(F)s2)c1S(=O)(=O)C1CC1]<br>(S)-2-(4-(cyclopropylsulfonyl)-5-methoxy-1H-indazol-1-yl)-N-(5-fluorothiazol-2-yl)-3-(tetrahydro-2H-pyran-4-yl)propanamide | See Cmpd. 15 | [M + H] calc'd for $C_{22}H_{26}FN_4O_5S_2$ 509, found 509 | $^1$H NMR (CHLOROFORM-d, 400 MHz): δ = 8.74 (s, 1H), 7.67 (d, J = 9.1 Hz, 1H), 7.33 (d, J = 9.3 Hz, 1H), 7.02 (d, J = 2.8 Hz, 1H), 5.37 (dd, J = 10.6, 4.8 Hz, 1H), 4.08 (s, 3H), 3.82-3.95 (m, 2H), 3.05-3.29 (m, 3H), 2.49 (ddd, J = 14.2, 10.5, 5.1 Hz, 1H), 2.23 (ddd, J = 14.0, 8.8, 4.8 Hz, 1H), 1.53-1.66 (m, 1H), 1.42-1.49 (m, 2H), 1.27-1.42 (m, 3H), 1.21 (dd, J = 7.5, 3.9 Hz, 1H), 1.02 ppm (dddd, J = 16.8, 8.1, 6.5, 4.9 Hz, 2H) |
| 83 | 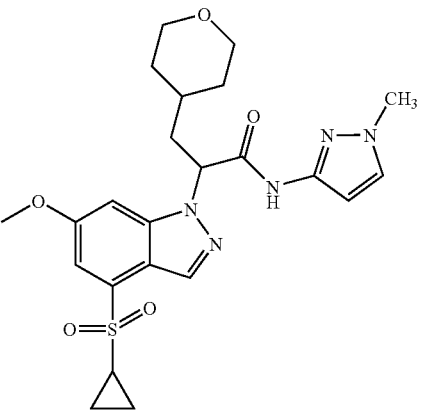<br>2-(4-(cyclopropylsulfonyl)-6-methoxy-1H-indazol-1-yl)-N-(1-methyl-1H-pyrazol-3-yl)-3-(tetrahydro-2H-pyran-4-yl)propanamide | See Cmpd. 10 | [M + H] calc'd for $C_{23}H_{30}N_5O_5S$ 488, found 488 | $^1$H NMR (CHLOROFORM-d, 400 MHz): δ = 10.28 (s, 1H), 8.45 (s, 1H), 7.42 (d, J = 1.8 Hz, 1H), 7.33 (d, J = 2.3 Hz, 1H), 7.12-7.18 (m, 1H), 6.77 (d, J = 2.5 Hz, 1H), 5.40 (dd, J = 10.1, 5.1 Hz, 1H), 3.93 (s, 3H), 3.90-4.04 (m, 2H), 3.85 (s, 3H), 3.21-3.40 (m, 2H), 2.48-2.66 (m, 2H), 2.22-2.34 (m, 1H), 1.68 (d, J = 12.4 Hz, 1H), 1.51-1.61 (m, 1H), 1.28-1.50 (m, 5H), 0.97-1.12 ppm (m, 2H) |
| 84 | 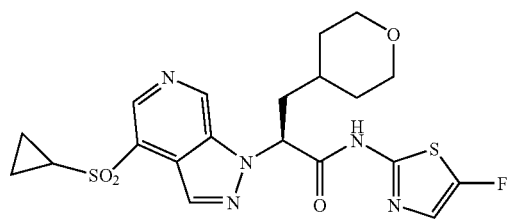<br>(S)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide | See Cmpd. 13 | [M + H] calc'd for $C_{20}H_{23}FN_5O_4S_2$ 480, found 480 | $^1$H NMR (400 MHz, CHLOROFORM-d) δ ppm 1.09-1.19 (m, 2H) 1.21-1.29 (m, 1H) 1.31-1.55 (m, 5H) 1.59-1.72 (m, 1H) 2.33 (ddd, J = 14.15, 8.34, 5.31 Hz, 1H), 2.42-2.56 (m, 1H) 2.64 (tt, J = 7.96, 4.80 Hz, 1H) 3.22 (m, J = 17.91, 11.64, 11.64, 2.27 Hz, 2H) 3.90 (ddd, J = 13.45, 11.43, 2.65 Hz, 2H) 5.61 (dd, J = 10.23, 5.43 Hz, 1H) 7.09 (d, J = 2.78 Hz, 1H) 8.65 (s, 1H) 8.87 (s, 1H) 9.34 (s, 1H) 9.99 (br. s., 1H) |

| Ex. | Structure | Method | LCMS | NMR data |
|---|---|---|---|---|
| 85 | 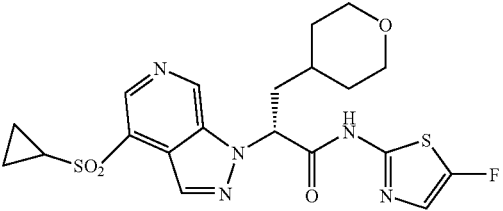<br>(R)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide | See Cmpd. 13 | [M + H] calc'd for $C_{20}H_{23}FN_5O_4S_2$ 480, found 480 | |
| 86 | 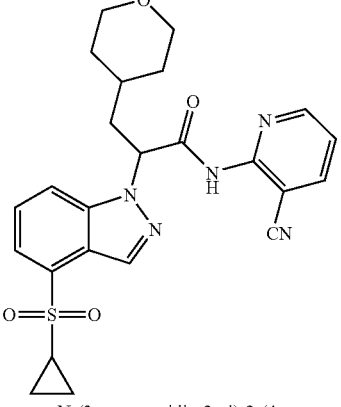<br>N-(3-cyanopyridin-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{24}H_{26}N_5O_4S$ 480.3, found 480.5 | $^1$H NMR (400 MHz, CHLOROFORM-d) δ ppm 0.89-1.05 (m, 2H) 1.18-1.45 (m, 5H) 1.49 (d, J = 9.60 Hz, 1H) 1.53-1.65 (m, 1H) 2.15-2.36 (m, 3H) 2.36-2.63 (m, 2H) 3.07-3.28 (m, 2H) 3.83 (t, J = 10.74 Hz, 2H) 5.44 (dd, J = 9.98, 5.18 Hz, 1H) 7.55 (dd, J = 8.72, 7.20 Hz, 1H), 7.73 (d, J = 7.58 Hz, 2H) 7.91 (d, J = 7.83 Hz, 1H) 8.62 (s, 1H), 9.50 (s, 1H) |
| 87 | 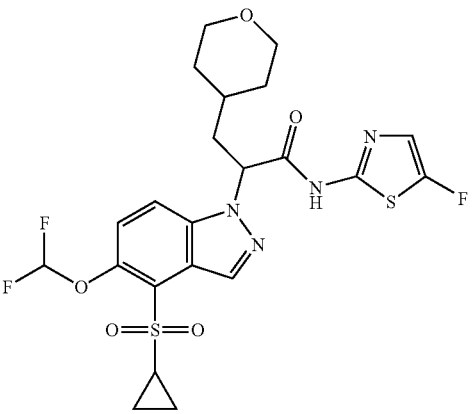 [SMILES: O=C(Nc1ncc(F)s1)C(CC1CCOCC1)n1ncc2c(S(=O)(=O)C3CC3)c(OC(F)F)ccc21]<br>2-(4-(cyclopropylsulfonyl)-5-(difluoromethoxy)-1H-indazol-1-yl)-N-(5-fluorothiazol-2-yl)-3-(tetrahydro-2H-pyran-4-yl)propanamide | See Cmpd. 12 | [M + H] calc'd for $C_{22}H_{24}F_3N_4O_5S_2$ 545, found 545 | $^1$H NMR (400 MHz, CHLOROFORM-d) δ ppm 1.02-1.13 (m, 2H) 1.34-1.49 (m, 4H) 1.50-1.61 (m, 1H) 1.65-1.76 (m, 1H) 2.24-2.35 (m, 1H) 2.47-2.60 (m, 1H) 2.66-2.77 (m, 2H) 3.20-3.36 (m, 2H) 3.89-3.99 (m, 2H) 5.46 (dd, J = 10.86, 4.80 Hz, 1H) 6.93 (s, 1H) 7.07-7.13 (m, 1H) 7.29-7.60 (m, 1H) 7.58-7.67 (m, 1H) 8.27 (s, 1H) |

| Ex. | Structure | Method | LCMS | NMR data |
|---|---|---|---|---|
| 88 | 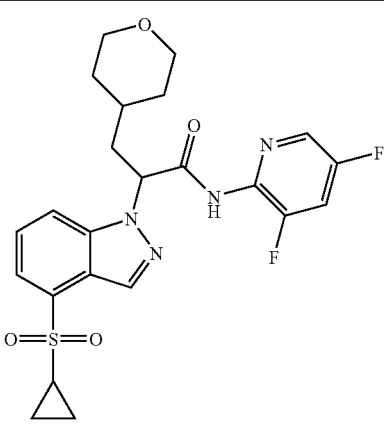<br>2-(4-(cyclopropylsulfonyl)-1H-indazol-1-yl)-N-(3,5-difluoropyridin-2-yl)-3-(tetrahydro-2H-pyran-4-yl)propanamide | See Cmpd. 10 | [M + H] calc'd for $C_{23}H_{25}F_2N_4O_4S$ 491.5, found 491.6 | $^1$H NMR (400 MHz, DMSO-$d_6$) δ ppm 0.94-1.13 (m, 2H) 1.13-1.37 (m, 4H) 1.47-1.59 (m, 1H) 1.66 (d, J = 10.11 Hz, 1H) 2.25 (d, J = 7.83 Hz, 1H) 2.34-2.47 (m, 1H) 2.92-3.22 (m, 4H) 3.71-3.86 (m, 2H) 5.82 (dd, J = 9.73, 5.43 Hz, 1H) 7.59-7.79 (m, 2H) 8.02 (ddd, J = 9.79, 8.40, 2.53 Hz, 1H) 8.21 (d, J = 8.34 Hz, 1H) 8.35 (d, J = 2.53 Hz, 1H) 8.39-8.51 (m, 1H) 10.73 (s, 1H) |
| 89 | 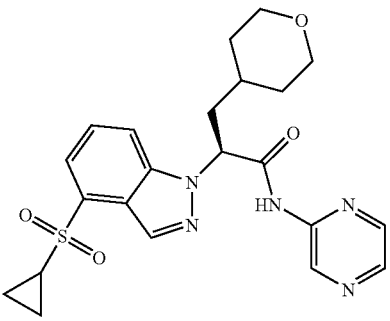 [SMILES: O=C(Nc1cnccn1)[C@H](CC1CCOCC1)n1ncc2c(S(=O)(=O)C3CC3)cccc21]<br>(S)-2-(4-(cyclopropylsulfonyl)-1H-indazol-1-yl)-N-(pyrazin-2-yl)-3-(tetrahydro-2H-pyran-4-yl)propanamide | See Cmpd. 10 | [M + H] calc'd for $C_{22}H_{26}N_5O_4S$ 456.53, found 456.5 | |
| 90 | 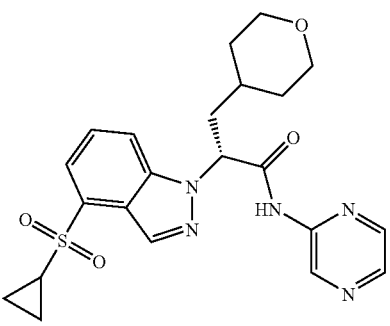 [SMILES: O=C(Nc1cnccn1)[C@@H](CC1CCOCC1)n1ncc2c(S(=O)(=O)C3CC3)cccc21]<br>(R)-2-(4-(cyclopropylsulfonyl)-1H-indazol-1-yl)-N-(pyrazin-2-yl)-3-(tetrahydro-2H-pyran-4-yl)propanamide | See Cmpd. 10 | [M + H] calc'd for $C_{22}H_{26}N_5O_4S$ 456.53, found 456.5 | |

| Ex. | Structure | Method | LCMS | NMR data |
|---|---|---|---|---|
| 91 | 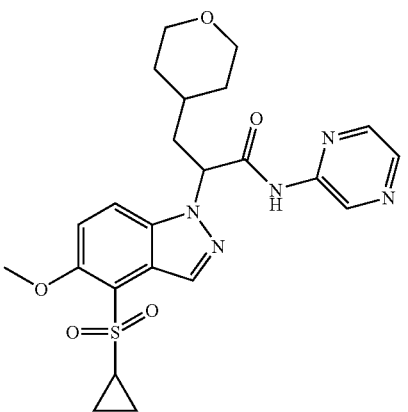<br>2-(4-(cyclopropylsulfonyl)-5-methoxy-1H-indazol-1-yl)-N-(pyrazin-2-yl)-3-(tetrahydro-2H-pyran-4-yl)propanamide | See Cmpd. 15 | [M + H] calc'd for $C_{23}H_{28}N_5O_5S$ 486, found 486 | $^1$H NMR (CHLOROFORM-d, 400 MHz): δ 9.49 (s, 1H), 9.20 (s, 1H), 8.79 (s, 1H), 8.32 (d, J = 1.5 Hz, 1H), 8.36 (d, J = 2.5 Hz, 1H), 7.71 (d, J = 9.3 Hz, 1H), 7.35 (d, J = 9.3 Hz, 1H), 5.34 (dd, J = 10.5, 4.9 Hz, 1H), 4.08 (s, 3H), 3.85-3.99 (m, 2H), 3.07-3.32 (m, 3H), 2.54 (d, J = 3.5 Hz, 1H), 2.28 (d, J = 5.3 Hz, 1H), 1.60 (br. s., 1H), 1.26-1.48 (m, 6H), 0.92-1.12 ppm (m, 2H) |
| 92 | 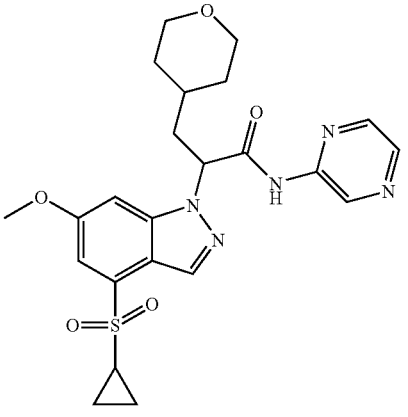 [SMILES: COc1cc(S(=O)(=O)C2CC2)c2cnn(C(CC3CCOCC3)C(=O)Nc3cnccn3)c2c1]<br>2-(4-(cyclopropylsulfonyl)-6-methoxy-1H-indazol-1-yl)-N-(pyrazin-2-yl)-3-(tetrahydro-2H-pyran-4-yl)propanamide | See Cmpd. 10 | [M + H] calc'd for $C_{23}H_{28}N_5O_5S$ 486, found 486 | $^1$H NMR (CHLOROFORM-d, 400 MHz): δ 9.50 (s, 1H), 9.22 (s, 1H), 8.55 (s, 1H), 8.33-8.41 (m, 1H), 8.28 (s, 1H), 7.44 (d, J = 2.0 Hz, 1H), 7.03 (d, J = 1.3 Hz, 1H), 5.31 (dd, J = 10.5, 4.9 Hz, 1H), 3.95 (s, 4H), 3.87-3.97 (m, 1H), 3.25-3.32 (m, 1H), 3.21 (td, J = 11.7, 2.5 Hz, 1H), 2.51-2.65 (m, 2H), 2.25-2.35 (m, 1H), 1.52-1.66 (m, 2H), 1.31-1.50 (m, 5H), 1.02-1.13 ppm (m, 2H) |
| 93 | 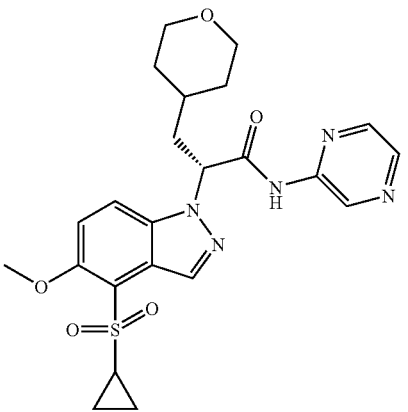 [SMILES: COc1ccc2c(cnn2[C@H](CC2CCOCC2)C(=O)Nc2cnccn2)c1S(=O)(=O)C1CC1]<br>(R)-2-(4-(cyclopropylsulfonyl)-5-methoxy-1H-indazol-1-yl)-N-(pyrazin-2-yl)-3-(tetrahydro-2H-pyran-4-yl)propanamide | See Cmpd. 15 | [M + H] calc'd for $C_{23}H_{28}N_5O_5S$ 486, found 486 | $^1$H NMR (CHLOROFORM-d, 400 MHz): δ = 9.49 (s, 1H), 9.20 (s, 1H), 8.79 (s, 1H), 8.32 (d, J = 1.5 Hz, 1H), 8.36 (d, J = 2.5 Hz, 1H), 7.71 (d, J = 9.3 Hz, 1H), 7.35 (d, J = 9.3 Hz, 1H), 5.34 (dd, J = 10.5, 4.9 Hz, 1H), 4.08 (s, 3H), 3.85-3.99 (m, 2H), 3.07-3.32 (m, 3H), 2.54 (d, J = 3.5 Hz, 1H), 2.28 (d, J = 5.3 Hz, 1H), 1.60 (br. s., 1H), 1.26-1.48 (m, 6H), 0.92-1.12 ppm (m, 2H) |

| Ex. | Structure | Method | LCMS | NMR data |
|---|---|---|---|---|
| 94 | 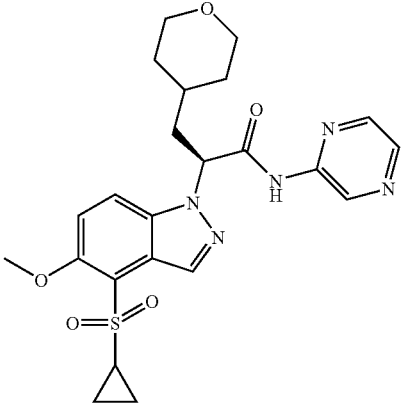 [SMILES: COc1ccc2c(cnn2[C@@H](CC2CCOCC2)C(=O)Nc2cnccn2)c1S(=O)(=O)C1CC1]<br>(S)-2-(4-(cyclopropylsulfonyl)-5-methoxy-1H-indazol-1-yl)-N-(pyrazin-2-yl)-3-(tetrahydro-2H-pyran-4-yl)propanamide | See Cmpd. 15 | [M + H] calc'd for $C_{23}H_{28}N_5O_5S$ 486, found 486 | $^1$H NMR (CHLOROFORM-d, 400 MHz): δ = 9.49 (s, 1H), 9.20 (s, 1H), 8.79 (s, 1H), 8.32 (d, J = 1.5 Hz, 1H), 8.36 (d, J = 2.5 Hz, 1H), 7.71 (d, J = 9.3 Hz, 1H), 7.35 (d, J = 9.3 Hz, 1H), 5.34 (dd, J = 10.5, 4.9 Hz, 1H), 4.08 (s, 3H), 3.85-3.99 (m, 2H), 3.07-3.32 (m, 3H), 2.54 (d, J = 3.5 Hz, 1H), 2.28 (d, J = 5.3 Hz, 1H), 1.60 (br. s., 1H), 1.26-1.48 (m, 6H), 0.92-1.12 ppm (m, 2H) |
| 95 | 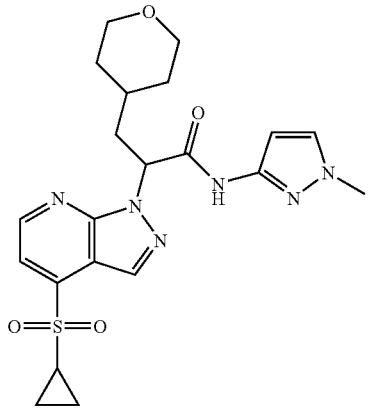 [SMILES: Cn1ccc(NC(=O)C(CC2CCOCC2)n2ncc3c(S(=O)(=O)C4CC4)ccnc32)n1]<br>2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide | See Cmpd. 16 | [M + H] calc'd for $C_{21}H_{27}N_6O_4S$ 459, found 459 | $^1$H NMR (400 MHz, METHANOL-d$_4$) δ ppm 1.08-1.18 (m, 2H) 1.28-1.44 (m, 5H) 1.54 (d, J = 9.35 Hz, 1H) 1.74 (dd, J = 10.11, 1.77 Hz, 1H) 2.17-2.27 (m, 1H) 2.67 (ddd, J = 14.21, 10.93, 3.66 Hz, 1H) 2.89 (tt, J = 7.86, 4.77 Hz, 1H) 3.10-3.28 (m, 2H) 3.76 (s, 3H) 3.85 (dd, J = 10.74, 4.93 Hz, 2H) 5.99 (dd, J = 10.99, 4.67 Hz, 1H) 6.42 (d, J = 2.53 Hz, 1H) 7.42 (d, J = 2.27 Hz, 1H) 7.69 (d, J = 4.80 Hz, 1H) 8.51 (s, 1H) 8.81 (d, 1H) |
| 96 | 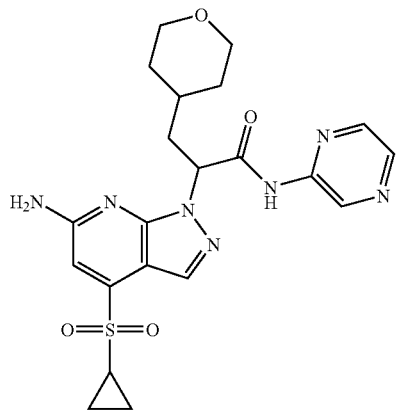 [SMILES: Nc1cc(S(=O)(=O)C2CC2)c2cnn(C(CC3CCOCC3)C(=O)Nc3cnccn3)c2n1]<br>2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 | [M + H] calc'd for $C_{21}H_{26}N_7O_4S$ 472, found 472 | $^1$H NMR (400 MHz, METHANOL-d$_4$) δ ppm 0.99-1.06 (m, 2H) 1.29-1.44 (m, 5H) 1.52 (d, J = 9.35 Hz, 1H) 1.71-1.79 (m, 1H) 2.13-2.22 (m, 1H) 2.56-2.66 (m, 1H) 2.90 (tt, J = 7.96, 4.80 Hz, 1H) 3.12-3.29 (m, 2H) 3.86 (t, J = 10.74 Hz, 2H) 5.90 (dd, J = 10.99, 4.42 Hz, 1H) 8.17 (s, 1H) 8.27-8.37 (m, 3H) 9.31 (s, 1H) |

| Ex. | Structure | Method | LCMS | NMR data |
|---|---|---|---|---|
| 97 | 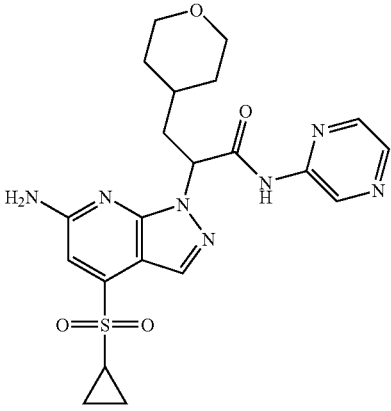<br>2-(4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 & 95 | [M + H] calc'd for $C_{21}H_{25}N_6O_4S$ 457, found 457 | $^1$H NMR (400 MHz, METHANOL-$d_4$) δ ppm 1.09-1.20 (m, 2H) 1.32-1.47 (m, 5H) 1.56 (dd, J = 9.47, 1.89 Hz, 1H) 1.76 (dd, J = 9.73, 1.89 Hz, 1H) 2.20-2.29 (m, 1H), 2.73 (ddd, J = 14.15, 11.12, 3.54 Hz, 1H) 2.91 (tt, J = 7.96, 4.80 Hz, 1H) 3.12-3.29 (m, 2H) 3.81-3.91 (m, 2H) 6.10 (dd, J = 11.12, 4.29 Hz, 1H) 7.71 (d, J = 4.55 Hz, 1H) 8.31 (d, J = 2.53 Hz, 1H) 8.36 (dd, J = 2.53, 1.52 Hz, 1H) 8.53 (s, 1H) 8.83 (d, J = 4.80 Hz, 1H) 9.29 (s, 1H) |
| 98 | 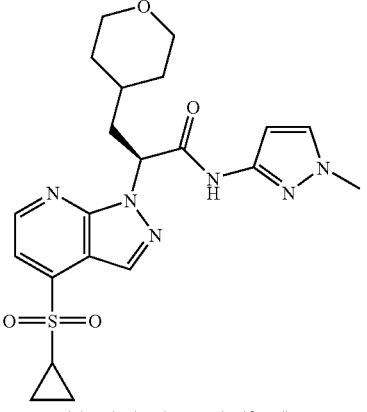<br>(S)-2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide | See Cmpd. 16 & 95 | [M + H] calc'd for $C_{21}H_{27}N_6O_4S$ 459, found 459 | $^1$H NMR (400 MHz, METHANOL-$d_4$) δ pmm 1.08-1.18 (m, 2H) 1.28-1.44 (m, 5H) 1.54 (d, J = 9.35 Hz, 1H) 1.74 (dd, J = 10.11, 1.77 Hz, 1H) 2.17-2.27 (m, 1H) 2.67 (ddd, J = 14.21, 10.93, 3.66 Hz, 1H) 2.89 (tt, J = 7.86, 4.77 Hz, 1H) 3.10-3.28 (m, 2H) 3.76 (s, 3H) 3.85 (dd, J = 10.74, 4.93 Hz, 2H) 5.99 (dd, J = 10.99, 4.67 Hz, 1H) 6.42 (d, J = 2.53 Hz, 1H) 7.42 (d, J = 2.27 Hz, 1H) 7.69 (d, J = 4.80 Hz, 1H) 8.51 (s, 1H) 8.81 (d, 1H) |
| 99 | 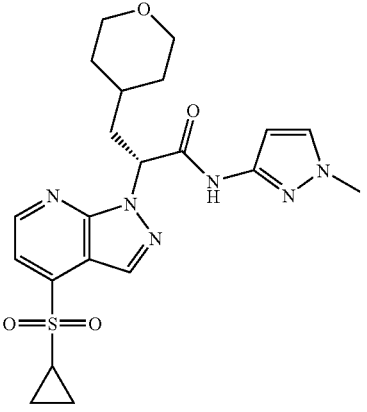<br>(R)-2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide | See Cmpd. 16 & 95 | [M + H] calc'd for $C_{21}H_{27}N_6O_4S$ 459, found 459 | $^1$H NMR (400 MHz, METHANOL-$d_4$) δ pmm 1.08-1.18 (m, 2H) 1.28-1.44 (m, 5H) 1.54 (d, J = 9.35 Hz, 1H) 1.74 (dd, J = 10.11, 1.77 Hz, 1H) 2.17-2.27 (m, 1H) 2.67 (ddd, J = 14.21, 10.93, 3.66 Hz, 1H) 2.89 (tt, J = 7.86, 4.77 Hz, 1H) 3.10-3.28 (m, 2H) 3.76 (s, 3H) 3.85 (dd, J = 10.74, 4.93 Hz, 2H) 5.99 (dd, J = 10.99, 4.67 Hz, 1H) 6.42 (d, J = 2.53 Hz, 1H) 7.42 (d, J = 2.27 Hz, 1H) 7.69 (d, J = 4.80 Hz, 1H) 8.51 (s, 1H) 8.81 (d, 1H) |

| Ex. | Structure | Method | LCMS | NMR data |
|---|---|---|---|---|
| 100 | 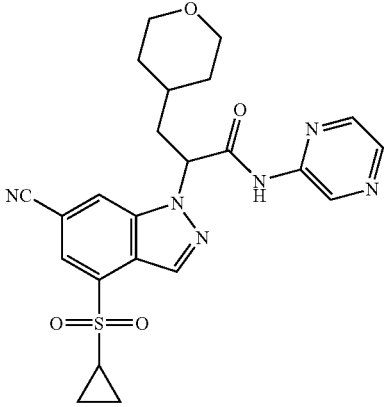<br>2-(6-cyano-4-(cyclopropylsulfonyl)-1H-indazol-1-yl)-N-(pyrazin-2-yl)-3-(tetrahydro-2H-pyran-4-yl)propanamide | See Cmpd. 19 | [M + H] calc'd for $C_{23}H_{25}N_6O_4S$ 481, found 481 | $^1$H NMR (CHLOROFORM-d, 400 MHz): δ = 9.55 (br. s., 1H), 9.40 (br. s., 1H), 8.74 (s, 1H), 8.45 (br. s., 1H), 8.37 (br. s., 1H), 8.22 (s, 1H), 7.99 (s, 1H), 5.52 (dd, J = 9.9, 5.8 Hz, 1H), 3.90-4.09 (m, 2H), 3.19-3.41 (m, 2H), 2.48-2.68 (m, 2H), 2.39 (dd, J = 13.8, 7.7 Hz, 1H), 1.68 (d, J = 12.1 Hz, 1H), 1.57-1.64 (m, 1H), 1.34-1.54 (m, 5H), 1.09-1.19 ppm (m, 2H) |
| 101 | 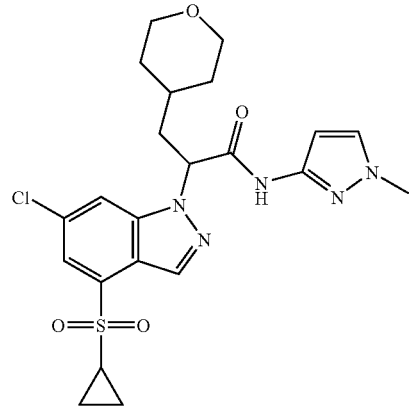 [SMILES: Cn1ccc(NC(=O)C(CC2CCOCC2)n2ncc3c(S(=O)(=O)C4CC4)cc(Cl)cc32)n1]<br>2-(6-chloro-4-(cyclopropylsulfonyl)-1H-indazol-1-yl)-N-(1-methyl-1H-pyrazol-3-yl)-3-(tetrahydro-2H-pyran-4-yl)propanamide | See Cmpd. 10 | [M + H] calc'd for $C_{22}H_{27}ClN_5O_4S$ 492, found 492 | $^1$H NMR (400 MHz, CHLOROFORM-d) δ 8.57 (s, 2H), 7.67-7.82 (m, 2H), 7.23 (d, J = 2.53 Hz, 1H), 6.62 (s, 1H), 5.28 (dd, J = 5.18, 10.23 Hz, 1H), 3.84-3.98 (m, 2H), 3.76 (s, 3H), 3.10-3.32 (m, 2H), 2.56-2.67 (m, 1H), 2.43-2.56 (m, 1H), 2.23-2.36 (m, 1H), 1.57-1.63 (m, 2H), 1.30-1.56 (m, 5H), 1.02-1.16 (m, 2H) |
| 102 | 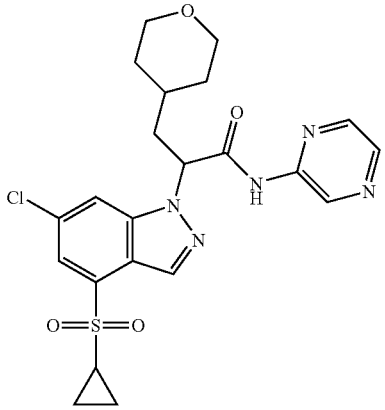 [SMILES: O=C(Nc1cnccn1)C(CC1CCOCC1)n1ncc2c(S(=O)(=O)C3CC3)cc(Cl)cc21]<br>2-(6-chloro-4-(cyclopropylsulfonyl)-1H-indazol-1-yl)-N-(pyrazin-2-yl)-3-(tetrahydro-2H-pyran-4-yl)propanamide | See Cmpd. 10 | [M + H] calc'd for $C_{22}H_{25}ClN_5O_4S$ 490, found 490 | $^1$H NMR (400 MHz, CHLOROFORM-d) δ 9.47-9.50 (m, 1H), 8.93 (s, 1H), 8.64 (s, 1H), 8.36 (d, J = 2.53 Hz, 1H), 8.23 (dd, J = 1.52, 2.53 Hz, 1H), 7.70-7.83 (m, 2H), 5.34 (dd, J = 5.31, 10.36 Hz, 1H), 3.80-3.97 (m, 2H), 3.14-3.35 (m, 2H), 2.47-2.67 (m, 2H), 2.27-2.38 (m, 1H), 1.53-1.65 (m, 2H), 1.31-1.52 (m, 5H), 1.04-1.16 (m, 2H) |

| Ex. | Structure | Method | LCMS | NMR data |
|---|---|---|---|---|
| 103 | 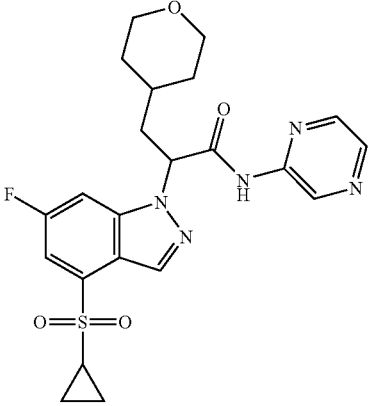 [SMILES: O=C(Nc1cnccn1)C(CC1CCOCC1)n1ncc2c(S(=O)(=O)C3CC3)cc(F)cc21]<br>2-(4-(cyclopropylsulfonyl)-6-fluoro-1H-indazol-1-yl)-N-(pyrazin-2-yl)-3-(tetrahydro-2H-pyran-4-yl)propanamide | See Cmpd. 10 | [M + H] calc'd for $C_{22}H_{25}FN_5O_4S$ 474, found 474 | $^1$H NMR (400 MHz, METHANOL-$d_4$) δ ppm 1.05-1.13 (m, 2H) 1.28-1.44 (m, 5H) 1.52 (dd, J = 9.47, 1.89 Hz, 1H) 1.68-1.77 (m, 1H) 2.19-2.28 (m, 1H) 2.55-2.65 (m, 1H) 2.81-2.90 (m, 1H) 3.16-3.29 (m, 2H) 3.80-3.92 (m, 2H) 5.73 (dd, J = 10.61, 5.05 Hz, 1H) 7.57 (dd, J = 8.34, 2.02 Hz, 1H) 7.89-7.94 (m, 1H) 8.32 (d, J = 2.53 Hz, 1H) 8.34-8.39 (m, 1H) 8.48 (s, 1H) 9.32 (d, 1H) |
| 104 | 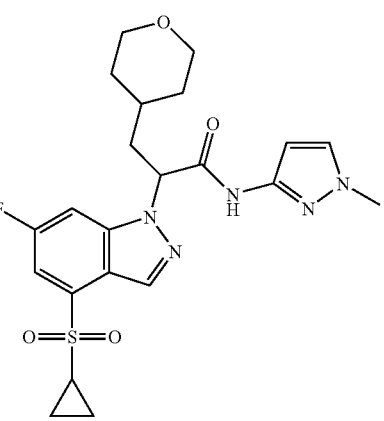<br>2-(4-(cyclopropylsulfonyl)-6-fluoro-1H-indazol-1-yl)-N-(1-methyl-1H-pyrazol-3-yl)-3-(tetrahydro-2H-pyran-4-yl)propanamide | See Cmpd. 10 | [M + H] calc'd for $C_{22}H_{27}FN_5O_4S$ 476, found 476 | $^1$H NMR (400 MHz, METHANOL-$d_4$) δ ppm 1.05-1.13 (m, 2H) 1.27-1.43 (m, 5H) 1.49-1.57 (m, 1H) 1.72 (dd, J = 10.23, 1.89 Hz, 1H) 2.18-2.27 (m, 1H) 2.50-2.59 (m, 1H) 2.81-2.89 (m, 1H) 3.16-3.29 (m, 2H) 3.77 (s, 3H) 3.81-3.91 (m, 2H) 5.60 (dd, J = 10.36, 5.31 Hz, 1H) 6.45 (d, J = 2.27 Hz, 1H) 7.43 (d, J = 2.27 Hz, 1H) 7.56 (dd, J = 8.34, 2.02 Hz, 1H) 7.90 (dd, J = 9.09, 1.01 Hz, 1H) 8.46 (s, 1H) |
| 105 | 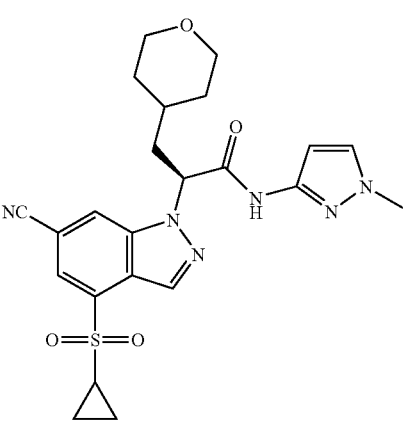<br>(S)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide | See Ex Cmpd. 19 | [M + H] calc'd for $C_{23}H_{27}N_6O_4S$ 483, found 483 | $^1$H NMR (CHLOROFORM-d, 400 MHz): δ = 8.68 (s, 1H), 8.45 (s, 1H), 8.17 (s, 1H), 7.95 (d, J = 1.0 Hz, 1H), 7.24 (d, J = 2.3 Hz, 1H), 6.62 (d, J = 2.3 Hz, 1H), 5.39 (dd, J = 9.9, 5.8 Hz, 1H), 3.91 (t, J = 11.7 Hz, 2H), 3.77 (s, 3H), 3.15-3.32 (m, 2H), 2.56-2.66 (m, 1H), 2.49 (s, 1H), 2.36 (d, J = 5.8 Hz, 1H), 1.62 (m, 1H), 1.31-1.50 (m, 6H), 1.08-1.19 ppm (m, 2H) |

| Ex. | Structure | Method | LCMS | NMR data |
|---|---|---|---|---|
| 106 | 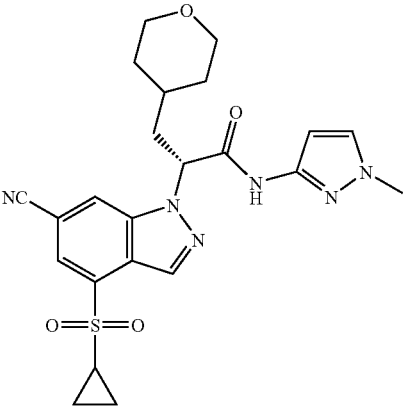<br>(R)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide | See Cmpd. 19 | [M + H] calc'd for $C_{23}H_{27}N_6O_4S$ 483, found 483 | $^1$H NMR (CHLOROFORM-d, 400 MHz): δ = 8.68 (s, 1H), 8.45 (s, 1H), 8.17 (s, 1H), 7.95 (d, J = 1.0 Hz, 1H), 7.24 (d, J = 2.3 Hz, 1H), 6.62 (d, J = 2.3 Hz, 1H), 5.39 (dd, J = 9.9, 5.8 Hz, 1H), 3.91 (t, J = 11.7 Hz, 2H), 3.77 (s, 3H), 3.15-3.32 (m, 2H), 2.56-2.66 (m, 1H), 2.49 (s, 1H), 2.36 (d, J = 5.8 Hz, 1H), 1.62 (m, 1H), 1.31-1.50 (m, 6H), 1.08-1.19 ppm (m, 2H) |
| 107 | 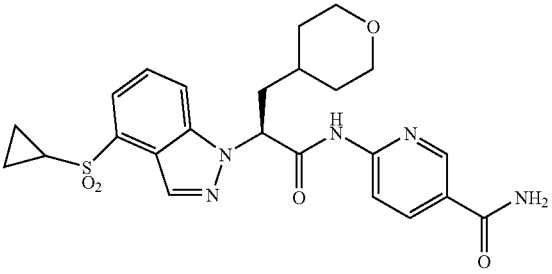 [SMILES: NC(=O)c1ccc(NC(=O)[C@H](CC2CCOCC2)n2ncc3c(S(=O)(=O)C4CC4)cccc32)nc1]<br>(S)-6-(2-(4-(cyclopropylsulfonyl)-1H-indazol-1-yl)-3-(tetrahydro-2H-pyran-4-yl)propanamido)nicotinamide | See Cmpd. 14 | [M + H] calc'd for $C_{24}H_{28}N_5O_5S$ 498.5, found 498.5 | |
| 108 | 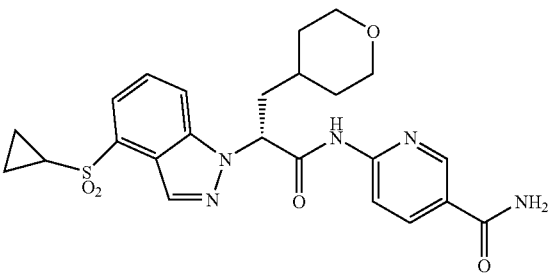 [SMILES: NC(=O)c1ccc(NC(=O)[C@@H](CC2CCOCC2)n2ncc3c(S(=O)(=O)C4CC4)cccc32)nc1]<br>(R)-6-(2-(4-(cyclopropylsulfonyl)-1H-indazol-1-yl)-3-(tetrahydro-2H-pyran-4-yl)propanamido)nicotinamide | See Cmpd. 14 | [M + H] calc'd for $C_{24}H_{28}N_5O_5S$ 498.5, found 498.5 | |

-continued

| Ex. | Structure | Method | LCMS | NMR data |
|---|---|---|---|---|
| 109 | 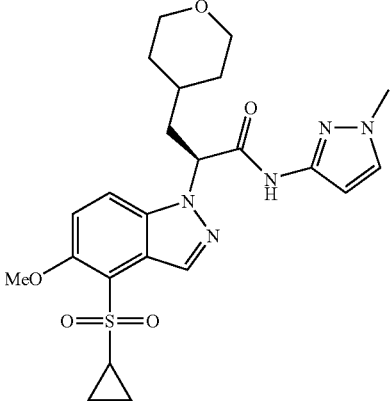 [SMILES: COc1ccc2c(cnn2[C@@H](CC2CCOCC2)C(=O)Nc2ccn(C)n2)c1S(=O)(=O)C1CC1]<br>(S)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide | See Cmpd. 15 | [M + H] calc'd for $C_{23}H_{29}N_5O_5S$ 488, found 488 | $^1$H NMR (CHLOROFORM-d, 400 MHz): δ = 8.72 (s, 1H), 8.64 (s, 1H), 7.67 (d, J = 9.3 Hz, 1H), 7.30 (d, J = 9.1 Hz, 1H), 7.22 (d, J = 2.5 Hz, 1H), 6.61 (d, J = 2.3 Hz, 1H), 5.27 (dd, J = 10.6, 4.8 Hz, 1H), 4.07 (s, 3H), 3.82-3.92 (m, 2H), 3.75 (s, 3H), 3.09-3.29 (m, 3H), 2.44-2.56 (m, 1H), 2.28 (d, J = 5.1 Hz, 1H), 1.42-1.52 (m, 2H), 1.29-1.40 (m, 3H), 1.21 (d, J = 6.1 Hz, 2H), 0.95-1.09 ppm (m, 2H) |
| 110 | 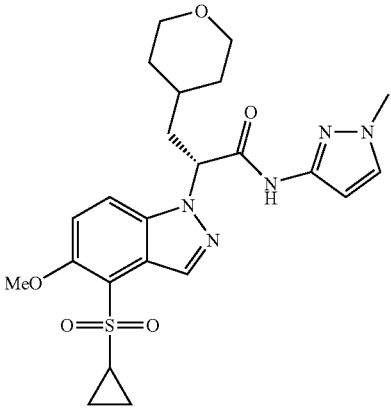 [SMILES: COc1ccc2c(cnn2[C@H](CC2CCOCC2)C(=O)Nc2ccn(C)n2)c1S(=O)(=O)C1CC1]<br>(R)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide | See Cmpd. 15 | [M + H] calc'd for $C_{23}H_{29}N_5O_5S$ 488, found 488 | $^1$H NMR (CHLOROFORM-d, 400 MHz): δ = 8.72 (s, 1H), 8.64 (s, 1H), 7.67 (d, J = 9.3 Hz, 1H), 7.30 (d, J = 9.1 Hz, 1H), 7.22 (d, J = 2.5 Hz, 1H), 6.61 (d, J = 2.3 Hz, 1H), 5.27 (dd, J = 10.6, 4.8 Hz, 1H), 4.07 (s, 3H), 3.82-3.92 (m, 2H), 3.75 (s, 3H), 3.09-3.29 (m, 3H), 2.44-2.56 (m, 1H), 2.28 (d, J = 5.1 Hz, 1H), 1.42-1.52 (m, 2H), 1.29-1.40 (m, 3H), 1.21 (d, J = 6.1 Hz, 2H), 0.95-1.09 ppm (m, 2H) |
| 111 | 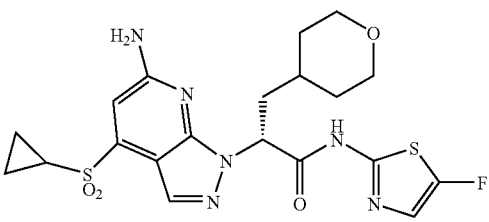 [SMILES: Nc1cc(S(=O)(=O)C2CC2)c2cnn([C@H](CC3CCOCC3)C(=O)Nc3ncc(F)s3)c2n1]<br>(R)-2-(6-amino-4-(cyclopropylsulfonyl)-1H-pyrazol[3,4-b]pyridin-1-yl)-N-(5-fluorothiazol-2-yl)-3-(tetrahydro-2H-pyran-4-yl)propanamide | See Cmpd. 16 | [M + H] calc'd for $C_{20}H_{24}FN_6O_4S_2$ 495.5, found 495.5 | $^1$H NMR (400 MHz, METHANOL-d$_4$) δ ppm 0.99-1.07 (m, 9H) 1.29-1.42 (m, 22H) 1.47-1.54 (m, 4H) 1.71-1.78 (m, 4H) 2.09-2.19 (m, 4H) 2.52-2.63 (m, 5H) 2.90 (tt, J = 8.08, 4.80 Hz, 5H) 3.12-3.28 (m, 9H) 3.80-3.90 (m, 9H) 5.86 (dd, J = 10.99, 4.42 Hz, 5H) 7.08 (d, J = 2.53 Hz, 4H) 8.15 (s, 4H) 8.32 (s, 4H). |

| Ex. | Structure | Method | LCMS | NMR data |
|---|---|---|---|---|
| 112 | 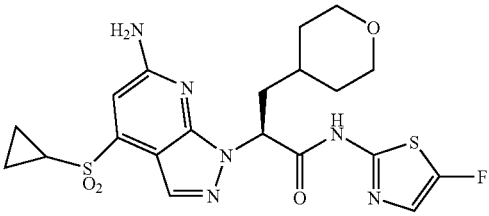 [SMILES: Nc1cc(S(=O)(=O)C2CC2)c2cnn([C@@H](CC3CCOCC3)C(=O)Nc3ncc(F)s3)c2n1]<br>(S)-2-(6-amino-4-(cyclopropylsulfonyl)-1H-pyrazol[3,4-b]pyridin-1-yl)-N-(5-fluorothiazol-2-yl)-3-(tetrahydro-2H-pyran-4-yl)propanamide | See Cmpd. 16 | [M + H] calc'd for $C_{20}H_{24}FN_6O_4S_2$ 495.5, found 495.5 | $^1$H NMR (400 MHz, METHANOL-$d_4$) δ ppm 0.99-1.07 (m, 9H) 1.29-1.42 (m, 22H) 1.47-1.54 (m, 4H) 1.71-1.78 (m, 4H) 2.09-2.19 (m, 4H) 2.52-2.63 (m, 5H) 2.90 (tt, J = 8.08, 4.80 Hz, 5H) 3.12-3.28 (m, 9H) 3.80-3.90 (m, 9H) 5.86 (dd, J = 10.99, 4.42 Hz, 5H) 7.08 (d, J = 2.53 Hz, 4H) 8.15 (s, 4H) 8.32 (s, 4H). |
| 113 | 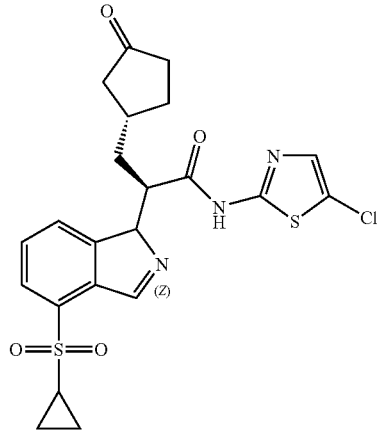 [SMILES: O=C1CC[C@H](C[C@@H](C(=O)Nc2ncc(Cl)s2)C2N=Cc3c2cccc3S(=O)(=O)C2CC2)C1]<br>(S)-N-(5-chlorothiazol-2-yl)-2-(4-(cyclopropylsulfonyl)-1H-indazol-1-yl)-3-((R)-3-oxocyclopentyl)propanamide | See Cmpd. 11 | [M + H] calc'd for $C_{21}H_{22}ClN_4O_4S_2$ 493.1, found 493.2 | |
| 114 | 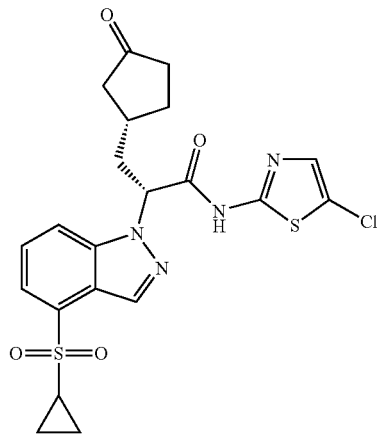 [SMILES: O=C1CC[C@H](C[C@H](C(=O)Nc2ncc(Cl)s2)n2ncc3c(S(=O)(=O)C4CC4)cccc32)C1]<br>(R)-N-(5-chlorothiazol-2-yl)-2-(4-(cyclopropylsulfonyl)-1H-indazol-1-yl)-3-((R)-3-oxocyclopentyl)propanamide | See Cmpd. 11 | [M + H] calc'd for $C_{21}H_{22}ClN_4O_4S_2$ 493.1, found 493.2 | $^1$H NMR (400 MHz, METHANOL-$d_4$) δ ppm 0.94-1.13 (m, 2H) 1.18-1.38 (m, 3H) 1.55-1.74 (m, 3H) 1.75-2.04 (m, 3H) 2.21-2.41 (m, 1H) 2.49-2.72 (m, 1H) 2.73-2.89 (m, 1H) 5.56-5.80 (m, 1H) 7.30 (s, 1H) 7.64 (dd, J = 8.59, 7.33 Hz, 1H) 7.75 (d, J = 7.07 Hz, 1H) 8.07 (dd, J = 8.59, 3.03 Hz, 1H) 8.48 (s, 1H) |

| Ex. | Structure | Method | LCMS | NMR data |
|---|---|---|---|---|
| 115 | 2-(4-(cyclopropylsulfonyl)-6-fluoro-1H-indazol-1-yl)-H-(5-fluorothiazol-2-yl)-3-(tetrahydro-2H-pyran-4-yl)propanamide | See Cmpd. 10 | [M + H] calc'd for $C_{21}H_{22}F_2N_4O_4S_3$ 498, found 498 | $^1$H NMR (400 MHz, METHANOL-d$_4$) δ ppm 1.05-1.13 (m, 2H) 1.25-1.37 (m, 5H) 1.45-1.53 (m, 1H) 1.67-1.75 (m, 1H) 2.17-2.27 (m, 1H) 2.55 (ddd, J = 14.46, 10.42, 4.42 Hz, 1H) 2.85 (tt, J = 7.96, 4.80 Hz, 1H) 3.15-3.28 (m, 2H) 3.79-3.91 (m, 2H) 5.69 (dd, J = 10.61, 5.05 Hz, 1H) 7.09 (d, J = 2.78 Hz, 1H) 7.57 (dd, J = 8.34, 2.02 Hz, 1H) 7.87 (dd, J = 9.09, 1.01 Hz, 1H) 8.46 (s, 1H) |
| 116 | 2-(4-(cyclopropylsulfonyl)-1H-indazol-1-yl)-N-(6-methylpyridazin-3-yl)-3-(tetrahydro-2H-pyran-4-yl)propanamide | See Cmpd. 10 | [M + H] calc'd for $C_{23}H_{27}N_5O_4S$ 471, found 471 | $^1$H NMR (400 MHz, METHANOL-d$_4$) δ ppm 1.02-1.09 (m, 2H) 1.25-1.44 (m, 5H) 1.49 (dd, J = 9.35, 1.77 Hz, 1H) 1.72 (d, J = 12.13 Hz, 1H) 2.21-2.30 (m, 1H) 2.62 (ddd, J = 14.15, 10.61, 3.79 Hz, 1H) 2.72 (s, 3H) 2.80 (tt, J = 7.89, 4.74 Hz, 1H) 3.13-3.27 (m, 2H) 3.79-3.91 (m, 2H) 5.84 (dd, J = 10.61, 4.80 Hz, 1H) 7.64 (dd, J = 8.46, 7.20 Hz, 1H) 7.75 (d, J = 6.57 Hz, 1H) 7.99 (d, J = 9.35 Hz, 1H) 8.10 (d, J = 8.59 Hz, 1H) 8.48 (s, 1H) 8.71 (d, 1H) |
| 117 | 6-(2-(4-(cyclopropylsulfonyl)-6-fluoro-1H-indazol-1-yl)-3-(tetrahydro-2H-pyran-4-yl)propanamido)nicotinamide | See Cmpd. 10 | [M + H] calc'd for $C_{24}H_{26}FN_5O_5S$ 517, found 517 | $^1$H NMR (400 MHz, DMSO-d$_6$) δ ppm 1.04-1.13 (m, 2H) 1.17-1.38 (m, 5H) 1.48-1.66 (m, 2H) 2.19-2.29 (m, 1H) 2.40-2.48 (m, 1H) 3.03-3.19 (m, 3H) 3.72-3.84 (m, 2H) 5.81 (dd, J = 9.73, 5.43 Hz, 1H) 7.48 (s, 1H) 7.60 (dd, J = 8.34, 2.02 Hz, 1H) 8.05 (s, 1H) 8.18-8.22 (m, 1H) 8.45 (s, 1H) 8.83 (d, J = 1.77 Hz, 1H) 11.26 (br. s., 1H) |
| 118 | (R)-2-(4-(cyclopropylsulfonyl)-1H-indazol-1-yl)-N-(1-methyl-1H-pyrazol-3-yl)-3-(tetrahydro-2H-pyrazol-4-yl)propanamide | See Cmpd. 10 | [M + H] calc'd for $C_{22}H_{27}N_5O_4S$ 459, found 459 | $^1$H NMR (400 MHz, METHANOL-d$_4$) δ ppm 1.02-1.09 (m, 2H) 1.25-1.42 (m, 5H) 1.53 (dd, J = 9.60, 1.77 Hz, 1H) 1.72 (dd, J = 9.98, 1.89 Hz, 1H) 2.18-2.28 (m, 1H) 2.54-2.63 (m, 1H) 2.81 (s, 1H) 3.15-3.28 (m, 2H) 3.76 (s, 3H) 3.81-3.90 (m, 2H) 5.67 (dd, J = 10.36, 5.31 Hz, 1H) 6.45 (d, J = 2.27 Hz, 1H) 7.43 (d, J = 2.27 Hz, 1H) 7.63 (dd, J = 8.34, 7.33 Hz, 1H) 7.75 (d, J = 6.57 Hz, 1H) 8.09 (d, J = 8.34 Hz, 1H) 8.48 (s, 1H) |

| Ex. | Structure | Method | LCMS | NMR data |
|---|---|---|---|---|
| 119 | (S)-2-(4-(cyclopropylsulfonyl)-1H-indazol-1-yl)-N-(1-methyl-1H-pyrazol-3-yl)-3-(tetrahydro-2H-pyrazol-4-yl)propanamide | See Cmpd. 10 | [M + H] calc'd for $C_{22}H_{27}N_5O_4S$ 459, found 459 | $^1$H NMR (400 MHz, METHANOL-$d_4$) δ ppm 1.02-1.09 (m, 2H) 1.25-1.42 (m, 5H) 1.53 (dd, J = 9.60, 1.77 Hz, 1H) 1.72 (dd, J = 9.98, 1.89 Hz, 1H) 2.18-2.28 (m, 1H) 2.54-2.63 (m, 1H) 2.81 (s, 1H) 3.15-3.28 (m, 2H) 3.76 (s, 3H) 3.81-3.90 (m, 2H) 5.67 (dd, J = 10.36, 5.31 Hz, 1H) 6.45 (d, J = 2.27 Hz, 1H) 7.43 (d, J = 2.27 Hz, 1H) 7.63 (dd, J = 8.34, 7.33 Hz, 1H) 7.75 (d, J = 6.57 Hz, 1H) 8.09 (d, J = 8.34 Hz, 1H) 8.48 (s, 1H) |
| 120 | 2-(6-cyano-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{22}FN_5O_4S_2$ 505, found 505 | $^1$H NMR (400 MHz, METHANOL-$d_4$) δ ppm 1.07-1.14 (m, 2H) 1.27-1.45 (m, 5H) 1.46-1.53 (m, 1H) 1.68-1.76 (m, 1H) 2.23-2.32 (m, 1H) 2.60 (ddd, J = 14.46, 10.42, 4.42 Hz, 1H) 2.89 (tt, J = 7.96, 4.80 Hz, 1H) 3.16-3.28 (m, 2H) 3.80-3.91 (m, 2H) 5.83 (dd, J = 10.61, 5.05 Hz, 1H) 7.10 (d, J = 2.78 Hz, 1H) 7.99 (d, J = 1.26 Hz, 1H) 8.59 (s, 1H) 8.64 (s, 1H) |
| 121 | 2-(6-chloro-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{23}ClFN_4O_4S_2$ 514.0, found 514.0 | $^1$H NMR (400 MHz, METHANOL-$d_4$) δ 8.55 (s, 1H), 8.34 (s, 1H), 7.92 (s, 1H), 7.00 (d, J = 2.78 Hz, 1H), 5.69 (dd, J = 5.43, 10.23 Hz, 1H), 3.82-3.92 (m, 2H), 3.16-3.29 (m, 2H), 2.53-2.71 (m, 2H), 2.16-2.28 (m, 1H), 1.67 (d, J = 12.13 Hz, 1H), 1.48-1.58 (m, 1H), 1.28-1.46 (m, 5H), 1.04-1.16 (m, 2H) |
| 122 | 2-(4-(cyclopropylsulfonyl)-6-methyl-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{26}FN_4O_4S_2$ 493.5, found 493.5 | $^1$H NMR (400 MHz, METHANOL-$d_4$) δ 8.45 (s, 1H), 8.27 (s, 1H), 7.71 (s, 1H), 7.09 (d, J = 2.53 Hz, 1H), 5.68 (dd, J = 5.05, 10.61 Hz, 1H), 3.79-3.91 (m, 2H), 3.66 (s, 1H), 3.14-3.27 (m, 2H), 2.84-2.92 (m, 4H), 2.57 (ddd, J = 4.29, 10.55, 14.46 Hz, 1H), 2.15-2.25 (m, 1H), 1.68-1.76 (m, 1H), 1.44-1.52 (m, 1H), 1.28-1.44 (m, 3H), 1.18-1.26 (m, 2H), 1.05-1.11 (m, 2H) |

| Ex. | Structure | Method | LCMS | NMR data |
|---|---|---|---|---|
| 123 | 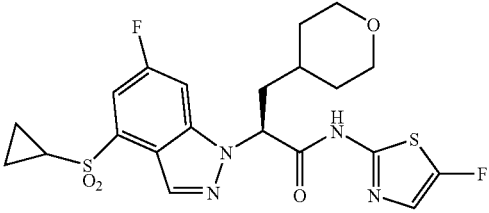 [SMILES: O=C(Nc1ncc(F)s1)[C@H](CC1CCOCC1)n1ncc2c(S(=O)(=O)C3CC3)cc(F)cc21]<br>(S)-2-(4-(cyclopropylsulfonyl)-6-fluoro-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{22}F_2N_4O_4S_2$ 498, found 498 | $^1$H NMR (400 MHz, METHANOL-$d_4$) δ ppm 1.05-1.13 (m, 2H) 1.26-1.37 (m, 5H) 1.45-1.52 (m, 1H) 1.67-1.75 (m, 1H) 2.17-2.27 (m, 1H) 2.55 (ddd, J = 14.46, 10.42, 4.42 Hz, 1H) 2.85 (tt, J = 7.96, 4.80 Hz, 1H) 3.15-3.28 (m, 2H) 3.79-3.91 (m, 2H) 5.69 (dd, J = 10.61, 5.05 Hz, 1H) 7.09 (d, J = 2.78 Hz, 1H) 7.57 (dd, J = 8.34, 2.02 Hz, 1H) 7.87 (dd, J = 9.09, 1.01 Hz, 1H) 8.46 (s, 1H) |
| 124 | 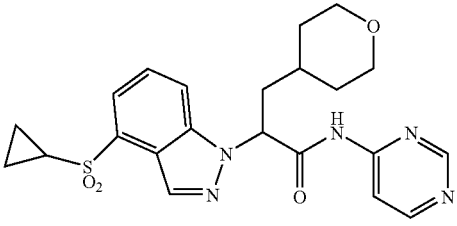 [SMILES: O=C(Nc1ccncn1)C(CC1CCOCC1)n1ncc2c(S(=O)(=O)C3CC3)cccc21]<br>2-(4-(cyclopropylsulfonyl)-1H-indazol-1-yl)-N-(pyrimidin-4-yl)-3-(tetrahydro-2H-pyran-4-yl)propanamide | See Cmpd. 10 | [M + H] calc'd for $C_{22}H_{25}N_5O_4S$ 457, found 457 | $^1$H NMR (400 MHz, METHANOL-$d_4$) δ ppm 1.02-1.12 (m, 2H) 1.25-1.41 (m, 5H) 1.41-1.53 (m, 1H) 1.68-1.76 (m, 1H) 2.18-2.30 (m, 1H) 2.59 (m, J = 14.31, 10.59, 10.59, 3.92 Hz, 1H) 2.77-2.87 (m, 1H) 3.12-3.27 (m, 2H) 3.78-3.91 (m, 2H) 5.62-5.86 (m, 1H) 7.58-7.68 (m, 1H) 7.70-7.79 (m, 1H) 8.05-8.12 (m, 1H) 8.24 (dd, J = 6.06, 1.26 Hz, 1H) 8.49 (s, 1H) 8.66 (d, J = 6.06 Hz, 1H) 8.92 (s, 1H) |
| 125 | 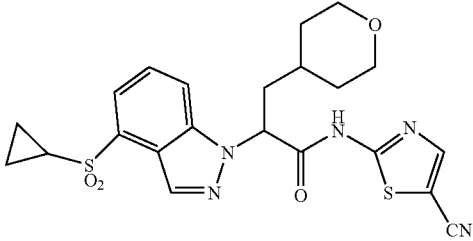 [SMILES: N#Cc1cnc(NC(=O)C(CC2CCOCC2)n2ncc3c(S(=O)(=O)C4CC4)cccc32)s1]<br>N-(5-cyanothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{22}H_{23}N_5O_4S_2$ 487, found 487 | $^1$H NMR (400 MHz, METHANOL-$d_4$) δ ppm 1.01-1.10 (m, 2H) 1.26-1.42 (m, 5H) 1.50 (dd, J = 9.35, 2.02 Hz, 1H) 1.70-1.77 (m, 1H) 2.23-2.32 (m, 1H) 2.58 (ddd, J = 14.27, 10.61, 3.92 Hz, 1H) 2.81 (tt, J = 7.96, 4.80 Hz, 1H) 3.15-3.27 (m, 2H) 3.79-3.90 (m, 2H) 5.77 (dd, J = 10.61, 4.80 Hz, 1H) 7.62 (dd, J = 8.46, 7.20 Hz, 1H) 7.74 (d, J = 6.57 Hz, 1H) 8.03-8.07 (m, 2H) 8.46 (s, 1H) |
| 126 | 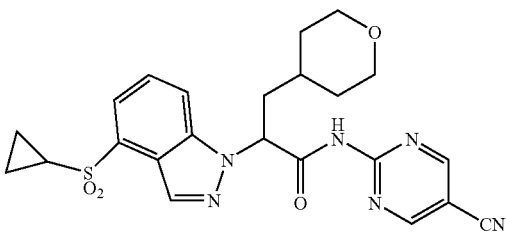 [SMILES: N#Cc1cnc(NC(=O)C(CC2CCOCC2)n2ncc3c(S(=O)(=O)C4CC4)cccc32)nc1]<br>N-(5-cyanopyrimidin-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{23}H_{24}N_6O_4S$ 482, found 482 | $^1$H NMR (400 MHz, METHANOL-$d_4$) δ ppm 1.02-1.11 (m, 2H) 1.26-1.41 (m, 5H) 1.42-1.52 (m, 1H) 1.70-1.79 (m, 1H) 2.18-2.30 (m, 1H) 2.53-2.65 (m, 1H) 2.77-2.87 (m, 1H) 3.12-3.27 (m, 2H) 3.79-3.91 (m, 2H) 5.65 (dd, J = 11.37, 4.29 Hz, 1H) 7.63 (dt, J = 8.59, 6.95 Hz, 1H) 7.74 (dd, J = 6.57, 5.05 Hz, 1H) 7.99-8.10 (m, 1H) 8.45 (d, J = 12.88 Hz, 1H) 8.54 (s, 1H) 8.95 (s, 1H) |

| Ex. | Structure | Method | LCMS | NMR data |
|---|---|---|---|---|
| 127 | 2-(4-(cyclopropylsulfonyl)-1H-pyrazolo[3,4-b]pyridin-1-yl)-N-(5-fluorothiazol-2-yl)-3-(tetrahydro-2H-pyran-4-yl)propanamide | See Cmpd. 16 & 95 | [M + H] calc'd for $C_{20}H_{22}FN_5O_4S_2$ 481, found 481 | $^1$H NMR (400 Mz, METHANOL-d$_4$) δ ppm 1.10-1.20 (m, 2H) 1.30-1.43 (m, 5H) 1.50-1.57 (m, 1H) 1.76 (dd, J = 10.23, 1.89 Hz, 1H) 2.16-2.26 (m, 1H) 2.67 (ddd, J = 14.27, 10.99, 3.79 Hz, 1H) 2.90 (tt, J = 7.93, 4.71 Hz, 1H) 3.11-3.28 (m, 2H) 3.81-3.90 (m, 2H) 6.05 (dd, J = 11.12, 4.29 Hz, 1H) 7.08 (d, J = 2.53 Hz, 1H) 7.71 (d, J = 4.80 Hz, 1H) 8.51 (s, 1H) 8.82 (d, 1H) |
| 128 | (S)-2-(4-(cyclopropylsulfonyl)-6-methoxy-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{26}FN_4O_5S_2$ 509, found 509 | $^1$H NMR (CHLOROFORM-d, 400 MHz): δ = 8.52 (s, 1H), 7.45 (d, J = 1.8 Hz, 1H), 7.00 (br. s., 1H), 6.96 (s, 1H), 5.30 (s, 1H), 3.95 (s, 3H), 3.78-3.93 (m, 2H), 3.13-3.30 (m, 2H), 2.57-2.73 (m, 1H), 2.50 (br. s., 1H), 2.25 (d, J = 5.6 Hz, 1H), 1.59 (d, J = 12.4 Hz, 1H), 1.44-1.55 (m, 2H), 1.28-1.44 (m, 4H), 1.01-1.16 ppm (m, 2H) |
| 129 | (R)-2-(4-(cyclopropylsulfonyl)-6-methoxy-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{26}FN_4O_5S_2$ 509, found 509 | $^1$H NMR (CHLOROFORM-d, 400 MHz): δ = 8.52 (s, 1H), 7.45 (d, J = 1.8 Hz, 1H), 7.00 (br. s., 1H), 6.96 (s, 1H), 5.30 (s, 1H), 3.95 (s, 3H), 3.78-3.93 (m, 2H), 3.13-3.30 (m, 2H), 2.57-2.73 (m, 1H), 2.50 (br. s., 1H), 2.25 (d, J = 5.6 Hz, 1H), 1.59 (d, J = 12.4 Hz, 1H), 1.44-1.55 (m, 2H), 1.28-1.44 (m, 4H), 1.01-1.16 ppm (m, 2H) |
| 130 | 2-(4-(cyclopropylsulfonyl)-6-hydroxy-1H-indazol-1-yl)-N-(5-fluorothiazol-2-yl)-3-(tetrahydro-2H-pyran-4-yl)propanamide | See Cmpd. 12 | [M + H] calc'd for $C_{21}H_{24}FN_4O_5S_2$ 495, found 495 | $^1$H NMR (DMSO-d$_6$, 400 MHz): δ = 12.70 (s, 1H), 10.48 (s, 1H), 8.23 (s, 1H), 7.33-7.36 (m, 2H), 7.23 (d, J = 1.8 Hz, 1H), 5.62 (d, J = 4.3 Hz, 1H), 3.71-3.85 (m, 3H), 3.06-3.21 (m, 2H), 2.24-2.41 (m, 1H), 2.09-2.24 (m, 1H), 1.54-1.63 (m, 1H), 1.48 (br. s., 1H), 1.28 (br. s., 3H), 1.16 (br. s., 2H), 1.06 ppm (dd, J = 7.8, 2.0 Hz, 2H) |

| Ex. | Structure | Method | LCMS | NMR data |
|---|---|---|---|---|
| 131 | 2-(4-(cyclopropylsulfonyl)-6-hydroxy-1H-indazol-1-yl)-N-(5-fluorothiazol-2-yl)-3-(tetrahydro-2H-pyran-4-yl)propanamide | See Cmpd. 12 | [M + H] calc'd for $C_{21}H_{24}FN_4O_5S_2$ 495, found 495 | $^1$H NMR (DMSO-d$_6$, 400 MHz): δ = 13.41 (br. s., 1H), 12.74 (s, 1H), 8.21 (s, 1H), 7.35 (d, J = 2.5 Hz, 1H), 7.30 (d, J = 2.0 Hz, 1H), 7.21 (d, J = 1.0 Hz, 1H), 5.18 (d, J =9.3 Hz, 1H), 3.79-3.87 (m, 2H), 3.21-3.35 (m, 2H), 2.93-3.02 (m, 1H), 1.92-2.00 (m, 1H), 1.84 (d, J = 3.5 Hz, 1H), 1.82 (br. s., 1H), 1.64 (br. s., 2H), 1.28 (br. s., 2H), 1.14-1.19 (m, 2H), 1.00-1.06 ppm (m, 2H) |
| 132 | (R)-2-(6-cyano-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{22}FN_5O_4S_2$ 505, found 505 | $^1$H NMR (400 MHz, METHANOL-d$_4$) δ ppm 1.07-1.14 (m, 2H) 1.27-1.45 (m, 5H) 1.46-1.53 (m, 1H) 1.68-1.76 (m, 1H) 2.23-2.32 (m, 1H) 2.60 (ddd, J = 14.46, 10.42, 4.42 Hz, 1H) 2.89 (tt, J = 7.96, 4.80 Hz, 1H) 3.16-3.28 (m, 2H) 3.80-3.91 (m, 2H) 5.83 (dd, J = 10.61, 5.05 Hz, 1H) 7.10 (d, J = 2.78 Hz, 1H) 7.99 (d, J = 1.26 Hz, 1H) 8.59 (s, 1H) 8.64 (s, 1H) |
| 133 | (S)-2-(6-cyano-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{22}H_{22}FN_5O_4S_2$ 505, found 505 | $^1$H NMR (400 MHz, METHANOL-d$_4$) δ ppm 1.07-1.14 (m, 2H) 1.27-1.45 (m, 5H) 1.46-1.53 (m, 1H) 1.68-1.76 (m, 1H) 2.23-2.32 (m, 1H) 2.60 (ddd, J = 14.46, 10.42, 4.42 Hz, 1H) 2.89 (tt, J = 7.96, 4.80 Hz, 1H) 3.16-3.28 (m, 2H) 3.80-3.91 (m, 2H) 5.83 (dd, J = 10.61, 5.05 Hz, 1H) 7.10 (d, J = 2.78 Hz, 1H) 7.99 (d, J = 1.26 Hz, 1H) 8.59 (s, 1H) 8.64 (s, 1H) |
| 134 | 2-(4-(cyclopropylsulfonyl)-1H-indazol-1-yl)-N-(1,5-dimethyl-1H-pyrazol-3-yl)-3-(tetrahydro-2H-pyran-4-yl)propanamide | See Cmpd. 10 | [M + H] calc'd for $C_{23}H_{29}N_5O_4S$ 473, found 473 | $^1$H NMR (400 MHZ, METHANOL-d$_4$) δ ppm 1.01-1.09 (m, 2H) 1.25-1.43 (m, 5H) 1.51 (d, J = 9.35 Hz, 1H) 1.71 (d, J = 11.87 Hz, 1H) 2.17-2.28 (m, 4H) 2.57 (ddd, J = 14.15, 10.36, 4.04 Hz, 1H) 2.81 (tt, J = 7.96, 4.80 Hz, 1H) 3.14-3.28 (m, 2H) 3.63-3.69 (m, 3H) 3.80-3.90 (m, 2H) 5.66 (dd, J = 10.36, 5.05 Hz, 1H) 6.24 (s, 1H) 7.61-7.66 (m, 1H) 7.74 (d, J = 6.57 Hz, 1H) 8.08 (d, J = 8.34 Hz, 1H) 8.48 (s, 1H) |

| Ex. | Structure | Method | LCMS | NMR data |
|---|---|---|---|---|
| 135 | N-(5-cyanopyridin-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{24}H_{25}N_5O_4S$ 481, found 481 | $^1$H NMR (400 MHz, METHANOL-$d_4$) δ ppm 1.01-1.09 (m, 2H) 1.25-1.43 (m, 5H) 1.50 (dd, J = 9.47, 1.89 Hz, 1H) 1.72 (d, J = 12.13 Hz, 1H) 2.18-2.27 (m, 1H) 2.60 (ddd, J = 14.15, 10.48, 3.92 Hz, 1H) 2.81 (tt, J = 7.96, 4.80 Hz, 1H) 3.13-3.27 (m, 2H) 3.79-3.90 (m, 2H) 5.79 (dd, J = 10.48, 4.93 Hz, 1H) 7.63 (dd, J = 8.59, 7.33 Hz, 1H) 7.74 (d, J = 6.57 Hz, 1H) 8.04-8.12 (m, 2H) 8.24 (d, J = 8.84 Hz, 1H) 8.49 (s, 1H) 8.60-8.64 (m, 1H) |
| 136 | (S)-N-(5-cyanothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{22}H_{23}N_5O_4S_2$ 487, found 487 | $^1$H NMR (400 MHz, METHANOL-$d_4$) δ ppm 1.01-1.10 (m, 2H) 1.26-1.42 (m, 5H) 1.50 (dd, J = 9.35, 2.02 Hz, 1H) 1.70-1.77 (m, 1H) 2.23-2.32 (m, 1H) 2.58 (ddd, J = 14.27, 10.61, 3.92 Hz, 1H) 2.81 (tt, J = 7.96, 4.80 Hz, 1H) 3.15-3.27 (m, 2H) 3.79-3.90 (m, 2H) 5.77 (dd, J = 10.61, 4.80 Hz, 1H) 7.62 (dd, J = 8.46, 7.20 Hz, 1H) 7.74 (d, J = 6.57 Hz, 1H) 8.03-8.07 (m, 2H) 8.46 (s, 1H) |
| 137 | (R)-N-(5-cyanothiazol-2-yl)-2-(4-(cyclopropylsulfonyl)-1H-indazol-1-yl)-3-(tetrahydro-2H-pyran-4-yl)propanamide | See Cmpd. 10 | [M + H] calc'd for $C_{22}H_{23}N_5O_4S_2$ 487, found 487 | $^1$H NMR (400 MHz, METHANOL-$d_4$) δ ppm 1.01-1.10 (m, 2H) 1.26-1.42 (m, 5H) 1.50 (dd, J = 9.35, 2.02 Hz, 1H) 1.70-1.77 (m, 1H) 2.23-2.32 (m, 1H) 2.58 (ddd, J = 14.27, 10.61, 3.92 Hz, 1H) 2.81 (tt, J = 7.96, 4.80 Hz, 1H) 3.15-3.27 (m, 2H) 3.79-3.90 (m, 2H) 5.77 (dd, J = 10.61, 4.80 Hz, 1H) 7.62 (dd, J = 8.46, 7.20 Hz, 1H) 7.74 (d, J = 6.57 Hz, 1H) 8.03-8.07 (m, 2H) 8.46 (s, 1H) |
| 138 | (S)-2-(4-(cyclopropylsulfonyl)-1H-pyrazol[3,4-b]pyridin-1-yl)-N-(5-fluorothiazol-2-yl)-3-(tetrahydro-2H-pyran-4-yl)propanamide | See Cmpd. 16 & 95 | [M + H] calc'd for $C_{20}H_{22}FN_5O_4S_2$ 481, found 481 | $^1$H NMR (400 Mz, METHANOL-$d_4$) δ ppm 1.10-1.20 (m, 2H) 1.30-1.43 (m, 5H) 1.50-1.57 (m, 1H) 1.76 (dd, J = 10.23, 1.89 Hz, 1H) 2.16-2.26 (m, 1H) 2.67 (ddd, J = 14.27, 10.99, 3.79 Hz, 1H) 2.90 (tt, J = 7.93, 4.71 Hz, 1H) 3.11-3.28 (m, 2H) 3.81-3.90 (m, 2H) 6.05 (dd, J = 11.12, 4.29 Hz, 1H) 7.08 (d, J = 2.53 Hz, 1H) 7.71 (d, J = 4.80 Hz, 1H) 8.51 (s, 1H) 8.82 (d, 1H) |

| Ex. | Structure | Method | LCMS | NMR data |
|---|---|---|---|---|
| 139 | 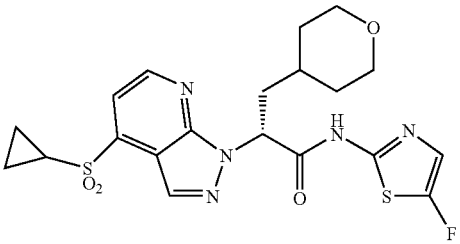 [SMILES: O=C(Nc1ncc(F)s1)[C@@H](CC1CCOCC1)n1ncc2c(S(=O)(=O)C3CC3)ccnc21]<br>(R)-2-(4-(cyclopropylsulfonyl)-1H-pyrazol[3,4-b]pyridin-1-yl)-N-(5-fluorothiazol-2-yl)-3-(tetrahydro-2H-pyran-4-yl)propanamide | See Cmpd. 16 & 95 | [M + H] calc'd for $C_{20}H_{22}FN_5O_4S_2$ 481, found 481 | $^1$H NMR (400 Mz, METHANOL-$d_4$) δ ppm 1.10-1.20 (m, 2H) 1.30-1.43 (m, 5H) 1.50-1.57 (m, 1H) 1.76 (dd, J = 10.23, 1.89 Hz, 1H) 2.16-2.26 (m, 1H) 2.67 (ddd, J = 14.27, 10.99, 3.79 Hz, 1H) 2.90 (tt, J = 7.93, 4.71 Hz, 1H) 3.11-3.28 (m, 2H) 3.81-3.90 (m, 2H) 6.05 (dd, J = 11.12, 4.29 Hz, 1H) 7.08 (d, J = 2.53 Hz, 1H) 7.71 (d, J = 4.80 Hz, 1H) 8.51 (s, 1H) 8.82 (d, 1H) |
| 140 | 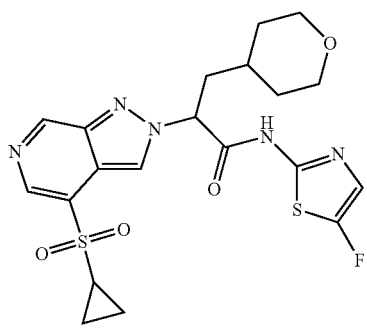 [SMILES: O=C(Nc1ncc(F)s1)C(CC1CCOCC1)n1cc2c(S(=O)(=O)C3CC3)cncc2n1]<br>2-(4-(cyclopropylsulfonyl)-2H-pyrazol[3,4-c]pyridin-2-yl)-N-(5-fluorothiazol-2-yl)-3-(tetrahydro-2H-pyran-4-yl)propanamide | See Cmpd. 13 | [M + H] calc'd for $C_{20}H_{23}FN_5O_4S_2$ 480, found 480 | |
| 141 | 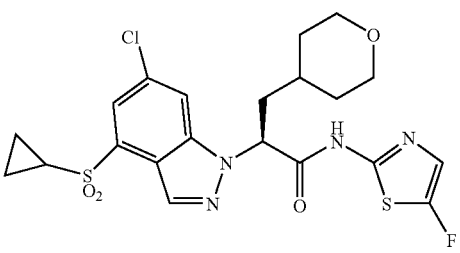 [SMILES: O=C(Nc1ncc(F)s1)[C@@H](CC1CCOCC1)n1ncc2c(S(=O)(=O)C3CC3)cc(Cl)cc21]<br>(S)-2-(6-chloro-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{23}ClFN_4O_4S_2$ 514.0, found 514.0 | |
| 142 | 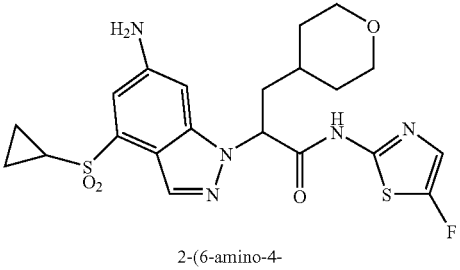<br>2-(6-amino-4-(cyclopropylsulfonyl)-1H-indazol-1-yl)-N-(5-fluorothiazol-2-yl)-3-(tetrahydro-2H-pyran-4-yl)propanamide | See Cmpd. 21 | [M + H] calc'd for $C_{21}H_{25}FN_5O_4S_2$ 494.1, found 494.4 | |

| Ex. | Structure | Method | LCMS | NMR data |
|---|---|---|---|---|
| 143 | 2-(4-(cyclopropylsulfonyl)-6-(difluoromethoxy)-1H-indazol-1-yl)-N-(5-fluorothiazol-2-yl)-3-(tetrahydro-2H-pyran-4-yl)propanamide | See Cmpd. 12 | [M + H] calc'd for $C_{22}H_{24}F_3N_4O_5S_2$ 545.1, found 545.3 | $^1$H NMR (400 MHz, METHANOL-$d_4$) δ ppm 1.03-1.14 (m, 2H) 1.23-1.45 (m, 5H) 1.45-1.55 (m, 1H) 1.72 (dd, J = 12.51, 2.40 Hz, 1H) 2.16-2.31 (m, 1H) 2.55 (ddd, J = 14.46, 10.42, 4.42 Hz, 1H) 2.86 (tt, J = 7.83, 4.80 Hz, 1H) 3.22 (m, J = 17.15, 11.57, 11.57, 2.15 Hz, 2H) 3.76-3.96 (m, 2H) 7.01 (d, J = 73.01 Hz, 1H) 7.10 (d, J = 2.53 Hz, 1H) 7.56 (d, J = 1.77 Hz, 1H) 7.87 (s, 1H) 8.47 (s, 1H) |
| 144 | 2-(4-(cyclopropylsulfonyl)-5-hydroxy-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{24}FN_4O_5S_2$ 495.1, found 495.3 | |
| 145 | (R)-2-(6-chloro-4-(cyclopropylsulfonyl)-1H-indazol-1-yl)-N-(5-fluorothiazol-2-yl)-3-(tetrahydro-2H-pyran-4-yl)propanamide | See Cmpd. 10 | [M + H] calc'd for $C_{21}H_{23}ClFN_4O_4S_2$ 514.0, found 514.0 | |
| 146 | 2-(4-(cyclopropylsulfonyl)-1H-indazol-1-yl)-N-(1-(methylsulfonyl)-1H-pyrazol-3-yl)-3-(tetrahydro-2H-pyran-4-yl)propanamide | See Cmpd. 10 | [M + H] calc'd for $C_{22}H_{28}N_5O_6S_2$ 522.1, found 522.1 | $^1$H NMR (400 MHz, CHLOROFORM-d) δ 9.00 (s, 1H), 8.66 (s, 1H), 7.92 (d, J = 3.03 Hz, 1H), 7.81 (d, J = 6.57 Hz, 1H), 7.74 (d, J = 8.84 Hz, 1H), 7.61 (dd, J = 7.33, 8.59 Hz, 1H), 7.02 (d, J = 2.78 Hz, 1H), 5.38 (dd, J = 5.05, 10.61 Hz, 1H), 3.89 (br. s., 2H), 3.09-3.30 (m, 5H), 2.60-2.71 (m, 1H), 2.46-2.59 (m, 1H), 2.29 (ddd, J = 5.05, 8.65, 14.08 Hz, 1H), 1.28-1.55 (m, 6H), 1.25 (br. s., 1H), 1.01-1.20 (m, 2H) |

| Ex. | Structure | Method | LCMS | NMR data |
| --- | --- | --- | --- | --- |
| 147 | 2-(4-(cyclopropylsulfonyl)-1H-indazol-1-yl)-N-(6-fluoropyridin-2-yl)-3-(tetrahydro-2H-pyran-4-yl)propanamide | See Cmpd. 10 | [M + H] calc'd for $C_{23}H_{26}FN_4O_4S$ 473.2, found 473.2 | $^1$H NMR (400 MHz, CHLOROFORM-d) δ 8.92 (s, 1H), 8.67 (s, 1H), 8.04 (dd, J = 1.64, 7.96 Hz, 1H), 7.73-7.86 (m, 3H), 7.60 (dd, J = 7.33, 8.59 Hz, 1H), 6.68 (dd, J = 2.27, 8.08 Hz, 1H), 5.39 (dd, J = 4.93, 10.48 Hz, 1H), 3.81-3.97 (m, 2H), 3.11-3.34 (m, 3H), 2.46-2.70 (m, 2H), 2.29 (ddd, J = 4.93, 8.59, 14.02 Hz, 1H), 1.62 (d, J = 12.88 Hz, 1H), 1.31-1.55 (m, 4H), 1.26 (qd, J = 4.29, 7.66 Hz, 1H), 0.96-1.15 (m, 2H) |
| 148 | 2-(4-(cyclopropylsulfonyl)-5-fluoro-2H-indazol-2-yl)-N-(5-fluorothiazol-2-yl)-3-(tetrahydro-2H-pyran-4-yl)propanamide | See Cmpd. 19 | [M + H] calc'd for $C_{21}H_{23}F_2N_4O_4S_2$ 497.1, found 497.1 | $^1$H NMR (400 MHz, CHLOROFORM-d) δ 8.61 (s, 1H), 8.04 (dd, J = 4.17, 9.22 Hz, 1H), 7.24-7.35 (m, 2H), 7.03 (br. s., 1H), 5.34 (dd, J = 5.43, 9.98 Hz, 1H), 3.91 (br. s., 2H), 3.18-3.34 (m, 2H), 2.80-2.97 (m, 1H), 2.37-2.53 (m, 1H), 2.20-2.37 (m, 1H), 1.68 (br. s., 1H), 1.45-1.55 (m, 2H), 1.26-1.45 (m, 4H), 1.00-1.15 (m, 2H) |
| 149 | 2-(4-(cyclopropylsulfonyl)-5-fluoro-1H-indazol-1-yl)-N-(5-fluorothiazol-2-yl)-3-(tetrahydro-2H-pyran-4-yl)propanamide | See Cmpd. 19 | [M + H] calc'd for $C_{21}H_{23}F_2N_4O_4S_2$ 497.1, found 497.1 | $^1$H NMR (400 MHz, CHLOROFORM-d) δ 8.72 (s, 1H), 7.73 (dd, J = 2.91, 9.22 Hz, 1H), 7.37 (t, J = 9.35 Hz, 1H), 7.07 (d, J = 2.27 Hz, 1H), 5.46 (dd, J = 4.93, 10.48 Hz, 1H), 3.92 (ddd, J = 2.53, 11.37, 13.39 Hz, 2H), 3.14-3.31 (m, 2H), 2.83-2.94 (m, 1H), 2.45-2.61 (m, 1H), 2.28 (ddd, J = 4.93, 8.78, 14.08 Hz, 1H), 1.58-1.69 (m, 1H), 1.32-1.58 (m, 5H), 1.21 (d, J = 3.79 Hz, 1H), 1.04-1.17 (m, 2H) |
| 150 | 2-(5-bromo-4-(cyclopropylsulfonyl)-1H-indazol-1-yl)-N-(5-fluorothiazol-2-yl)-3-(tetrahydro-2H-pyran-4-yl)propanamide | See Cmpd. 19 | [M + H] calc'd for $C_{21}H_{23}BrFN_4O_4S_2$ 558, found 558 | $^1$H NMR (400 MHz, DMSO-$d_6$) δ 9.00 (s, 1H), 7.82 (d, J = 7.58 Hz, 1H), 7.56 (d, J = 7.58 Hz, 1H), 7.38 (d, J = 2.53 Hz, 1H), 5.82 (dd, J = 5.68, 9.73 Hz, 1H), 3.73-3.86 (m, 2H), 3.09-3.20 (m, 2H), 2.89-3.04 (m, 1H), 2.45-2.61 (m, 1H) 2.20-2.36 (m, 1H), 1.64 (d, J = 7.83 Hz, 1H), 1.51 (d, J = 13.14 Hz, 1H), 1.20-1.37 (m, 5H), 0.97-1.09 (m, 2H) |

| Ex. | Structure | Method | LCMS | NMR data |
|---|---|---|---|---|
| 151 | 2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide | See Cmpd. 13 | [M + H] calc'd for $C_{21}H_{26}H_6O_4S$ 460, found 460 | $^1$H NMR (400 MHz, DMSO-$d_6$) δ ppm 1.03-1.13 (m, 2H) 1.17-1.36 (m, 5H) 1.48-1.70 (m, 2H) 2.28 (d, J = 6.82 Hz, 1H) 2.44 (br. s., 1H) 3.03-3.23 (m, 3H) 3.69-3.84 (m, 5H) 5.87 (d, J = 3.54 Hz, 1H) 6.37 (d, J = 2.02 Hz, 1H) 7.55 (d, J = 2.02 Hz, 1H) 8.51 (s, 1H) 8.68 (s, 1H) 9.67 (s, 1H) 11.08 (s, 1H) |
| 152 | 2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide | See Cmpd. 22 | [M + H] calc'd for $C_{22}H_{27}FN_5O_4S$ 476, found 476 | $^1$H NMR (CHLOROFORM-d, 400 MHz): δ = 8.58-8.83 (m, 2H), 7.74 (dd, J = 9.1, 3.0 Hz, 1H), 7.34 (t, J = 9.3 Hz, 1H), 7.23 (d, J = 2.0 Hz, 1H), 6.61 (d, J = 2.3 Hz, 1H), 5.33 (dd, J = 10.4, 5.1 Hz, 1H), 3.81-3.94 (m, 2H), 3.76 (s, 3H), 3.08-3.32 (m, 2H), 2.90 (dd, J = 4.8, 3.3 Hz, 1H), 2.49 (d, J = 3.8 Hz, 1H), 2.22-2.37 (m, 1H), 1.59 (d, J = 12.4 Hz, 1H), 1.19-1.55 (m, 5H), 1.04-1.19 (m, 2H), 0.78-0.93 ppm (m, 1H) |
| 153 | 2-(4-(cyclopropylsulfonyl)-5-fluoro-2H-indazol-2-yl)-N-(1-methyl-1H-pyrazol-3-yl)-3-(tetrahydro-2H-pyran-4-yl)propanamide | See Cmpd. 22 | [M + H] calc'd for $C_{22}H_{27}FN_5O_4S$ 476, found 476 | $^1$H NMR (CHLOROFORM-d, 400 MHz): δ = 9.16 (s, 1H), 8.59 (s, 1H), 8.04 (dd, J = 9.3, 3.5 Hz, 1H), 7.28 (d, 1H), 7.24 (d, J = 2.5 Hz, 1H), 6.63 (d, J = 2.3 Hz, 1H), 5.27 (dd, J = 9.9, 5.6 Hz, 1H), 3.93 (dd, J = 11.4, 2.3 Hz, 1H), 3.87 (d, J = 10.9 Hz, 1H), 3.77 (s, 3H), 3.23-3.37 (m, 2H), 2.78-2.94 (m, 1H), 2.42 (dd, J = 9.6, 4.5 Hz, 1H), 2.27-2.37 (m, 1H), 1.59-1.84 (m, 2H), 1.28-1.52 (m, 5H), 0.95-1.18 ppm (m, 2H) |
| 154 | 2-(4-(cyclopropylsulfonyl)-5-fluoro-1H-indazol-1-yl)-N-(pyrazin-2-yl)-3-(tetrahydro-2H-pyran-4-yl)propanamide | See Cmpd. 22 | [M + H] calc'd for $C_{22}H_{25}FN_5O_4S$ 474, found 474 | $^1$NMR (CHLOROFORM-d, 400 MHz): δ = 9.39-9.52 (m, 1H), 9.05 (s, 1H), 8.80 (s, 1H), 8.31-8.40 (m, 1H), 8.18-8.29 (m, 1H), 7.77 (dd, J = 9.2, 2.9 Hz, 1H), 7.39 (t, J = 9.5 Hz, 1H), 5.39 (dd, J = 10.4, 5.1 Hz, 1H), 3.76-4.00 (m, 2H), 3.09-3.33 (m, 2H), 2.74-2.96 (m, 1H), 2.43-2.62 (m, 1H), 2.19-2.43 (m, 1H), 1.57-1.66 (m, 1H), 1.24-1.55 (m, 6H), 1.03-1.19 ppm (m, 2H) |

| Ex. | Structure | Method | LCMS | NMR data |
|---|---|---|---|---|
| 155 | 2-(4-(cyclopropylsulfonyl)-5-fluoro-1H-indazol-1-yl)-N-(1-ethyl-1H-pyrazol-3-yl)-3-(tetrahydro-2H-pyran-4-yl)propanamide | See Cmpd. 22 | [M + H] calc'd for $C_{23}H_{29}FN_5O_4S$ 490, found 490 | $^1$H NMR (CHLOROFORM-d, 400 MHz): δ = 9.38 (s, 1H), 8.71 (s, 1H), 7.75-7.78 (m, 1H), 7.23-7.36 (m, 2H), 6.67-6.72 (m, 1H), 5.25-5.46 (m, 1H), 4.00-4.12 (m, 2H), 3.83-3.95 (m, 2H), 3.12-3.34 (m, 2H), 2.81-2.94 (m, 1H), 2.39-2.59 (m, 1H), 2.23-2.39 (m, 1H), 1.32-1.54 (m, 10H), 0.96-1.19 ppm (m, 2H) |
| 156 | 2-(4-(cyclopropylsulfonyl)-5-fluoro-2H-indazol-2-yl)-N-(pyrazin-2-yl)-3-(tetrahydro-2H-pyran-4-yl)proanamide | See Cmpd. 22 | [M + H] calc'd for $C_{22}H_{25}FN_5O_4S$ 474, found 474 | $^1$H NMR (CHLOROFORM-d, 400 MHz): δ = 9.53 (s, 2H), 8.81 (s, 1H), 8.42 (d, J = 3.0 Hz, 2H), 7.78 (dd, J = 9.0, 3.4 Hz, 1H), 7.41 (t, J = 9.5 Hz, 1H), 5.43 (dd, J = 10,1, 5.3 Hz, 1H), 3.89-4.13 (m, 2H), 3.18-3.42 (m, 2H), 2.78-2.96 (m, 1H), 2.52 (dd, J = 9.9, 4.5 Hz, 1H), 2.21-2.41 (m, 1H), 1.65 (d, J = 12.6 Hz, 1H), 1.38-1.56 (m, 5H), 1.31-1.37 (m, 1H), 1.11-1.24 ppm (m, 2H) |
| 157 | 2-(4-(cyclopropylsulfonyl)-5-methyl-1H-indazol-1-yl)-N-(pyrazin-2-yl)-3-(tetrahydro-2H-pyran-4-yl)propanamide | See Cmpd. 22 | [M + H] calc'd for $C_{23}H_{28}N_5O_4S$ 470, found 470 | $^1$H NMR (CHLOROFORM-d, 400 MHz): δ = 9.53 (br. s., 1H), 9.31 (br. s., 1H), 8.77 (s, 1H), 8.27-8.50 (m, 2H), 7.64 (d, J = 8.6 Hz, 1H), 7.43 (d, J = 8.8 Hz, 1H), 5.38 (dd, J = 10.4, 5.1 Hz, 1H), 3.80-4.00 (m, 2H), 3.11-3.34 (m, 2H), 2.86 (s, 3H), 2.69 (tt, J = 8.0, 4.8 Hz, 1H), 2.44-2.60 (m, 1H), 2.29 (ddd, J = 13.9, 8.3, 5.1 Hz, 1H), 1.62 (d, J = 12.6 Hz, 1H), 1.34-1.55 (m, 5H), 1.25-1.33 (m, 1H), 0.96-1.14 ppm (m, 2H |
| 158 | 2-(4-(cyclopropylsulfonyl)-5-methyl-1H-indazol-1-yl)-N-(1-methyl-1H-pyrazol-3-yl)-3-(tetrahydro-2H-pyran-4-yl)propanamide | See Cmpd. 22 | [M + H] calc'd for $C_{23}H_{30}N_5O_4S$ 472, found 472 | $^1$H NMR (CHLOROFORM-d, 400 MHz): δ = 9.26 (s, 1H), 8.67 (s, 1H), 7.64 (d, J = 8.8 Hz, 1H), 7.38 (d, J = 8.6 Hz, 1H), 7.15-7.32 (m, 1H), 6.67 (d, J = 2.5 Hz, 1H), 5.34 (dd, J = 10.5, 4.9 Hz, 1H), 3.88 (td, J = 11.2, 2.7 Hz, 2H), 3.78 (s, 3H), 3.08-3.31 (m, 2H), 2.85 (s, 3H), 2.60-2.80 (m, 1H), 2.39-2.60 (m, 1H), 2.27 (ddd, J = 14.0, 8.5, 5.1 Hz, 1H), 1.62 (d, J = 12.6 Hz, 1H), 1.30-1.51 (m, 5H), 1.21-1.29 (m, 1H), 1.03 (d, J = 7.3 Hz, 1H), 1.02 ppm (s, 1H) |

| Ex. | Structure | Method | LCMS | NMR data |
|---|---|---|---|---|
| 159 | (S)-2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide | See Cmpd. 13 | [M + H] calc'd for $C_{21}H_{26}H_6O_4S$ 460, found 460 | $^1$H NMR (400 MHz, DMSO-$d_6$) δ ppm 1.03-1.13 (m, 2H) 1.17-1.36 (m, 5H) 1.48-1.70 (m, 2H) 2.28 (d, J = 6.82 Hz, 1H) 2.44 (br. s., 1H) 3.03-3.23 (m, 3H) 3.69-3.84 (m, 5H) 5.87 (d, J = 3.54 Hz, 1H) 6.37 (d, J = 2.02 Hz, 1H) 7.55 (d, J = 2.02 Hz, 1H) 8.51 (s, 1H) 8.68 (s, 1H) 9.67 (s, 1H) 11.08 (s, 1H) |
| 160 | (R)-2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide | See Cmpd. 13 | [M + H] calc'd for $C_{21}H_{26}H_6O_4S$ 460, found 460 | $^1$H NMR (400 MHz, DMSO-$d_6$) δ ppm 1.03-1.13 (m, 2H) 1.17-1.36 (m, 5H) 1.48-1.70 (m, 2H) 2.28 (d, J = 6.82 Hz, 1H) 2.44 (br. s., 1H) 3.03-3.23 (m, 3H) 3.69-3.84 (m, 5H) 5.87 (d, J = 3.54 Hz, 1H) 6.37 (d, J = 2.02 Hz, 1H) 7.55 (d, J = 2.02 Hz, 1H) 8.51 (s, 1H) 8.68 (s, 1H) 9.67 (s, 1H) 11.08 (s, 1H) |
| 161 | (R)-2-(4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 & 92 | [M + H] calc'd for $C_{21}H_{24}H_6O_4S$ 458, found 458 | $^1$H NMR (400 MHz, METHANOL-$d_4$) δ ppm 1.09-1.19 (m, 2H) 1.33-1.46 (m, 5H) 1.56 (dd, J = 9.47, 1.89 Hz, 1H) 1.76 (dd, J = 9.73, 1.89 Hz, 1H) 2.20-2.30 (m, 1H) 2.73 (ddd, J = 14.15, 11.12, 3.54 Hz, 1H) 2.91 (tt, J = 7.96, 4.80 Hz, 1H) 3.11-3.28 (m, 2H) 3.81-3.90 (m, 2H) 6.10 (dd, J = 11.12, 4.29 Hz, 1H) 7.71 (d, J = 4.55 Hz, 1H) 8.31 (d, J = 2.53 Hz, 1H) 8.36 (dd, J = 2.53, 1.52 Hz, 1H) 8.53 (s, 1H) 8.83 (d, J = 4.80 Hz, 1H) 9.29 (s, 1H) |
| 162 | (S)-2-(4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 & 92 | [M + H] calc'd for $C_{21}H_{24}H_6O_4S$ 458, found 458 | $^1$H NMR (400 MHz, METHANOL-$d_4$) δ ppm 1.09-1.19 (m, 2H) 1.33-1.46 (m, 5H) 1.56 (dd, J = 9.47, 1.89 Hz, 1H) 1.76 (dd, J = 9.73, 1.89 Hz, 1H) 2.20-2.30 (m, 1H) 2.73 (ddd, J = 14.15, 11.12, 3.54 Hz, 1H) 2.91 (tt, J = 7.96, 4.80 Hz, 1H) 3.11-3.28 (m, 2H) 3.81-3.90 (m, 2H) 6.10 (dd, J = 11.12, 4.29 Hz, 1H) 7.71 (d, J = 4.55 Hz, 1H) 8.31 (d, J = 2.53 Hz, 1H) 8.36 (dd, J = 2.53, 1.52 Hz, 1H) 8.53 (s, 1H) 8.83 (d, J = 4.80 Hz, 1H) 9.29 (s, 1H) |

| Ex. | Structure | Method | LCMS | NMR data |
|---|---|---|---|---|
| 163 | 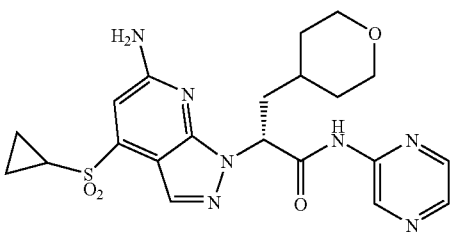 [SMILES: Nc1cc(S(=O)(=O)C2CC2)c2cnn([C@H](CC3CCOCC3)C(=O)Nc3cnccn3)c2n1]<br>(R)-2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 | [M + H] calc'd for $C_{21}H_{25}N_7O_4S$ 473, found 473 | $^1$H NMR (400 MHz, METHANOL-$d_4$) δ ppm 0.99-1.06 (m, 2H) 1.29-1.42 (m, 5H) 1.52 (d, J = 9.35 Hz, 1H) 1.71-1.79 (m, 1H) 2.13-2.23 (m, 1H) 2.57-2.66 (m, 1H) 2.90 (tt, J = 7.96, 4.80 Hz, 1H) 3.13-3.27 (m, 2H) 3.86 (t, J = 10.74 Hz, 2H) 5.90 (dd, J = 10.99, 4.42 Hz, 1H) 8.17 (s, 1H) 8.27-8.38 (m, 3H) 9.31 (s, 1H) |
| 164 | 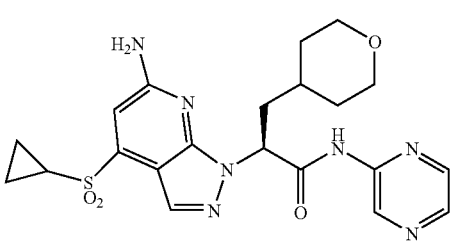 [SMILES: Nc1cc(S(=O)(=O)C2CC2)c2cnn([C@@H](CC3CCOCC3)C(=O)Nc3cnccn3)c2n1]<br>(S)-2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide | See Cmpd. 16 | [M + H] calc'd for $C_{21}H_{25}N_7O_4S$ 473, found 473 | $^1$H NMR (400 MHz, METHANOL-$d_4$) δ ppm 0.99-1.06 (m, 2H) 1.29-1.42 (m, 5H) 1.52 (d, J = 9.35 Hz, 1H) 1.71-1.79 (m, 1H) 2.13-2.23 (m, 1H) 2.57-2.66 (m, 1H) 2.90 (tt, J = 7.96, 4.80 Hz, 1H) 3.13-3.27 (m, 2H) 3.86 (t, J = 10.74 Hz, 2H) 5.90 (dd, J = 10.99, 4.42 Hz, 1H) 8.17 (s, 1H) 8.27-8.38 (m, 3H) 9.31 (s, 1H) |
| 165 | 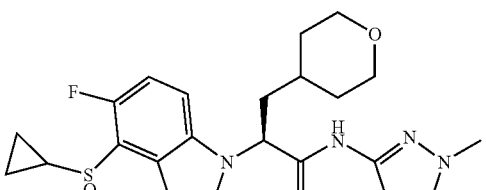<br>(S)-2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide | See Cmpd. 22 | [M + H] calc'd for $C_{22}H_{27}FN_5O_4S$ 476, found 476 | $^1$H NMR (CHLOROFORM-d, 400 MHz): δ = 8.58-8.83 (m, 2H), 7.74 (dd, J = 9.1, 3.0 Hz, 1H), 7.34 (t, J = 9.3 Hz, 1H), 7.23 (d, J = 2.0 Hz, 1H), 6.61 (d, J = 2.3 Hz, 1H), 5.33 (dd, J = 10.4, 5.1 Hz, 1H), 3.81-3.94 (m, 2H), 3.76 (s, 3H), 3.08-3.32 (m, 2H), 2.90 (dd, J = 4.8, 3.3 Hz, 1H), 2.49 (d, J = 3.8 Hz, 1H), 2.22-2.37 (m, 1H), 1.59 (d, J = 12.4 Hz, 1H), 1.19-1.55 (m, 5H), 1.04-1.19 (m, 2H), 0.78-0.93 ppm (m, 1H) |
| 166 | 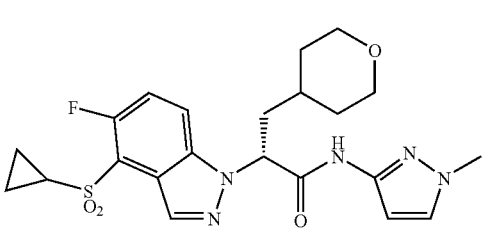 [SMILES: Cn1ccc(NC(=O)[C@@H](CC2CCOCC2)n2ncc3c(S(=O)(=O)C4CC4)c(F)ccc32)n1]<br>(R)-2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide | See Cmpd. 22 | [M + H] calc'd for $C_{22}H_{27}FN_5O_4S$ 476, found 476 | $^1$H NMR (CHLOROFORM-d, 400 MHz): δ = 8.58-8.83 (m, 2H), 7.74 (dd, J = 9.1, 3.0 Hz, 1H), 7.34 (t, J = 9.3 Hz, 1H), 7.23 (d, J = 2.0 Hz, 1H), 6.61 (d, J = 2.3 Hz, 1H), 5.33 (dd, J = 10.4, 5.1 Hz, 1H), 3.81-3.94 (m, 2H), 3.76 (s, 3H), 3.08-3.32 (m, 2H), 2.90 (dd, J = 4.8, 3.3 Hz, 1H), 2.49 (d, J = 3.8 Hz, 1H), 2.22-2.37 (m, 1H), 1.59 (d, J = 12.4 Hz, 1H), 1.19-1.55 (m, 5H), 1.04-1.19 (m, 2H), 0.78-0.93 ppm (m, 1H) |

-continued

| Ex. | Structure | Method | LCMS | NMR data |
|---|---|---|---|---|
| 167 | 2-(6-chloro-4-(cyclopropylsulfonyl)-2H-indazol-2-yl)-N-(1-methyl-1H-pyrazol-3-yl)-3-(tetrahydro-2H-pyran-4-yl)propanamide | See Cmpd. 10 | [M + H] calc'd for $C_{22}H_{27}ClN_5O_4S$ 492, found 492 | $^1$H NMR (400 MHz, CHLOROFORM-d) δ 9.17 (s, 1H), 8.47 (d, J = 1.01 Hz, 1H), 8.04 (d, J = 1.01 Hz, 1H), 7.69 (d, J = 1.77 Hz, 1H), 7.18-7.31 (m, 1H), 6.62 (d, J = 2.27 Hz, 1H), 5.26 (dd, J = 5.81, 9.85 Hz, 1H), 3.82-4.00 (m, 2H), 3.72-3.81 (m, 3H), 3.26 (td, J = 1.89, 11.43 Hz, 2H), 2.48-2.62 (m, 1H), 2.25-2.48 (m, 2H), 1.61-1.76 (m, 1H), 1.47-1.55 (m, 1H), 1.26-1.47 (m, 5H), 0.97-1.11 (m, 2H) |
| 168 | 2-(6-chloro-4-(cyclopropylsulfonyl)-2H-indazol-2-yl)-N-(pyrazin-2-yl)-3-(tetrahydro-2H-pyran-4-yl)propanamide | See Cmpd. 10 | [M + H] calc'd for $C_{22}H_{25}ClN_5O_4S$ 490.1, found 490.1 | $^1$H NMR (400 MHz, CHLOROFORM-d) δ 9.59 (s, 1H), 9.49 (br. s., 1H), 8.52 (s, 1H), 8.38 (br. s., 1H), 8.26 (s, 1H), 8.08 (s, 1H), 7.71 (d, J = 1.52 Hz, 1H), 5.33 (dd, J = 5.81, 9.85 Hz, 1H), 3.81-4.02 (m, 2H), 3.18-3.32 (m, 2H), 2.42-2.66 (m, 2H), 2.26-2.42 (m, 1H), 1.70 (d, J = 12.13 Hz, 1H), 1.62 (br. s., 1H), 1.49-1.58 (m, 1H), 1.29-1.49 (m, 4H), 1.00-1.14 (m, 2H) |
| 169 | 2-(4-(cyclopropylsulfonyl)-2H-pyrazolo[3,4-c]pyridin-2-yl)-N-(pyrazin-2-yl)-3-(tetrahydro-2H-pyran-4-yl)propanamide | See Cmpd. 13 & 140 | [M + H] calc'd for $C_{21}H_{24}N_6O_4S$ 458, found 458 | $^1$H NMR (400 MHz, DMSO-d$_6$) δ ppm 1.04-1.14 (m, 2H) 1.17-1.40 (m, 5H) 1.48-1.71 (m, 2H) 2.23-2.35 (m, 1H) 2.53-2.60 (m, 1H) 3.02-3.21 (m, 3H) 3.70-3.88 (m, 2H) 5.97 (dd, J = 9.85, 5.56 Hz, 1H) 8.38-8.49 (m, 2H) 8.57 (s, 1H) 9.00 (s, 1H) 9.27 (d, J = 1.26 Hz, 1H) 9.56 (s, 1H) 11.56 (s, 1H) |
| 170 | 2-(6-amino-4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide | See Cmpd. 16 | [M + H] calc'd for $C_{21}H_{27}N_7O_4S$ 475, found 475 | $^1$H NMR (400 MHz, METHANOL-d$_4$) δ ppm 1.11-1.19 (m, 2H) 1.28-1.44 (m, 5H) 1.49-1.56 (m, 1H) 1.73-1.81 (m, 1H) 2.24 (ddd, J = 13.77, 8.97, 4.55 Hz, 1H) 2.67-2.77 (m, 1H) 2.85-2.95 (m, 1H) 3.10-3.28 (m, 2H) 3.79-3.90 (m, 5H) 6.08 (dd, J = 11.37, 4.29 Hz, 1H) 7.72 (d, J = 4.80 Hz, 1H) 7.75 (s, 1H) 8.53 (s, 1H) 8.84 (d, 1H) |

-continued

| Ex. | Structure | Method | LCMS | NMR data |
|---|---|---|---|---|
| 171 | 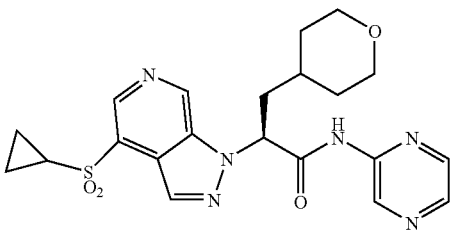 [SMILES: O=C(Nc1cnccn1)[C@H](CC1CCOCC1)n1ncc2c(S(=O)(=O)C3CC3)cncc21]<br>(S)-2-(4-(cyclopropylsulfonyl)-1H-pyrazolo[3,4-c]pyridin-1-yl)-N-(pyrazin-2-yl)-3-(tetrahydro-2H-pyran-4-yl)propanamide | See Cmpd. 20 | [M + H] calc'd for $C_{21}H_{25}H_6O_4S$ 458, found 458 | $^1$H NMR (400 MHz, DMSO-$d_6$) δ 1.06-1.12 (m, 2H) 1.20-1.37 (m, 5H) 1.50 (d, J = 11.62 Hz, 1H) 1.66 (d, J = 11.12 Hz, 1H) 2.25-2.35 (m, 1H) 2.52-2.58 (m, 1H) 3.04-3.17 (m, 3H) 3.71-3.83 (m, 2H) 6.06 (dd, J = 10.11, 5.31 Hz, 1H) 8.40 (d, J = 2.53 Hz, 1H) 8.42-8.46 (m, 1H) 8.55 (s, 1H) 8.70 (s, 1H) 9.24 (d, J = 1.26 Hz, 1H) 9.68 (s, 1H). |
| 172 | 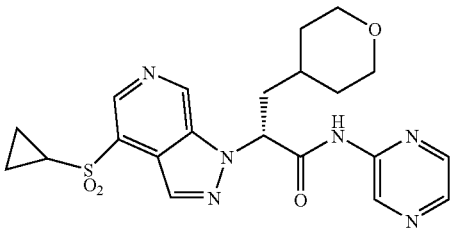 [SMILES: O=C(Nc1cnccn1)[C@@H](CC1CCOCC1)n1ncc2c(S(=O)(=O)C3CC3)cncc21]<br>(R)-2-(4-(cyclopropylsulfonyl)-1H-pyrazolo[3,4-c]pyridin-1-yl)-N-(pyrazin-2-yl)-3-(tetrahydro-2H-pyran-4-yl)propanamide | See Cmpd. 20 | [M + H] calc'd for $C_{21}H_{25}H_6O_4S$ 458, found 458 | $^1$H NMR (400 MHz, DMSO-$d_6$) δ 1.06-1.12 (m, 2H) 1.20-1.37 (m, 5H) 1.50 (d, J = 11.62 Hz, 1H) 1.66 (d, J = 11.12 Hz, 1H) 2.25-2.35 (m, 1H) 2.52-2.58 (m, 1H) 3.04-3.17 (m, 3H) 3.71-3.83 (m, 2H) 6.06 (dd, J = 10.11, 5.31 Hz, 1H) 8.40 (d, J = 2.53 Hz, 1H) 8.42-8.46 (m, 1H) 8.55 (s, 1H) 8.70 (s, 1H) 9.24 (d, J = 1.26 Hz, 1H) 9.68 (s, 1H). |

Biological Testing

The activity of compounds as glucokinase activators may be assayed in vitro, in vivo or in a cell line. Provided below is an enzymatic glucokinase activity assay.

Purified glucokinase may be obtained as follows. DNA encoding residues 12-465 of the full-length sequence of the human enzyme may be amplified by PCR and cloned into the HindIII and EcoRT sites of pFLAG-CTC (Sigma). SEQ. I.D. No. 1 corresponds to residues 12-465 of glucokinase.

The expression of recombinant glucokinase protein may be carried out by transformation and growth of DH10b-T1r E. coli cells incorporating the (pFLAG-CTC) plasmid in LB media. Protein expression can be induced in this system by the addition of IPTG to the culture medium.

Recombinant protein may be isolated from cellular extracts by passage over Sepharose Q Fast Flow resin (Pharmacia). This partially purified GK extract may then be further purified by a second passage over Poros HQ10 (Applied Biosystems). The purity of GK may be determined on denaturing SDS-PAGE gel. Purified GK may then be concentrated to a final concentration of 20.0 mg/ml. After flash freezing in liquid nitrogen, the proteins can be stored at −78° C. in a buffer containing 25 mM TRIS-HCl pH 7.6, 50 mM NaCl, and 0.5 mM TCEP.

It should be noted that a variety of other expression systems and hosts are also suitable for the expression of glucokinase, as would be readily appreciated by one of skill in the art.

The activation properties of compounds for GK may be determined using a black 384-well-plate format under the following reaction conditions: 25 mM Hepes pH 7.2, 25 mM NaCl, 10 mM $MgCl_2$, 0.01% Brij35, 1 mM DTT, 5 μM ATP, 5 mM Glucose 2% DMSO. The amount of ATP consumed may be determined quantitatively by addition of equal volume of luciferase reagent (luciferase+beetle luciferin—KinaseGlo Luminescent Kinase Assay kit from Promega). The luminescence intensity may be measured by using the Analyst HT from LJL Biosystems.

The assay reaction may be initiated as follows: 4 μl of substrate mixture (12.5 μM ATP and 12.5 mM Glucose) was added to each well of the plate, followed by the addition of 2 μl of activator (2 fold serial dilutions for 11 data points for each activator) containing 10% DMSO. 4 μL of 1.25 nM GK solution may be added to initiate the reaction. The reaction mixture may then be incubated at room temperature for 60 min, and quenched and developed by addition of 10 μL of luciferase reagent. Luminescence intensities of the resulting reaction mixtures may be measured after a 10 min incubation at room temperature. The luminescence intensity may be measured by using the Analyst HT from LJL Biosystems.

$pK_{act}$ and % $ACT_{max}$ values may be calculated by non-linear curve fitting of the compound concentrations and luminescence intensities to a standard inhibition/activation equation. $K_{act}$ is the concentration that displays 50% of the maximal increase in GK activity observed using a saturating activator concentration. % $Act_{max}$ represents the calculated maximal gain in GK enzyme activity at a saturating concentration of the compound. $pK_{act}$ and % $ACT_{max}$ values for select compounds of the present invention are given in Table 1.

TABLE 1

$pK_{act}$ and % $ACT_{max}$ of Exemplified Compounds Against GK

| Compound | $pK_{act}$ | % $ACT_{max}$ |
|---|---|---|
| 1 | ≤4.8 | ≤90 |
| 2 | ≤4.8 | ≤90 |
| 3 | ≤4.8 | ≤90 |
| 4 | 4.9-5.4 | 101-105 |
| 5 | 5.9-6.4 | ≥111 |
| 6 | 4.9-5.4 | ≥111 |

TABLE 1-continued pK$_{act}$ and % ACT$_{max}$ of Exemplified Compounds Against GK

| Compound | pK$_{act}$ | % ACT$_{max}$ |
|---|---|---|
| 7 | 4.9-5.4 | ≤90 |
| 8 | 4.9-5.4 | ≤90 |
| 9 | 4.9-5.4 | ≤90 |
| 10 | 5.5-5.8 | ≥111 |
| 11 | ≥6.5 | 101-105 |
| 12 | 5.5-5.8 | ≤90 |
| 13 | ≥6.5 | 106-110 |
| 14 | ≥6.5 | ≥111 |
| 15 | 5.9-6.4 | 90-100 |
| 16 | ≥6.5 | 106-110 |
| 19 | ≥6.5 | ≤90 |
| 20 (Free Base) | 5.9-6.4 | 101-105 |
| 20 (TFA Salt) | 5.5-5.8 | 106-110 |
| 22 | ≥6.5 | ≥111 |
| 23 | ≥6.5 | ≥111 |
| 24 | ≤4.8 | ≤90 |
| 25 | ≤4.8 | ≤90 |
| 26 | ≤4.8 | ≤90 |
| 27 | 5.5-5.8 | ≤90 |
| 28 | 4.9-5.4 | ≥111 |
| 29 | 5.9-6.4 | ≥111 |
| 30 | 4.9-5.4 | ≤90 |
| 31 | ≤4.8 | ≤90 |
| 32 | 4.9-5.4 | 101-105 |
| 33 | 5.5-5.8 | ≥111 |
| 34 | 5.5-5.8 | ≥111 |
| 35 | ≤4.8 | ≤90 |
| 36 | 5.5-5.8 | ≥111 |
| 37 | 5.5-5.8 | ≥111 |
| 38 | ≤4.8 | ≥111 |
| 39 | 5.5-5.8 | ≥111 |
| 40 | ≤4.8 | ≤90 |
| 41 | 5.5-5.8 | ≤90 |
| 42 | 5.5-5.8 | ≥111 |
| 43 | ≤4.8 | ≤90 |
| 44 | 5.9-6.4 | ≥111 |
| 45 | 4.9-5.4 | ≥111 |
| 46 | ≤4.8 | 101-105 |
| 47 | 4.9-5.4 | ≥111 |
| 48 | 5.9-6.4 | ≥111 |
| 49 | 4.9-5.4 | 90-100 |
| 50 | ≤4.8 | ≤90 |
| 51 | 5.9-6.4 | ≥111 |
| 52 | ≤4.8 | 90-100 |
| 53 | ≤4.8 | ≤90 |
| 54 | 4.9-5.4 | ≤90 |
| 55 | 4.9-5.4 | ≤90 |
| 56 | ≤4.8 | ≤90 |
| 57 | 4.9-5.4 | 101-105 |
| 58 | ≤4.8 | 101-105 |
| 59 | ≥6.5 | 106-110 |
| 60 | ≤4.8 | ≤90 |
| 61 | 5.9-6.4 | 90-100 |
| 62 | 5.9-6.4 | 90-100 |
| 63 | 4.9-5.4 | ≥111 |
| 64 | ≥6.5 | ≥111 |
| 65 | 5.9-6.4 | 90-100 |
| 66 | ≥6.5 | 101-105 |
| 67 | ≥6.5 | 106-110 |
| 68 | 4.9-5.4 | 101-105 |
| 69 | ≥6.5 | 106-110 |
| 70 | 5.5-5.8 | 101-105 |
| 71 | 5.5-5.8 | ≤90 |
| 72 | ≥6.5 | ≤90 |
| 73 | ≤4.8 | 90-100 |
| 74 | 5.5-5.8 | 90-100 |
| 75 | 5.9-6.4 | 90-100 |
| 76 | ≥6.5 | 106-110 |
| 77 | ≤4.8 | 101-105 |
| 78 | 5.5-5.8 | 90-100 |
| 79 | ≥6.5 | 90-100 |
| 80 | ≥6.5 | 101-105 |
| 81 | 4.9-5.4 | 101-105 |
| 82 | ≥6.5 | 106-110 |
| 83 | 4.9-5.4 | ≤90 |
| 84 | ≥6.5 | 106-110 |
| 85 | 5.5-5.8 | 90-100 |
| 86 | ≤4.8 | ≤90 |
| 87 | 5.5-5.8 | 90-100 |
| 88 | ≤4.8 | ≤90 |
| 89 | 5.5-5.8 | 101-105 |
| 90 | ≤4.8 | 90-100 |
| 91 | 5.9-6.4 | 101-105 |
| 92 | 4.9-5.4 | ≤90 |
| 93 | ≤4.8 | ≤90 |
| 94 | ≥6.5 | 90-100 |
| 95 | 5.5-5.8 | 101-105 |
| 96 | 5.9-6.4 | 101-105 |
| 97 | 5.9-6.4 | 106-110 |
| 98 | 5.9-6.4 | 90-100 |
| 99 | 4.9-5.4 | 90-100 |
| 100 | 5.9-6.4 | ≤90 |
| 101 | 5.9-6.4 | 90-100 |
| 102 | 5.9-6.4 | 90-100 |
| 103 | 5.5-5.8 | 101-105 |
| 104 | 5.5-5.8 | 90-100 |
| 105 (TFA Salt) | 5.9-6.4 | ≤90 |
| 105 (Free Base) | ≥6.5 | ≤90 |
| 106 | ≤4.8 | 90-100 |
| 107 | ≥6.5 | ≥111 |
| 108 | 4.9-5.4 | ≥111 |
| 109 | ≥6.5 | 101-105 |
| 110 | ≤4.8 | 106-110 |
| 111 | 5.9-6.4 | 106-110 |
| 112 | ≥6.5 | 106-110 |
| 113 | 5.9-6.4 | 101-105 |
| 114 | ≥6.5 | 101-105 |
| 115 | ≥6.5 | 106-110 |
| 116 | 4.9-5.4 | ≤90 |
| 117 | ≥6.5 | 106-110 |
| 118 | ≤4.8 | ≤90 |
| 119 | 5.9-6.4 | 90-100 |
| 120 | ≥6.5 | 90-100 |
| 121 | ≥6.5 | 90-100 |
| 122 | 4.9-5.4 | ≥111 |
| 123 | ≥6.5 | ≥111 |
| 124 | 4.9-5.4 | ≥111 |
| 125 | 5.5-5.8 | ≥111 |
| 126 | ≤4.8 | ≤90 |
| 127 | ≥6.5 | 101-105 |
| 128 | ≥6.5 | 90-100 |
| 129 | 4.9-5.4 | ≤90 |
| 130 | ≥6.5 | 101-105 |
| 131 | ≤4.8 | ≤90 |
| 132 | 5.5-5.8 | 90-100 |
| 133 | ≥6.5 | 101-105 |
| 134 | 5.5-5.8 | ≥111 |
| 135 | 5.9-6.4 | 106-110 |
| 136 | 5.9-6.4 | ≥111 |
| 137 | 4.9-5.4 | ≤90 |
| 138 | 5.9-6.4 | 90-100 |
| 139 | ≤4.8 | 106-110 |
| 140 | ≤4.8 | ≤90 |
| 141 | ≥6.5 | 90-100 |
| 142 | ≥6.5 | 101-105 |
| 143 | ≥6.5 | ≤90 |
| 144 | ≥6.5 | 106-110 |
| 145 | 4.9-5.4 | ≤90 |
| 146 | 4.9-5.4 | ≤90 |
| 147 | 5.5-5.8 | ≥111 |
| 148 | 4.9-5.4 | ≤90 |
| 149 | ≥6.5 | ≥111 |
| 150 | 5.9-6.4 | ≥111 |
| 151 | 5.5-5.8 | 90-100 |
| 152 | ≥6.5 | 106-110 |
| 153 | ≤4.8 | 106-110 |
| 154 | ≥6.5 | 106-110 |
| 155 | ≥6.5 | 106-110 |
| 156 | ≥6.5 | 101-105 |
| 157 | 5.9-6.4 | ≥111 |
| 158 | 5.9-6.4 | ≥111 |
| 159 | 5.5-5.8 | 101-105 |

TABLE 1-continued pK$_{act}$ and % ACT$_{max}$ of Exemplified Compounds Against GK

| Compound | pK$_{act}$ | % ACT$_{max}$ |
|---|---|---|
| 160 | 4.9-5.4 | 90-100 |
| 161 | ≤4.8 | ≤90 |
| 162 | 5.5-5.8 | 106-110 |
| 163 | 5.5-5.8 | ≤90 |
| 164 | 5.9-6.4 | 106-110 |
| 165 | ≥6.5 | 90-100 |
| 166 | 4.9-5.4 | 90-100 |
| 167 | 4.9-5.4 | ≤90 |
| 168 | ≤4.8 | ≤90 |
| 169 | ≤4.8 | ≤90 |
| 170 | ≤4.8 | ≤90 |
| 171 | 5.5-5.8 | 106-110 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound of the formula:

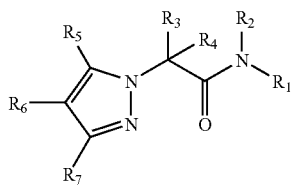

or a tautomer, enantiomer or pharmaceutically acceptable salt thereof, wherein $R_1$ is heteroaryl optionally substituted through available valencies with one or more substituents independently selected from the group consisting of halo, nitro, cyano, hydroxy, alkoxy, amino, $(C_{1-10})$alkyl, halo$(C_{1-10})$alkyl, amino$(C_{1-10})$alkyl, imino$(C_{1-3})$alkyl, oxa$(C_{1-5})$alkyl, oxo$(C_{1-5})$alkyl, and -$L_1$-$R_{22}$;

$R_2$ is hydrogen;

$R_3$ is -L-$R_{18}$;

$R_4$ is hydrogen;

$R_5$ is selected from the group consisting of hydrogen, halo, nitro, cyano, hydroxy, $(C_{1-10})$alkoxy, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, and imino$(C_{1-10})$alkyl;

$R_6$ is selected from the group consisting of hydrogen, halo, nitro, cyano, hydroxy, $(C_{1-10})$alkoxy, amino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, imino$(C_{1-10})$alkyl, and -$L_1$-$R_{22}$;

or $R_5$ and $R_6$ together with the atoms to which they are attached form an aryl or heteroaryl ring which has 6 ring members and is optionally substituted through available valencies with one or more substituents independently selected from the group consisting of halo, nitro, cyano, hydroxy, alkoxy, amino, $(C_{1-10})$alkyl, halo$(C_{1-10})$alkyl, amino$(C_{1-10})$alkyl, imino$(C_{1-10})$alkyl, and -$L_1$-$R_{22}$;

$R_7$ is selected from the group consisting of hydrogen, halo, nitro, cyano, hydroxy, $(C_{1-10})$alkoxy, amino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, imino$(C_{1-10})$alkyl, and -$L_1$-$R_{22}$;

L is —$(CH_2)$—;

$L_1$ at each occurrence is independently absent or a linker providing 1, 2, 3, 4, 5 or 6 atom separation between $R_{22}$ and the ring to which $L_1$ is attached, wherein, when present, $L_1$ is selected from the group consisting of —$(CH_2)_s$—, —NH—, —O—, —CO—, —$SO_2$—, and combinations thereof;

s at each occurrence is independently selected from the group consisting of 1, 2, 3, 4, 5 and 6;

$R_{18}$ is tetrahydro-2H-pyran-4-yl; and $R_{22}$ at each occurrence is independently selected from the group consisting of hydroxy, amino, $(C_{1-10})$alkyl, halo$(C_{1-10})$alkyl, hydroxy$(C_{1-10})$alkyl, $(C_{3-12})$cycloakyl, and phenyl optionally substituted with halo.

2. The compound of claim 1 having the formula:

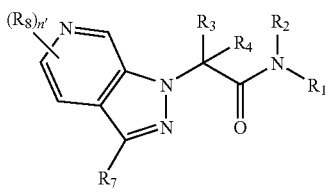

or a pharmaceutically acceptable salt thereof, wherein
n' is selected from the group consisting of 0, 1, 2 and 3; and
$R_8$ at each occurrence is independently selected from the group consisting of hydrogen, halo, nitro, cyano, hydroxy, alkoxy, amino, $(C_{1-10})$alkyl, halo$(C_{1-10})$alkyl, amino$(C_{1-10})$alkyl, imino $(C_{1-3})$alkyl, and -$L_1$-$R_{22}$.

3. The compound or pharmaceutically acceptable salt according to claim 2, wherein each $R_8$ is independently selected from the group consisting of hydrogen, halo,
$(C_{1-3})$alkyl,
$(C_{1-3})$alkylsulfonyl, and
$(C_{3-12})$cycloalkylsulfonyl.

4. The compound or pharmaceutically acceptable salt according to claim 2, wherein each $R_8$ is independently selected from the group consisting of methylsulfonyl, cyclopropylsulfonyl, and cyclopentylsulfonyl.

5. The compound or pharmaceutically acceptable salt according to claim 2, wherein
$R_8$ is -$L_1$-$R_{22}$.

6. The compound or pharmaceutically acceptable salt according to claim 2, wherein $R_8$ is —$SO_2$—$R_{22}$.

7. The compound or pharmaceutically acceptable salt according to claim 2, wherein $R_8$ is cyclopropylsulfonyl.

8. The compound of claim 1 having the formula:

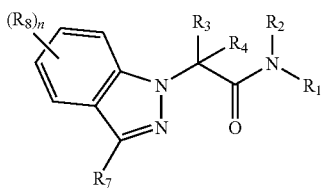

or a pharmaceutically acceptable salt thereof, wherein
n is selected from the group consisting of 0, 1, 2, 3 and 4; and
$R_8$ at each occurrence is independently selected from the group consisting of hydrogen, halo, nitro, cyano, hydroxy, alkoxy, amino, $(C_{1-10})$alkyl, halo$(C_{1-10})$alkyl, amino$(C_{1-10})$alkyl, imino$(C_{1-3})$alkyl, and -$L_1$-$R_{22}$.

9. The compound or pharmaceutically acceptable salt according to claim 8, wherein each $R_8$ is independently selected from the group consisting of hydrogen, halo,
$(C_{1-3})$alkyl,
$(C_{1-3})$alkylsulfonyl, and
$(C_{3-12})$cycloalkylsulfonyl.

10. The compound or pharmaceutically acceptable salt according to claim 8, wherein each $R_8$ is independently selected from the group consisting of methylsulfonyl, cyclopropylsulfonyl, and cyclopentylsulfonyl.

11. The compound or pharmaceutically acceptable salt according to claim 8, wherein
$R_8$ is -$L_1$-$R_{22}$.

12. The compound or pharmaceutically acceptable salt according to claim 8, wherein $R_8$ is —$SO_2$—$R_{22}$.

13. The compound or pharmaceutically acceptable salt according to claim 8, wherein $R_8$ is cyclopropylsulfonyl.

14. The compound of claim 1 having the formula:

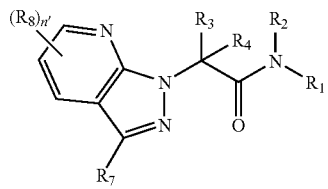

or a pharmaceutically acceptable salt thereof, wherein
n' is selected from the group consisting of 0, 1, 2 and 3; and
$R_8$ at each occurrence is independently selected from the group consisting of hydrogen, halo, nitro, cyano, hydroxy, alkoxy, amino, $(C_{1-10})$alkyl, halo$(C_{1-10})$alkyl, amino$(C_{1-10})$alkyl, imino$(C_{1-3})$alkyl, and -$L_1$-$R_{22}$.

15. The compound or pharmaceutically acceptable salt according to claim 14, wherein each $R_8$ is independently selected from the group consisting of hydrogen, halo,
$(C_{1-3})$alkyl,
$(C_{1-3})$alkylsulfonyl, and
$(C_{3-12})$cycloalkylsulfonyl.

16. The compound or pharmaceutically acceptable salt according to claim 14, wherein $R_8$ is selected from the group consisting of methylsulfonyl, cyclopropylsulfonyl, and cyclopentylsulfonyl.

17. The compound or pharmaceutically acceptable salt according to claim 14, wherein
$R_8$ is -$L_1$-$R_{22}$.

18. The compound or pharmaceutically acceptable salt according to claim 14, wherein $R_8$ is —$SO_2$—$R_{22}$.

19. The compound or pharmaceutically acceptable salt according to claim 14, wherein $R_8$ is cyclopropylsulfonyl.

20. The compound or pharmaceutically acceptable salt according to claim 1, wherein $R_1$ is selected from the group consisting of thiazolyl, pyrazinyl, pyrazolyl, and pyridyl, each optionally substituted through available valencies with one or more substituents independently selected from the group consisting of halo, nitro, cyano, hydroxy, alkoxy, amino, $(C_{1-10})$alkyl, halo$(C_{1-10})$alkyl, amino$(C_{1-10})$alkyl, imino$(C_{1-3})$alkyl, oxa$(C_{1-5})$alkyl, oxo$(C_{1-5})$alkyl, and -$L_1$-$R_{22}$.

21. The compound or pharmaceutically acceptable salt according to claim 1, wherein $R_1$ is selected from the group consisting of thiazol-2-yl, 2-pyridyl, 5-methyl-thiazol-2-yl, 6-methyl-pyrid-2-yl, 4-methyl-pyrid-2-yl, 5-bromo-6-methyl-pyrid-2-yl, 5-phenyl-pyrid-2-yl, benzothiazol-2-yl, a nicotinic acid methyl ester, 5-bromo-pyrid-2-yl, 2-pyrazinyl, 1-methyl-pyrazol-3-yl, and 5-fluoro-thiazol-2-yl.

22. The compound or pharmaceutically acceptable salt according to claim 1, wherein $R_1$ is selected from the group consisting of:

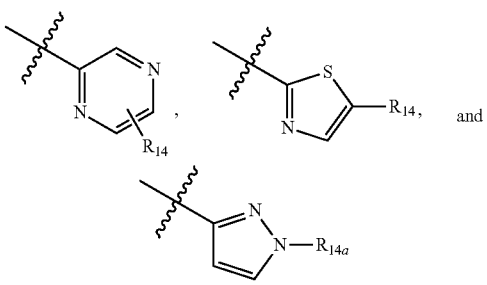

wherein
R$_{14}$ is selected from the group consisting of hydrogen, halo, nitro, cyano, hydroxy, alkoxy, amino, (C$_{1-10}$)alkyl, halo(C$_{1-10}$)alkyl, amino(C$_{1-10}$)alkyl, imino(C$_{1-3}$)alkyl, oxa(C$_{1-5}$)alkyl, oxo(C$_{1-5}$)alkyl, and -L$_1$-R$_{22}$; and R$_{14a}$ is selected from the group consisting of hydrogen, (C$_{1-10}$)alkyl, halo(C$_{1-10}$)alkyl, amino(C$_{1-10}$)alkyl, imino(C$_{1-3}$)alkyl, oxa(C$_{1-5}$)alkyl, and oxo(C$_{1-5}$)alkyl.

23. The compound or pharmaceutically acceptable salt according to claim 1, wherein R$_5$ is selected from the group consisting of hydrogen, halo, and (C$_{1-3}$)alkyl.

24. The compound or pharmaceutically acceptable salt according to claim 1, wherein R$_6$ is selected from the group consisting of hydrogen, halo, (C$_{1-3}$)alkyl, (C$_{1-3}$)alkylsulfony, and (C$_{3-6}$)cycloalkylsulfonyl.

25. The compound or pharmaceutically acceptable salt according to claim 1, wherein
R$_6$ is -L$_1$-R$_{22}$.

26. The compound or pharmaceutically acceptable salt according to claim 1, wherein R$_7$ is selected from the group consisting of hydrogen, halo, and (C$_{1-3}$)alkyl.

27. The compound or pharmaceutically acceptable salt according to claim 1, wherein
R$_7$ is -L$_1$-R$_{22}$.

28. The compound or pharmaceutically acceptable salt according to claim 1, wherein each R$_{22}$ is independently selected from the group consisting of (C$_{1-5}$)alkyl optionally substituted with halo; (C$_{3-6}$)cycloalkyl; and phenyl optionally substituted with halo.

29. The compound or pharmaceutically acceptable salt according to claim 1, wherein R$_{22}$ is cyclopropyl.

30. The compound or pharmaceutically acceptable salt according to claim 1, wherein
R$_{22}$ is amino.

31. The compound or pharmaceutically acceptable salt according to claim 1, wherein L$_1$ is —SO$_2$—.

32. The compound according to claim 1, wherein the compound is in the form of a pharmaceutically acceptable salt.

33. A compound according to claim 1, which is selected from the following group of compounds:
- 2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide;
- (S)-2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide;
- (R)-2-(3-(cyclopropylsulfonyl)-1H-pyrazol-1-yl)-N-(5-methoxythiazolo[5,4-b]pyridin-2-yl)-3-(tetrahydro-2H-pyran-4-yl)propanamide ;
- N-(5-chlorothiazol-2-yl)-2-(4-(cyclopropylsulfonyl)-1H-pyrazol-1-yl)-3-(tetrahydro-2H-pyran-4-yl)propanamide;
- N-(5-chlorothiazol-2-yl)-2-(4-(cyclopentylsulfonyl)-1H-pyrazol-1-yl)-3-(tetrahydro-2H-pyran-4-yl)propanamide;
- 4-chloro-1-(1-(5-chlorothiazol-2-ylamino)-1-oxo-3-(tetrahydro-2H-pyran-4-yl)propan-2-yl)-N-cyclopropyl-1H-pyrazole-3-carboxamide;
- N-(5-chlorothiazol-2-yl)-2-(4-(cyclopropanesulfonamido)-1H-pyrazol-1-yl)-3-(tetrahydro-2H-pyran-4-yl)propanamide;
- N-(5-chlorothiazol-2-yl)-2-(5-(cyclopropylsulfonyl)-1H-indazol-1-yl)-3-(tetrahydro-2H-pyran-4-yl)propanamide;
- 2-(4-(cyclopropylsulfonyl)-6-(difluoromethoxy)-1H-indazol-1-yl)-N-(1-methyl-1H-pyrazol-3-yl)-3-(tetrahydro-2H-pyran-4-yl)propanamide;
- 2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide;
- 6-(2-(4-(cyclopropylsulfonyl)-1H-indazol-1-yl)-3-(tetrahydro-2H-pyran-4-yl)propanamido)nicotinamide;
- 2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide;
- 2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;
- 2-(6-cyano-4-(cyclopropylsulfonyl)-1H-indazol-1-yl)-N-(1-methyl-1H-pyrazol-3-yl)-3-(tetrahydro-2H-pyran-4-yl)propanamide;
- 2-(4-(cyclopropylsulfonyl)-1H-pyrazolo[3,4-c]pyridin-1-yl)-N-(pyrazin-2-yl)-3-(tetrahydro-2H-pyran-4-yl)propanamide;
- 4-(cyclopropylsulfonyl)-1-(1-(5-fluorothiazol-2-ylamino)-1-oxo-3-(tetrahydro-2H-pyran-4-yl)propan-2-yl)-1H-indazole-6-carboxylic acid;
- 2-(5-chloro-4-(cyclopropylsulfonyl)-1H-indazol-1-yl)-N-(5-fluorothiazol-2-yl)-3-(tetrahydro-2H-pyran-4-yl)propanamide;
- 2-(7-chloro-4-(cyclopropylsulfonyl)-1H-indazol-1-yl)-N-(5-fluorothiazol-2-yl)-3-(tetrahydro-2H-pyran-4-yl)propanamide;
- 2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide;
- (R)-2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide;
- (S)-2-(4-(cyclopropylsulfonyl)-1H-pyrazol-1-yl)-N-(5-methoxythiazolo[5,4-b]pyridin-2-yl)-3-(tetrahydro-2H-pyran-4-yl)propanamide;
- 2-(4-(cyclopropylsulfonyl)-3,5-dimethyl-1H-pyrazol-1-yl)-N-(5-fluorothiazol-2-yl)-3-(tetrahydro-2H-pyran-4-yl)propanamide;
- 2-(4-(cyclopropylsulfonyl)-1H-pyrazol-1-yl)-N-(5-fluorothiazol-2-yl)-3-(tetrahydro-2H-pyran-4-yl)propanamide;
- 2-(4-(4-chlorophenylsulfonyl)-1H-pyrazol-1-yl)-N-(5-fluorothiazol-2-yl)-3-(tetrahydro-2H-pyran-4-yl)propanamide;
- 2-(4-(4-chlorophenylsulfonyl)-1H-pyrazol-1-yl)-N-(5-methoxythiazolo[5,4-b]pyridin-2-yl)-3-(tetrahydro-2H-pyran-4-yl)propanamide;
- (R)-2-(4-(cyclopropylsulfonyl)-1H-pyrazol-1-yl)-N-(5-fluorothiazol-2-yl)-3-(tetrahydro-2H-pyran-4-yl)propanamide;

(S)-2-(4-(cyclopropylsulfonyl)-1H-pyrazol-1-yl)-N-(5-fluorothiazol-2-yl)-3-(tetrahydro-2H-pyran-4-yl)propanamide;

2-(4-(cyclopentylsulfonyl)-1H-pyrazol-1-yl)-N-(5-fluorothiazol-2-yl)-3-(tetrahydro-2H-pyran-4-yl)propanamide;

(R)-N-(5-chlorothiazol-2-yl)-2-(4-(cyclopropylsulfonyl)-1H-pyrazol-1-yl)-3-(tetrahydro-2H-pyran-4-yl)propanamide;

N-(5-fluorothiazol-2-yl)-2-(4-(methylsulfonyl)-1H-indazol-1-yl)-3-(tetrahydro-2H-pyran-4-yl)propanamide;

(S)-N-(5-chlorothiazol-2-yl)-2-(4-(cyclopropylsulfonyl)-1H-pyrazol-1-yl)-3-(tetrahydro-2H-pyran-4-yl)propanamide;

(R)-2-(4-(cyclopentylsulfonyl)-1H-pyrazol-1-yl)-N-(5-fluorothiazol-2-yl)-3-(tetrahydro-2H-pyran-4-yl)propanamide;

(S)-2-(4-(cyclopentylsulfonyl)-1H-pyrazol-1-yl)-N-(5-fluorothiazol-2-yl)-3-(tetrahydro-2H-pyran-4-yl)propanamide;

N-(5-chloropyridin-2-yl)-2-(4-(cyclopropylsulfonyl)-1H-pyrazol-1-yl)-3-(tetrahydro-2H-pyran-4-yl)propanamide;

2-(4-(cyclopropylsulfonyl)-1H-pyrazol-1-yl)-N-(pyrazin-2-yl)-3-(tetrahydro-2H-pyran-4-yl)propanamide;

(R)-N-(5-chlorothiazol-2-yl)-2-(5-(cyclopropylsulfonyl)-1H-indazol-1-yl)-3-(tetrahydro-2H-pyran-4-yl)propanamide;

(S)-N-(5-chlorothiazol-2-yl)-2-(5-(cyclopropylsulfonyl)-1H-indazol-1-yl)-3-(tetrahydro-2H-pyran-4-yl)propanamide;

2-(4-(tert-butylsulfonyl)-1H-pyrazol-1-yl)-N-(5-fluorothiazol-2-yl)-3-(tetrahydro-2H-pyran-4-yl)propanamide;

(R)-2-(4-(tert-butylsulfonyl)-1H-pyrazol-1-yl)-N-(5-fluorothiazol-2-yl)-3-(tetrahydro-2H-pyran-4-yl)propanamide;

(S)-2-(4-(tert-butylsulfonyl)-1H-pyrazol-1-yl)-N-(5-fluorothiazol-2-yl)-3-(tetrahydro-2H-pyran-4-yl)propanamide;

(R)-N-(5-chlorothiazol-2-yl)-2-(4-(cyclopentylsulfonyl)-1H-pyrazol-1-yl)-3-(tetrahydro-2H-pyran-4-yl)propanamide;

N-(5-chlorothiazol-2-yl)-2-(4-(cyclopropylsulfonyl)-1H-indazol-1-yl)-3-(tetrahydro-2H-pyran-4-yl)propanamide;

N-(5-chlorothiazol-2-yl)-2-(6-(cyclopropylsulfonyl)-1H-indazol-1-yl)-3-(tetrahydro-2H-pyran-4-yl)propanamide;

(R)-N-(5-chlorothiazol-2-yl)-2-(4-(cyclopropylsulfonyl)-1H-indazol-1-yl)-3-(tetrahydro-2H-pyran-4-yl)propanamide;

(S)-N-(5-chlorothiazol-2-yl)-2-(4-(cyclopropylsulfonyl)-1H-indazol-1-yl)-3-(tetrahydro-2H-pyran-4-yl)propanamide;

2-(4-(cyclopropylsulfonyl)-1H-indazol-1-yl)-N-(pyrazin-2-yl)-3-(tetrahydro-2H-pyran-4-yl)propanamide;

2-(4-(cyclopropylsulfonyl)-1H-indazol-1-yl)-N-(5-fluorothiazol-2-yl)-3-(tetrahydro-2H-pyran-4-yl)propanamide;

N-(5-chlorothiazol-2-yl)-2-(4-(cyclopropylsulfonyl)-6-fluoro-1H-indazol-1-yl)-3-(tetrahydro-2H-pyran-4-yl)propanamide;

(R)-2-(4-(cyclopropylsulfonyl)-1H-indazol-1-yl)-N-(5-fluorothiazol-2-yl)-3-(tetrahydro-2H-pyran-4-yl)propanamide;

(S)-2-(4-(cyclopropylsulfonyl)-1H-indazol-1-yl)-N-(5-fluorothiazol-2-yl)-3-(tetrahydro-2H-pyran-4-yl)propanamide;

2-(4-(cyclopropylsulfonyl)-6-methoxy-1H-indazol-1-yl)-N-(5-fluorothiazol-2-yl)-3-(tetrahydro-2H-pyran-4-yl)propanamide;

(S)-2-(4-(cyclopropylsulfonyl)-6-hydroxy-1H-indazol-1-yl)-N-(5-fluorothiazol-2-yl)-3-(tetrahydro-2H-pyran-4-yl)propanamide;

(R)-2-(4-(cyclopropylsulfonyl)-6-hydroxy-1H-indazol-1-yl)-N-(5-fluorothiazol-2-yl)-3-(tetrahydro-2H-pyran-4-yl)propanamide;

2-(4-(cyclopropylsulfonyl)-5-methoxy-1H-indazol-1-yl)-N-(5-fluorothiazol-2-yl)-3-(tetrahydro-2H-pyran-4-yl)propanamide;

(R)-2-(4-(cyclopropylsulfonyl)-5-methoxy-1H-indazol-1-yl)-N-(5-fluorothiazol-2-yl)-3-(tetrahydro-2H-pyran-4-yl)propanamide;

(S)-2-(4-(cyclopropylsulfonyl)-5-methoxy-1H-indazol-1-yl)-N-(5-fluorothiazol-2-yl)-3-(tetrahydro-2H-pyran-4-yl)propanamide;

2-(4-(cyclopropylsulfonyl)-6-methoxy-1H-indazol-1-yl)-N-(1-methyl-1H-pyrazol-3-yl)-3-(tetrahydro-2H-pyran-4-yl)propanamide;

(S)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide;

(R)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide;

N-(3-cyanopyridin-2-yl)-2-(4-(cyclopropylsulfonyl)-1H-indazol-1-yl)-3-(tetrahydro-2H-pyran-4-yl)propanamide;

2-(4-(cyclopropylsulfonyl)-5-(difluoromethoxy)-1H-indazol-1-yl)-N-(5-fluorothiazol-2-yl)-3-(tetrahydro-2H-pyran-4-yl)propanamide;

2-(4-(cyclopropylsulfonyl)-1H-indazol-1-yl)-N-(3,5-difluoropyridin-2-yl)-3-(tetrahydro-2H-pyran-4-yl)propanamide;

(S)-2-(4-(cyclopropylsulfonyl)-1H-indazol-1-yl)-N-(pyrazin-2-yl)-3-(tetrahydro-2H-pyran-4-yl)propanamide;

(R)-2-(4-(cyclopropylsulfonyl)-1H-indazol-1-yl)-N-(pyrazin-2-yl)-3-(tetrahydro-2H-pyran-4-yl)propanamide;

2-(4-(cyclopropylsulfonyl)-5-methoxy-1H-indazol-1-yl)-N-(pyrazin-2-yl)-3-(tetrahydro-2H-pyran-4-yl)propanamide;

2-(4-(cyclopropylsulfonyl)-6-methoxy-1H-indazol-1-yl)-N-(pyrazin-2-yl)-3-(tetrahydro-2H-pyran-4-yl)propanamide;

(R)-2-(4-(cyclopropylsulfonyl)-5-methoxy-1H-indazol-1-yl)-N-(pyrazin-2-yl)-3-(tetrahydro-2H-pyran-4-yl)propanamide;

(S)-2-(4-(cyclopropylsulfonyl)-5-methoxy-1H-indazol-1-yl)-N-(pyrazin-2-yl)-3-(tetrahydro-2H-pyran-4-yl)propanamide;

2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide;

2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide;

2-(4-(cyclopropylsulfonyl)-1H-pyrazolo[3,4-b]pyridin-1-yl)-N-(pyrazin-2-yl)-3-(tetrahydro-2H-pyran-4-yl)propanamide;

(S)-2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide;

(R)-2-(4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide;

2-(6-cyano-4-(cyclopropylsulfonyl)-1H-indazol-1-yl)-N-(pyrazin-2-yl)-3-(tetrahydro-2H-pyran-4-yl)propanamide;

2-(6-chloro-4-(cyclopropylsulfonyl)-1H-indazol-1-yl)-N-(1-methyl-1H-pyrazol-3-yl)-3-(tetrahydro-2H-pyran-4-yl)propanamide;

2-(6-chloro-4-(cyclopropylsulfonyl)-1H-indazol-1-yl)-N-(pyrazin-2-yl)-3-(tetrahydro-2H-pyran-4-yl)propanamide;

2-(4-(cyclopropylsulfonyl)-6-fluoro-1H-indazol-1-yl)-N-(pyrazin-2-yl)-3-(tetrahydro-2H-pyran-4-yl)propanamide;

2-(4-(cyclopropylsulfonyl)-6-fluoro-1H-indazol-1-yl)-N-(1-methyl-1H-pyrazol-3-yl)-3-(tetrahydro-2H-pyran-4-yl)propanamide;

(S)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide;

(R)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide;

(S)-6-(2-(4-(cyclopropylsulfonyl)-1H-indazol-1-yl)-3-(tetrahydro-2H-pyran-4-yl)propanamido)nicotinamide;

(R)-6-(2-(4-(cyclopropylsulfonyl)-1H-indazol-1-yl)-3-(tetrahydro-2H-pyran-4-yl)propanamido)nicotinamide;

(S)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide;

(R)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide;

(R)-2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;

(S)-2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;

2-(4-(cyclopropylsulfonyl)-6-fluoro-1H-indazol-1-yl)-N-(5-fluorothiazol-2-yl)-3-(tetrahydro-2H-pyran-4-yl)propanamide;

2-(4-(cyclopropylsulfonyl)-1H-indazol-1-yl)-N-(6-methylpyridazin-3-yl)-3-(tetrahydro-2H-pyran-4-yl)propanamide;

6-(2-(4-(cyclopropylsulfonyl)-6-fluoro-1H-indazol-1-yl)-3-(tetrahydro-2H-pyran-4-yl)propanamido)nicotinamide;

(R)-2-(4-(cyclopropylsulfonyl)-1H-indazol-1-yl)-N-(1-methyl-1H-pyrazol-3-yl)-3-(tetrahydro-2H-pyran-4-yl)propanamide;

(S)-2-(4-(cyclopropylsulfonyl)-1H-indazol-1-yl)-N-(1-methyl-1H-pyrazol-3-yl)-3-(tetrahydro-2H-pyran-4-yl)propanamide;

2-(6-cyano-4-(cyclopropylsulfonyl)-1H-indazol-1-yl)-N-(5-fluorothiazol-2-yl)-3-(tetrahydro-2H-pyran-4-yl)propanamide;

2-(6-chloro-4-(cyclopropylsulfonyl)-1H-indazol-1-yl)-N-(5-fluorothiazol-2-yl)-3-(tetrahydro-2H-pyran-4-yl)propanamide;

2-(4-(cyclopropylsulfonyl)-6-methyl-1H-indazol-1-yl)-N-(5-fluorothiazol-2-yl)-3-(tetrahydro-2H-pyran-4-yl)propanamide;

(S)-2-(4-(cyclopropylsulfonyl)-6-fluoro-1H-indazol-1-yl)-N-(5-fluorothiazol-2-yl)-3-(tetrahydro-2H-pyran-4-yl)propanamide;

2-(4-(cyclopropylsulfonyl)-1H-indazol-1-yl)-N-(pyrimidin-4-yl)-3-(tetrahydro-2H-pyran-4-yl)propanamide;

N-(5-cyanothiazol-2-yl)-2-(4-(cyclopropylsulfonyl)-1H-indazol-1-yl)-3-(tetrahydro-2H-pyran-4-yl)propanamide;

N-(5-cyanopyrimidin-2-yl)-2-(4-(cyclopropylsulfonyl)-1H-indazol-1-yl)-3-(tetrahydro-2H-pyran-4-yl)propanamide;

2-(4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;

(S)-2-(4-(cyclopropylsulfonyl)-6-methoxy-1H-indazol-1-yl)-N-(5-fluorothiazol-2-yl)-3-(tetrahydro-2H-pyran-4-yl)propanamide;

(R)-2-(4-(cyclopropylsulfonyl)-6-methoxy-1H-indazol-1-yl)-N-(5-fluorothiazol-2-yl)-3-(tetrahydro-2H-pyran-4-yl)propanamide;

2-(4-(cyclopropylsulfonyl)-6-hydroxy-1H-indazol-1-yl)-N-(5-fluorothiazol-2-yl)-3-(tetrahydro-2H-pyran-4-yl)propanamide;

(R)-2-(6-cyano-4-(cyclopropylsulfonyl)-1H-indazol-1-yl)-N-(5-fluorothiazol-2-yl)-3-(tetrahydro-2H-pyran-4-yl)propanamide;

(S)-2-(6-cyano-4-(cyclopropylsulfonyl)-1H-indazol-1-yl)-N-(5-fluorothiazol-2-yl)-3-(tetrahydro-2H-pyran-4-yl)propanamide;

2-(4-(cyclopropylsulfonyl)-1H-indazol-1-yl)-N-(1,5-dimethyl-1H-pyrazol-3-yl)-3-(tetrahydro-2H-pyran-4-yl)propanamide;

N-(5-cyanopyridin-2-yl)-2-(4-(cyclopropylsulfonyl)-1H-indazol-1-yl)-3-(tetrahydro-2H-pyran-4-yl)propanamide;

(S)-N-(5-cyanothiazol-2-yl)-2-(4-(cyclopropylsulfonyl)-1H-indazol-1-yl)-3-(tetrahydro-2H-pyran-4-yl)propanamide;

(R)-N-(5-cyanothiazol-2-yl)-2-(4-(cyclopropylsulfonyl)-1H-indazol-1-yl)-3-(tetrahydro-2H-pyran-4-yl)propanamide;

(S)-2-(4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;

(R)-2-(4-(cyclopropylsulfonyl)-1H-pyrazolo[3,4-b]pyridin-1-yl)-N-(5-fluorothiazol-2-yl)-3-(tetrahydro-2H-pyran-4-yl)propanamide;

(S)-2-(6-chloro-4-(cyclopropylsulfonyl)-1H-indazol-1-yl)-N-(5-fluorothiazol-2-yl)-3-(tetrahydro-2H-pyran-4-yl)propanamide;

2-(6-amino-4-(cyclopropylsulfonyl)-1H-indazol-1-yl)-N-(5-fluorothiazol-2-yl)-3-(tetrahydro-2H-pyran-4-yl)propanamide;

2-(4-(cyclopropylsulfonyl)-6-(difluoromethoxy)-1H-indazol-1-yl)-N-(5-fluorothiazol-2-yl)-3-(tetrahydro-2H-pyran-4-yl)propanamide;

2-(4-(cyclopropylsulfonyl)-5-hydroxy-1H-indazol-1-yl)-N-(5-fluorothiazol-2-yl)-3-(tetrahydro-2H-pyran-4-yl)propanamide;

(R)-2-(6-chloro-4-(cyclopropylsulfonyl)-1H-indazol-1-yl)-N-(5-fluorothiazol-2-yl)-3-(tetrahydro-2H-pyran-4-yl)propanamide;

2-(4-(cyclopropylsulfonyl)-1H-indazol-1-yl)-N-(1-(methylsulfonyl)-1H-pyrazol-3-yl)-3-(tetrahydro-2H-pyran-4-yl)propanamide;

2-(4-(cyclopropylsulfonyl)-1H-indazol-1-yl)-N-(6-fluoropyridin-2-yl)-3-(tetrahydro-2H-pyran-4-yl)propanamide;
2-(4-(cyclopropylsulfonyl)-5-fluoro-1H-indazol-1-yl)-N-(5-fluorothiazol-2-yl)-3-(tetrahydro-2H-pyran-4-yl)propanamide;
2-(5-bromo-4-(cyclopropylsulfonyl)-1H-indazol-1-yl)-N-(5-fluorothiazol-2-yl)-3-(tetrahydro-2H-pyran-4-yl)propanamide;
2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide;
2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide;
2-(4-(cyclopropylsulfonyl)-5-fluoro-1H-indazol-1-yl)-N-(pyrazin-2-yl)-3-(tetrahydro-2H-pyran-4-yl)propanamide;
2-(4-(cyclopropylsulfonyl)-5-fluoro-1H-indazol-1-yl)-N-(1-ethyl-1H-pyrazol-3-yl)-3-(tetrahydro-2H-pyran-4-yl)propanamide;
2-(4-(cyclopropylsulfonyl)-5-methyl-1H-indazol-1-yl)-N-(pyrazin-2-yl)-3-(tetrahydro-2H-pyran-4-yl)propanamide;
2-(4-(cyclopropylsulfonyl)-5-methyl-1H-indazol-1-yl)-N-(1-methyl-1H-pyrazol-3-yl)-3-(tetrahydro-2H-pyran-4-yl)propanamide;
(S)-2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide;
(R)-2-(4-(cyclopropylsulfonyl)-1H-pyrazolo[3,4-c]pyridin-1-yl)-N-(1-methyl-1H-pyrazol-3-yl)-3-(tetrahydro-2H-pyran-4-yl)propanamide;
(R)-2-(4-(cyclopropylsulfonyl)-1H-pyrazolo[3,4-b]pyridin-1-yl)-N-(pyrazin-2-yl)-3-(tetrahydro-2H-pyran-4-yl)propanamide;
(S)-2-(4-(cyclopropylsulfonyl)-1H-pyrazolo[3,4-b]pyridin-1-yl)-N-(pyrazin-2-yl)-3-(tetrahydro-2H-pyran-4-yl)propanamide;
(R)-2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide;
(S)-2-(6-amino-4-(cyclopropylsulfonyl)-1H-pyrazolo[3,4-b]pyridin-1-yl)-N-(pyrazin-2-yl)-3-(tetrahydro-2H-pyran-4-yl)propanamide;
(S)-2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide;
(R)-2-(4-(cyclopropylsulfonyl)-5-fluoro-1H-indazol-1-yl)-N-(1-methyl-1H-pyrazol-3-yl)-3-(tetrahydro-2H-pyran-4-yl)propanamide;
2-(6-amino-4-(cyclopropylsulfonyl)-1H-pyrazolo[3,4-b]pyridin-1-yl)-N-(1-methyl-1H-pyrazol-3-yl)-3-(tetrahydro-2H-pyran-4-yl)propanamide;
(S)-2-(4-(cyclopropylsulfonyl)-1H-pyrazolo[3,4-c]pyridin-1-yl)-N-(pyrazin-2-yl)-3-(tetrahydro-2H-pyran-4-yl)propanamide;
(R)-2-(4-(cyclopropylsulfonyl)-1H-pyrazolo[3,4-c]pyridin-1-yl)-N-(pyrazin-2-yl)-3-(tetrahydro-2H-pyran-4-yl)propanamide; and
a pharmaceutically acceptable salt of any one of the aforementioned compounds.

34. A compound according to claim 1, which is 2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide or a pharmaceutically acceptable salt thereof.

35. A compound according to claim 1, which is (S)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide or a pharmaceutically acceptable salt thereof.

36. A compound according to claim 1, which is (R)-2-(4-(cyclopropylsulfonyl)-1H-pyrazolo[3,4-c]pyridin-1-yl)-N-(5-fluorothiazol-2-yl)-3-(tetrahydro-2H-pyran-4-yl)propanamide or a pharmaceutically acceptable salt thereof.

37. A compound according to claim 1, which is 6-(2-(4-(cyclopropylsulfonyl)-1H-indazol-1-yl)-3-(tetrahydro-2H-pyran-4-yl)propanamido)nicotinamide or a pharmaceutically acceptable salt thereof.

38. A compound according to claim 1, which is (S)-6-(2-(4-(cyclopropylsulfonyl)-1H-indazol-1-yl)-3-(tetrahydro-2H-pyran-4-yl)propanamido)nicotinamide or a pharmaceutically acceptable salt thereof.

39. A compound according to claim 1, which is (R)-6-(2-(4-(cyclopropylsulfonyl)-1H-indazol-1-yl)-3-(tetrahydro-2H-pyran-4-yl)propanamido)nicotinamide or a pharmaceutically acceptable salt thereof.

40. A compound according to claim 1, which is 2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide or a pharmaceutically acceptable salt thereof.

41. A compound according to claim 1, which is (S)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide or a pharmaceutically acceptable salt thereof.

42. A compound according to claim 1, which is (R)-2-(4-(cyclopropylsulfonyl)-5-methoxy-1H-indazol-1-yl)-N-(1-methyl-1H-pyrazol-3-yl)-3-(tetrahydro-2H-pyran-4-yl)propanamide or a pharmaceutically acceptable salt thereof.

43. A compound according to claim 1, which is 2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide or a pharmaceutically acceptable salt thereof.

44. A compound according to claim 1, which is (R)-2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide or a pharmaceutically acceptable salt thereof.

45. A compound according to claim 1, which is (S)-2-(6-amino-4-(cyclopropylsulfonyl)-1H-pyrazolo[3,4-b]pyridin-1-yl)-N-(5-fluorothiazol-2-yl)-3-(tetrahydro-2H-pyran-4-yl)propanamide or a pharmaceutically acceptable salt thereof.

46. A compound according to claim 1, which is 2-(6-cyano-4-(cyclopropylsulfonyl)-1H-indazol-1-yl)-N-(1-methyl-1H-pyrazol-3-yl)-3-(tetrahydro-2H-pyran-4-yl)propanamide or a pharmaceutically acceptable salt thereof.

47. A compound according to claim 1, which is (S)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide or a pharmaceutically acceptable salt thereof.

48. A compound according to claim 1, which is (R)-2-(6-cyano-4-(cyclopropylsulfonyl)-1H-indazol-1-yl)-N-(1-methyl-1H-pyrazol-3-yl)-3-(tetrahydro-2H-pyran-4-yl)propanamide or a pharmaceutically acceptable salt thereof.

49. A compound according to claim 1, which is 2-(4-(cyclopropylsulfonyl)-1H-pyrazolo[3,4-c]pyridin-1-yl)-N-(pyrazin-2-yl)-3-(tetrahydro-2H-pyran-4-yl)propanamide or a pharmaceutically acceptable salt thereof.

50. A compound according to claim 1, which is (S)-2-(4-(cyclopropylsulfonyl)-1H-pyrazolo[3,4-c]pyridin-1-yl)-N-(pyrazin-2-yl)-3-(tetrahydro-2H-pyran-4-yl)propanamide or a pharmaceutically acceptable salt thereof.

51. A compound according to claim 1, which is (R)-2-(4-(cyclopropylsulfonyl)-1H-pyrazolo[3,4-c]pyridin-1-yl)-N-

(pyrazin-2-yl)-3-(tetrahydro-2H-pyran-4-yl)propanamide or a pharmaceutically acceptable salt thereof.

52. A pharmaceutical composition comprising a compound or pharmaceutically acceptable salt as defined in any one of the preceding claims, and a pharmaceutically acceptable excipient.

* * * * *

SEQUENCE LISTING

```
<160> NUMBER OF SEQ ID NOS: 1

<210> SEQ ID NO 1
<211> LENGTH: 458
<212> TYPE: PRT
<213> ORGANISM: Homo sapiens
<220> FEATURE:
<221> NAME/KEY: MISC_FEATURE
<222> LOCATION: (5)..(458)
<223> OTHER INFORMATION: Amino Acid Sequence residues 12-465 of human
      Glucokinase

<400> SEQUENCE: 1

Met Lys Leu Met Ala Leu Thr Leu Val Glu Gln Ile Leu Ala Glu Phe
1               5                   10                  15

Gln Leu Gln Glu Glu Asp Leu Lys Lys Val Met Arg Arg Met Gln Lys
                20                  25                  30

Glu Met Asp Arg Gly Leu Arg Leu Glu Thr His Glu Glu Ala Ser Val
            35                  40                  45

Lys Met Leu Pro Thr Tyr Val Arg Ser Thr Pro Glu Gly Ser Glu Val
        50                  55                  60

Gly Asp Phe Leu Ser Leu Asp Leu Gly Gly Thr Asn Phe Arg Val Met
65                  70                  75                  80

Leu Val Lys Val Gly Glu Gly Glu Gly Gln Trp Ser Val Lys Thr
                85                  90                  95

Lys His Gln Met Tyr Ser Ile Pro Glu Asp Ala Met Thr Gly Thr Ala
                100                 105                 110

Glu Met Leu Phe Asp Tyr Ile Ser Glu Cys Ile Ser Asp Phe Leu Asp
            115                 120                 125

Lys His Gln Met Lys His Lys Leu Pro Leu Gly Phe Thr Phe Ser
        130                 135                 140

Phe Pro Val Arg His Glu Asp Ile Asp Lys Gly Ile Leu Leu Asn Trp
145                 150                 155                 160

Thr Lys Gly Phe Lys Ala Ser Gly Ala Glu Gly Asn Asn Val Val Gly
                165                 170                 175

Leu Leu Arg Asp Ala Ile Lys Arg Arg Gly Asp Phe Glu Met Asp Val
                180                 185                 190

Val Ala Met Val Asn Asp Thr Val Ala Thr Met Ile Ser Cys Tyr Tyr
            195                 200                 205

Glu Asp His Gln Cys Glu Val Gly Met Ile Val Gly Thr Gly Cys Asn
        210                 215                 220
```

-continued

```
Ala Cys Tyr Met Glu Glu Met Gln Asn Val Glu Leu Val Glu Gly Asp
225                 230                 235                 240

Glu Gly Arg Met Cys Val Asn Thr Glu Trp Gly Ala Phe Gly Asp Ser
                245                 250                 255

Gly Glu Leu Asp Glu Phe Leu Leu Glu Tyr Asp Arg Leu Val Asp Glu
                260                 265                 270

Ser Ser Ala Asn Pro Gly Gln Gln Leu Tyr Glu Lys Leu Ile Gly Gly
            275                 280                 285

Lys Tyr Met Gly Glu Leu Val Arg Leu Val Leu Leu Arg Leu Val Asp
    290                 295                 300

Glu Asn Leu Leu Phe His Gly Glu Ala Ser Glu Gln Leu Arg Thr Arg
305                 310                 315                 320

Gly Ala Phe Glu Thr Arg Phe Val Ser Gln Val Glu Ser Asp Thr Gly
                325                 330                 335

Asp Arg Lys Gln Ile Tyr Asn Ile Leu Ser Thr Leu Gly Leu Arg Pro
                340                 345                 350

Ser Thr Thr Asp Cys Asp Ile Val Arg Arg Ala Cys Glu Ser Val Ser
        355                 360                 365

Thr Arg Ala Ala His Met Cys Ser Ala Gly Leu Ala Gly Val Ile Asn
    370                 375                 380

Arg Met Arg Glu Ser Arg Ser Glu Asp Val Met Arg Ile Thr Val Gly
385                 390                 395                 400

Val Asp Gly Ser Val Tyr Lys Leu His Pro Ser Phe Lys Glu Arg Phe
                405                 410                 415

His Ala Ser Val Arg Arg Leu Thr Pro Ser Cys Glu Ile Thr Phe Ile
            420                 425                 430

Glu Ser Glu Glu Gly Ser Gly Arg Gly Ala Ala Leu Val Ser Ala Val
            435                 440                 445

Ala Cys Lys Lys Ala Cys Met Leu Gly Gln
            450                 455
```